(12) United States Patent
DeBusk et al.

(10) Patent No.: US 6,314,556 B1
(45) Date of Patent: Nov. 6, 2001

(54) MODULAR HEALTH CARE INFORMATION MANAGEMENT SYSTEM UTILIZING REUSABLE SOFTWARE OBJECTS

(75) Inventors: Brian C. DeBusk, Clinton; Michael C. Cofer, Knoxville; Mark W. Shanks, Knoxville; Wil Francis Lukens, Knoxville, all of TN (US)

(73) Assignee: DeRoyal Business Systems, LLC, Powell, TN (US)

( * ) Notice: Subject to any disclaimer, the term of this patent is extended or adjusted under 35 U.S.C. 154(b) by 0 days.

(21) Appl. No.: 09/382,710

(22) Filed: Aug. 24, 1999

Related U.S. Application Data

(63) Continuation-in-part of application No. 08/965,788, filed on Nov. 7, 1997, now Pat. No. 5,995,937.

(51) Int. Cl.[7] .................................................. G06F 17/60
(52) U.S. Cl. ........................................ 717/1; 705/2
(58) Field of Search ........................................ 717/1; 705/2

(56) References Cited

U.S. PATENT DOCUMENTS

| | | | |
|---|---|---|---|
| 5,301,320 | 4/1994 | McAtee et al. | 705/9 |
| 5,319,543 | 6/1994 | Wilhelm | 705/3 |
| 5,583,758 | 12/1996 | McIlroy et al. | 705/2 |
| 5,596,502 | 1/1997 | Koski et al. | 364/468.01 |
| 5,721,913 | 2/1998 | Ackroff et al. | 707/103 |
| 5,724,575 * | 3/1998 | Hoover et al. | 707/10 |
| 5,732,401 | 3/1998 | Conway | 705/29 |
| 5,748,907 | 5/1998 | Crane | 705/2 |
| 5,826,239 | 10/1998 | Du et al. | 705/8 |
| 5,842,173 | 11/1998 | Strum et al. | 705/1 |
| 5,845,254 | 12/1998 | Lockwood et al. | 705/2 |

OTHER PUBLICATIONS

Sethi, Ravi. Programming Languages. New York: Addison Wesley. 1989, pp. 169–173 and 178–185.

Biggerstaff et al. Software Reusability. New York: Addison Wesley. 1989, vol. 2, pp. 269–287.

* cited by examiner

Primary Examiner—Mark Powell
Assistant Examiner—John Q. Chavis
(74) Attorney, Agent, or Firm—Luedeka, Neely & Graham, P.C.

(57) ABSTRACT

A health care information management system that utilizes modular and reusable software objects to allow for user configuration. The disclosed information management system allows for the creation by the user of software objects representative of specific events and resources which will occur or be utilized during the provision of health care to patients. These user configured software modules then allow the user to track the provision of health care, the utilization of resources during the provision of health care, the allocation of resources to perform medical procedures and identify opportunities for enhancing efficiencies in the provision of health care services. In one embodiment of the invention described, the system allows for the user to create, manage and maintain software modules representing specific procedural pathways to be performed in a health care institution. The user creates these modules using user configurable software objects that function to represent containers, resources and data. The software objects are modular and re-usable and allow the user to select components for creation of the modules. The created modules may then be used to provide information management relating to the provision of the medical procedures represented by the procedural pathway modules.

36 Claims, 147 Drawing Sheets

| | Part | Description | Consume | Scrap | Return | Cost |
|---|---|---|---|---|---|---|
| 1 | 125382 | Anesthesia Prep Kit | 2.00 | .00 | .00 | na |
| 2 | 117237 | CAN,SUCT 2500CC W/SPT/TBG/1 | 1.00 | | | |
| 3 | 112393 | SUTURE ETHILON 5-0 P-3 BLK | 2 | | | |
| 4 | 112465 | SUTURE,ETHILON 3/0 PSL NDL | 2.00 | .00 | .00 | na |
| 5 | 125353 | Warming Blanket | 1.00 | .00 | .00 | na |
| 6 | 125142 | COBE Oxygenator | 1.00 | | | |
| 7 | 118025 | BLD,DEBAKEY,8MM WIDTH | 2.00 | .00 | .00 | na |

Care Event: Open Heart Anesthesia Care

636

304 — OK    Cancel

Show Kit Detail

11/04/1997   3:48 PM

MODULAR HEALTH CARE INFORMATION MANAGEMENT SYSTEM UTILIZING REUSABLE SOFTWARE OBJECTS

This application is a continuation in part of application Ser. No. 08/965,788, filed Nov. 7, 1997, entitled Modular Health-Care Information Management System Utilizing Reusable Software Objects, which issued on Nov. 30, 1999 as U.S. Pat. No. 5,995,937.

FIELD OF THE INVENTION

This invention relates to the field of information systems for use in the health care environment and in particular to an information system incorporating software for supply, scheduling and resource utilization management in the health care environment. This specification includes a microfiche appendix of 50 slides with a capacity of 96 frames each, with a total of 1,450 frames. This application is a continuation in part of application 08/965,788, filed Nov. 7, 1997, entitled Modular Health-Care Information Management System Utilizing Reusable Software Objects, which issued on Nov. 30, 1999 as U.S. Pat. 5,995,937.

BACKGROUND OF THE INVENTION

One important consideration in the provision of health care is the allocation, utilization and consumption of resources such as labor, durable equipment, reusable supplies and disposable supplies. For example, one way for supplies to be obtained by hospitals is for a central supply service to order the individual supplies anticipated to be needed for a given time period. These supplies are maintained in a supply room until needed for a given procedure. Once a procedure is scheduled, a pick list (a list of supplies) is generated. A hospital employee then uses the pick list to withdraw the desired items from inventory and place them in the operating room where the procedure takes place. After the procedure is completed, unused supplies are returned to inventory, a list of used supplies is provided to the billing department, and the used supplies are disposed of or re-sterilized. However, this system is costly and inefficient.

For example, a relatively large inventory of supplies has to be maintained, particularly for standard items such as drapes, sponges, sutures, clamps, etc., which could be used in a large variety of procedures. The inventory of such items has to be large in order to insure that sufficient quantities are on hand for every procedure. Furthermore, the act of picking items for surgery and, later, restocking unused items, is onerous and expensive since relatively highly skilled labor is utilized to insure that the proper items were collected and that the restocked items are placed in the proper location. In particular, the restocking of unused items is a substantial burden on the hospital. Each item pulled from inventory has to be either used and billed for, or restocked and not billed for. If an item is not used during the procedure and is billed for anyway, the billing for that product could be considered fraud on the reimburser. Since items are often individually wrapped, the restocking procedure could be very time consuming, particularly where sufficient quantities of items are picked from inventory to cover any situation during surgery. For example, it is not uncommon to withdraw ten clamps from inventory and use only three or four, except in situations where heavy bleeding is encountered, which might necessitate the use of all ten.

What is needed, therefore, is an integrated information system for use in healthcare institutions for managing, optimizing and analyzing the use of resources within that institution.

SUMMARY OF THE INVENTION

The above and further objects are met in the exemplar embodiment of the present invention, having an information management system for managing information relating to providing health care services, including a general purpose computer system having storage means for storing data corresponding to the information, processing means for processing management instructions, display means for visually presenting the information, and input means for receiving the management instructions and the information. Information management software is installed on the general purpose computer system, which software includes software objects, where each of the software objects provides a health care information management function and corresponds to an aspect of providing health care services.

In various preferred embodiments the software objects include software objects of many different types. Node software objects are for creating, altering characteristics of, and the management of the software objects. Container software objects are for containing the software objects, and correspond to at least one of health care procedures, health care information, and health care resource groups. Types of container software objects include care event container software objects for containing the software objects, and which correspond to health care procedures, and bundle container software objects to contain the software objects, which correspond to health care resource groups.

Resource software objects correspond to resources to be used in the provision of health care services, and also are of several types. Equipment resource software objects correspond to equipment to be used in the provision of health care services. Personnel resource software objects correspond to personnel to be used in the provision of health care services, and supply resource software objects correspond to supplies to be used in the provision of health care services. Finally, data software objects correspond to health care information associated with the provision of health care services.

The node software objects, container software objects, resource software objects, and data software objects may be combined in different structures, including procedural pathways corresponding to sets of health care procedures, cases corresponding to sets of health care procedures designated for a patient, and libraries. The cases may be selectively designated as open, corresponding to health care procedures that are planned for a patient, or selectively designated as closed, corresponding to health care procedures that are completed for a patient. The libraries may be of predefined care event containers corresponding to predefined health care procedures, or predefined bundle containers corresponding to predefined health care resource groups, or a combination of the two. Libraries can also include predefined data software objects, corresponding to the predetermined sets of health care information to be gathered and recorded.

Further, the node software objects, container software objects, resource software objects, and data software objects may be combined in a library of procedural pathways having predefined care event containers corresponding to predefined health care procedures and predefined bundle containers corresponding to predefined health care resource groups, which procedural pathways correspond to predefined sets of health care procedures. The procedural pathways may contain data objects, corresponding to health care information to be gathered and recorded. The data objects may be used to selectively include a portion of the predefined bundle containers.

The node software objects, container software objects, resource software objects, and data software objects may be provided in a hierarchical form, corresponding to a sequential order of health care procedures to be performed, health care resources to be provided, and health care information to be gathered and recorded.

In an alternate embodiment of a system for managing health care services, a computing means has input means for receiving patient health care information, storage means for storing data corresponding to the patient health care information, processing means for processing software objects corresponding to health care services management instructions and the patient health care information and producing health care services management output, and display means for visually presenting the health care services output.

The software objects include data software objects, resource software objects, and node software objects. The data software objects have means for receiving the patient health care information and means for providing the patient health care information through a standardized interface.

The resource software objects associate resources with information relating to the resources, and are of several different types. Personnel resource software objects have means for associating a health care personnel resource with information relating to the health care personnel resource, including at least one of a personnel resource billing rate, a personnel resource pay rate, and a personnel resource time requirement, and means for providing the information relating to the health care personnel resource through the standardized interface.

Equipment resource software objects have means for associating a health care equipment resource with information relating to the health care equipment resource, including at least one of an equipment resource billing rate, an equipment resource cost, and an equipment resource time requirement, and means for providing the information relating to the health care equipment resource through the standardized interface.

Supply resource software objects include bundle supply resource software objects and conditional bundle supply resource software objects. The bundle supply resource software objects have means for associating health care supply resources with information relating to health care supply resources, including at least one of a supply resource billing rate and a supply resource cost, and means for providing the information relating to heath care supply resources through the standardized interface. The conditional bundle supply resource software objects have means for associating health care supply resources with information relating to health care supply resources, including at least one of supply resource billing rates and supply resource costs, and means for selectively providing the information relating to health care supply resources through the standardized interface based at least in part on the patient health care information provided by at least one of the data software objects.

The node software objects include at least a pathway node software object having means for selectively creating the data software objects and means for selectively creating the resource software objects. Means selectively link the standardized interface of the data software objects and resource software objects into configurable procedural pathways associated with health care treatment plans. Means also selectively adapt the information provided through the standardized interface of the data software objects, and resource software objects. Means further provide the data software objects and resource software objects with a first set of functions specifically adapted to the pathway node software object.

In a preferred embodiment, container software objects are also included, having means for selectively associating groups of data software objects, resource software objects, and container software objects, and means for associating the groups with information relating to at least one of a health care procedure and a health care resource kit.

BRIEF DESCRIPTION OF THE DRAWINGS

The foregoing embodiments of the present invention may be best understood with reference to the following Detailed Description of the Preferred Embodiments and the drawings, wherein.

DETAILED DESCRIPTION OF THE PREFERRED EMBODIMENTS

Figure 1:
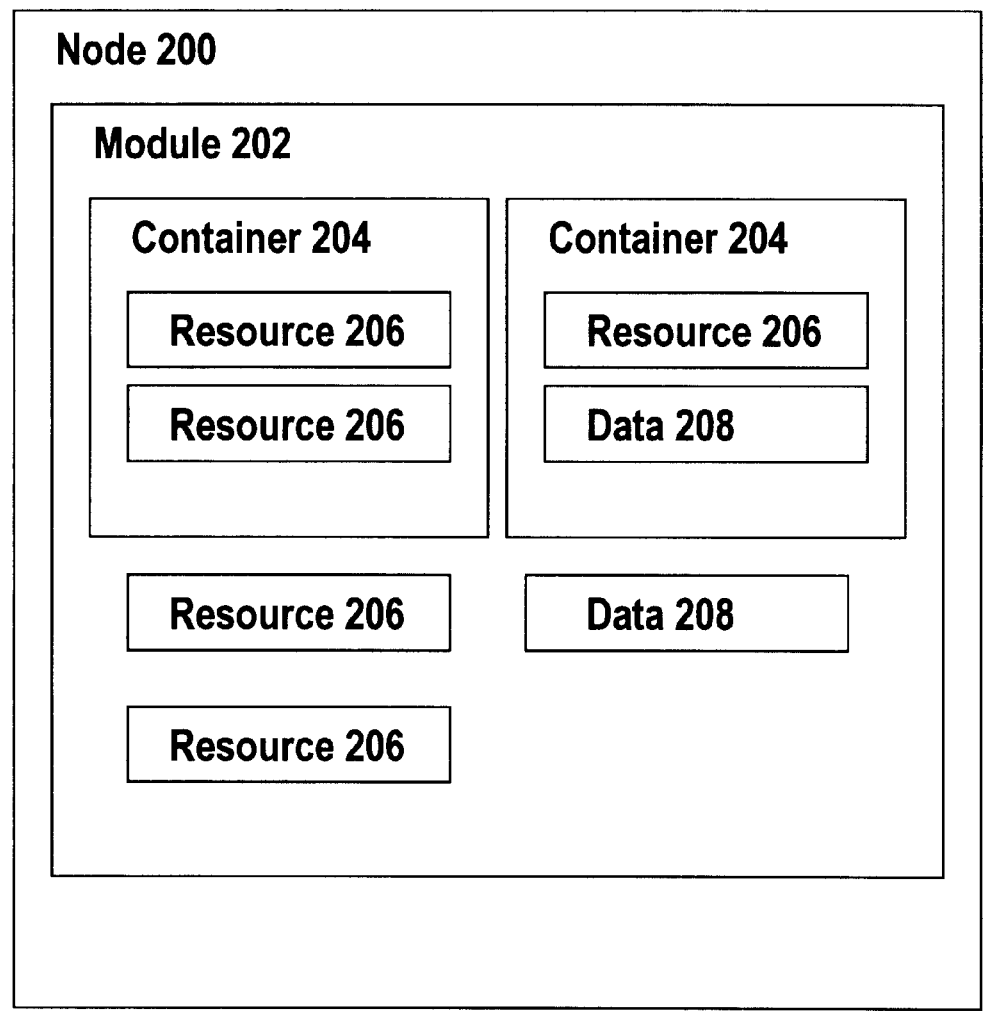
FIG. 1 is a block diagram showing the generic form of the present invention.

DeRoyal Industries, Inc., the assignee of U.S. patent application Ser. No. 08/846,798, filed Apr. 30, 1997, entitled, Method and System for the Tracking and Profiling of Supply Usage in a Health Care Environment, U.S. patent application Ser. No. 08/936,780, filed Sep. 24, 1997, entitled Method for the Analysis and Standardization of Bills of Resources, and U.S. application Ser. No. 08/889,948, filed Jul. 10, 1997, entitled Method for the Supply of Medical Supplies to a Health care Institution Based on a Nested Bill of Materials on a Procedure Level, which is a continuation-in-part of U.S. Pat. No. 5,682,728, issued Nov. 4, 1997, entitled Method for the Supply of Medical Supplies to a Health care Institution Based on a Nested Bill of Materials on a Procedure Level, the entire disclosures of which are hereby incorporated by reference thereto as if fully set forth herein, has been developing a resource utilization paradigm based upon the concept of the procedural pathway.

In the provision of medical services, the process by which medical services are provided may be described as a procedural pathway. Any given treatment regimen or clinical procedure may be easily described as a related series of care events. Each care event has some relation to at least one of either the preceding or the following care events that is logical and reasonable. For example, take a simple procedure such as suturing a wound. The task of suturing a wound can be described as a series of care events: 1) examination of the wound; 2) cleansing of the wound; 3) anesthesia; 4) suturing of the wound; and 5) dressing the sutured wound. Thus, each of these related care events make up a procedural pathway for the procedure of suturing a wound. Each of the care events could be broken down into a more detailed series of sub care events, thus, the concept of the procedural pathway is scaleable; that is, any given care event may be made of a series of care events and can therefore be described as a procedural pathway.

The concept of the procedural pathway may also be expanded to more involved procedures. For example, a patient might go to her doctor complaining of particular symptoms. The doctor might then make an examination or order tests. Based upon the result of the examination or tests, the doctor makes a diagnosis and prescribes a treatment regimen. The treatment regimen may include a surgical procedure to be performed in a hospital, as well as follow up care. In this case, the procedural pathway might look like: 1) patient induction (basic administration getting the patient into the doctor's system); 2) examination; 3) testing; 4) diagnosis; 5) prescription of treatment; 6) admission to the hospital; 7) pre-surgical testing; 8) pre-operative preparation; 9) anesthesia; 10) surgery; 11) post operative recovery; 12) discharge from hospital; 13) follow up treatment; 14) final discharge. Once again, each care event in the given example might be further broken down into smaller incremental care events, and thus represent a procedural pathway of its own. For example, the surgery could be broken down into each step associated with the surgery from the initial incision until the incision is closed.

Each care event represents the provision of some type of medical (or administrative) service, and each care event may also require the allocation of some type of resources in order to be performed. These resources may be in the form of labor (doctor, nurse, technician, data clerk, etc.), equipment (x-ray machine, respirator, vital signs monitors, etc.), or supplies (sponges, surgical instruments, drapes, x-ray film, sutures, medications, etc.). Thus, for each care event it is possible to identify the allocation of resources necessary for completion of the care event. For example, for the examination step described in the second example, the allocation of resources could be: 15 minutes of doctor's time, use of a specimen collector, use of a specimen container, and the use of a blood collection kit. Likewise, the testing step might include the use of an imaging device (such as an x-ray or MRI machine), thirty minutes of technician's time, use of x-ray film, use of an x-ray developer and associated chemical supplies, and fifteen minutes of a radiologist's time to interpret the images.

By describing events in the context of a procedural pathway, a framework is provided which allows for the systematic classification of the steps necessary to treat a particular patient as well as identifying the resource allocation necessary to properly complete the procedural pathway.

Basing an information system around the procedural pathway, as opposed to just tying services, supplies and other resources used to the patient, with no real relation to the pathway, provides an inherent ability to use the information more efficiently and to allow for greater cost accountability in the provision of medical services.

To illustrate the efficiency of the procedural pathway, it is best to analyze generally a hospital stay for a given patient. Initially, the patient will be admitted, have some blood work done, be assigned a room, possibly be subject to some diagnostic screenings, possibly have a surgical procedure done, spend a period of time recovering from the procedure and be discharged. Also, the procedural pathway may extend beyond the hospital stay and include follow up care such as periodic check ups or rehabilitation. Each step along the procedural pathway can be broken down into increasingly fine detail as series of more and more detailed sub procedures. For example, the surgical procedure can be further broken down into surgical preparation, anesthesia, the surgical procedure itself, closing and post operative anesthesia recovery. Each of these sub procedures could be further broken down into specific tasks to be performed at each stage.

As can be seen from the procedural pathway model, each stage of the procedural pathway is going to require the utilization of resources. These resources may be labor resources, consumable supply items, durable equipment, reusable supply items, particular rooms (i.e. patient rooms, OR's, recovery rooms, etc.) or services. For example, the blood work will require a technician to draw the blood, the disposable equipment for drawing blood, a labor resource to deliver the blood to the laboratory, the consumable and reusable supplies for handling and testing the blood, durable medical equipment for testing the blood, labor resources for testing the blood and generating the report, and a labor resource for providing the report to the patient's chart. As can be seen, each resource can be analyzed and tied to a particular care event along the procedural pathway.

Each procedural pathway is going to have some unique characteristics which will vary based upon the reason the patient is in the health care facility (the type of procedure), the doctor performing the procedure and the characteristics of the patient. The procedural pathway is preferably different for someone having heart bypass surgery from someone having out patient orthopedic surgery. Likewise, preferences vary from one doctor to another in performing the same surgery; i.e. one doctor may prefer the feel of one brand of scalpel while another doctor may prefer another. Finally, the patient will often dictate variation within a given procedure; i.e. one patient may have certain physical characteristics that require using certain supplies and equipment and another patient may require different supplies and equipment.

The present invention provides an information system for use in the health care environment that utilizes the procedural pathway paradigm for the input of data, the organization of data, the retrieval of data and the analysis of the data. In addition to storing unique data for each procedural pathway (historical data), the present invention also provides for the development of procedural pathways for certain medical procedures which have been analyzed and standard pathways developed. These procedural pathways, which are created from modular software objects configured by the user of the software associate the anticipated resource allocation to a given procedure and allow for the anticipation of resource consumption for each upcoming standard procedure.

For example, if a procedural pathway is developed for a hip replacement surgery, the procedural pathway for a given patient coming in for hip surgery is easily developed from the template. The information system user merely enters the identifying information about the patient and the surgeon performing the procedure, and the standard template generates a procedural pathway showing the resources required for that patient. At a further level of detail, departure points from the standard template can be identified and the alternate resource allocation for the departure points may also be provided in the information system.

For example, in co-pending application Ser. No. 08/846, 798, the disclosure of which has been incorporated by reference, this feature is described as a conditional bundle. For example, in the hip replacement surgery described above, variations in resource requirements may vary from doctor to doctor because of differing techniques, requirements and subjective preferences. Thus, the standard template for a hip replacement surgery may be substantially the same for two different doctors, but vary on a few items. The conditional bundles can be used to account for the departure from the standard template for each doctor and, by entering the doctor performing the procedure, the information system can automatically associate the appropriate conditional bundle with the standard template to form the procedural pathway for a given patient.

In terms of resource management, there are two basic types of resources which will be needed to perform a medical procedure at a given location: 1) those resources which will need to be brought in from outside the location for the procedure and 2) those resources which are maintained by the location and which must be scheduled for a given procedure (for the purposes of this application, although doctors are not usually employed by the hospital, we will assume that they are resources associated with the location, since they are typically driving the scheduling of a procedure at a location). The management of outside and inside resources requires the consideration of two different sets of problems. Typically, the outside resources will primarily include the supplies which must be ordered from outside vendors, be delivered to the location and be provided at the appropriate time and place for the performance of the procedure. The inside resources will include the labor resources, equipment owned and maintained by the location and facilities at the location such as OR's, radiology, laboratories, etc.

In managing the outside resources there are two competing interests, the desire to have sufficient quantities of everything readily available, which necessitates a large inventory of supplies along with skilled personnel to maintain the inventory and deliver it for performance of the procedure, and the desire to minimize inventory, which minimizes inventory carrying costs, the risk that inventory will expire before use, tied up capital and the skilled labor necessary to maintain the inventory and pull it for each procedure.

In managing inside resources the goal is to maximize the utilization of each available resource while carrying only the minimum amount of required resources to get the job done. Management of these resources necessitates that efficient resource allocation tools be used so that the location is not carrying costs associated with labor, equipment and facilities which are not being fully used, while insuring that all of the procedures can be performed in a timely fashion. For example, idle employees, equipment, OR's, etc. all carry a substantial cost. However, overworked employees, overused equipment and overbooked facilities reduce the efficiency and efficacy of the performance of the procedures and result in additional costs. Thus, precise scheduling and resource utilization management software is necessary to allow for the maximum productivity from resources, while minimizing inefficiency caused by overbooked resources and overworked employees. Additionally, software which allows for the detailed analysis of historical resource utilization will allow for the prediction of when new labor and other resources will be needed and allow for the most effective way of acquiring those resources, often saving money as opposed to the last minute recognition and rush acquisition of such resources.

Description of the Preferred Embodiment

In the preferred embodiment, the information management system consists of a series of software objects implemented using Microsoft ActiveX controls which may be configured and linked by a user to build a custom configured health care information management system. Preferably, the information system is implemented on a Windows NT or Windows 95 based personal computer, which may or may not be networked. In order to maintain a database of information related to this information system, a database program such as Microsoft SQL/Server or Microsoft Access is used in background. The information system of the preferred embodiment generates data and communicates through an interface compatible with the background database program. Typically, the software objects which will be described are coded in Visual C++ or Visual Basic, and adhere to the framework of ActiveX or OLE controls so as to maintain the ability to be implemented as compatible software objects in a component based software architecture.

In general, the software provides a number of "nodes," each of which correspond to a particular function of the information system. For example, if the system will have functions for developing and maintaining software based procedural pathways, maintaining and logging resource consumption on a case by case basis, and studying resource consumption for logged cases, each of these functions represent one node. Each of these nodes uses the feature of ActiveX controls to allow objects created in one node to provide necessary information or form the basis for a new object in another node. The interaction of objects from one node to another will be described more fully hereinafter.

Referring now to FIG. 1, each node 200, as described, provides for a particular information management function in the present invention. Also, each node 200 represents a software object which will allow the user to perform certain functions and tasks relative to the information system function provided for the node 200. In general, the function of each node will be to allow the user to generate specific templates, or software object modules 202 which will organize additional software objects into custom configurations representative of the information to be managed. Under each node 200, the user will have access to further software objects, by copying from previously generated templates, by creating the objects or copying them from an object library, in order to access the functionality of the node 200.

The software objects available to the user will be of three specific types: 1) container objects 204, 2) resource objects 206 and 3) data objects 208. Each of these objects represent ActiveX software objects which function as miniature software programs to perform a specific function. Container objects 204 function as receptacles of other objects and act to organize the other objects in accordance with the user's specifications. Additionally, container objects 204 will be customized by the input of data from the user based upon what the container object 204 is designed to hold, the specific use to which the container object is subjected by the user and other usage specific data which the user will provide.

Resource objects 206 are software objects which represent resources to be utilized in the provision of the health care. Resource objects 206 typically represent supplies, or kits of supplies, equipment, personnel, pharmaceuticals, or any other resource which will be utilized during the provision of health care. Each resource object 206 will be populated with data relevant to that object and will communicate that information as required.

Data objects 208 are software objects which will be used by the user to collect specific information for use by the template or the information system. For example, it may be necessary to gather certain procedure specific information at some point in a procedural pathway and a data object 208 may be inserted at that point in a module 202 to collect such data and make it available to the appropriate software objects.

Figure 2:
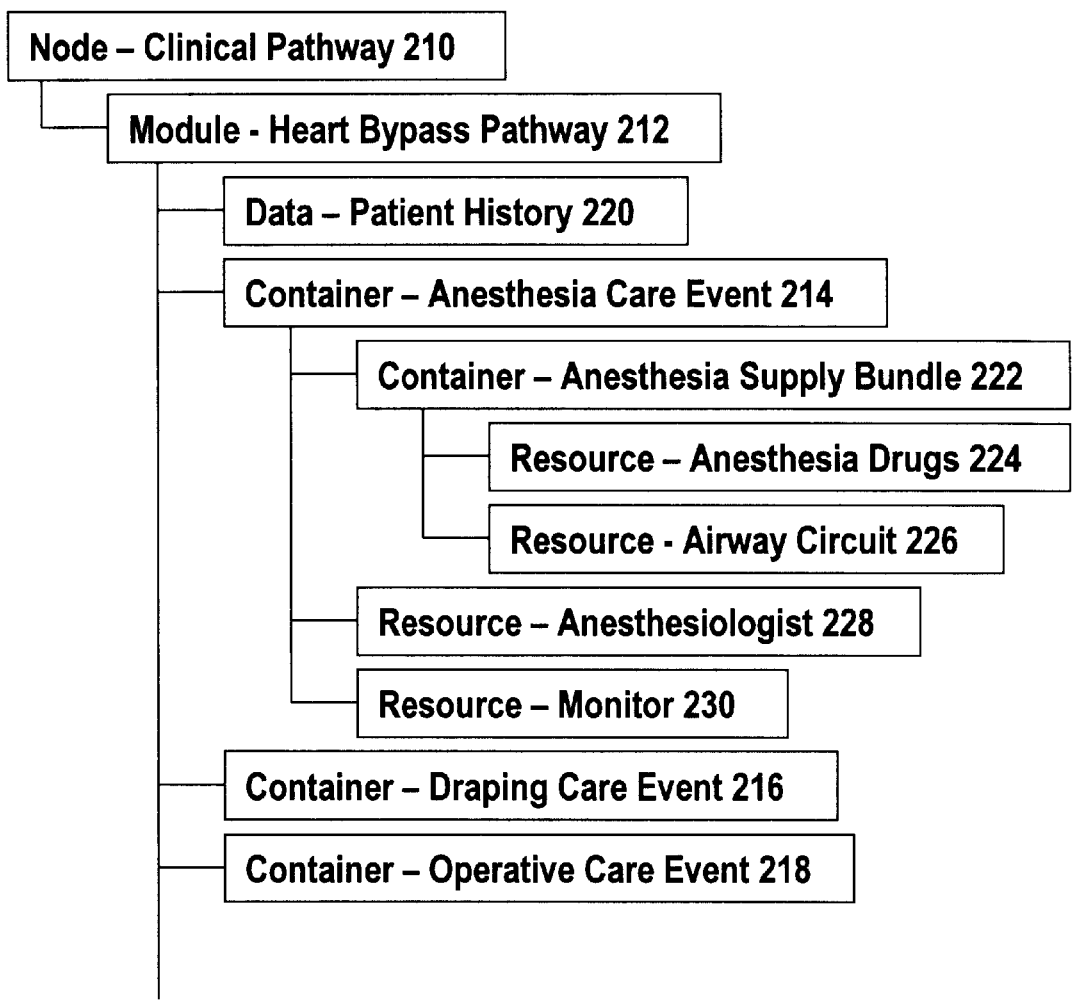
FIG. 2 is a tree diagram showing the organization of a preferred form of the present invention.

Use of the software objects is best understood by a general reference to one function of the information system. Referring now to FIG. 2, the first node 210 of the software represents the function of generation, modification and maintenance of software templates for procedural pathways using the objects previously described. This node 210 allows the user to create software modules 212, made up of user selected objects, which represent in software a health care procedure or procedural pathway. In general, as described previously, the procedural pathway will be broken down into a series of related care events, representing discrete sub procedures along the procedural pathway. Using the functionality provided by the procedural pathway node 210, the user develops a new module 212 by making an appropriate selection from the menu of the software. The user is prompted to input information relevant to the procedural pathway generally, such as the name of the procedural pathway, any hospital or other codes used to identify the type of procedure, doctors who perform that type of procedure, etc.

Once the module 210 is defined and created, the user breaks the procedure down into a series of care events. For example, if the procedure is a heart bypass operation, then various care events can be identified such as 1) anesthesia care event, 2) draping care event and 3) the operative care event. Each of these care events is implemented in the procedural pathway module 212 by the selection or creation of care event container objects corresponding to each care event 214, 216, and 218. These objects require the input of information relevant to the care event and function as containers for additional container, resource, or data care events.

Once the care event containers 214, 216 and 218 are created in the module 212, the user fills out each of the associated care events for the module. For example, a patient history data object 220 might be associated with the module 212, which prompts the user to obtain patient specific data when the procedural pathway is used relative to a particular patient. Resources are then associated with each care event.

For example, the Anesthesia Care Event container 214 may contain an anesthesia supply bundle container 222, which in turn can contain resources such as anesthesia drugs 224 and an airway circuit 226. Other resources, provided by a resource object, such as an anesthesiologist 228 and patient monitor 230, which are related to the anesthesia care event 214 are also associated with the anesthesia care event 230. In the example, the anesthesia drugs resource 224 represents a pharmaceutical resource object, which contains certain information relevant to the specific drugs to be delivered, while the airway resource 226 represent specific supplies to be used in the anesthesia care event object 214.

These two items, because they will be used together, are combined in a supply bundle container 222 which may be reused for other procedures, which include an anesthesia care event. The anesthesiologist resource 228 represents a personnel resource object and will contain information concerning the anesthesiologist, including identification, time to be allotted for the procedure and scheduling information. The patient monitor resource object 230 represents an equipment resource, which contains information about its availability and utilization.

This process is repeated until each of the remaining care events 216 and 218 for the procedural pathway is completed (a more complete description of a procedural pathway, including examples of multiple care events which have been completed is provided in the Description of an Exemplar Embodiment below). The user of the information system then has a software module 212 configured for the heart bypass procedural pathway, which consists of container, resource and data objects. Each of the software objects encapsulates information particular to that object and communicates that information via a standard interface to other software objects as such information is required.

For example, after constructing a particular procedural pathway module, the user might desire to schedule a procedure for a particular patient using the procedural pathway. By utilizing a node designed to manage information for individual cases, the user could select the appropriate procedural pathway module, which transfers the data from the procedural pathway module for that procedure into a case module. The case module then contains all of the information from the objects from the selected procedural pathway module and provides a ready listing of resources to be utilized in performing the procedure. With this information, schedules of supplies, equipment, etc. could be generated in order to facilitate the performance of the procedure.

Additionally, as will be described more fully hereinafter, by creating a case module, the user has available the case node functionality which allows for the tracking of resource utilization in performing the procedure and creation of a consumption record for use in analyzing resource utilization, generating cost information for cost recovery and allows the user to perform other case node specific functions. Also, to the extent that objects created in the procedural pathway have utility for other procedural pathways, the created objects may be reused to develop additional procedural pathways.

As will be described in greater detail below, the various types of objects are predefined in the overall software system. Container objects are available to represent care events, supply bundles and conditional supply bundles. Each type of container may then be configured by the user to reflect the particulars of the procedural pathway to be represented. Care event containers will be configured with specific information for each care event in the procedural pathway and will contain information relevant to that care event. Supply bundles will be provisioned with supply resource objects and will have information specific to that supply bundle contained therein. Conditional supply bundles will be provisioned with supplies and a condition, which will determine if that conditional supply bundle will be used; for example, a conditional supply bundle may be developed for a particular surgeon and will have supplies used only by that surgeon provided therein. Then, if the condition is met when a case is scheduled, such as the particular surgeon is assigned to the case, that conditional bundle will automatically be added to the list of objects associated with that case.

Similarly, various types of resource objects are provided as standard templates for configuration by the user. Examples of such types of resource objects are supplies, kits (which are pre-packaged groups of supplies), equipment, personnel and pharmaceuticals. When configuring resource objects for a procedural pathway, the user selects the appropriate supply type for the resource to be represented and inputs the prompted information. For example, the user might be able to look up a database of listed supplies and select a particular supply for inclusion in the procedural pathway. Alternatively, the user could create a new supply from scratch by inputting prompted information to create a new supply resource object. The type of information varies from resource type to resource type, but a standard template is provided for each resource type to prompt the user to input the appropriate information for each resource to be added.

Additionally, while the user has the option to create various container, resource and data objects from scratch for use in the information system, the user, to the extent appropriate, can reuse previously created objects. For example, the user might create a library of standard pre-configured objects which are frequently re-used in various procedural pathways. Thus, when a new pathway is being created, these library objects may be selected for inclusion in the new pathway. Likewise, information concerning a variety of resources may be maintained in various database systems maintained by a health care institution. The supply department may maintain a database of available supplies, or dealers may provide databases of available supplies, by providing standard database program interfaces for these sources of information. Data from these source may then be automatically read into the present system in order to configure resource software objects for use therein.

As described, the use of software objects to represent events, bundles, resources and data objects in a health care information management system allows the user to readily create software modules which represent specific health care procedures which are much more functional then with traditional health care database systems. Furthermore, the module object approach to the system makes it more readily customizable for particular installations. For example, if the standard configuration of any software object is not readily adapted for a particular installation, a programmer will not be required to modify a monolithic source code listing to implement the new configuration. For customization, the user will only have to reconfigure a particular object. As long as the standardized data interface for the object is retained, there will not need to be any change in configuration in the remaining source code for the system.

Additionally, the use of the software object framework allows for the ready implementation of new functionality, without requiring the rewrite of the majority of the code for the system. For example, if a new functionality is required, a new functional node may be added which will utilize, to the extent possible, already existing software objects. One example might be to add a scheduling node to the above described software to allow for the ready scheduling of personnel, equipment, supplies, etc. Most of the scheduling information for any given procedure will be available in the procedural pathway module for that procedure. Thus, to create a scheduling node, the user creates a software object that queries existing objects for data relevant to scheduling and organizes that data in a useful manner. In the context of the present invention, such a node could create scheduling objects for various resources indicating their utilization schedule (as received from the object representing such resources) which would automatically query scheduled resources, check their availability and establish a calendar for each. Other functionality could be created by the creation of other nodes.

For example, the functionality of tracking resource utilization in the manner described in application Ser. No. 08/846,798, filed Apr. 30, 1997, entitled Method and System for the Tracking and Profiling of Supply Usage in a Health Care Environment, may be provided as a functional node software object. In implementing such a node, each individual procedural pathway as described in that application may be copied from a procedural pathway constructed as described above with reference to FIG. 2. A further type of node functionality is described in U.S. patent application Ser. No. 08/936,780, filed Sep. 24, 1997, entitled Method for the Analysis and Standardization of Bills of Resources, which provides from the conversion of case software module objects into models which could then be analyzed for resource utilization efficiency and the standardization of bills of resource. Furthermore, the output of the node functionality described in application Ser. No. 08/936,780, could then be used to create an optimized procedural pathway under the procedural pathway node described with reference to FIG. 2.

The functionality described above is implemented in the Meridian™ information management system marketed by DeRoyal Business Systems, 200 DeBusk Lane, Powell, Tenn., 37849, which is an affiliate of the assignee hereof, DeRoyal Industries, Inc.

Description of an Exemplar Embodiment

The foregoing functionality may be best described with reference to the following exemplar embodiment. The exemplar embodiment is available as the Meridian™ software package available from the assignee hereof, DeRoyal Industries, Inc. The software of the exemplar embodiment hereof is preferably run under the Windows 95 or Windows NT operating systems and interfaces with a SQL compliant database such as Microsoft SQL/Server or Microsoft Access. Much of the information maintained by the exemplar embodiment described herein will be maintained in tables which are created and managed using the background database software.

Figure 3:
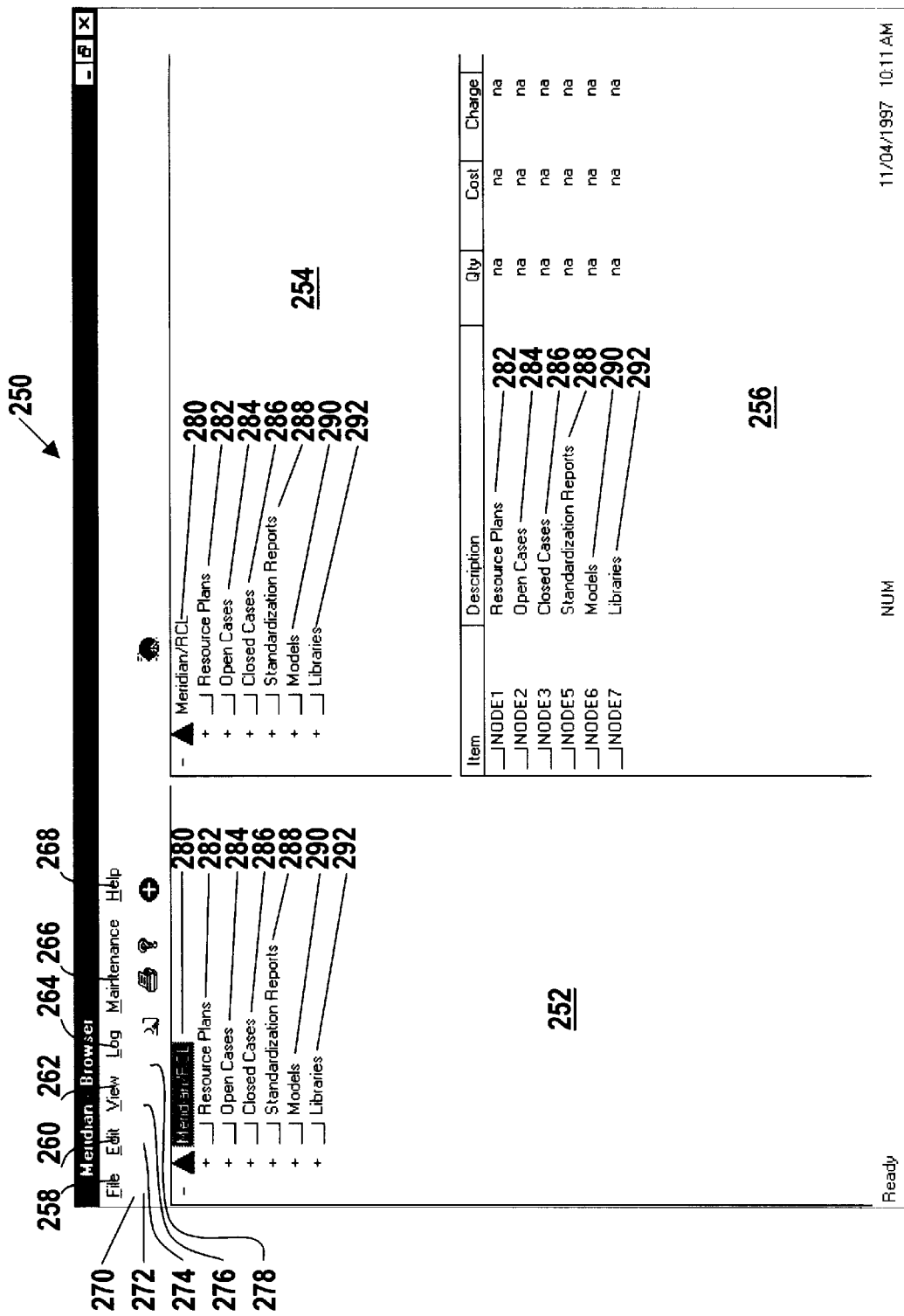
FIGS. 3–147 are screen shots of a computer program of an exemplar embodiment of the present invention.

Referring now to FIG. 3, there is shown the Meridian™ Browser window 250. The Browser window 250 is similar in appearance to the Windows Explorer window provided in the Windows 95 and Windows NT environments and maintains similar functionality. To the left of the window 250 is a Nested Tree view 252, which allows the user to see the Meridian™ nodes, depicted as folders, and other objects. In the top right of the window 250 is a Second Tree view 254, which provides similar functionality. The provision of the dual tree views 252 and 254 is to allow the user to move items from one location in the tree to another location, using drag and drop, in the event that the two locations are separated by more than one window's distance (in the instance where the source folder and destination folder are not both displayed in the same window). Furthermore, this dual tree view allows the user to look at different items at the same time. In the lower right hand side of the window 250 is the List view 256, which displays the contents of whatever item is highlighted in the tree view 252 or 254. It should be further noted that the mouse functionality of Windows 95 or Windows NT is maintained in the Meridian™ software; that is, the standard features of highlighting selected folders, files or objects, dragging and dropping and right clicking are retained.

At the top of the Browser window 250 are drop down menus File 258, Edit 260, view 262, Log 264, Maintenance 266 and Help 268. The File 258, Edit 260, view 262 and Help 268 drop down menus maintain the standard functionality of any Windows™ program with some Meridian™ specific features. The remaining drop down menus deal with functions specific to the exemplar embodiment.

Below the drop down menus is the Meridian™ tool bar 270 which is provisioned with buttons to allow shortcut implementation of common functions which are also provided in the drop down menus and other menus. However, the cut 272, copy 274, paste 276 and paste shortcut 278 buttons function in the standard Windows™ environment.

In the tree views 252, 254, the top level is the Meridian™/RCL software itself 280, under this level are functional nodes relating to various information management functions to be performed by the software. The nodes shown in this embodiment are Resource Plans 282, Open Cases 284, Closed Cases 286, Standardization Reports 288, Models 290 and Libraries 292. Each node represents a different functionality or acts as a folder for storing various information. Functional nodes (as opposed to mere folders) are provided as software objects. In most cases, the function of the node software objects is to allow for the creation, management and maintenance of additional software objects which perform specific information management tasks.

Figure 4:
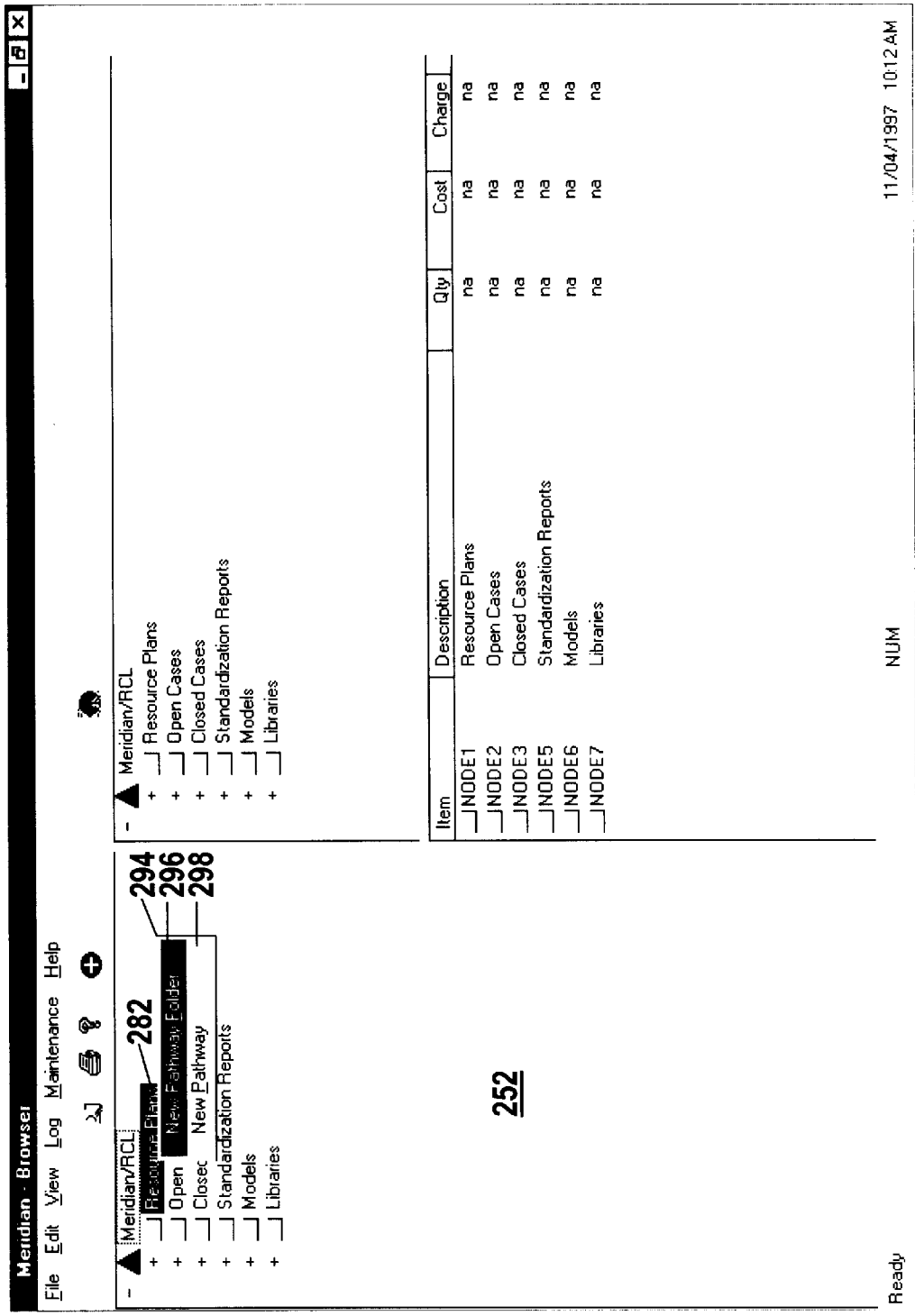

Referring now to FIG. 4, the Resource Plans software node 282 is highlighted and its menu functions activated by a right click of the mouse. As shown in FIG. 4, by right clicking on the Resource Plans node 282, the Resource Plans menu 294 is activated. The user may then select one of the menu functions, either New Pathway Folder 296 or New Pathway 298, to activate a function. In FIG. 4, the user has selected the New Pathway Folder 296 function, depicted as inverted text.

Figure 5:
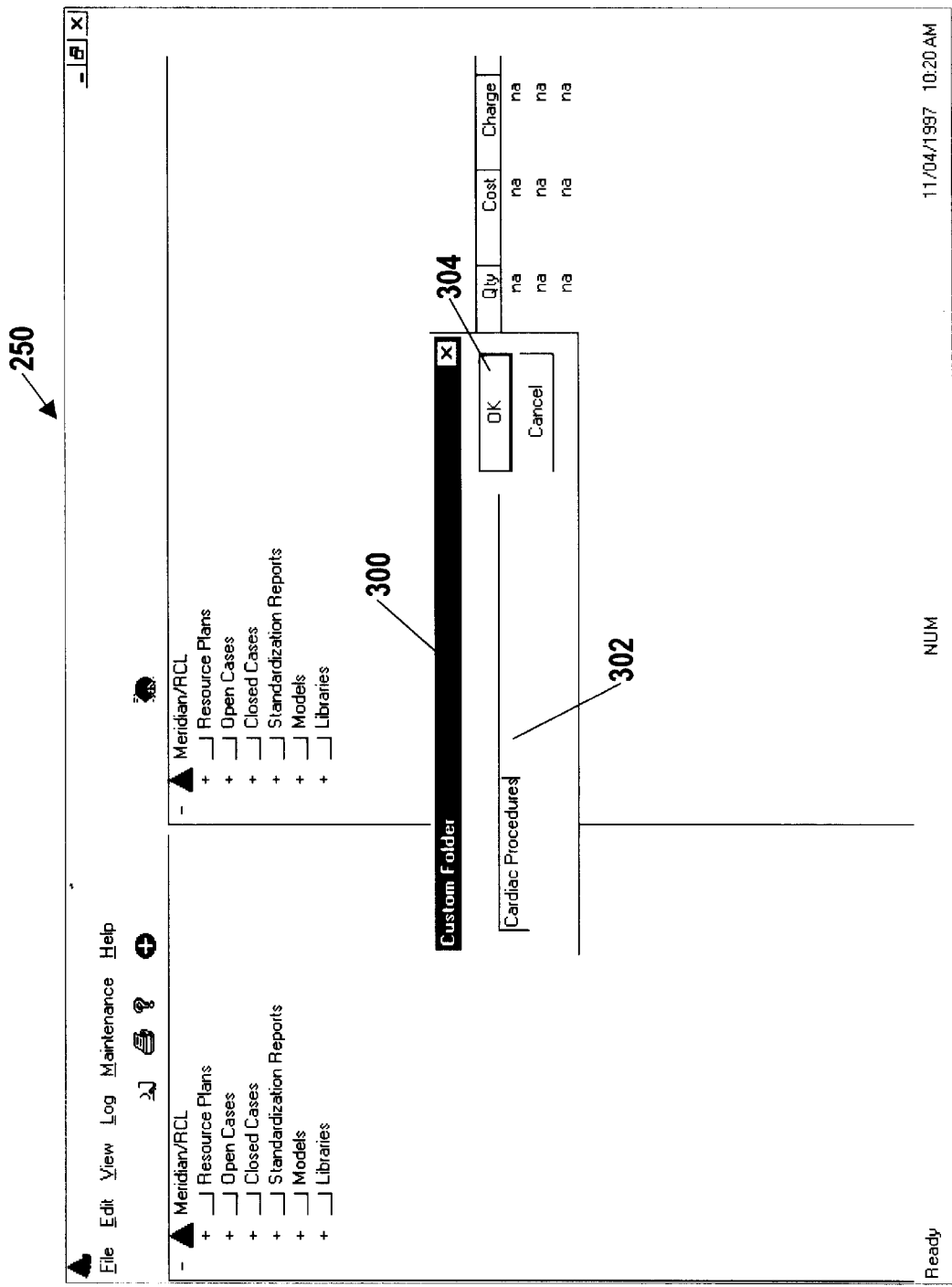

Referring now to FIG. 5, after the user has selected the New Pathway Folder function 296 of FIG. 4, a Custom Folder window 300 is presented, which allows the user to enter the name for the new pathway folder. The name of the new folder is entered into the description window 302 and the user then selects the OK button 304 to finish the creation of the new folder.

Figure 6:
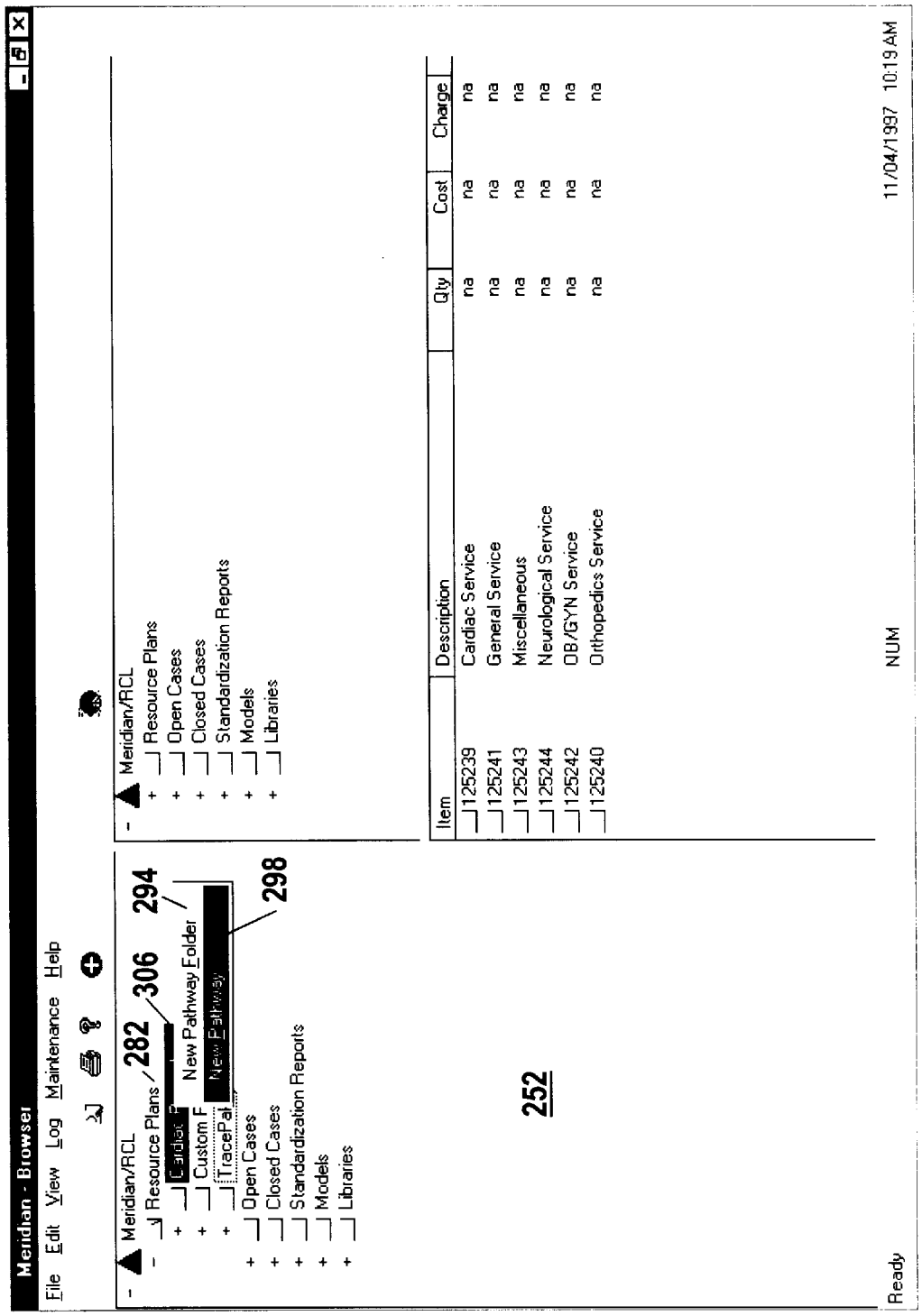

Referring now to FIG. 6, it can be seen that the new Cardiac Procedures folder 306 has appeared under the Resource Plans node 282. In FIG. 6, the user has right clicked on the Cardiac Procedures folder 306 and activated the Resource Plans node menu 294 and has selected the New Pathway function 298, which will allow the user to create a new procedural pathway module software object.

Figure 7:
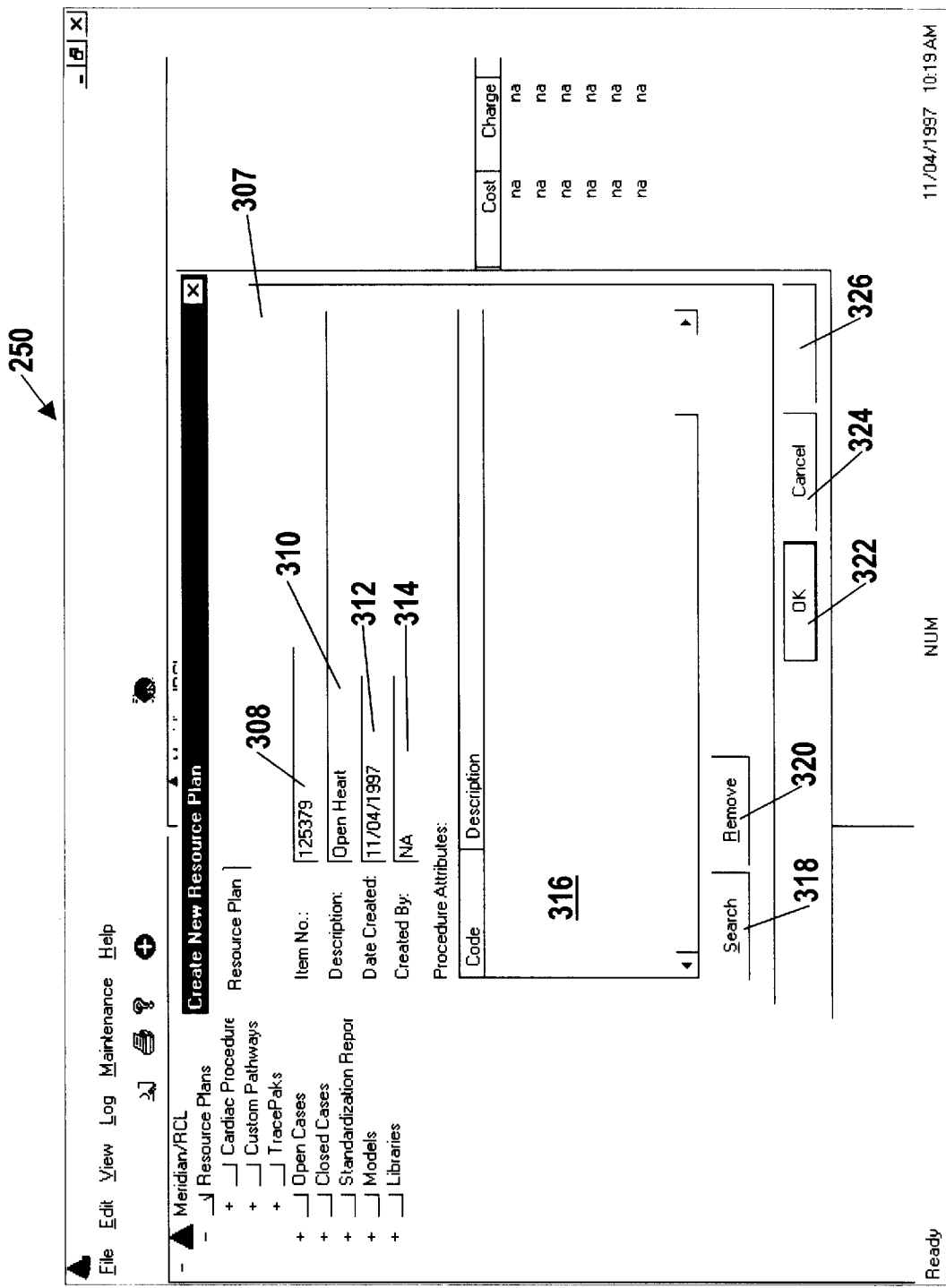

In FIG. 7, the Create New Resource Plan window 307 has appeared in response to the user selection of the New Pathway function 298 described in FIG. 6. The Create New Resource Plan window 307 prompts the user to input information concerning the software module to be created. In the Item No. field 308, the user inputs the desired identifying number for the new pathway (or, alternatively, the software will provide the next number in sequence which has not yet been used). In the Description field 310, the user types in the desired description for the pathway. Other fields which may be completed are the Date Created field 312 (the default date will be the current date) and the Created By field 314. Finally, the Procedure Attributes field 316 is provided which will allow the user to select standardized procedure codes, such as the AMA IC9 code and description, for the procedure to be represented by the pathway.

This function is provided with a database search capability, by the Search button 318, which allows the user to search a pre-configured procedure code database for the appropriate procedure information. The Remove button 320 allows the user to remove selected procedure codes from the Procedure Attributes field 316 if an inappropriate selection is made. The OK button 322 allows the user to approve the input and exit the Create New Resource Plan window 307 while saving the information. The Cancel button 324 allows the user to exit the Create New Resource Plan window 307 without saving the information. The Apply button 326 serves to update database records concerning the new pathway upon activation. In the present case, the user, upon completion of the information, selects the OK button 322 to exit the Create Resource Plan window 307 and return to the Browser window 250.

Figure 8:
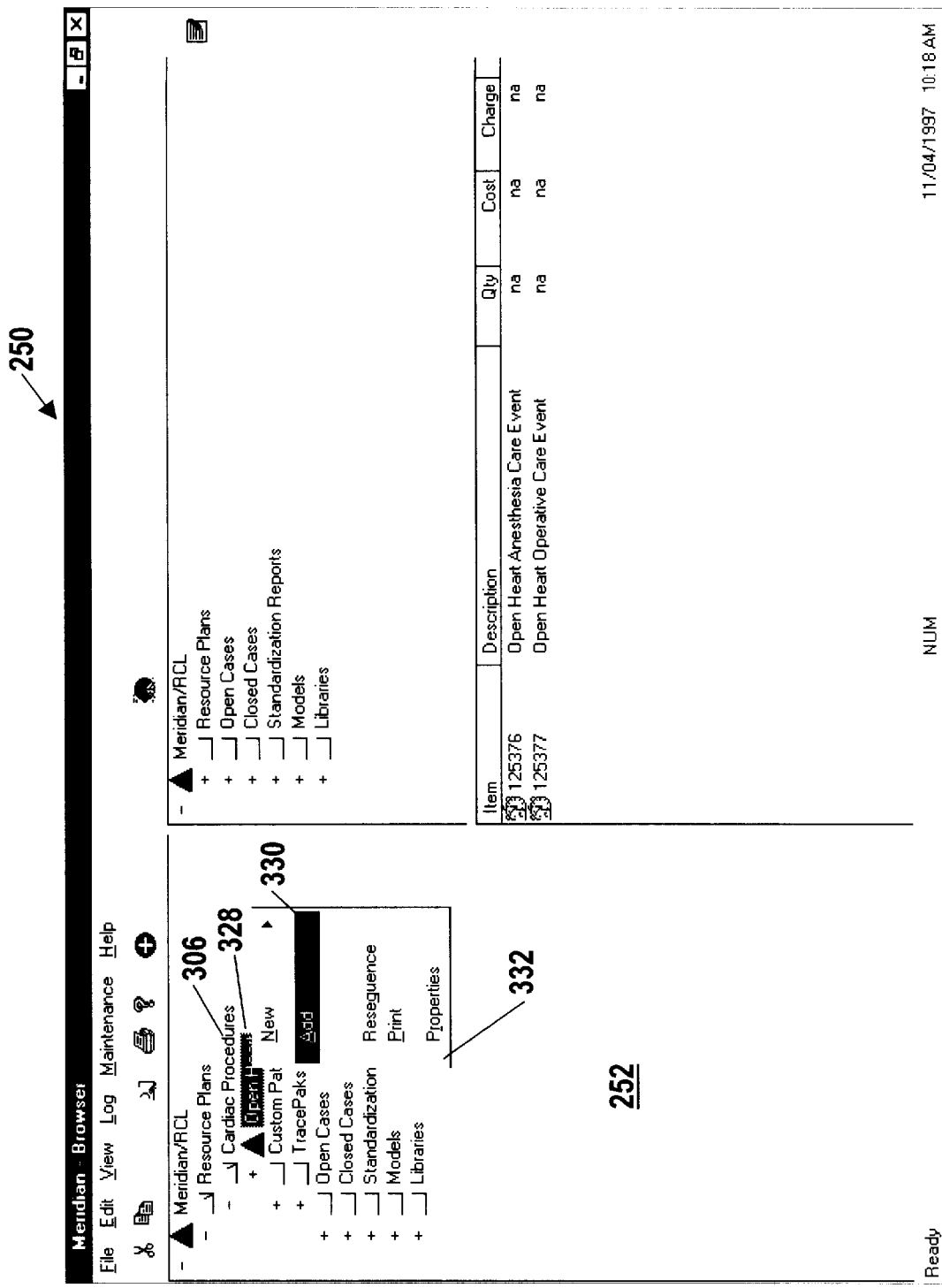

Once the new procedure is added, an Open Heart icon 328 appears under the appropriate Cardiac Procedures folder 306 to indicate the new Open Heart procedural pathway software module as is seen in FIG. 8. In FIG. 8 the user has selected the Open Heart icon 328 and right clicked on the mouse to call up the Procedural pathway module menu 330, which provides functions related to the creation, management and maintenance of the various procedural pathway software modules created by the user. In FIG. 8 the user has selected the Add function 332 from the Procedural pathway module menu 330, which will allow the user to add items to the Open Heart procedural pathway 328.

As described previously, using the procedural pathway paradigm, a medical procedure is broken down into a series of related care events. Typically, the user of the present invention first adds the various care events to the pathway software module and provisions them later. The following description provides a walk through of how to add various care event containers to the pathway.

Figure 9:
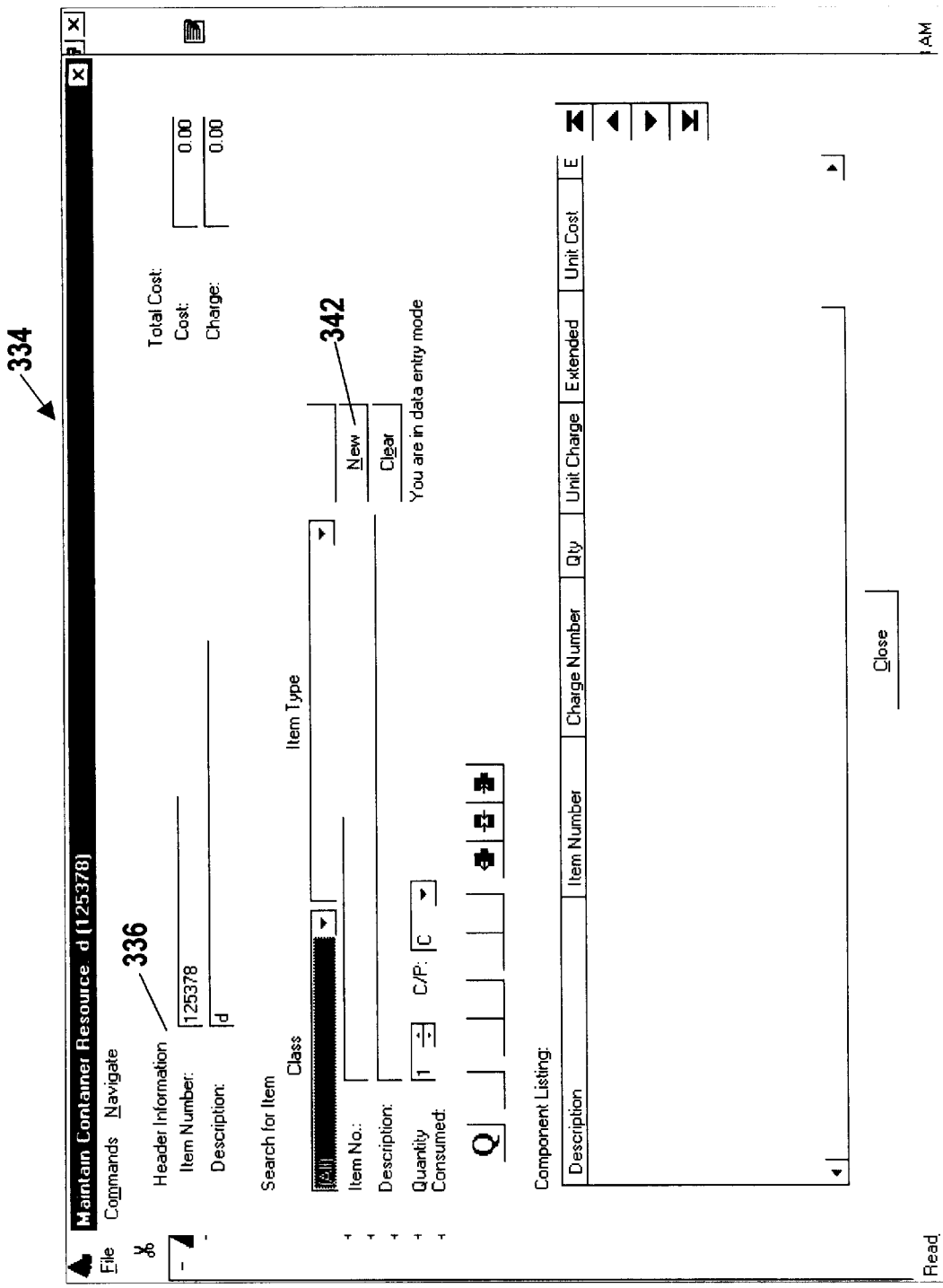

Referring now to FIG. 9, the Maintain Container Resource window 334 appears in response to selecting the Add function 332 from the Procedural pathway module menu 330. The Maintain Container Resource window 334 has Header Information 336 which provides the user with information specific to the procedural pathway module which is being maintained. The remaining portions of the Maintain Container Resource window 334 are devoted to the creation and searching of available container resources for addition to the procedural pathway module.

Figure 10:
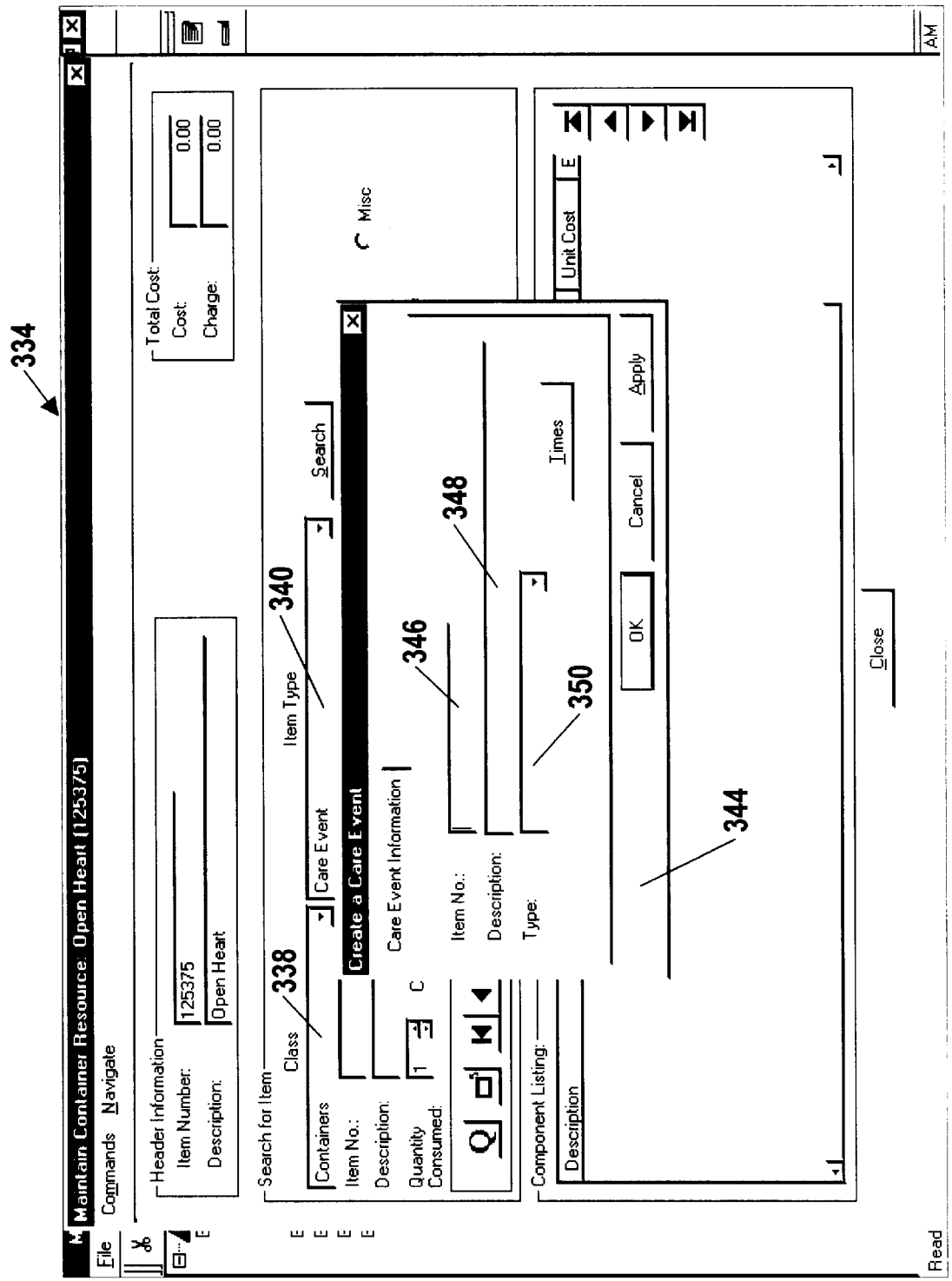
Figure 11:
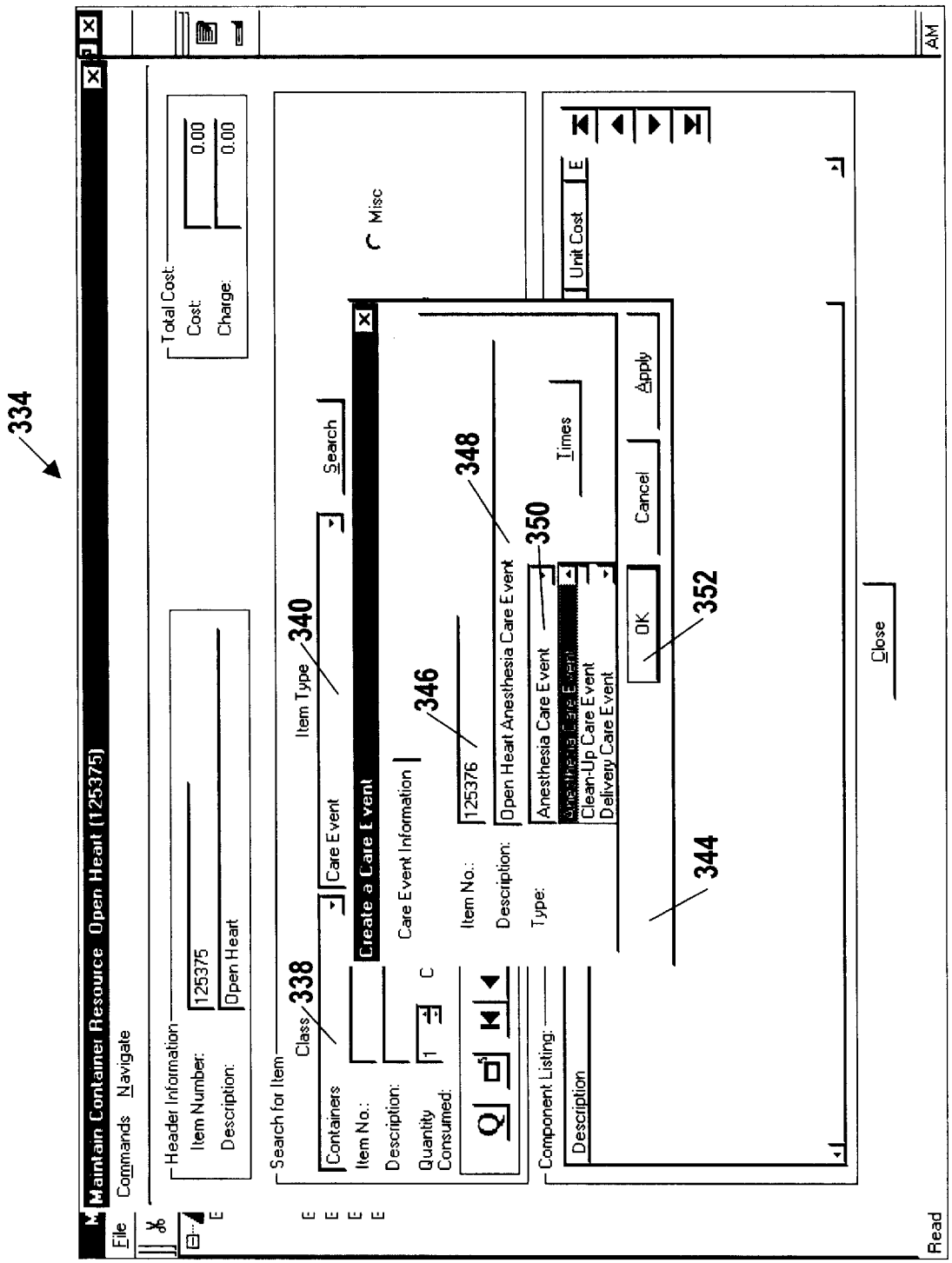

In FIG. 10, the user has selected the designation of Containers in the Class field 338 and the designation of Care Event in the Item Type field 340, and selected the New function 342 (depicted in FIG. 9). These selections cause the Create a Care Event window 344 to appear. The Create a Care Event window 344 allows the user to input information into the Item No. field 346, Description field 348 and select the type of the new care event to be added to the procedural pathway module in the Type field 350. As shown in FIG. 11, the user has entered the appropriate information into the fields, and by selecting the OK button 352 may proceed.

Figure 12:
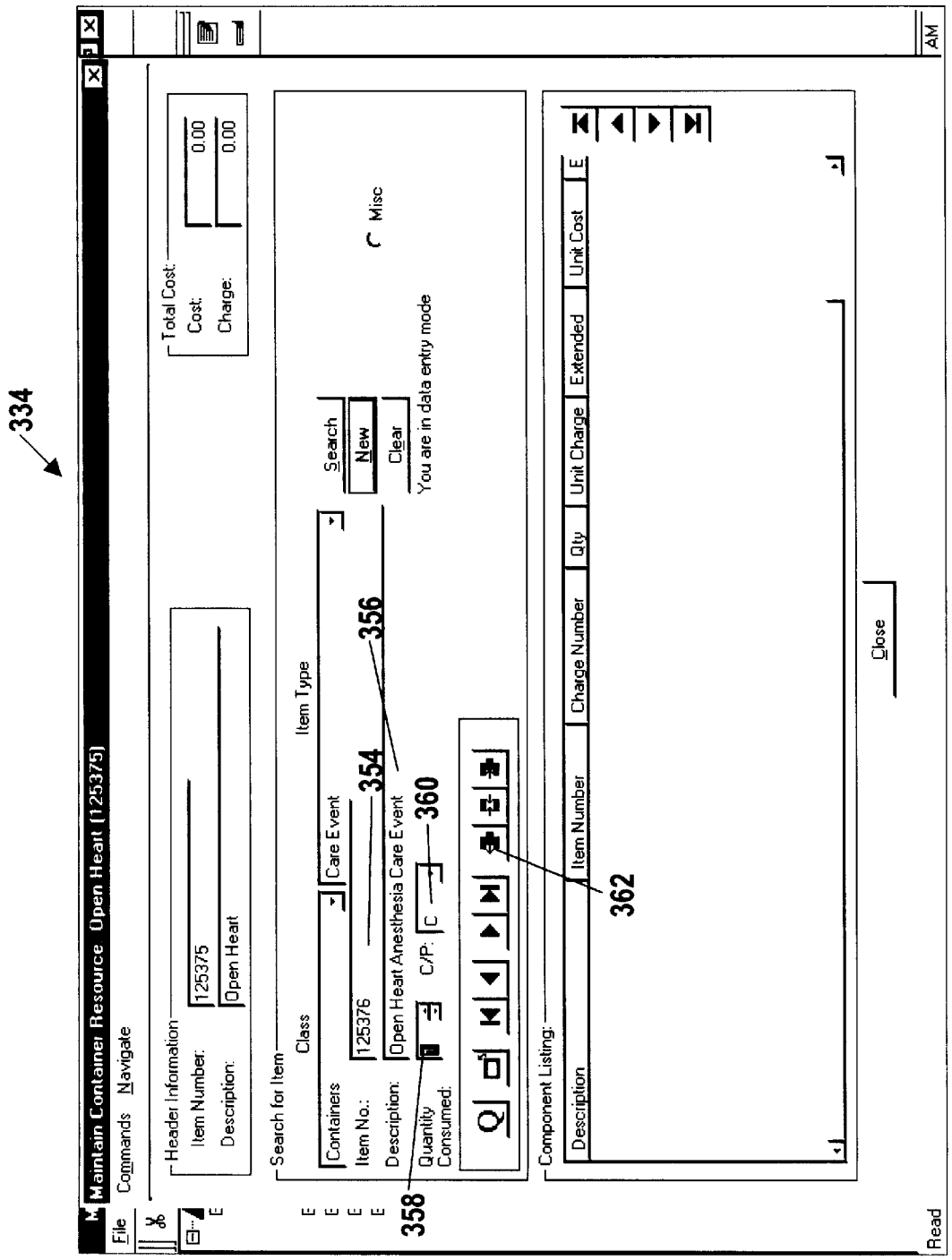
Figure 13:
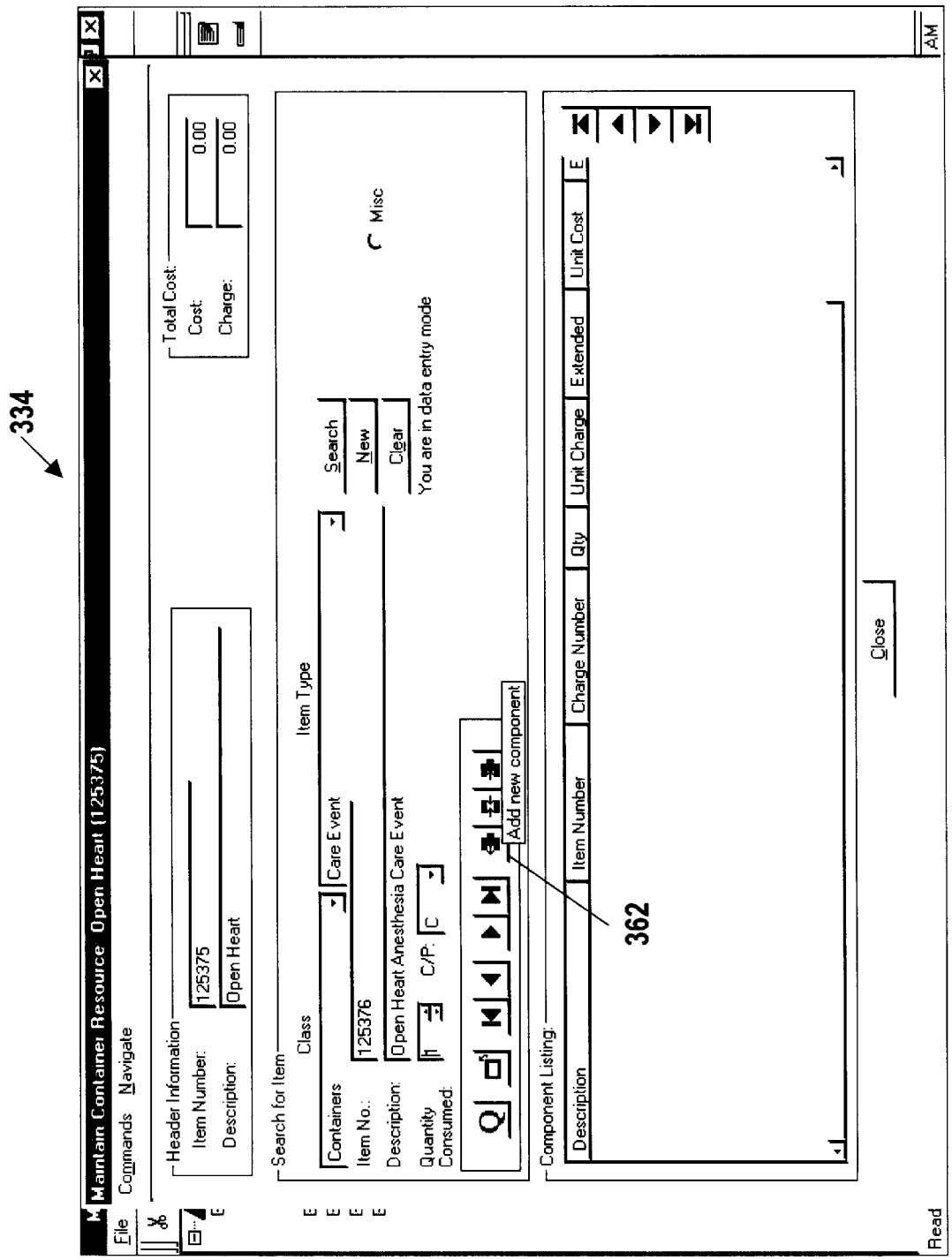
Figure 14:
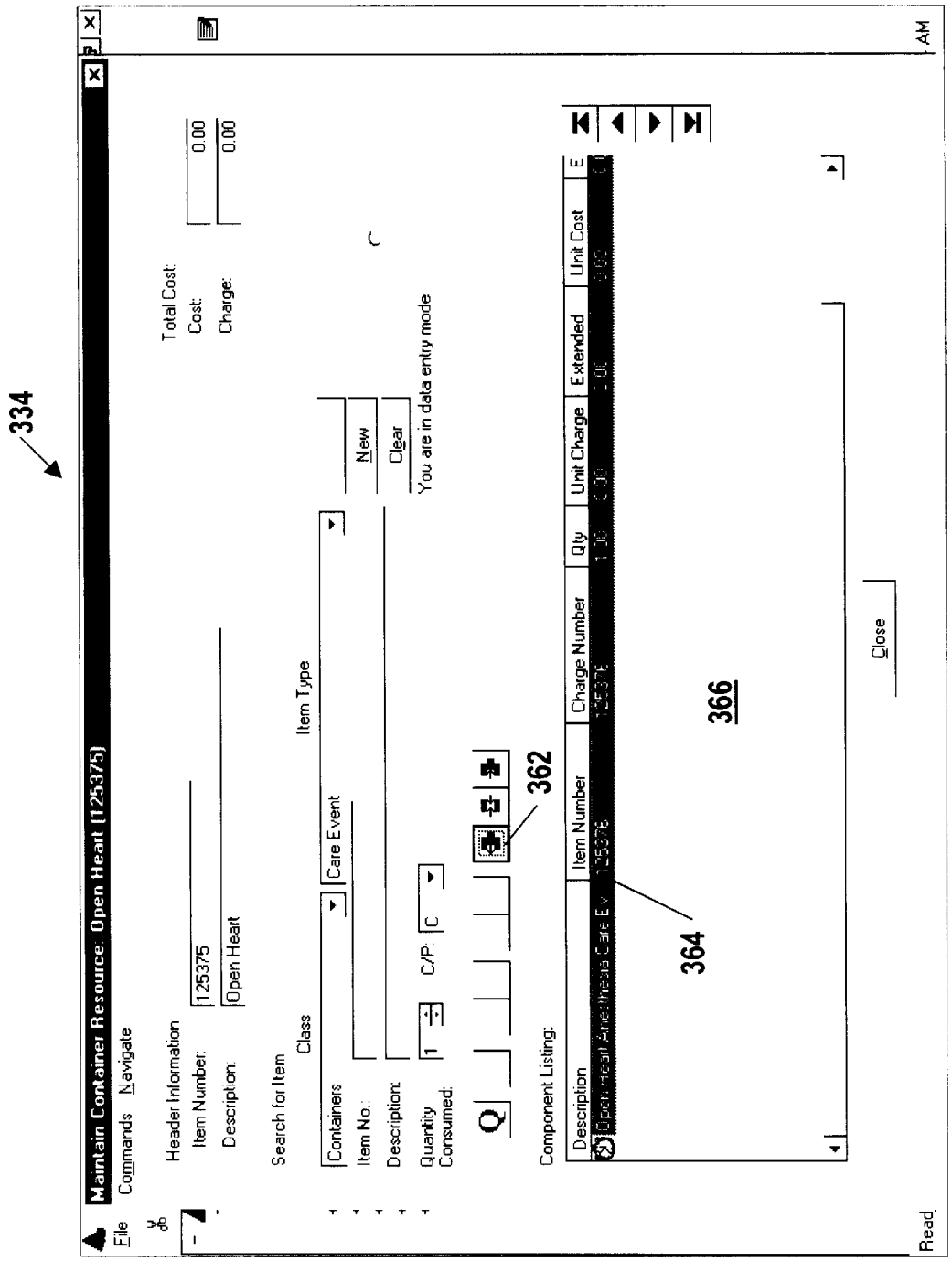

After selecting the OK function 352, the user is returned to the Maintain Container Resource window 334, shown in FIG. 12. As can be seen in FIG. 12, the newly created open heart anesthesia care event information is provided in the Item No. field 354 and Description field 356. Other user configurable fields, Quantity Consumed field 358 and C/P field 360 allow the user to select the number of the selected items which will appear in the component listing. By selecting the Add New Component button 362, as depicted in FIG. 13, the Open Heart Anesthesia Care Event 364 appears in the Component Listing field 366, shown in FIG. 14. This process may be repeated as required for new care events to provision the procedural pathway module.

Figure 15:
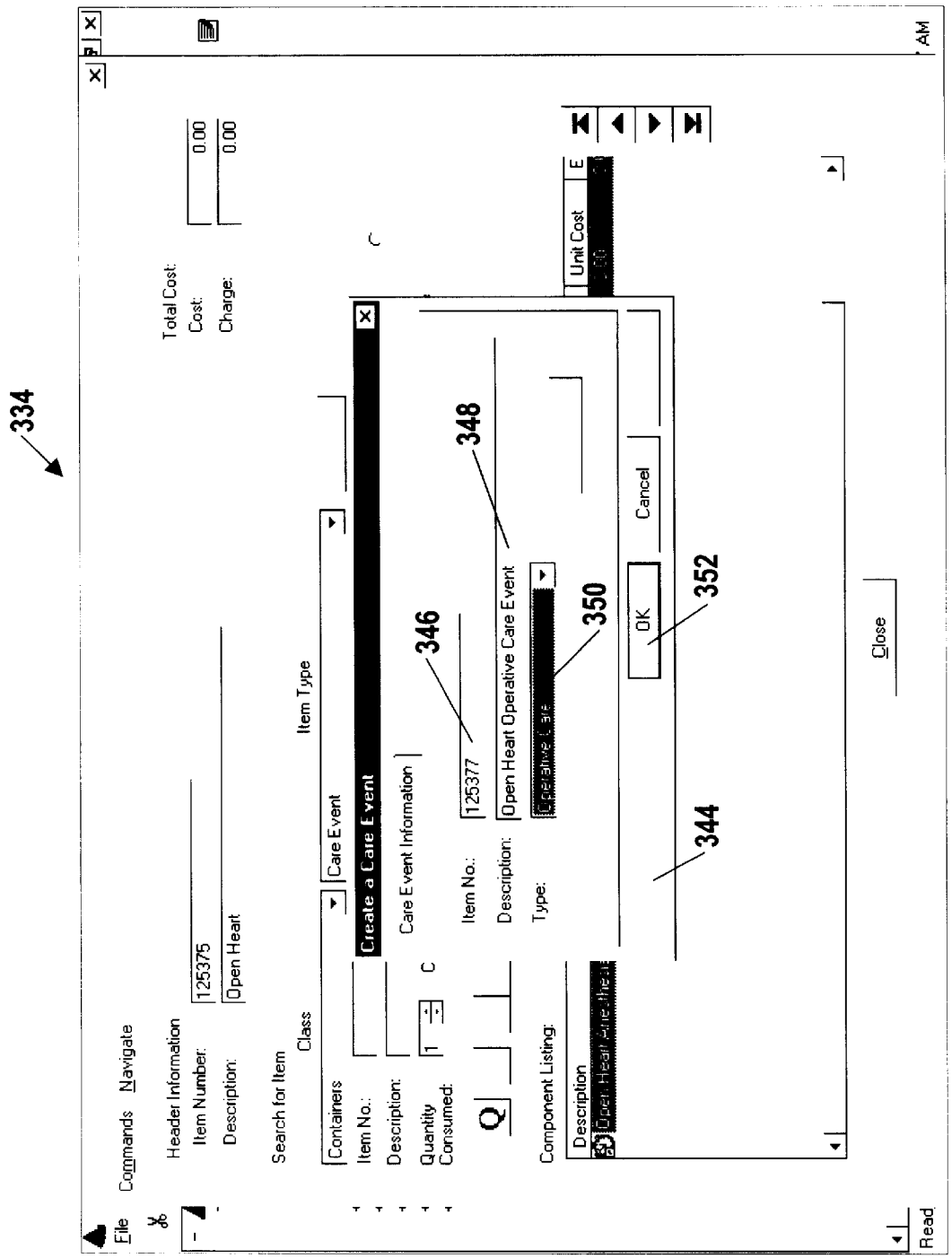

As seen in FIG. 15, an additional new care event called the Open Heart Operative Care Event may be created in the same manner by selecting the New button 342 in the Maintain Container Resource window 334 and entering the appropriate information in the Create a Care Event window 344. This new care event can then be added to the Open Heart Procedural pathway 328 as described previously for the open heart anesthesia care event.

Each created care event is a software object of the container type. As such, each care event is a self contained module relating to the specific care event and is designed to hold additional container, resource and data objects relating to that particular care event. As a software object, once created, care events may be re-used where appropriate. For example, if the user has created a standard anesthesia care event, and desires to use it in other procedural pathway software modules, it may be selected and used without the step of creating a new care event. In fact, the user may create libraries of re-usable software objects which allow for the faster and easier creation of new procedural pathways.

Figure 16:
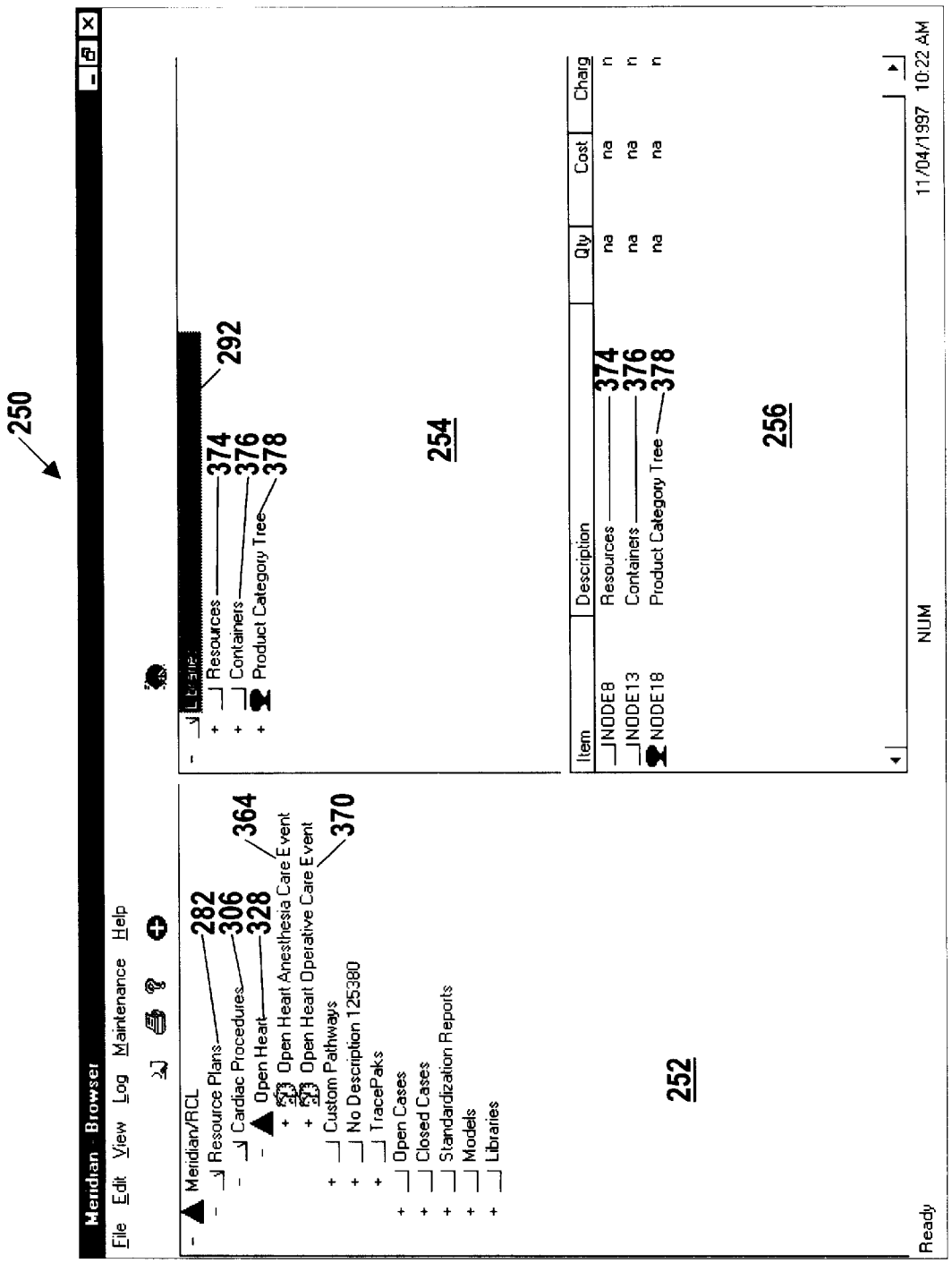
Figure 17:
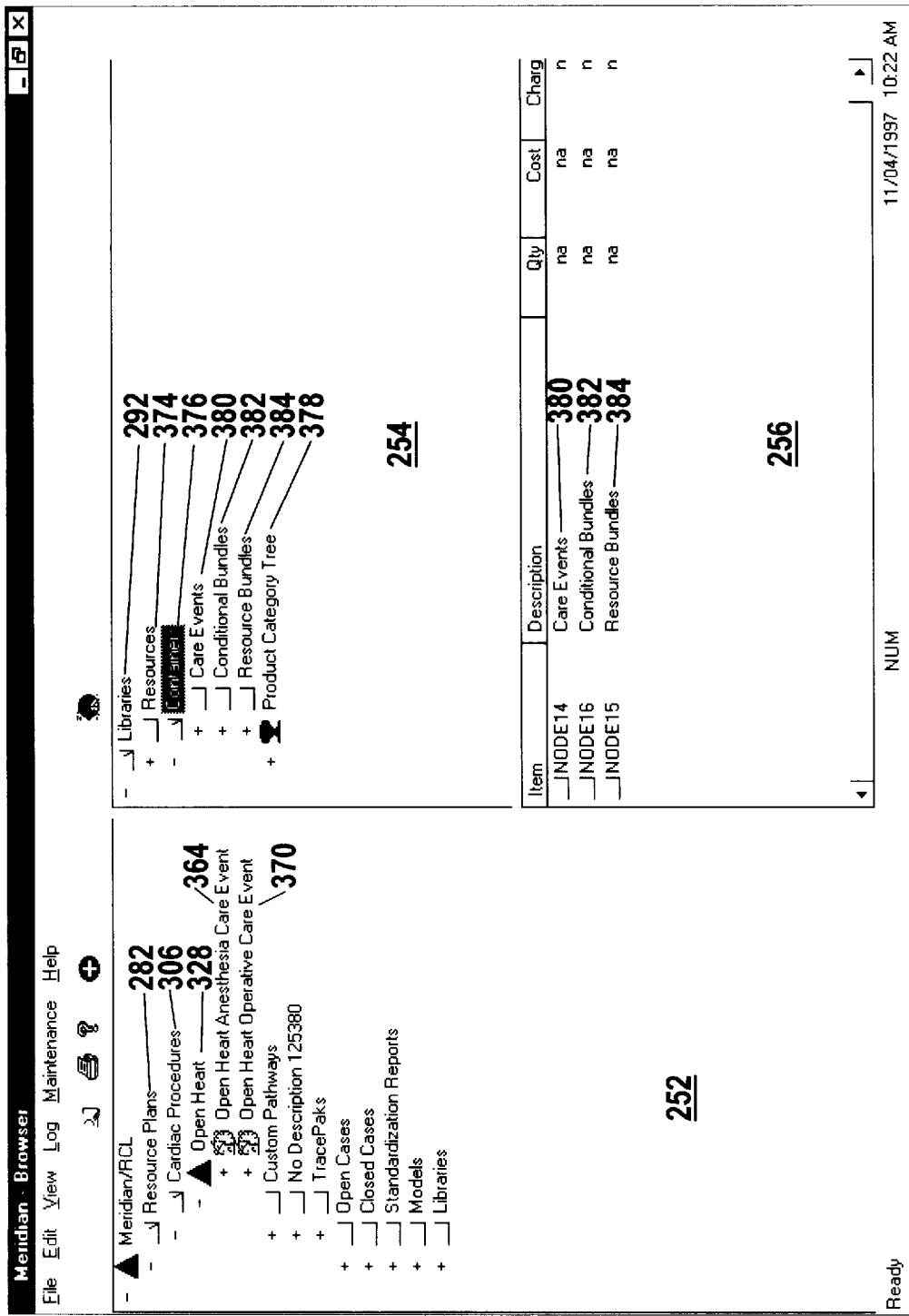

Referring now to FIG. 16, the Browser window 250 shows the Open Heart module 328 including the added Open Heart Anesthesia Care Event object 364 and Open Heart Operative Care Event object 370 in the Nested Tree view 252. In the Second Tree view 254 the user has selected the Libraries node 292, and the List view 256 shows the items and subfolders available under the Libraries node 292. Shown in the List view 256 are subfolders for Resources 374 and Containers 376 and the Product Category Tree 378, which is a hierarchical taxonomy of products classified by type. In FIG. 17, the Containers folder 376 is expanded to show additional subfolders of different types of containers: 1) Care Events 380, 2) Conditional Bundles 382 and 3) Resource Bundles 384.

Figure 18:
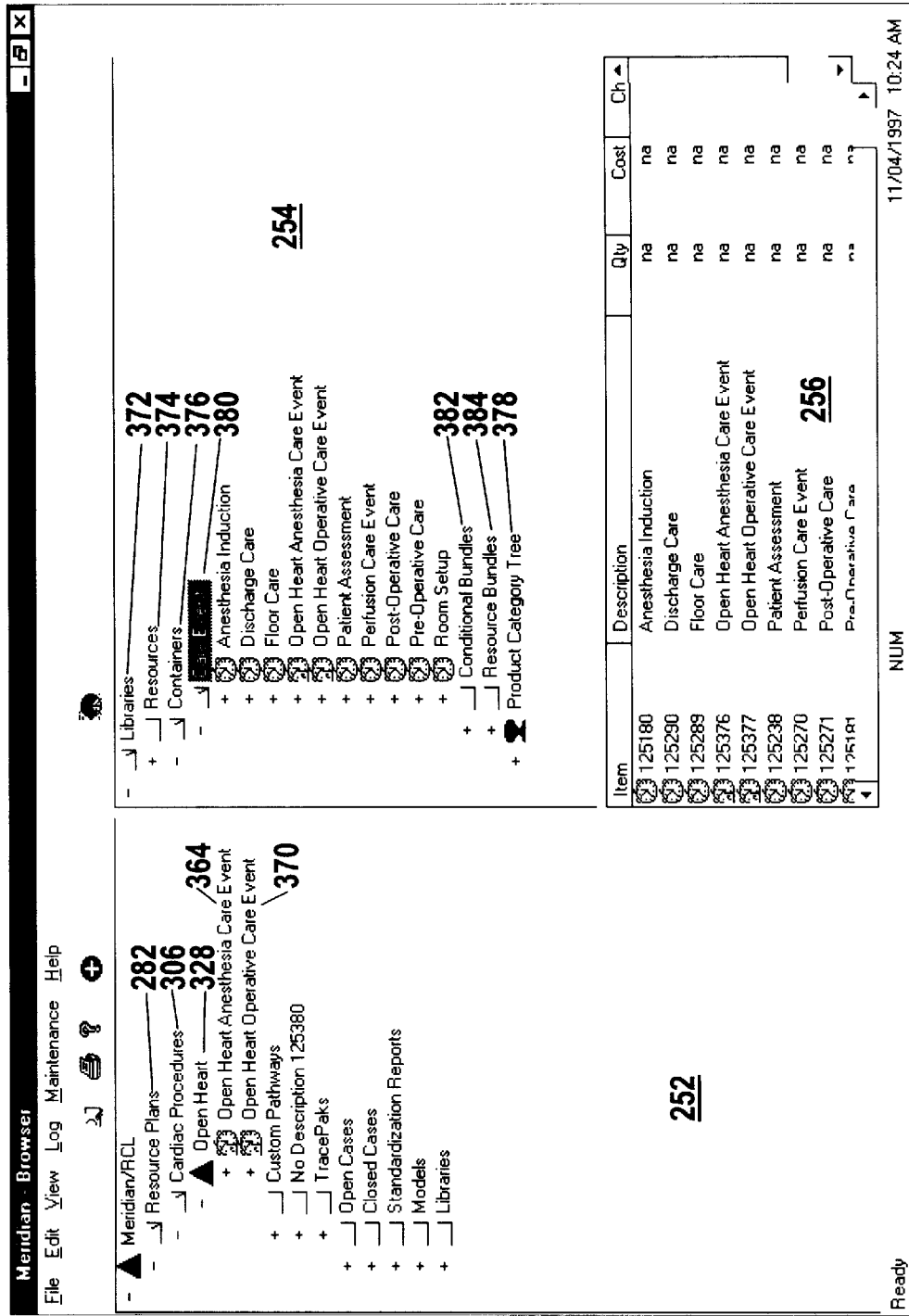
Figure 19:
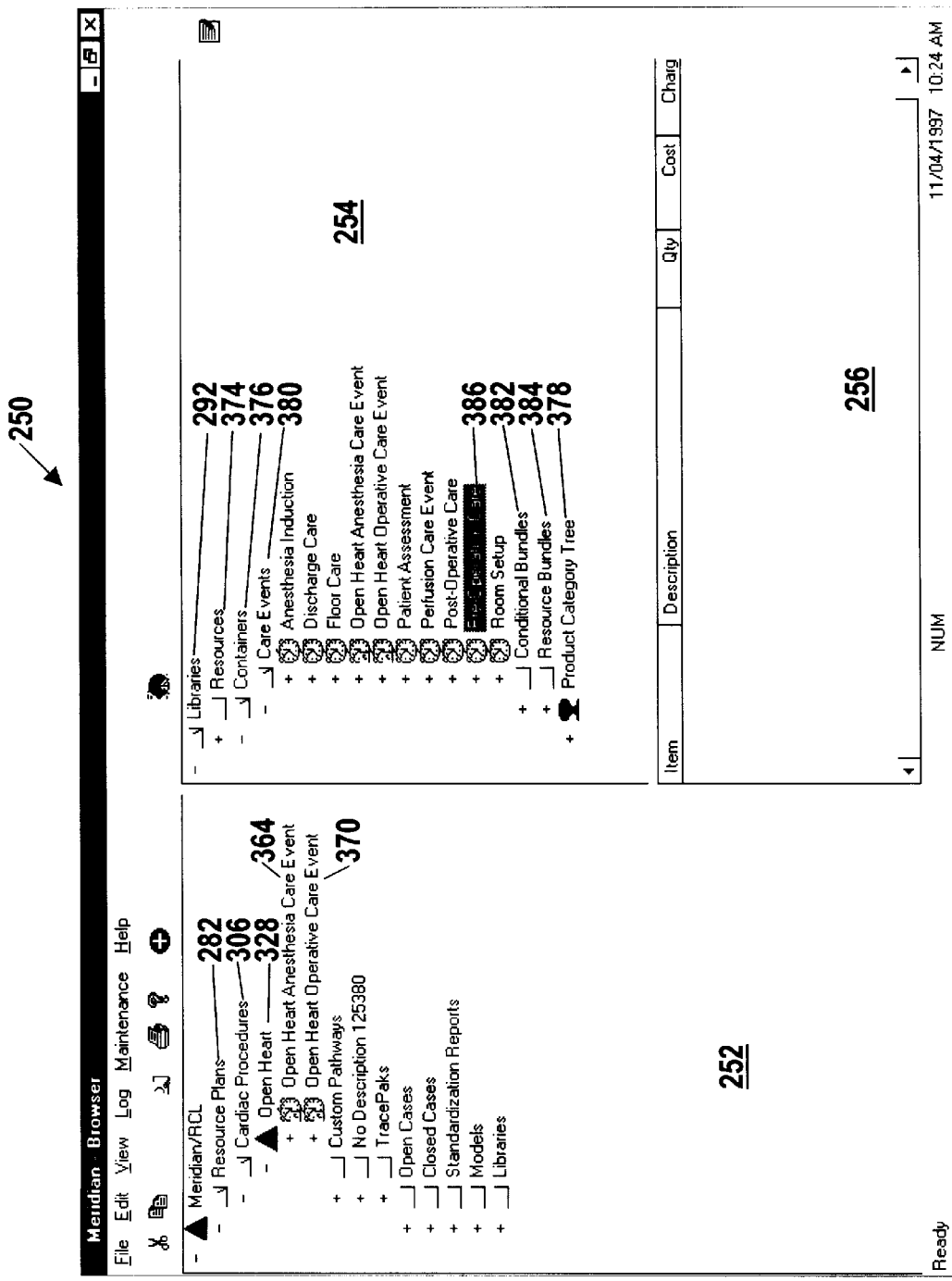
Figure 20:
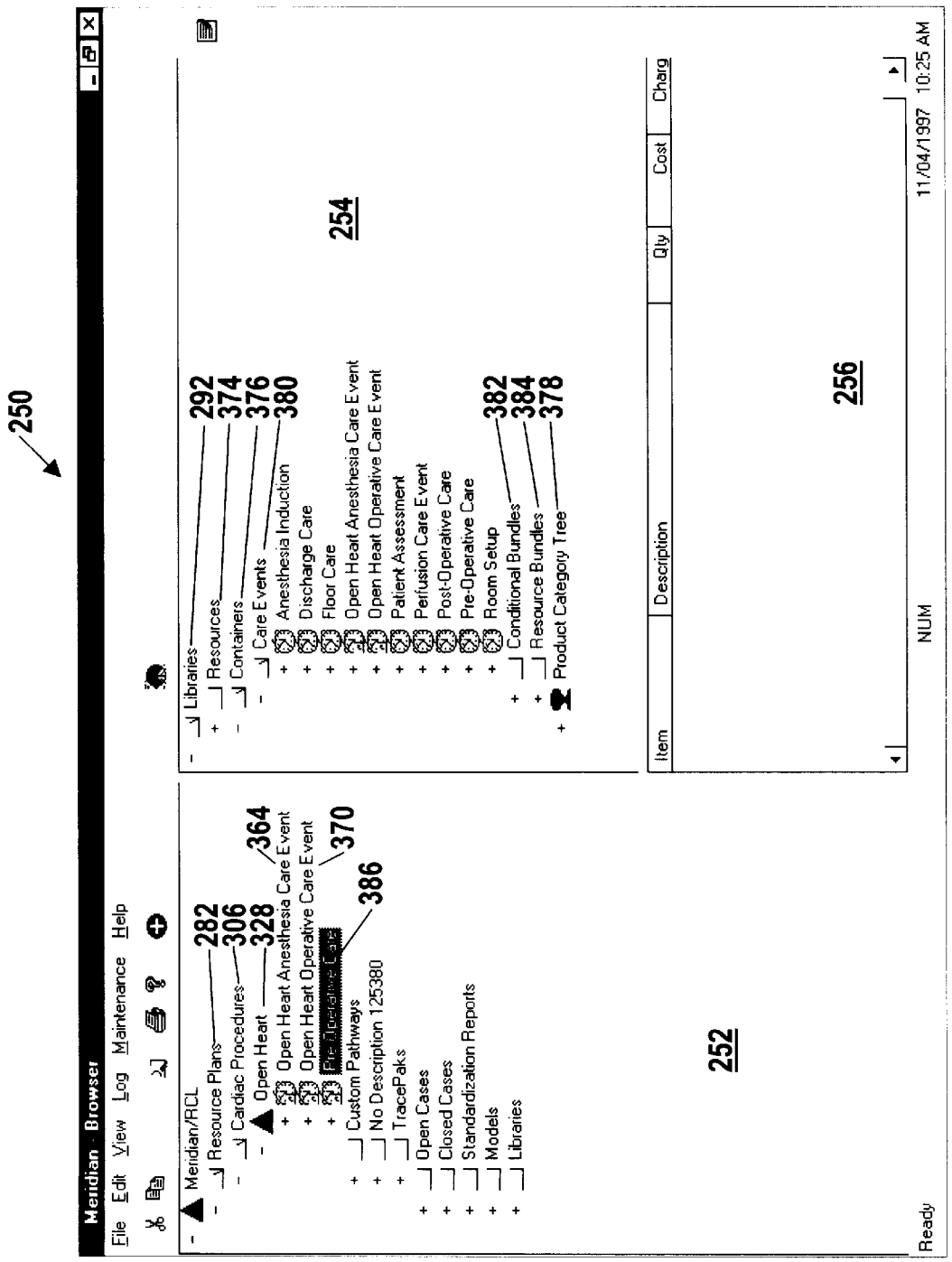

In FIG. 18, the Care Events subfolder 380 is expanded to show the pre-configured care event objects which are available. In FIG. 19, the user has selected the Pre-Operative Care event 386 for addition to the Open Heart procedural pathway 328. By dragging and dropping using the mouse, the user may copy the Pre-Operative Care Event 386 into the Open Heart procedural pathway 328 where it appears in FIG. 20. This procedure has allowed the user to select a pre-configured care event software object and add it to a procedural pathway module without requiring the creation of a new care event from scratch. The library of pre-configured software objects allows the user to maintain a set of re-usable objects representing standard items for inclusion in procedural pathways.

Figure 21:
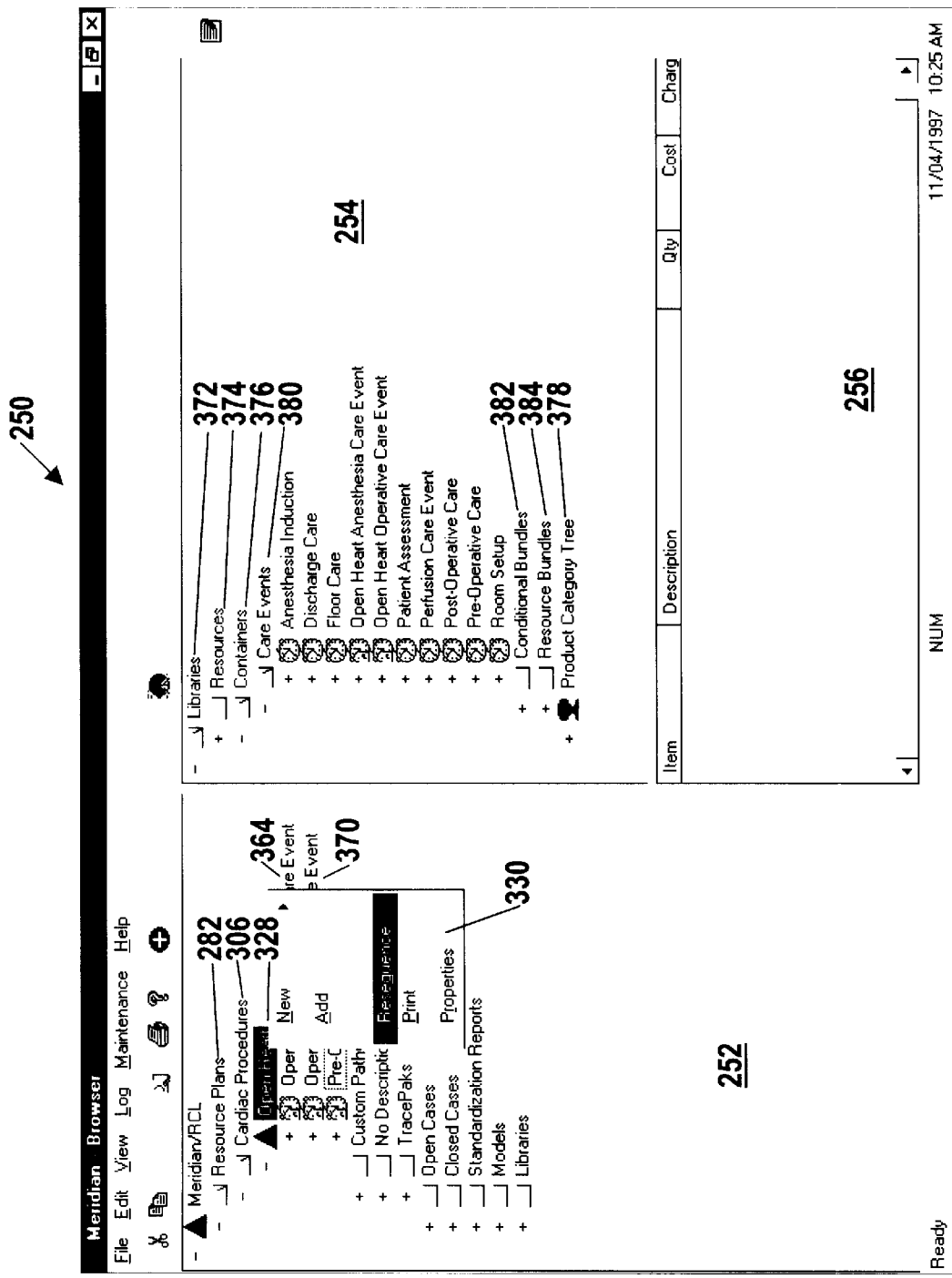
Figure 22:
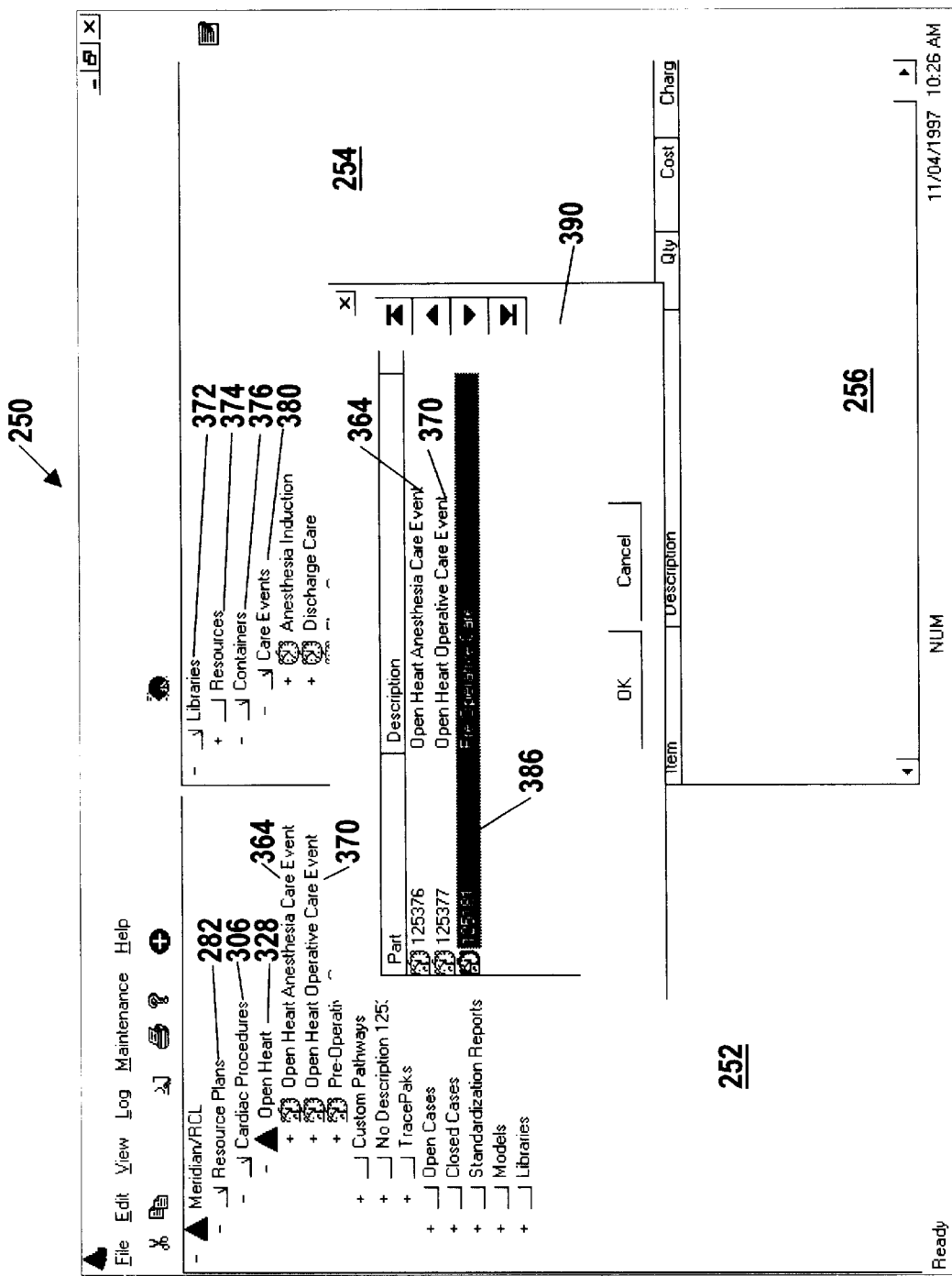
Figure 23:
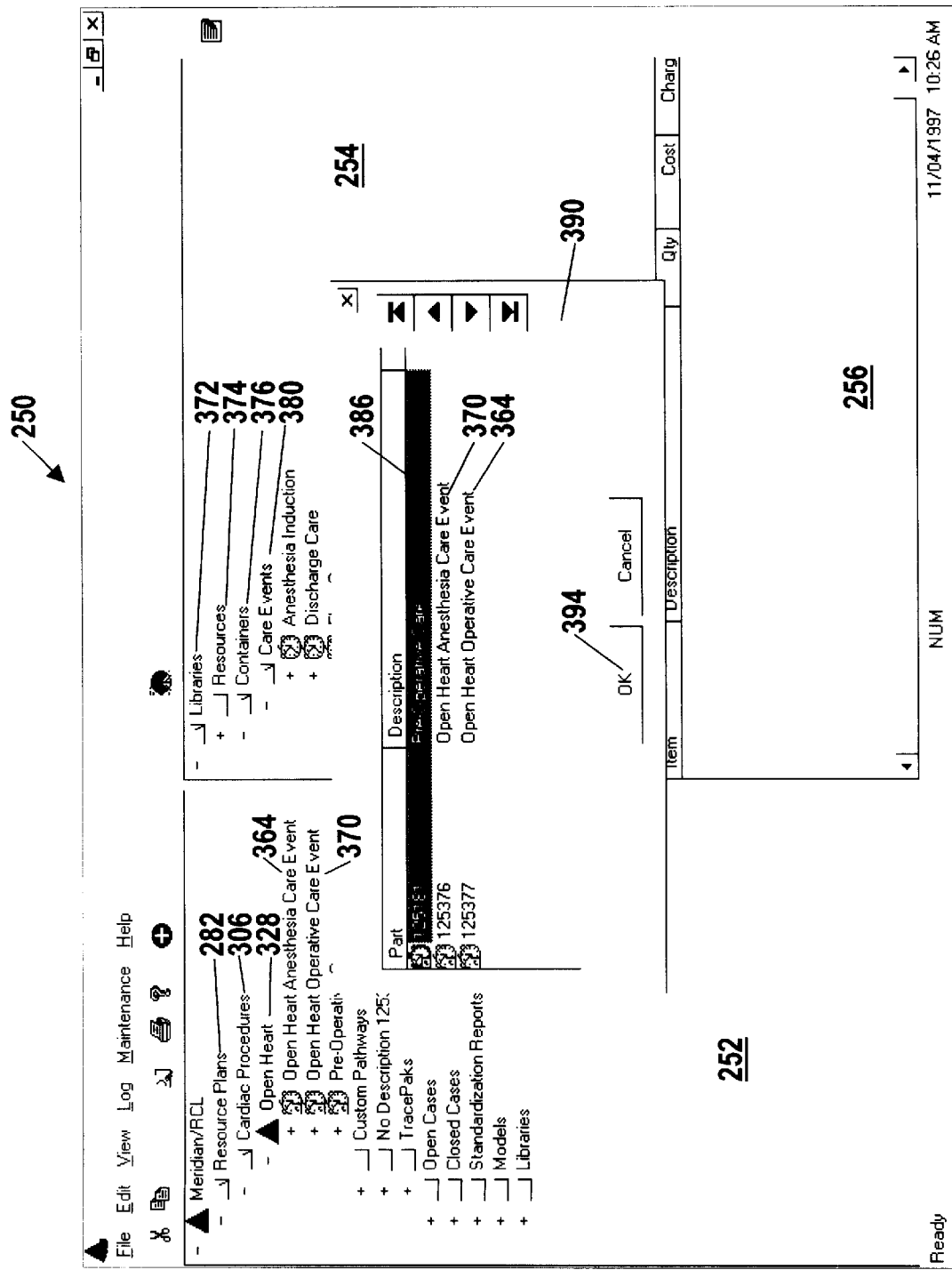
Figure 24:
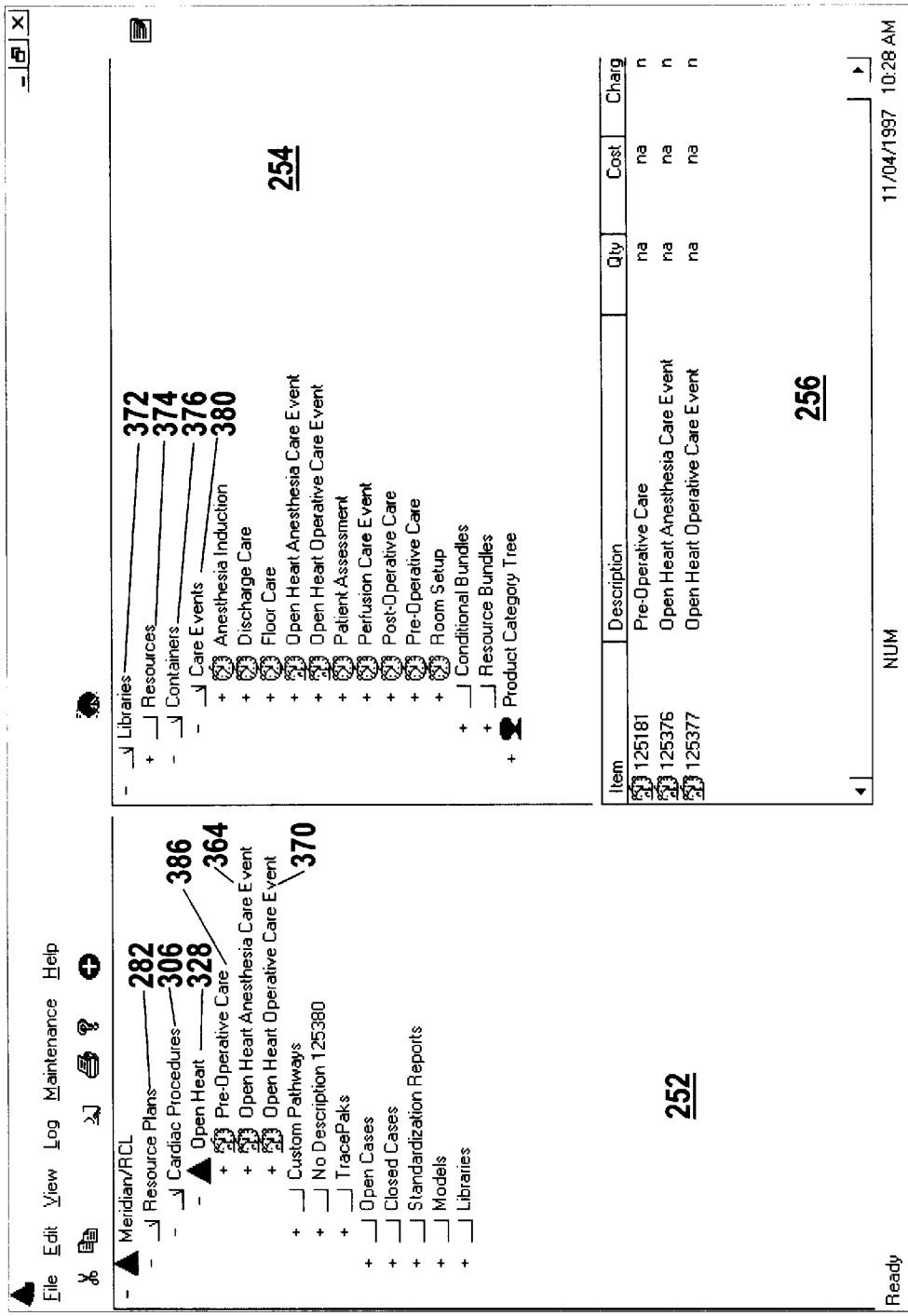

In FIG. 21, the user has selected the Open Heart procedural pathway 328 and called up the Procedural pathway module menu 330 and selected the Resequence function 388. This function allows the user to change the order of the items shown under the Open Heart procedural pathway 328. By selecting the Resequence function 388, the user is presented with the Resequence Components window 390, shown in FIG. 22. This window 390 shows the items under the Open Heart procedural pathway 328 and by selecting the desired care event, such as the Pre-Operative Care Event 386, and using the arrow keys to the right of the window 390 the user may move the selected care event 386 to the desired location, shown in FIG. 23. Once the desired sequence is achieved, the user exits the Resequence Components window 390 by selecting the OK button 394. As shown in the Browser window 250 of FIG. 24, the new care event sequence has appeared under the Open Heart procedural pathway 328 with the Pre-Operative Care Event object 386 appearing first, followed by the Open Heart Anesthesia Care Event object 364 and the Open Heart Operative Care Event object 370.

Figure 25:
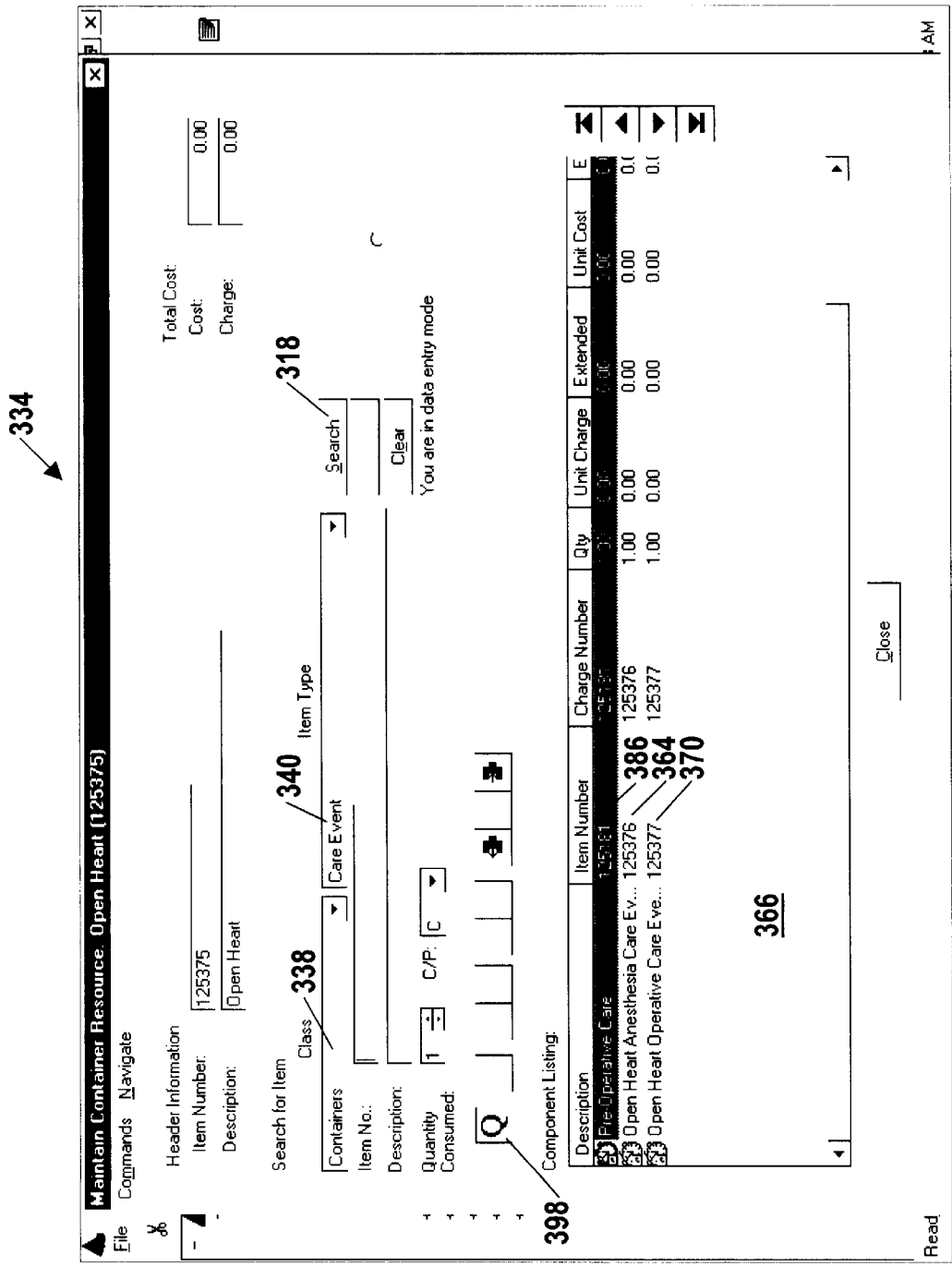
Figure 26:
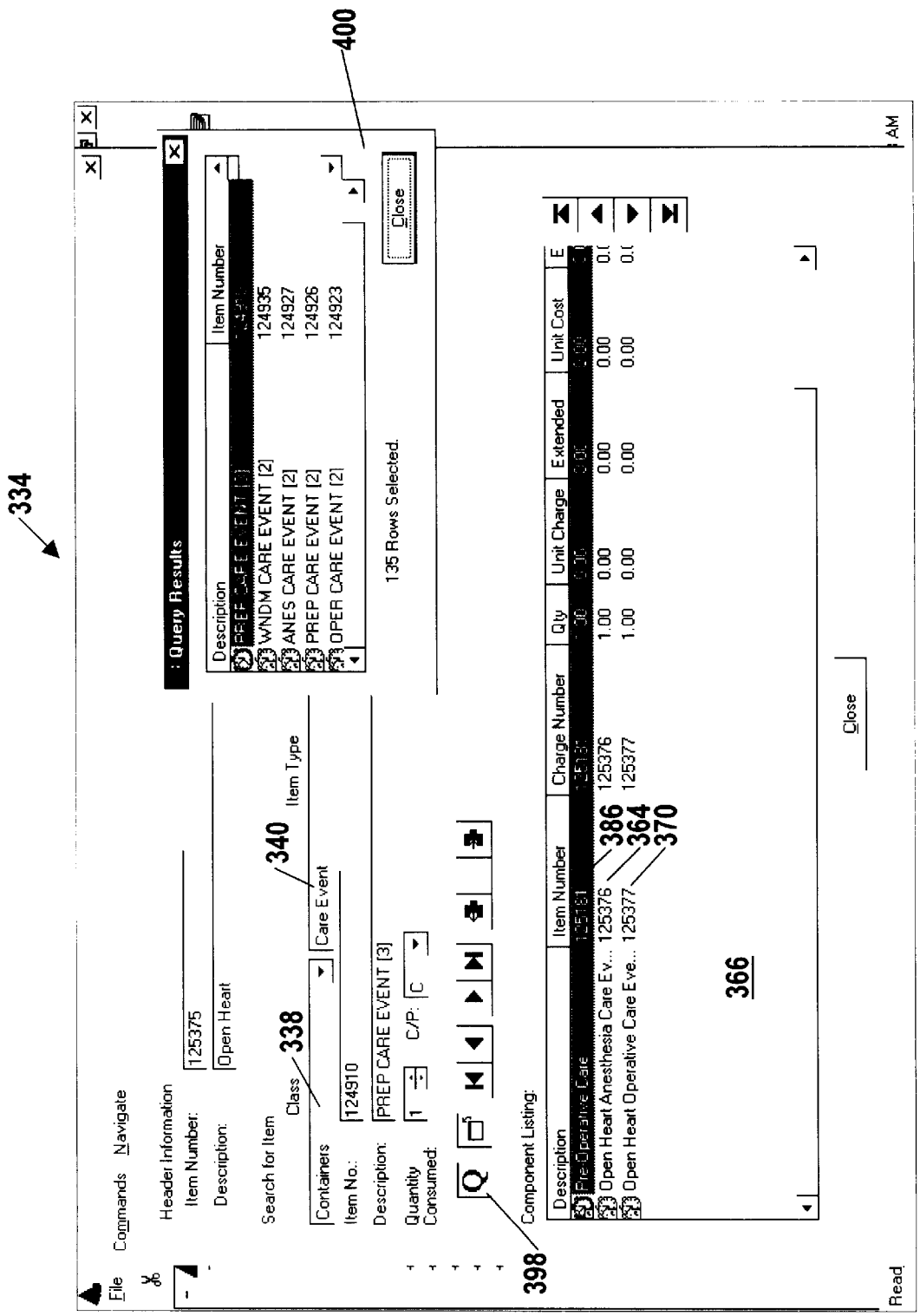

Containers may be added by using the database search functions of the Maintain Container Resource window 334 as well. Shown in FIG. 25, the user has entered the Maintain Container Resource window 334 as previously described. The Maintain Container Resource window 334 displays the care events which are added to the Open Heart procedural pathway 328 in the Component Listing field 366. From the Maintain Container Resource window 334, the user may search the database related to the information system to add components which have already been created, by selecting the Query mode button 398. By selecting the class of the object in the Class field 338 and the item type of the object in the Item Type field 340 the user may search the database for all objects having those attributes by selecting the Search button 318. The results of the query appear in the Query Results window 400 shown in FIG. 26.

Figure 27:
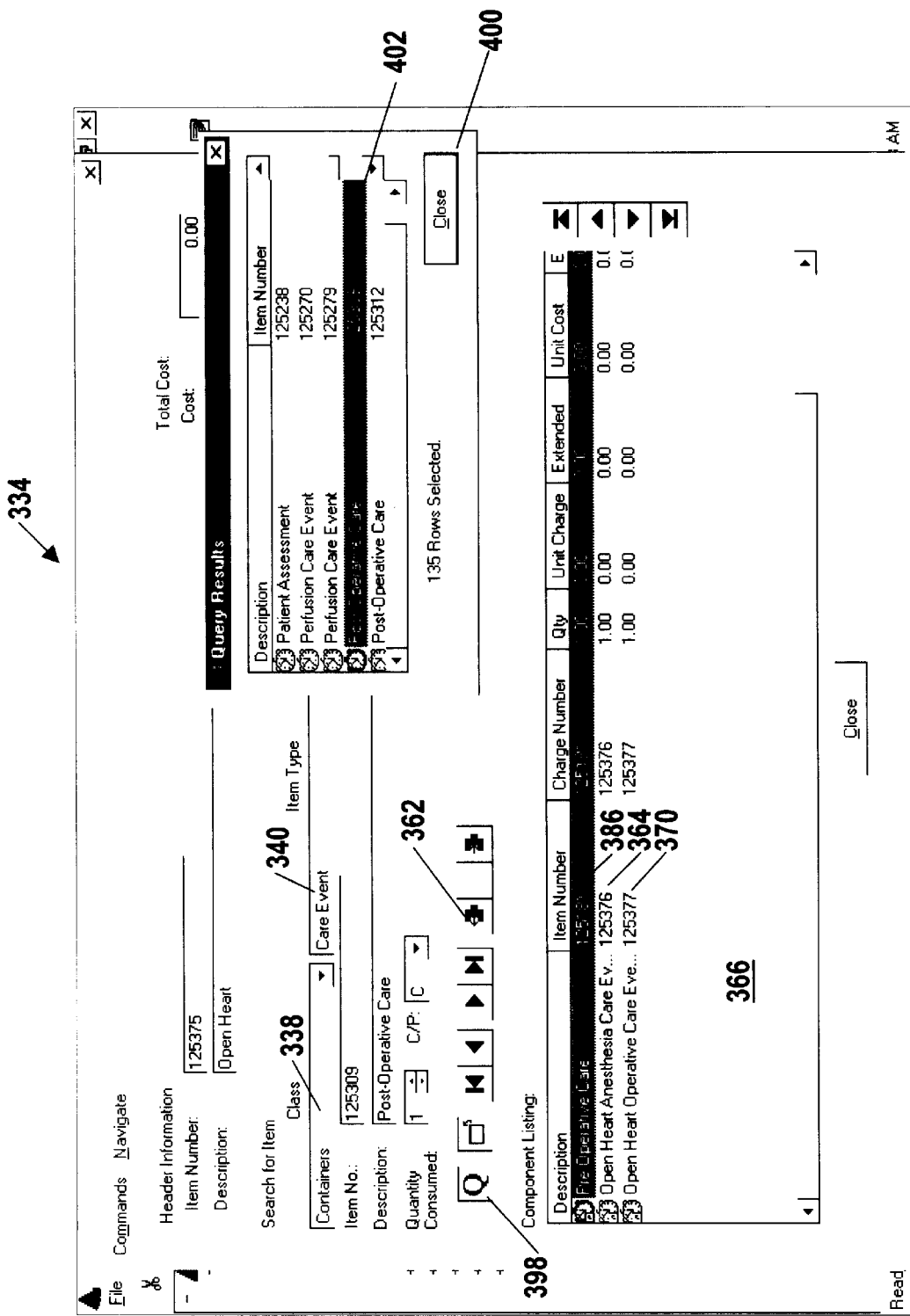
Figure 28:
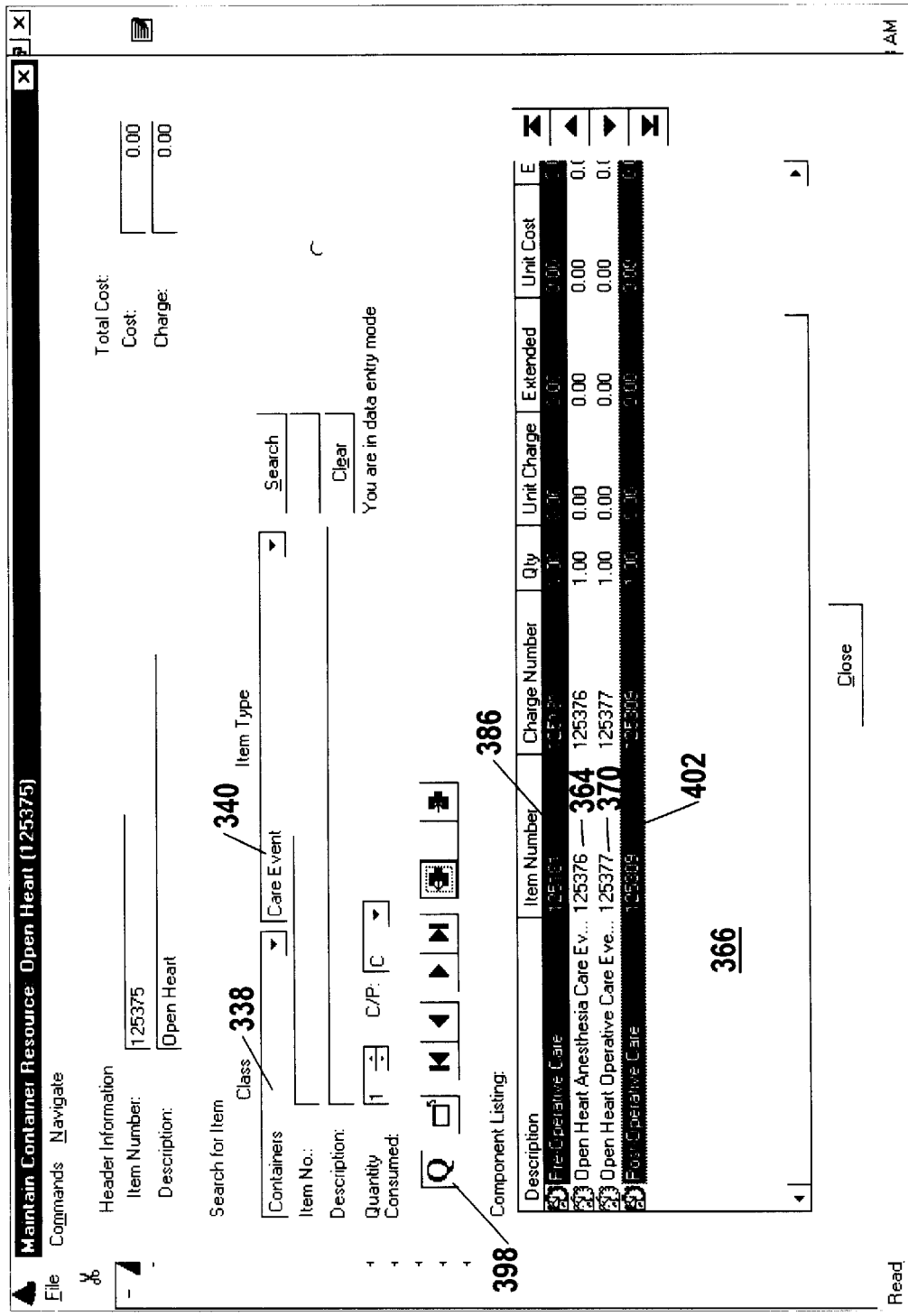
Figure 29:
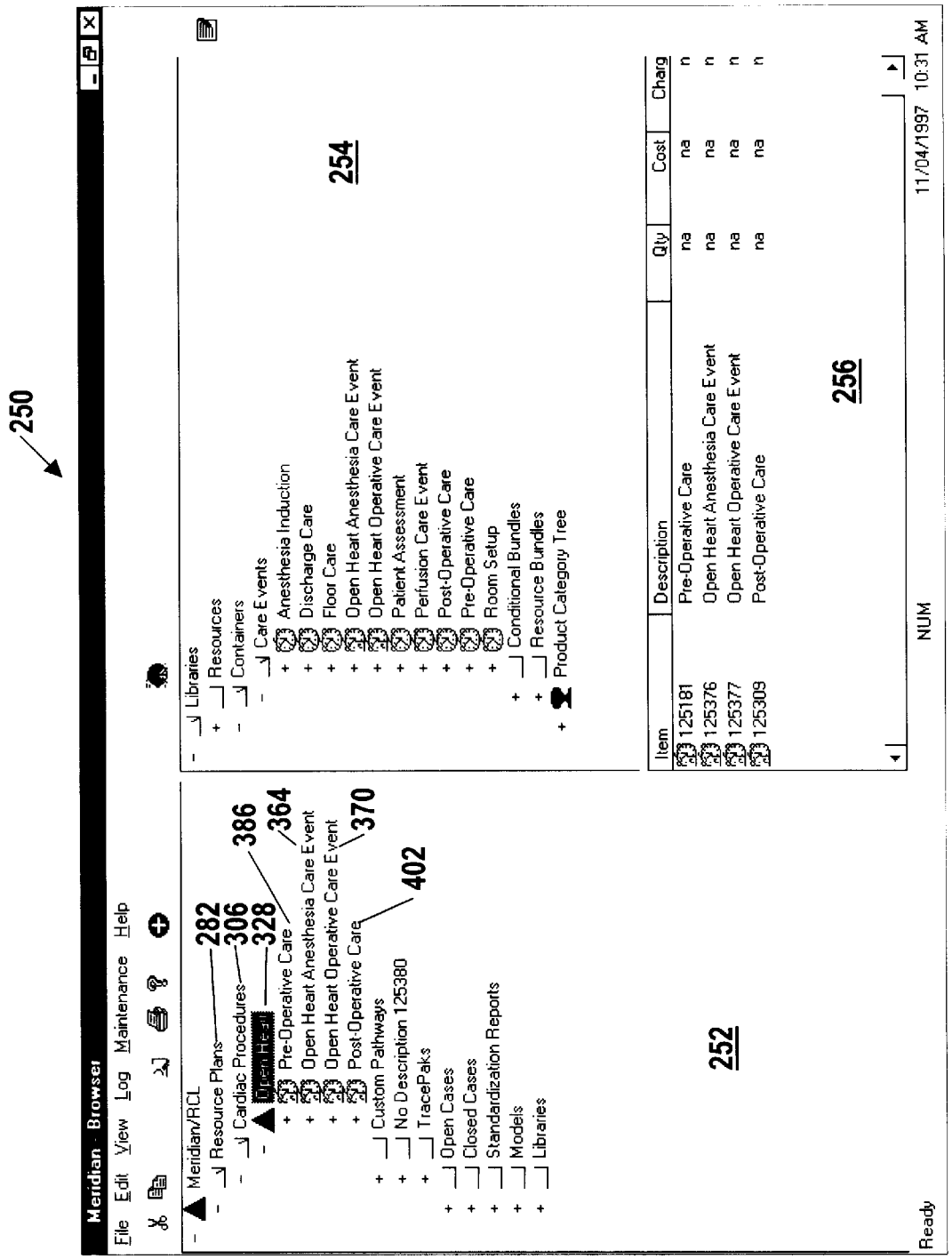

The Query Results window 400 shows all objects which meet the search criteria entered into the Maintain Container Resource window 334. The user may then highlight a desired object, in this case the Post Operative Care Event 402, in the Query Results window 400, as shown in FIG. 27. The user adds the desired Post Operative Care Event 402 by selecting the Add New Component button 362 as previously described. As shown in FIG. 28, the newly selected Post Operative Care Event 402 is then copied to the Open Heart Procedural pathway 328 and shows up in the Component Listing window 366. As is seen in FIG. 29, the new Post Operative Care Event 402 appears under the Open Heart procedural pathway 328.

One of the features of the exemplar embodiment is the fact that each of the containers, resources and data software objects, once created, are reusable with other software module objects, or even other functional nodes. For example, in the previous description, the Pre-Operative Care Event 386 and the Post Operative Care Event 402 each maintain their contained information upon addition to the Open Heart Procedural pathway 328.

Figure 30:
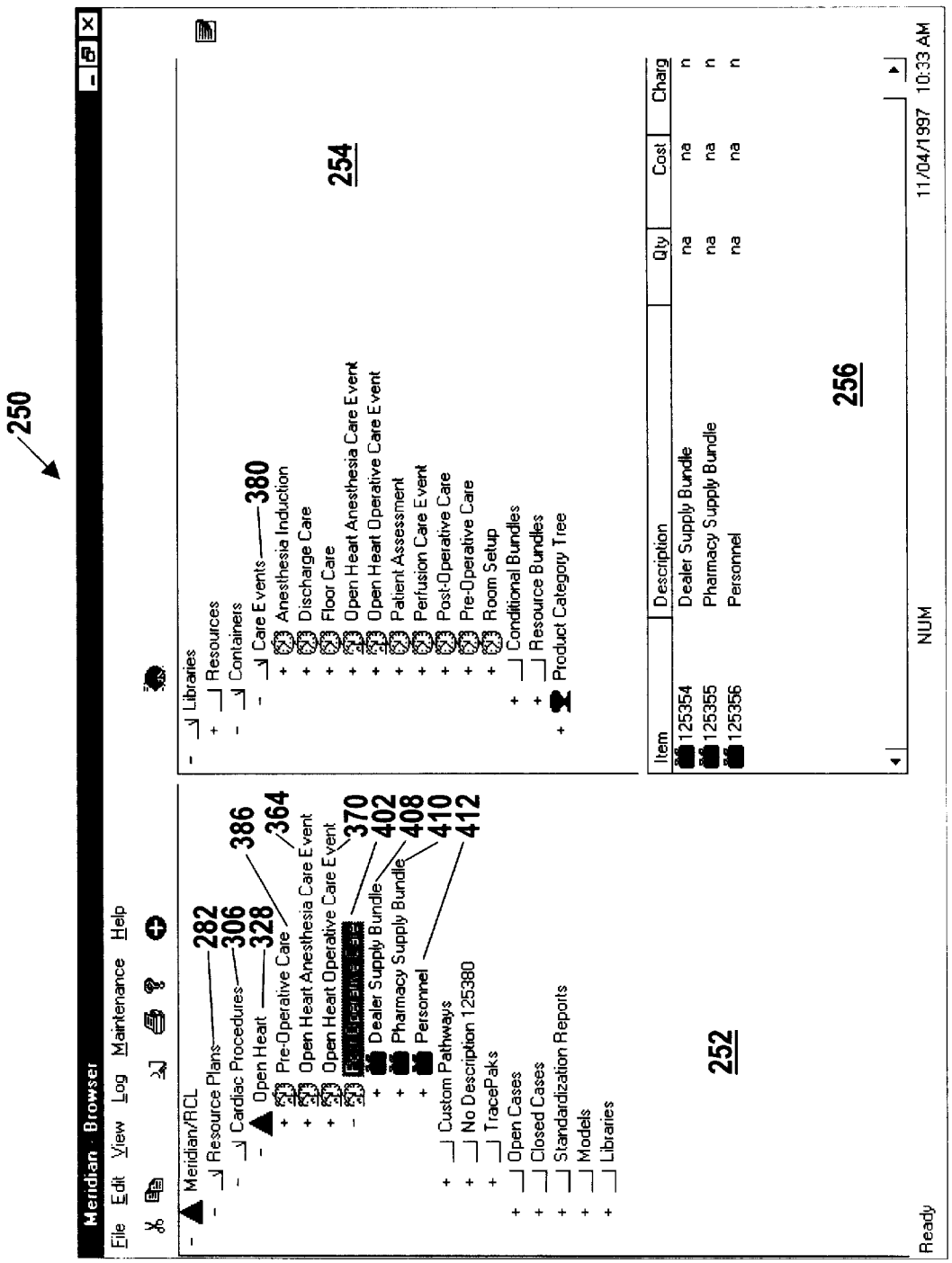
Figure 31:
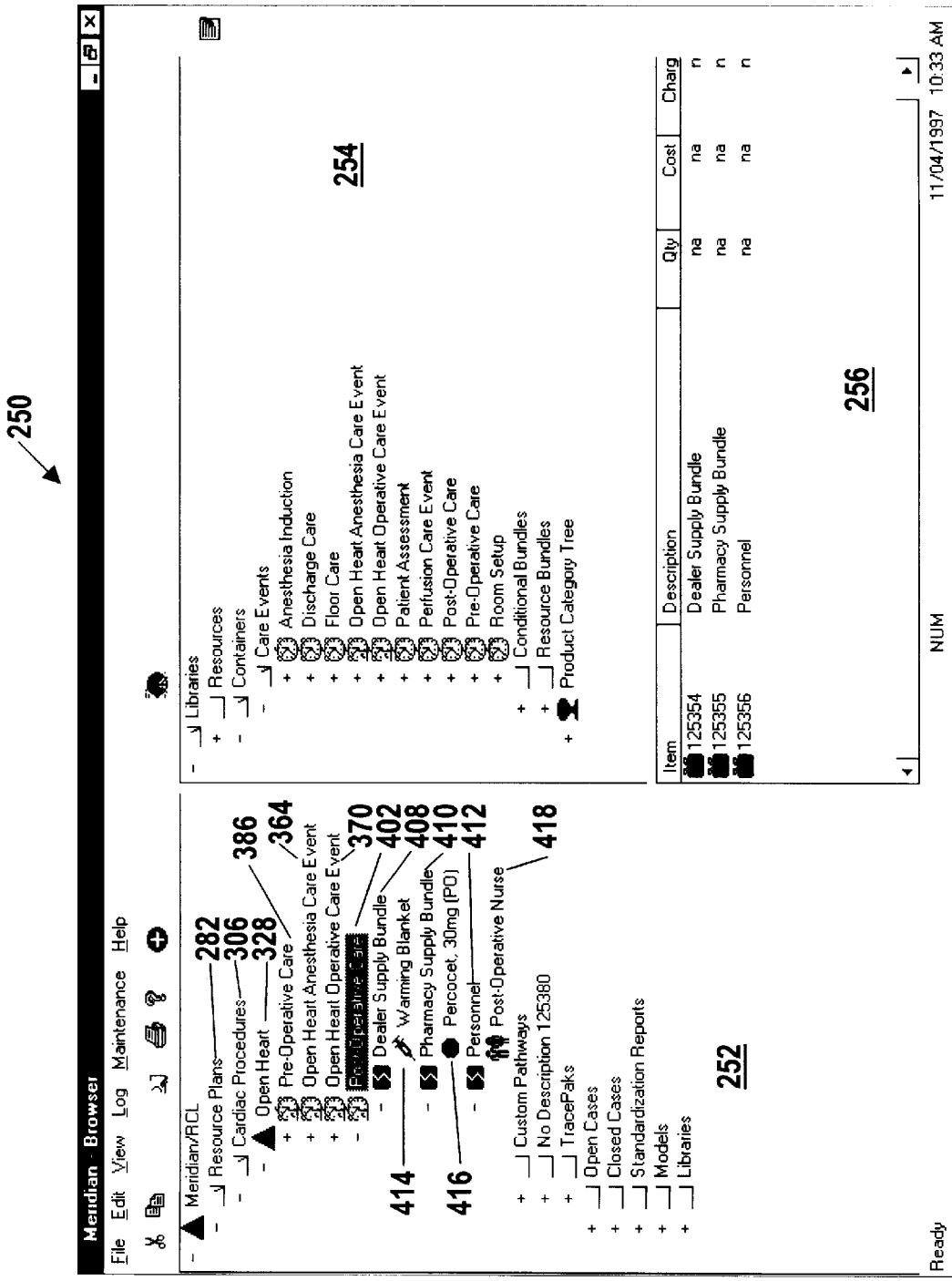

Referring to FIGS. 30 and 31, the Post Operative Care Event 402 is expanded to show its contents. Unlike the Open Heart Anesthesia Care Event 364 and the Open Heart Operative Care Event 370, since the Post Operative Care Event 402 is retrieved from the list of pre-configured care events 380 in the Second Tree view 254, it has contents that were added at the time that this care event was created. Shown in FIG. 30 is an expanded view of the Post Operative Care Event 402 showing its contents, which include three bundle container objects, the Dealer Supply Bundle 408, the Pharmacy Supply Bundle 410 and the Personnel bundle 412. Each of these container objects, as will be described later, are configured by the user to group resource objects, which are commonly used together.

As shown in FIG. 31, the various bundles 408, 410 and 412 are expanded to show their contents. The Dealer Supply Bundle 408 contains a Warming Blanket resource object 414, the Pharmacy Supply Bundle 410 contains a pharmacy resource object 416, which is a 30 milligram tablet of Percocet, and the Personnel bundle 412 contains a Post Operative Nurse personnel resource object 418. The objects that form the content of the Post Operative Care Event 402 all maintain their original contents from their creation by the user, and by copying the care event container to the Open Heart Procedural pathway object 328, the contents of the container are included as well.

Figure 32:
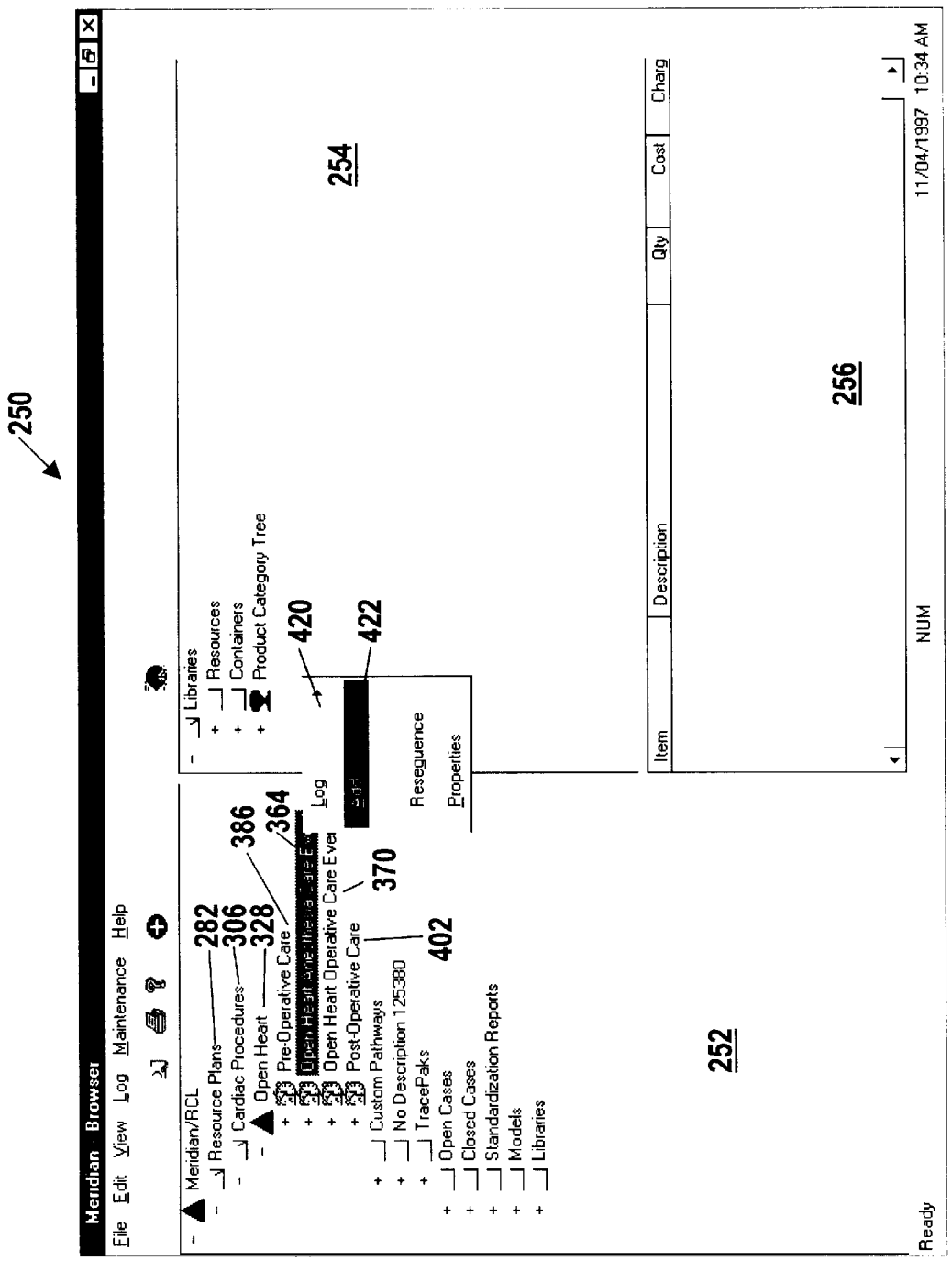
Figure 33:
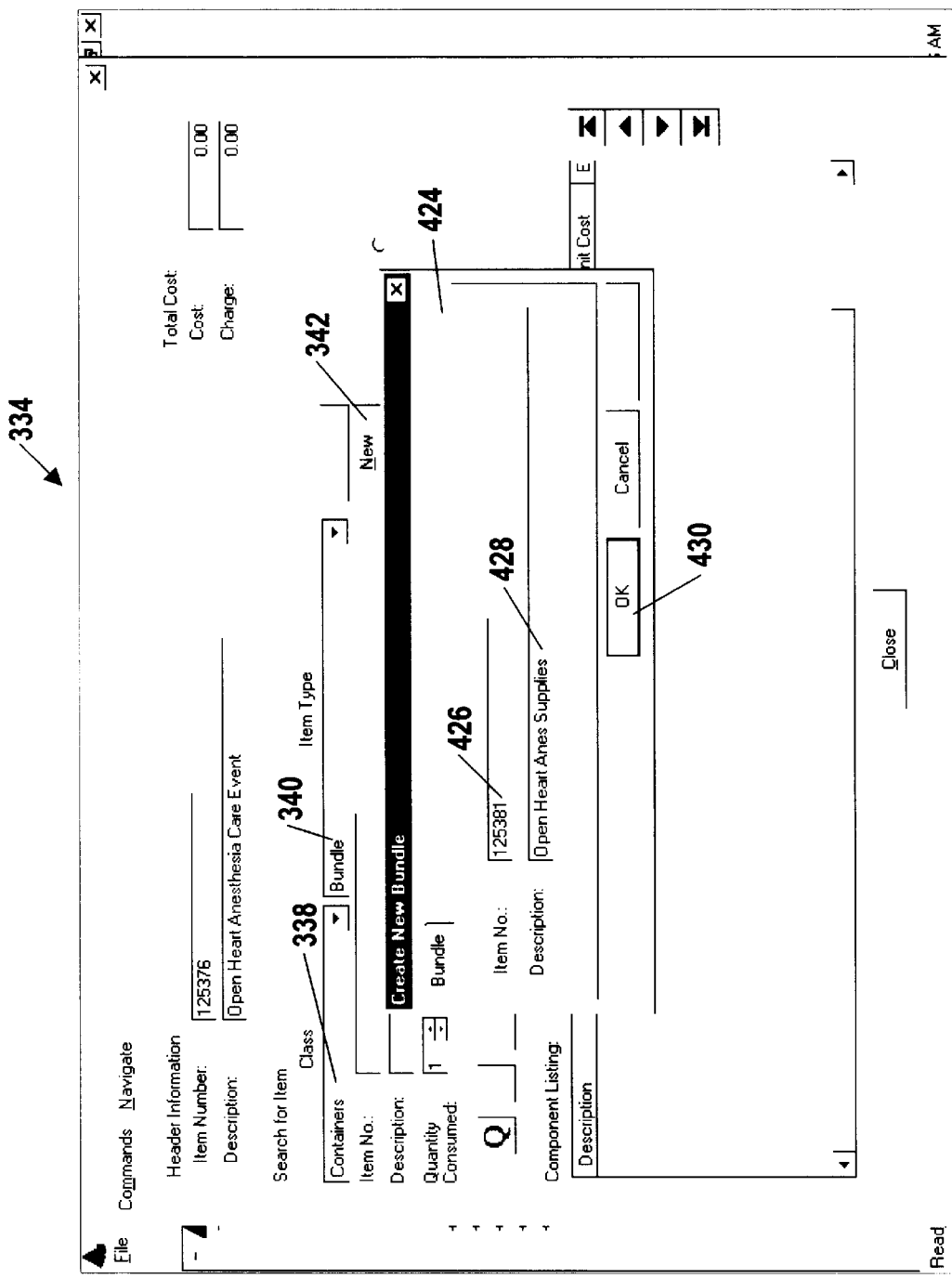

With respect to created care event containers, once the container objects are created, the user then populates the containers with other container, resource and data objects related to the particular care event. Referring now to FIG. 32, the user has selected the Open Heart Anesthesia Care Event object 364 and right clicked to call up the Care Event Menu 420 and has selected the Add function 422. This function will allow the user to add other objects to the selected care event container. As is shown in FIG. 33, selecting the Add function 422 from the Care Event Menu 420 will provide the user with the Maintain Container Resource window 334. Previously, this window 334 was described with respect to the Open Heart Procedural pathway 328. Since the Open Heart Anesthesia Care Event object 364 was selected at the time the Maintain Container Resource window 334 was opened, the Open Heart Anesthesia Care Event object 364 information is reflected in the Header Information 336.

Figure 34:
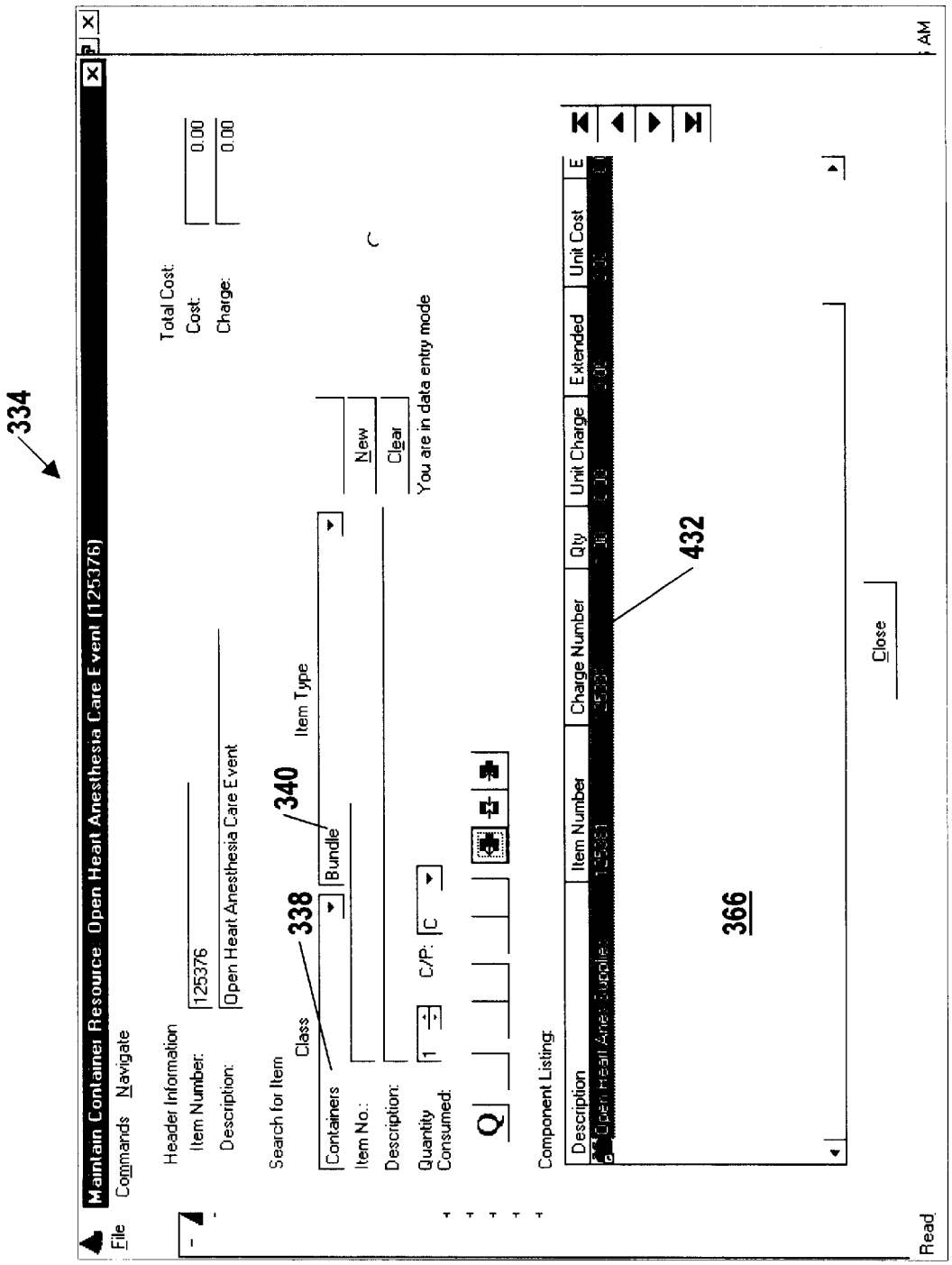

In this example of FIG. 33, the user has selected the class type of Containers in the Class field 338 and the item type of Bundle in the Item Type field 340. The user then selects the New button 342 which causes the Create New Bundle window 424 to appear. This window 424 allows the user to create a new bundle container object to hold other related objects. In the example, the user provides the item number and the bundle description in the Item No. field 426 and Description field 428, and by selecting the OK button 430 creates the new bundle object. As shown in FIG. 34, the Open Heart Anesthesia Supplies bundle object 432 appears in the Component Listing field 366.

Figure 35:
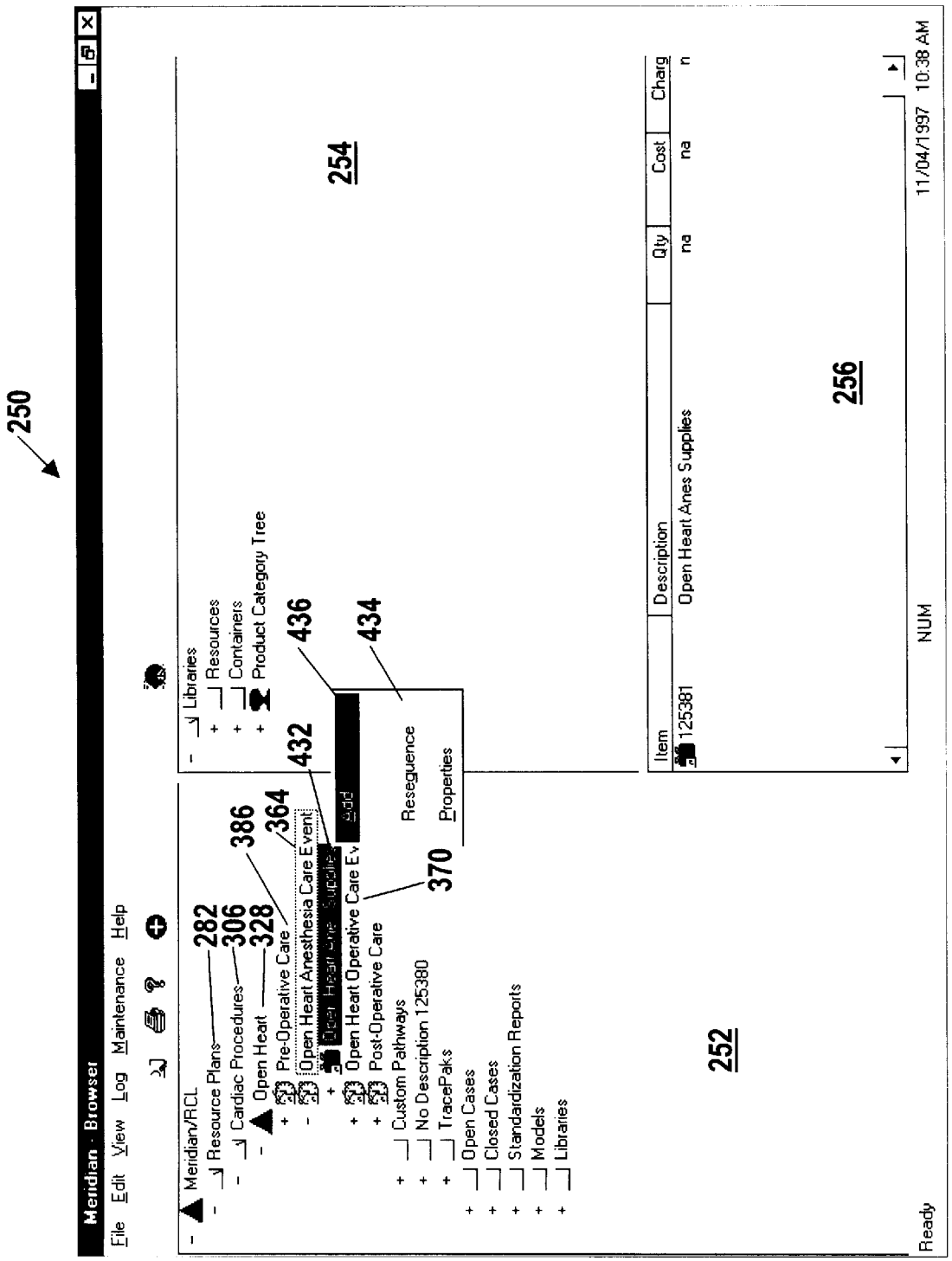
Figure 36:
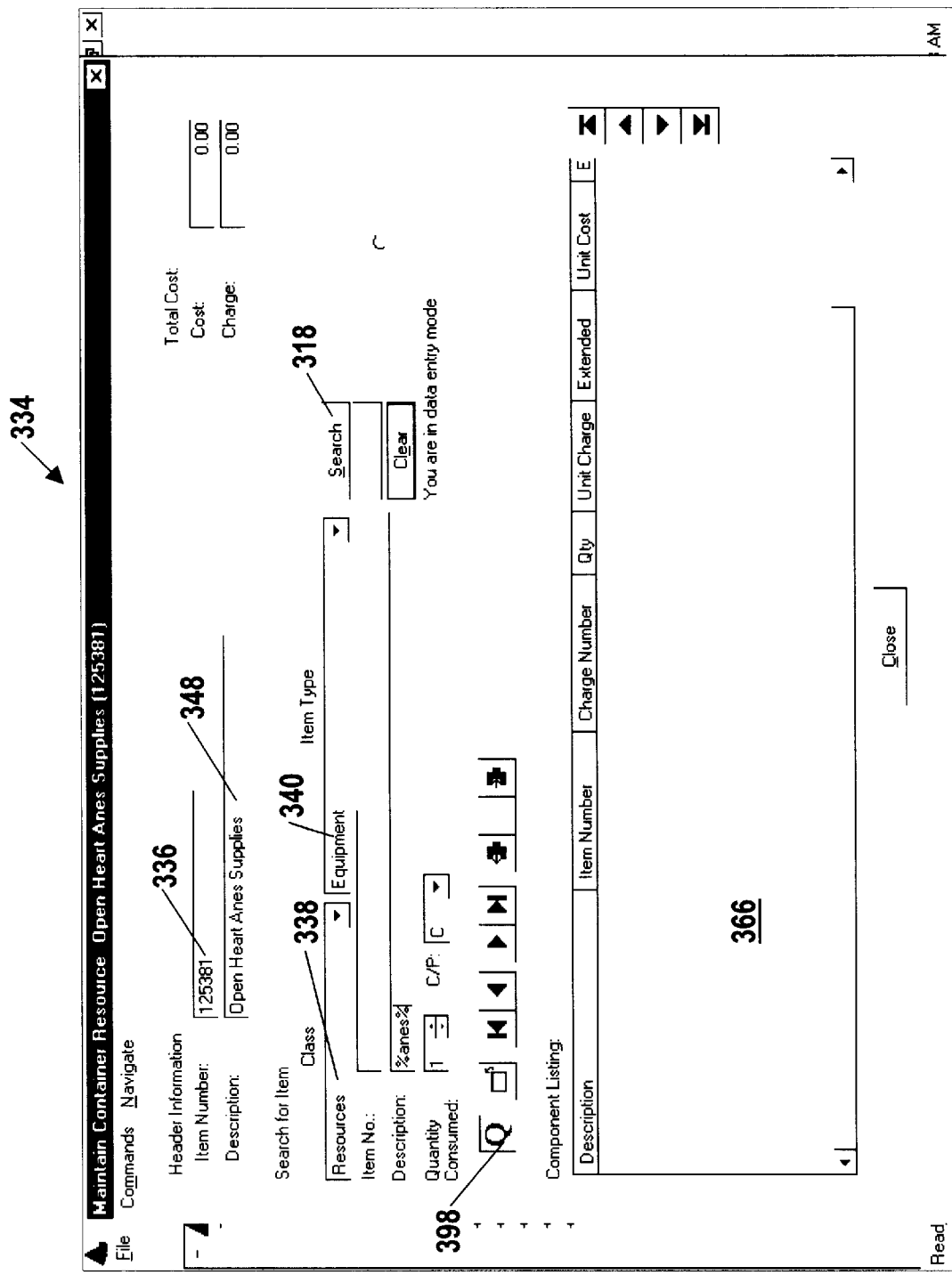

Referring now to FIG. 35, once the new Open Heart Anesthesia Supplies bundle object 432 is created and added to the Open Heart Anesthesia Care Event container object 364, the new bundle object 432 appears under the care event object 364 in the Nested Tree view 252 of the Browser window 250, By selecting the Open Heart Anesthesia Supplies bundle object 432 and right clicking, the user can call up the Bundle Object Menu 434 in order to maintain the bundle object 432. In the example of FIG. 35, the user selects the Add function 436, which allows the user to maintain the contents of the Open Heart Anesthesia Supplies bundle object 432. Selecting the Add function 436 calls up the Maintain Container Resource window 334, with the Header Information 336 reflecting the maintenance of the Open Heart Anesthesia Supplies bundle object 432, as shown in the Description field 348, as depicted in FIG. 36.

The user may then proceed with provisioning the bundle object 432 with resource objects relating to the provision of anesthesia in the open heart procedure. In the example of FIG. 36, the user has selected the class of objects as resources in the Class field 338 and the item type of equipment in the Item Type field 340. By selecting the Query mode button 398 and selecting the Search button 318 the user retrieves a list of all previously created equipment resource objects, which allows the user to utilize preconfigured equipment resource objects in the Open Heart Anesthesia Supplies bundle object 432.

Figure 37:
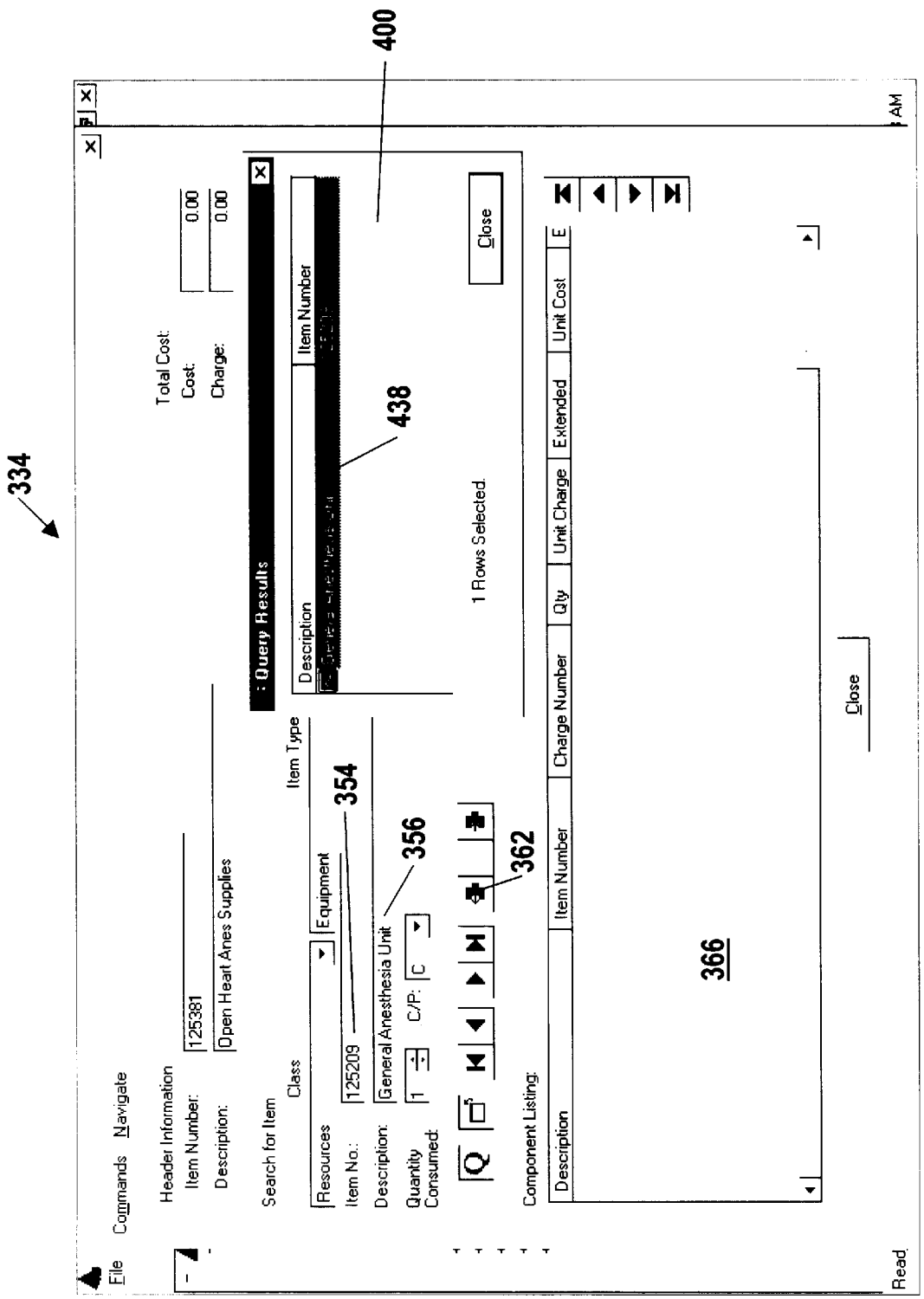
Figure 38:
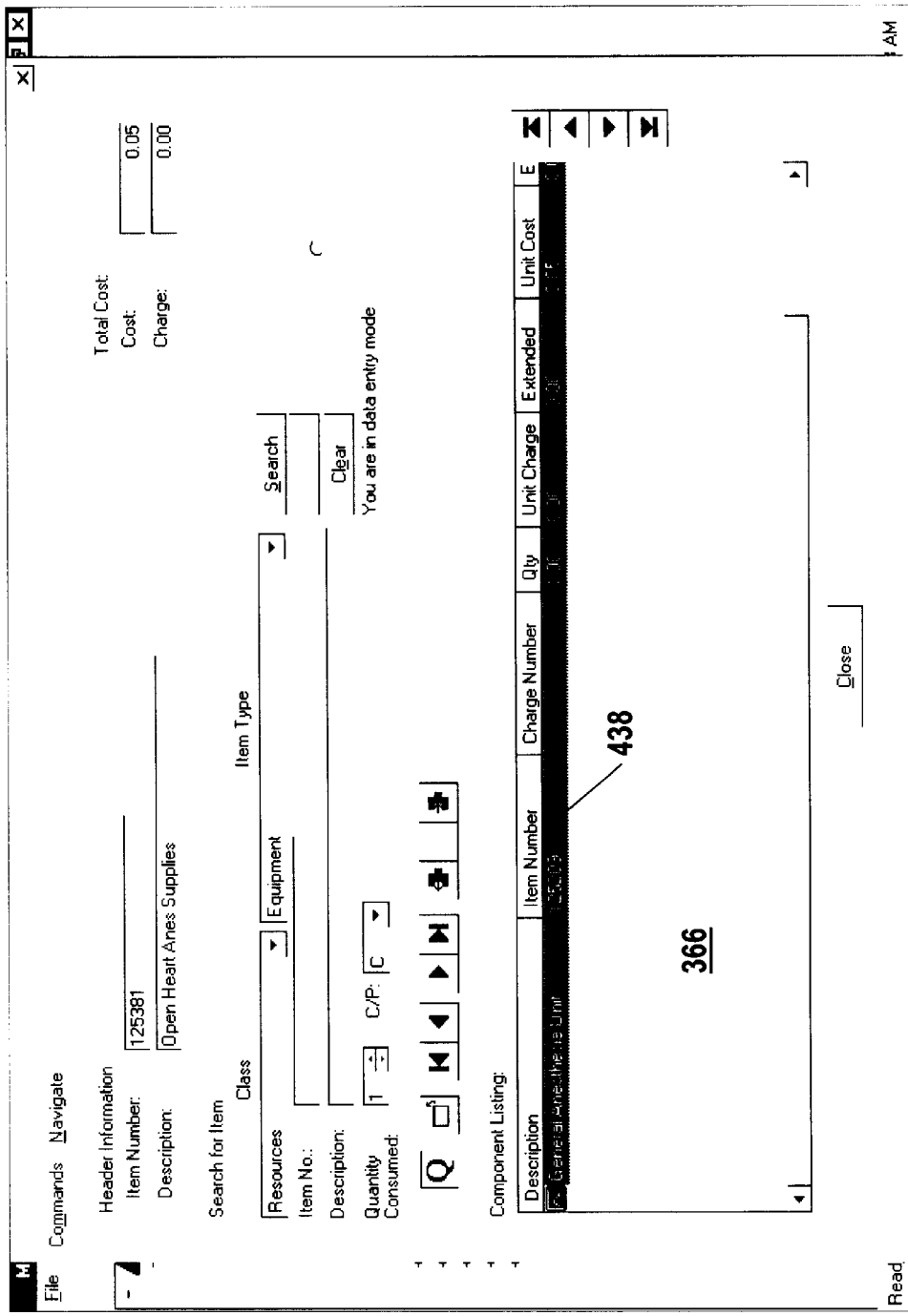

FIG. 37 shows the results of the database search in the Query Results window 400. By selecting the desired equipment object, in this case a General Anesthesia Unit 438, the relevant information will appear in the Item No. field 354 and Description field 356 in the Maintain Container Resource window 334. By then selecting the Add New Component button 362 the General Anesthesia Unit object 438 will appear in the Component Listing field 366, as shown in FIG. 38.

Figure 39:
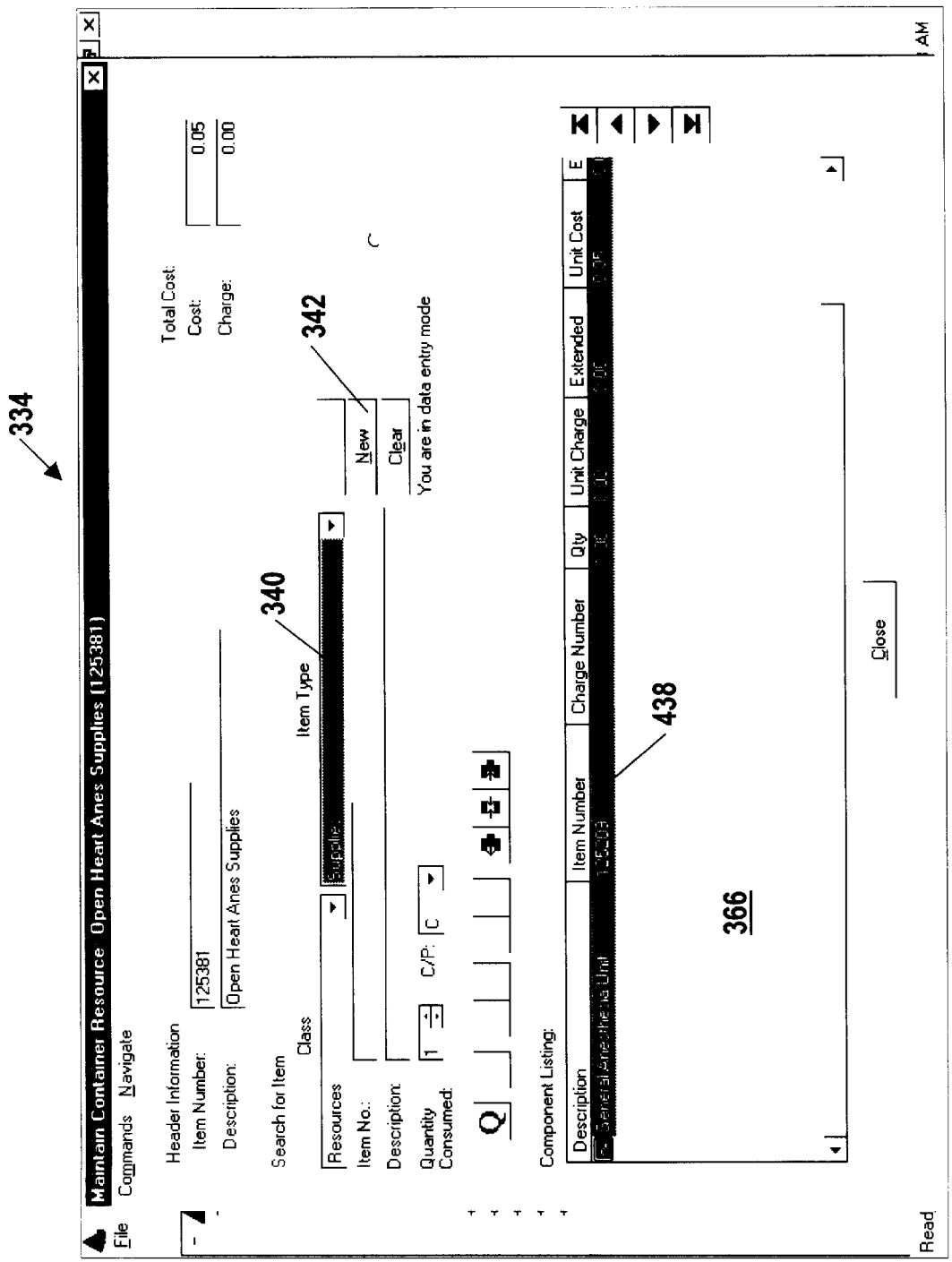
Figure 40:
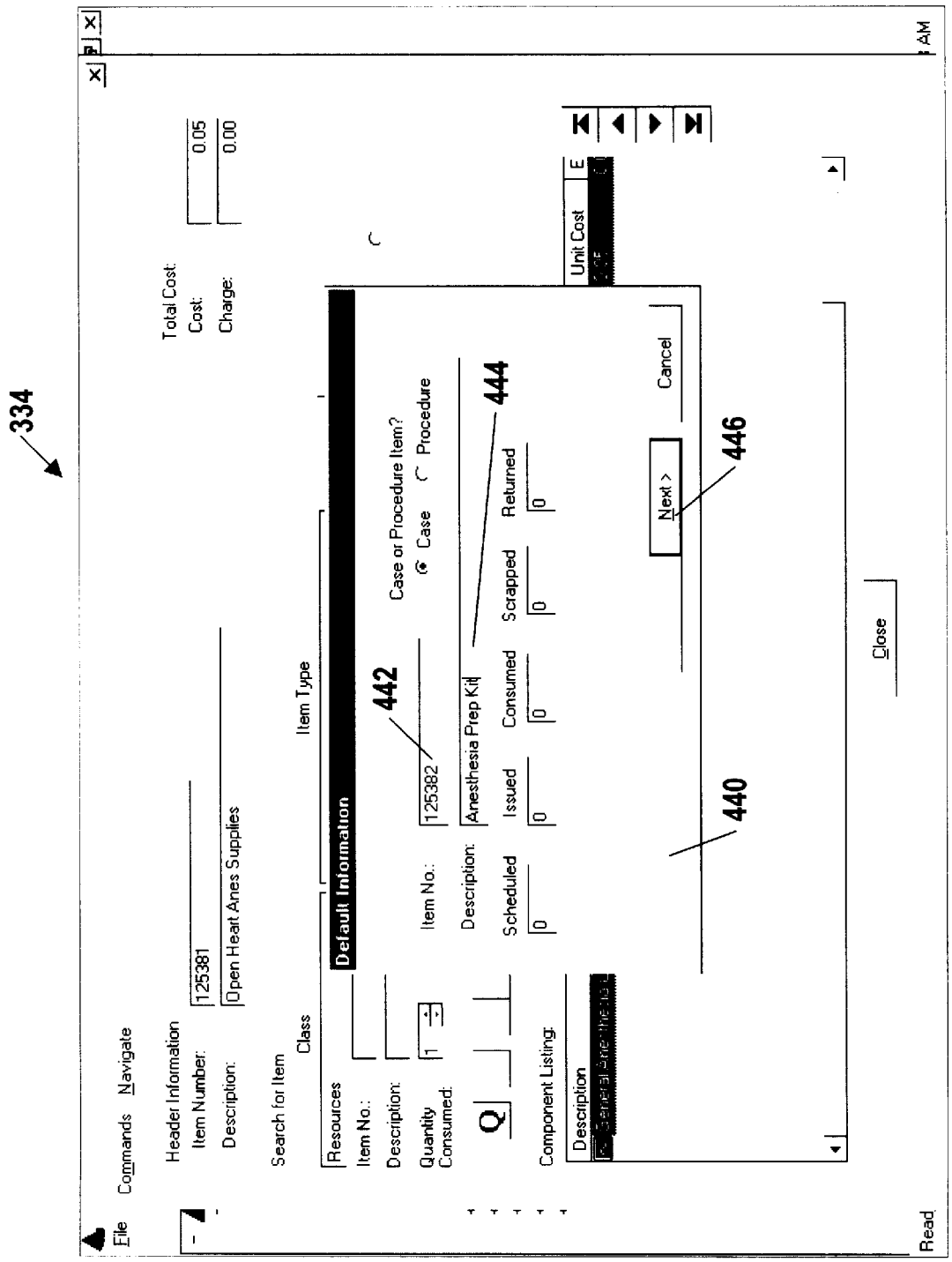

Referring now to FIG. 39 the addition of other objects to the Open Heart Anesthesia supplies bundle container object 432 will be described. In FIG. 39 the Item Type field 340 and the supplies object type are selected. Clicking on the New button 342 brings up the supply object Default Information window 440, as depicted in FIG. 40. In this window 440 the desired supply object can be called up by either entering an existing supply object item number in the Item Number field 442, or entering an existing supply object description in the Description field 444. Alternately, a new item number is entered or automatically assigned in the Item Number field 442, and the name of a new supply object is entered into the Description field 444. In the example depicted in FIG. 40, the new supply object is given the name of "Anesthesia Prep Kit," which is entered into the Description field 444.

Figure 41:
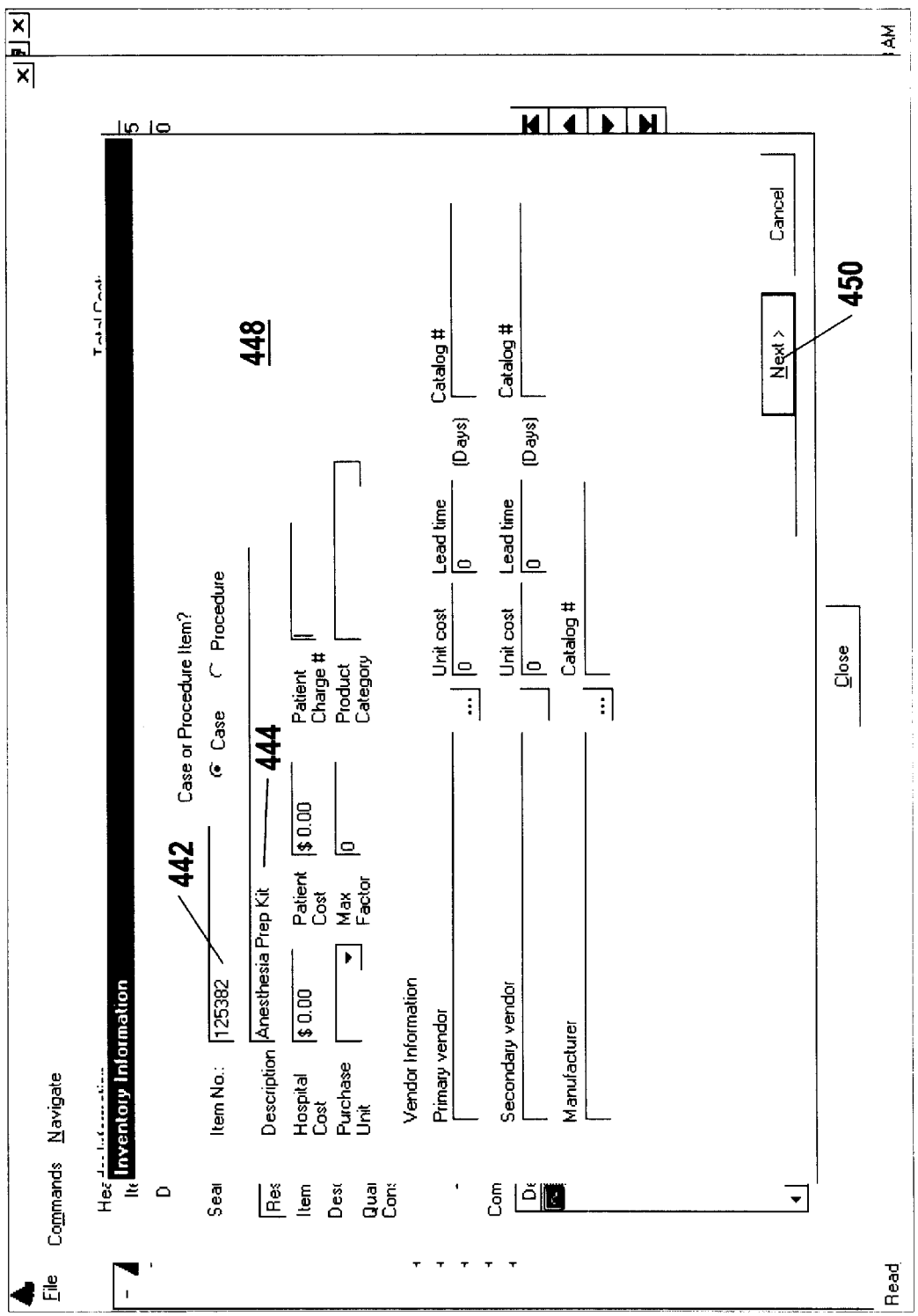

The information management system of the exemplar embodiment automatically prompts the user for all of the information necessary and desirable to fully specify the new supply object. The windows to provide this information are invoked by the user by pressing the Next button 446, which causes the display of the Inventory Information window 448, as depicted in FIG. 41. The item number and description of the supply object are automatically carried forward from the Default Information window 440, depicted in FIG. 40, to the Inventory Information window 448, depicted in FIG. 41, and are displayed within the persistent Item Number field 442 and Description field 444.

The management information system user may enter specific inventory management information about the supply object using the Inventory Information window 448. For example, a patient charge number and catalog number may be entered, as well as other information that may be necessary for the proper tracking of the supply object. The Inventory Information window 448 also displays other information about the supply object, which information cannot be edited by the user at this point. However, if the information is already entered, it is displayed in the Inventory Information window 448. When the desired user editable information has been entered into the Inventory Information window 448, the user proceeds by pressing the Next button 450.

Figure 42:
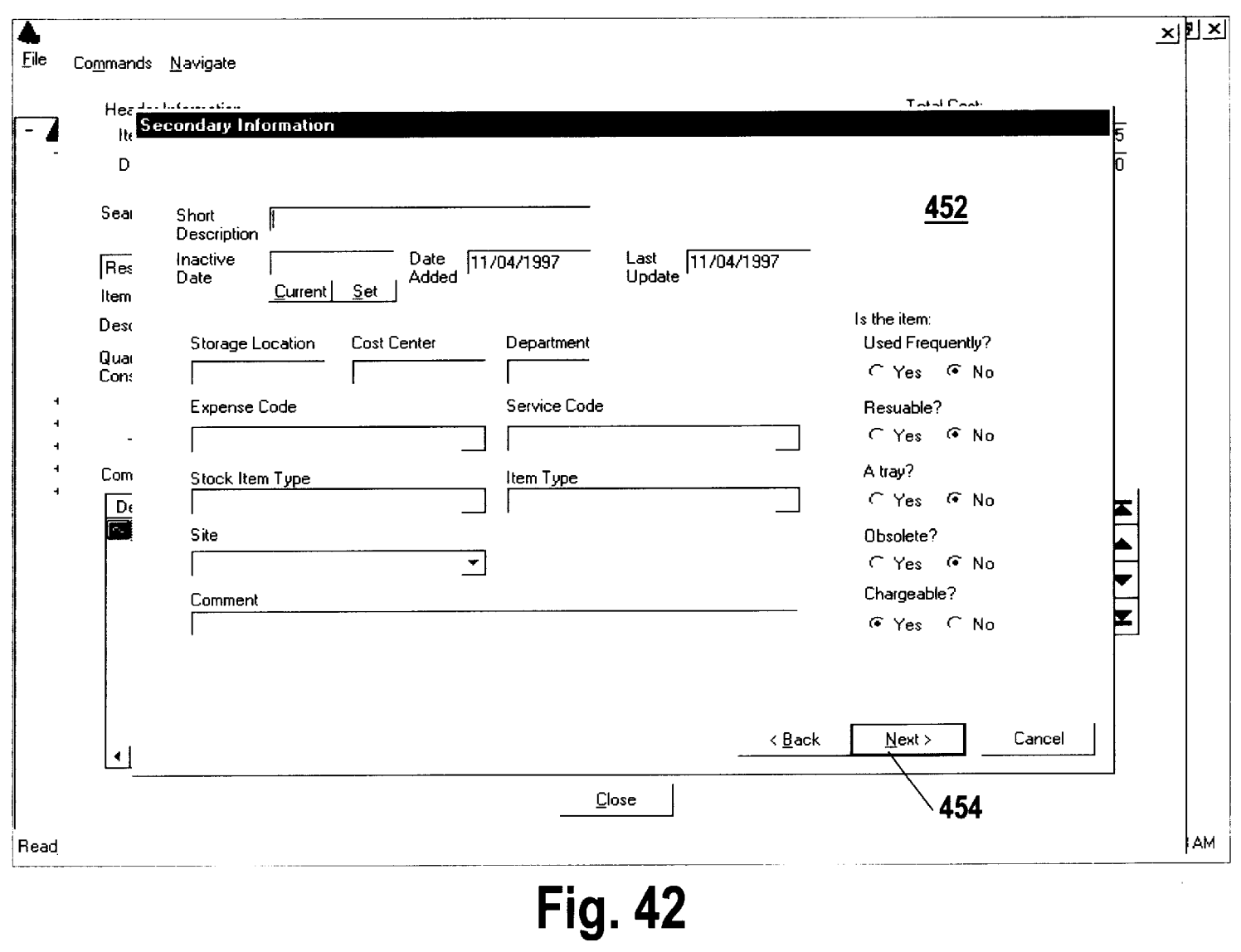

FIG. 42 depicts the Secondary Information window 452, in which further information about the supply object is entered. For example, a short description of the supply object may be entered. If the supply object has a shelf life, the inactive date of the supply object may also be entered. Other inventory tracking information, such as storage location, cost center, department, site, and other information may also be entered. When the user has entered all of the desired information into the Secondary Information window 452, the data entry process for the supply object is resumed by pressing the Next button 454.

Figure 43:
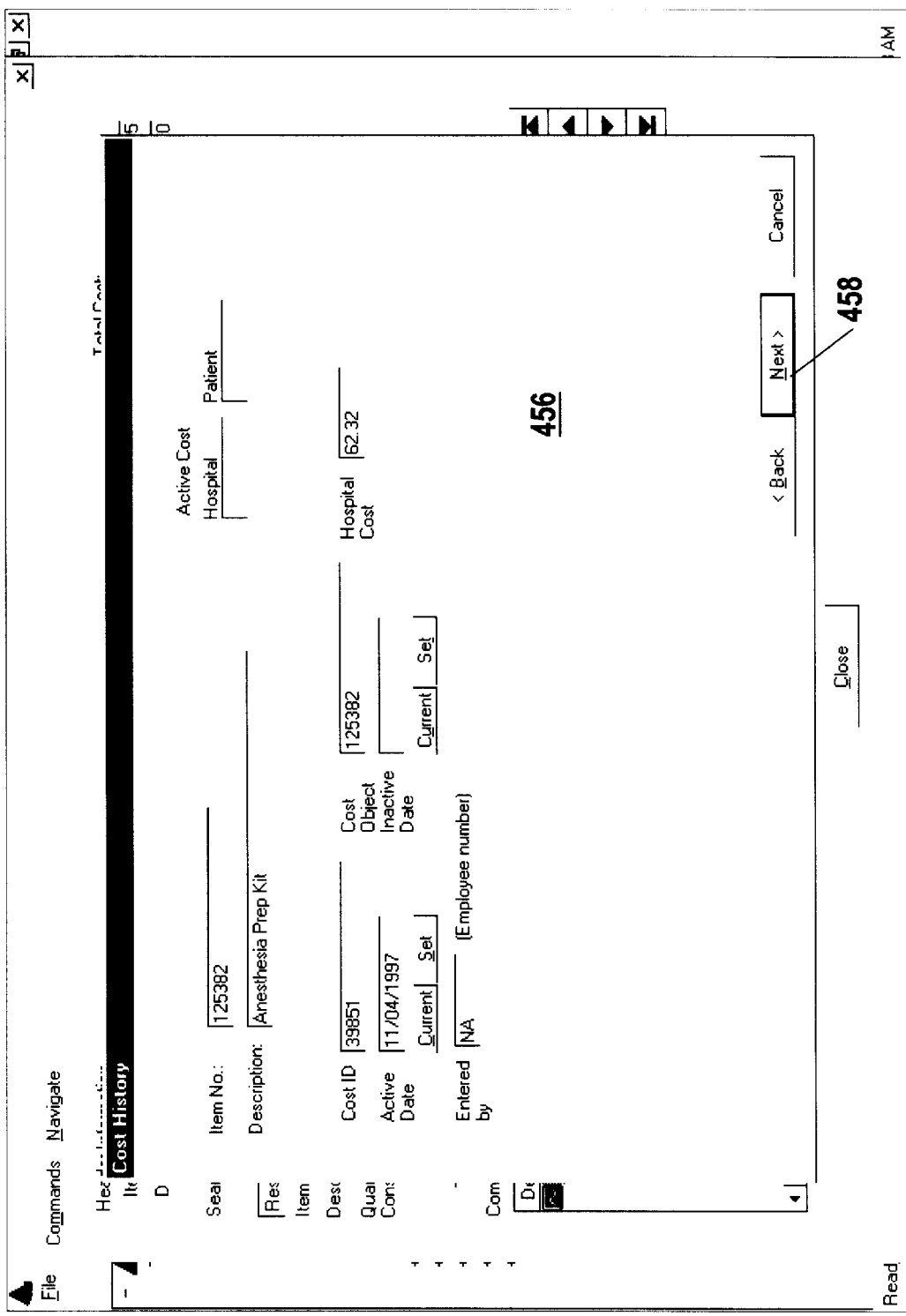
Figure 44:

The next step of data entry for the supply object in the exemplar embodiment is depicted in FIG. 43, in which the Hospital Cost History window 456 is displayed. In this window, information as to the cost to the hospital of purchasing the supply object is entered. When this information has been entered, the user continues the data entry process for the supply object by pressing the Next button 458, which brings up the Patient Cost History window 460, as depicted in FIG. 44. In this window, information as to the cost to the patient of purchasing the supply object is entered. Thus, by using the data entered on these two windows, the user is able to track the cost of specific supply objects used in the various procedures developed and specify at what cost the supply objects will be billed out to the patients who use them.

Figure 45:
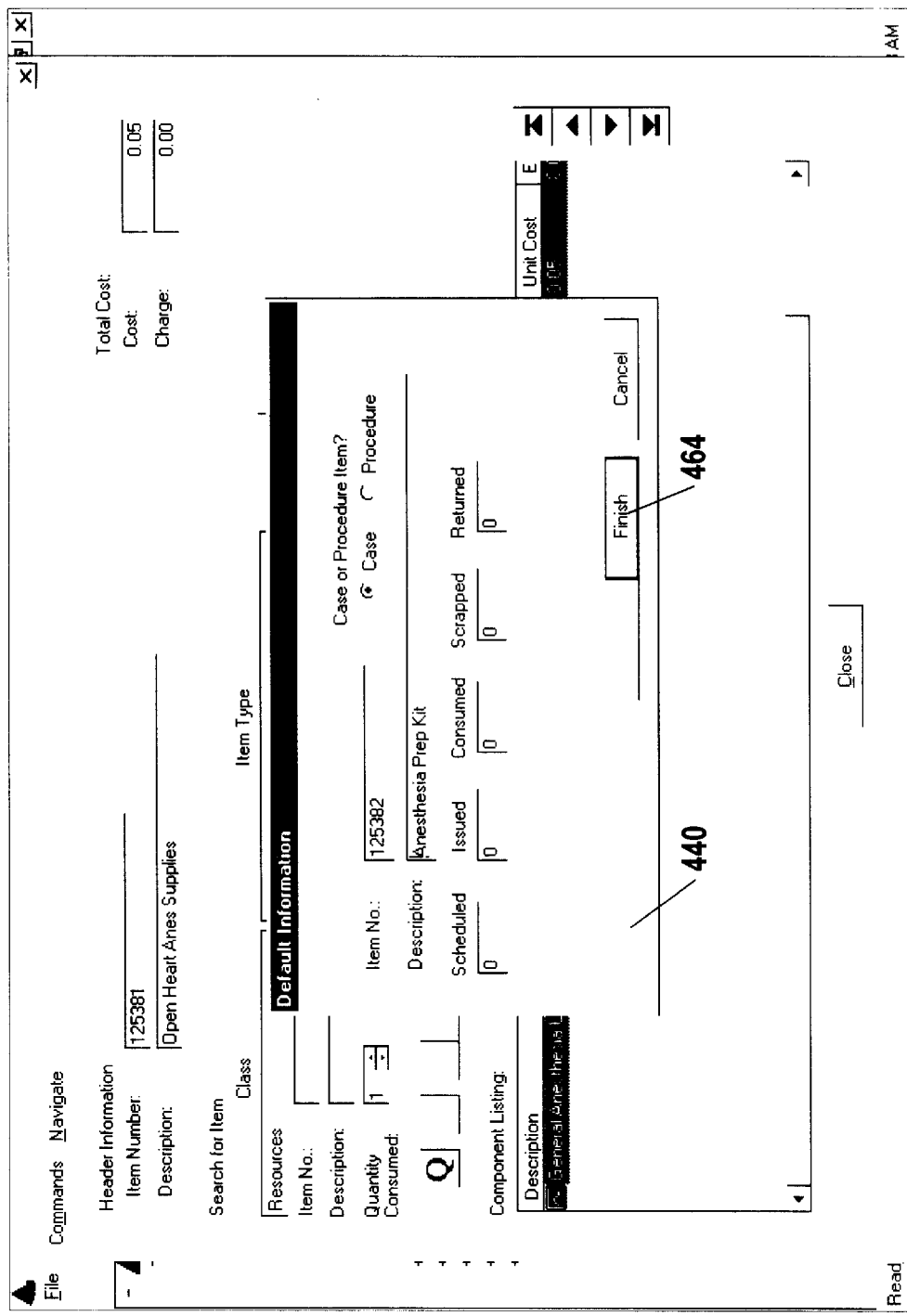
Figure 46:
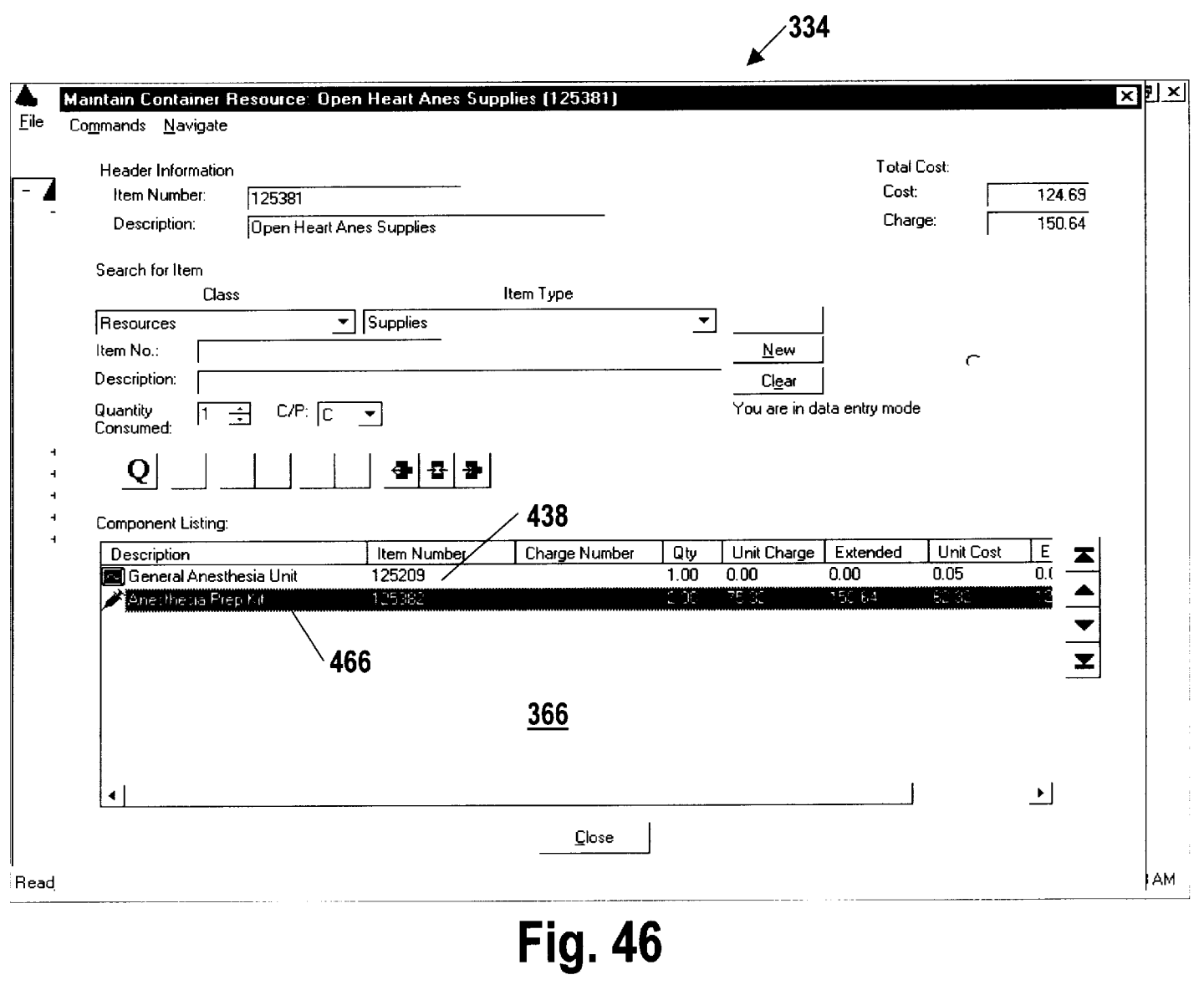
Figure 47:
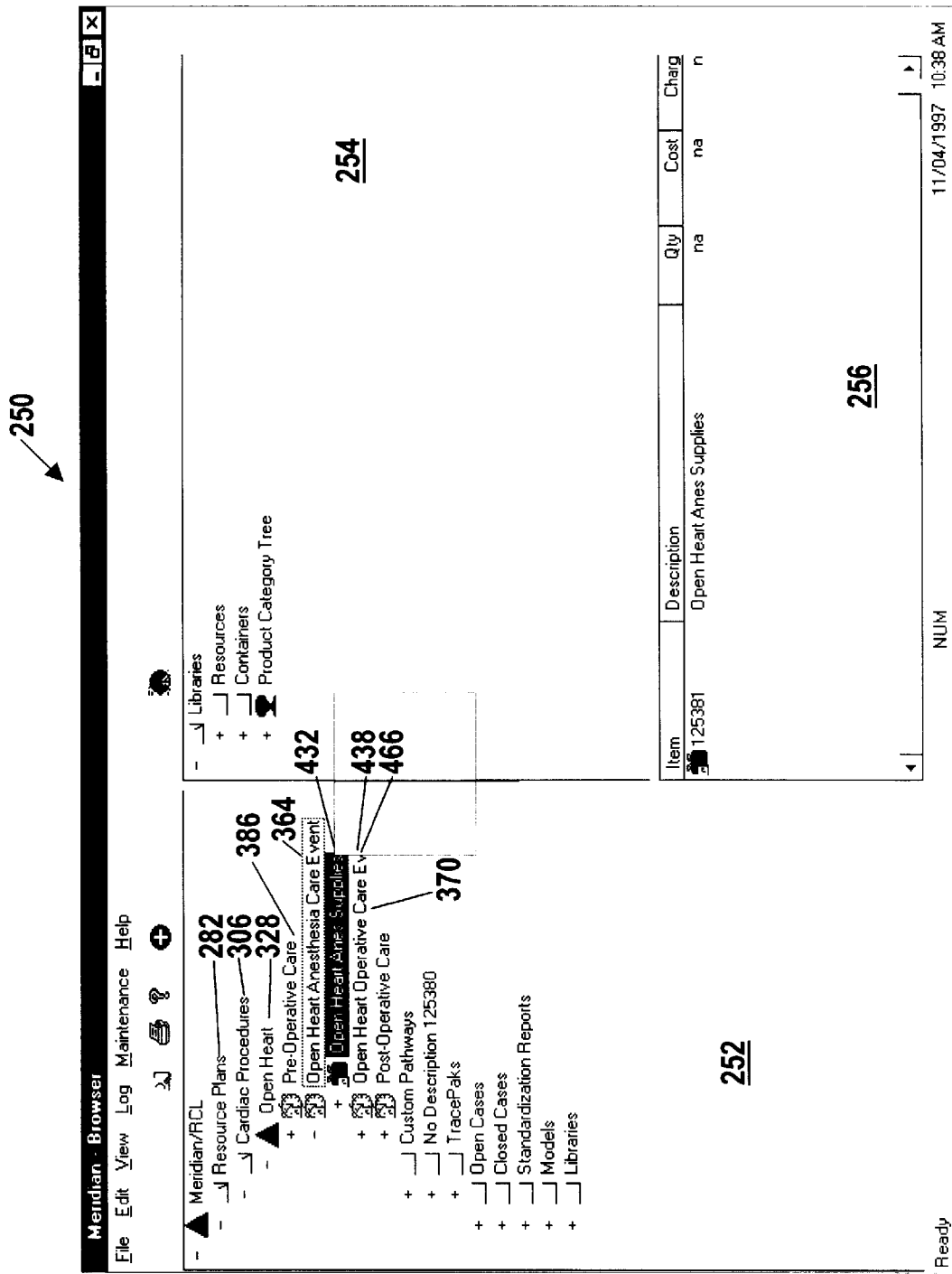

Data entry for the supply object is completed by pressing the Finish button 462, which redisplays the Default Information window 440, as depicted in FIG. 45. The Anesthesia Prep Kit supply object is then added to the Open Heart Anesthesia Supplies Bundle container object 432 by pressing the Finish button 464. The completed Anesthesia Prep Kit supply object 466 is displayed in the Component Listing field 366, as depicted in FIG. 46. Returning to the Browser window 250, as depicted in FIG. 47, the two new supply objects 438 and 466 are displayed under the Open Heart Anesthesia Supplies container object 364.

Figure 48:
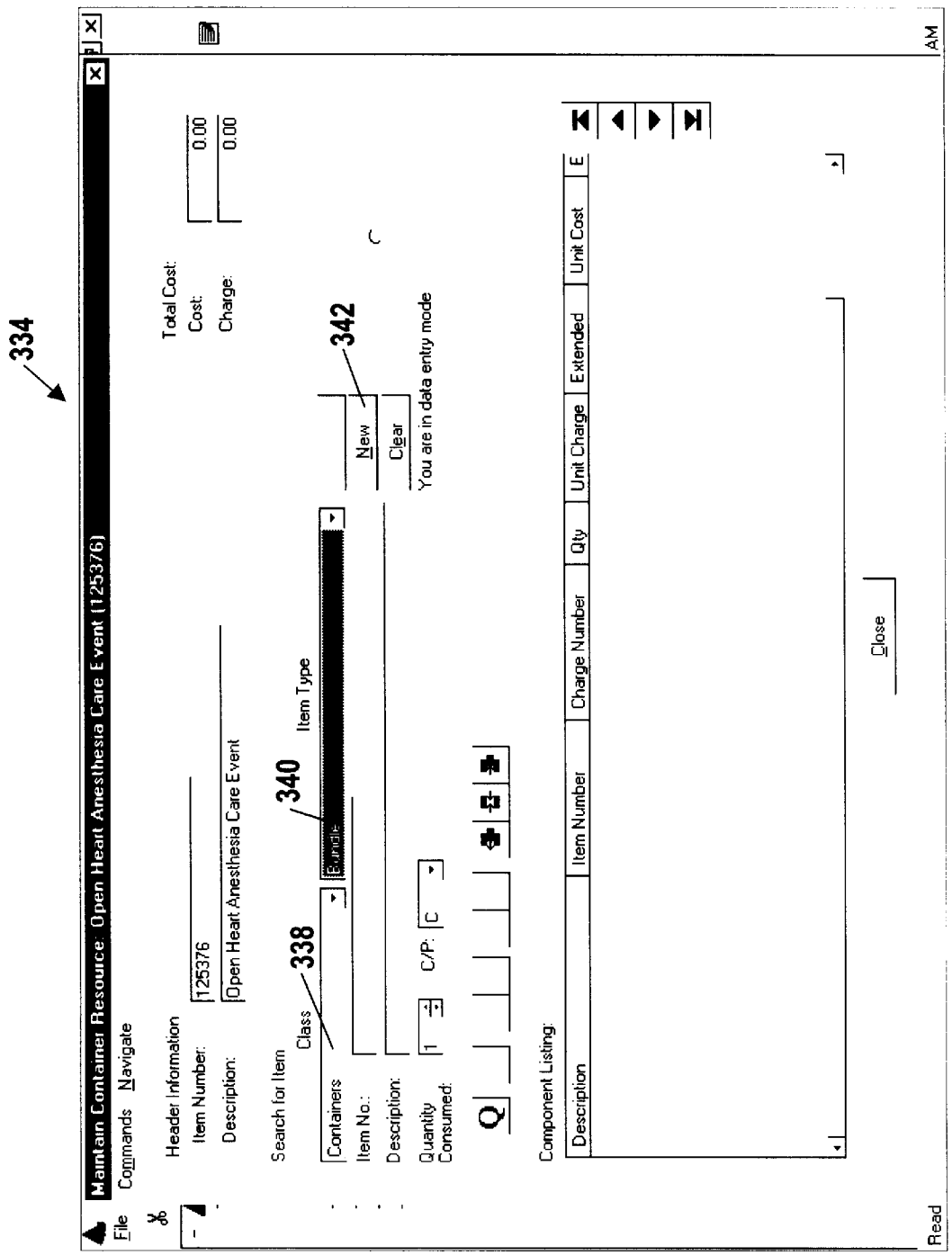

FIG. 48 depicts the Maintain Container Resource window 334 for the Open Heart Anesthesia Care Event 364. The Maintain Container Resource window 334 has been opened from the Browser window 250 as described several times above, the procedure for which will not be rehearsed at this point. The next series of figures depicts the creation of a new bundle object, which is to be made a part of the Open Heart Anesthesia Care Event 364. This process is initiated by selecting the Containers class within the Class field 338 and the Bundle type within the Item Type field 340, and pressing the New button 342.

Figure 49:
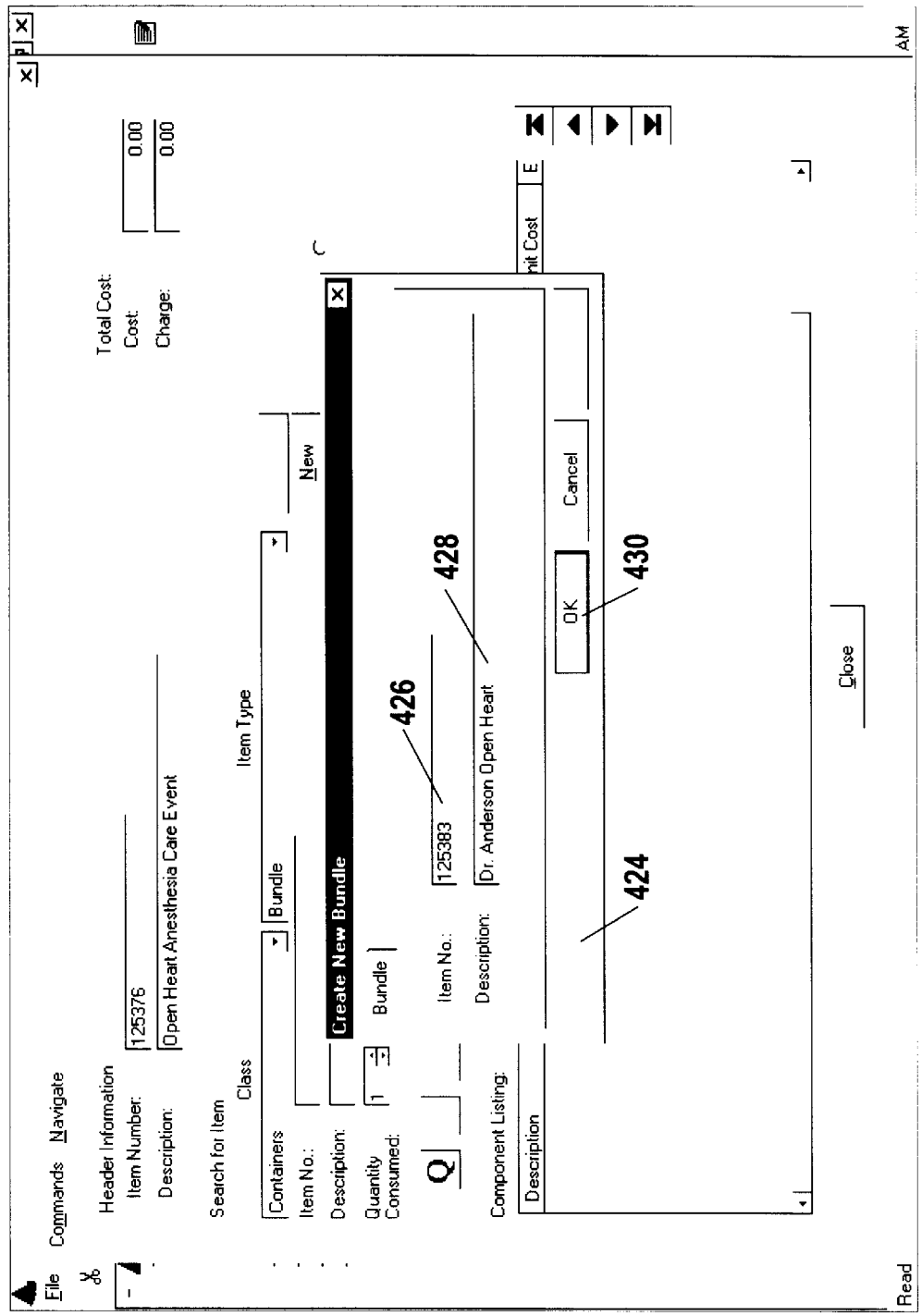

This action causes the display of the Create New Bundle window 424, as depicted in FIG. 49. As previously described, the Item Number field 426 initially contains an automatically assigned item number or, alternately, a new or existing item number can be entered, which will either create a new bundle object or pull up an existing bundle object, as described above at length. In the example of FIG. 49, the automatically assigned new item number is displayed in the Item Number field 426, and the new bundle object is given the name of "Dr. Anderson Open Heart" in the Description field 428. Thus, the new bundle object to be created is a bundle object that is specific to a specific doctor, and may contain the items which this doctor desires to have for the specified procedure.

Therefore, the information management system of the exemplar embodiment provides for the preferences of individual doctors. For example, the supplies which are common to all doctors may be put into one bundle object for a given procedure, and then the additional and varying supplies that may be requested by various doctors may be provided in additional bundle objects that are specific to each doctor. Of course, this is just one example of how the information management system adapts to the particular needs and procedures of a hospital, and the user of the information management system may adapt the system according to the various methods described above as suits him best.

Figure 50:
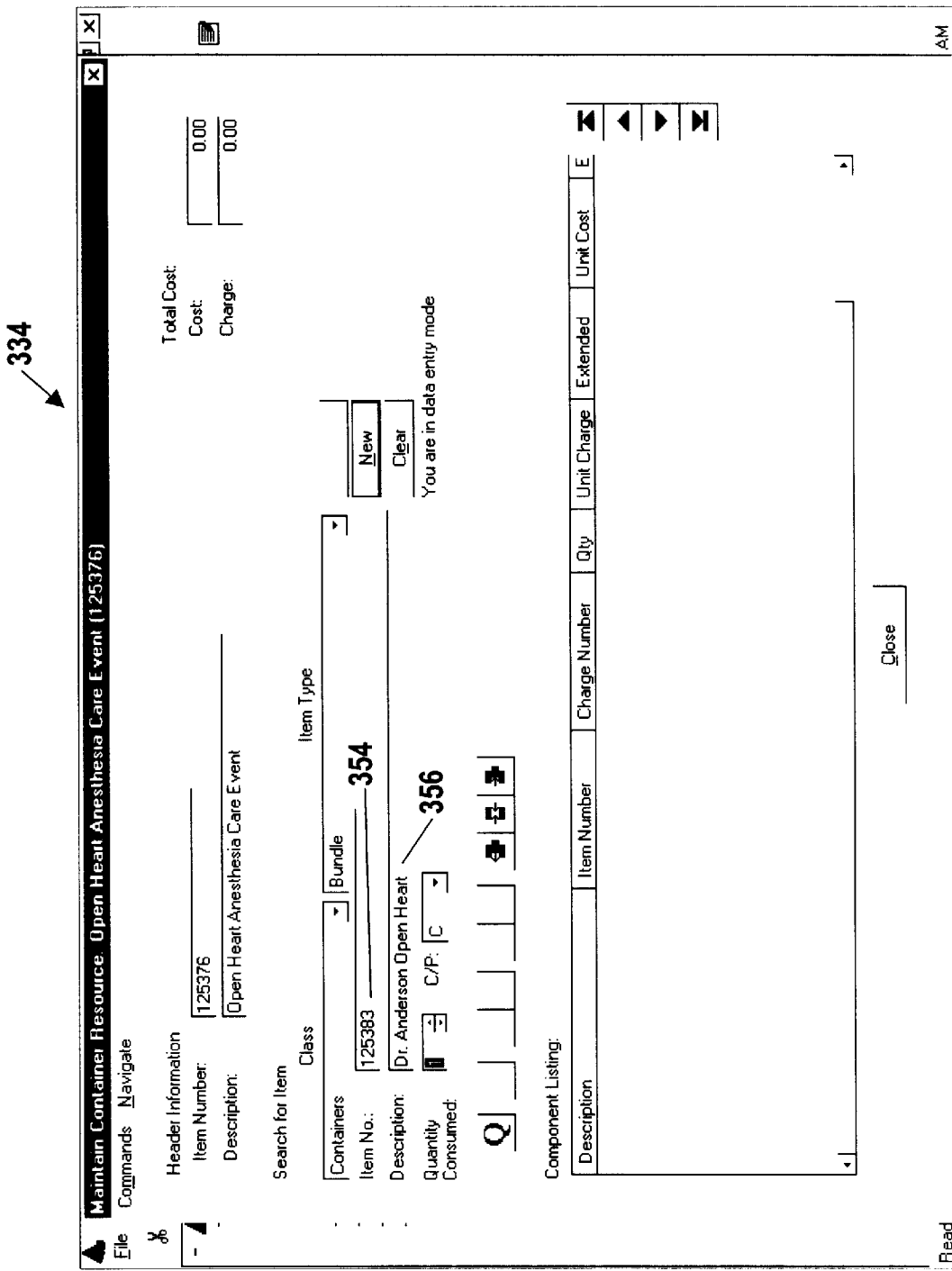
Figure 51:
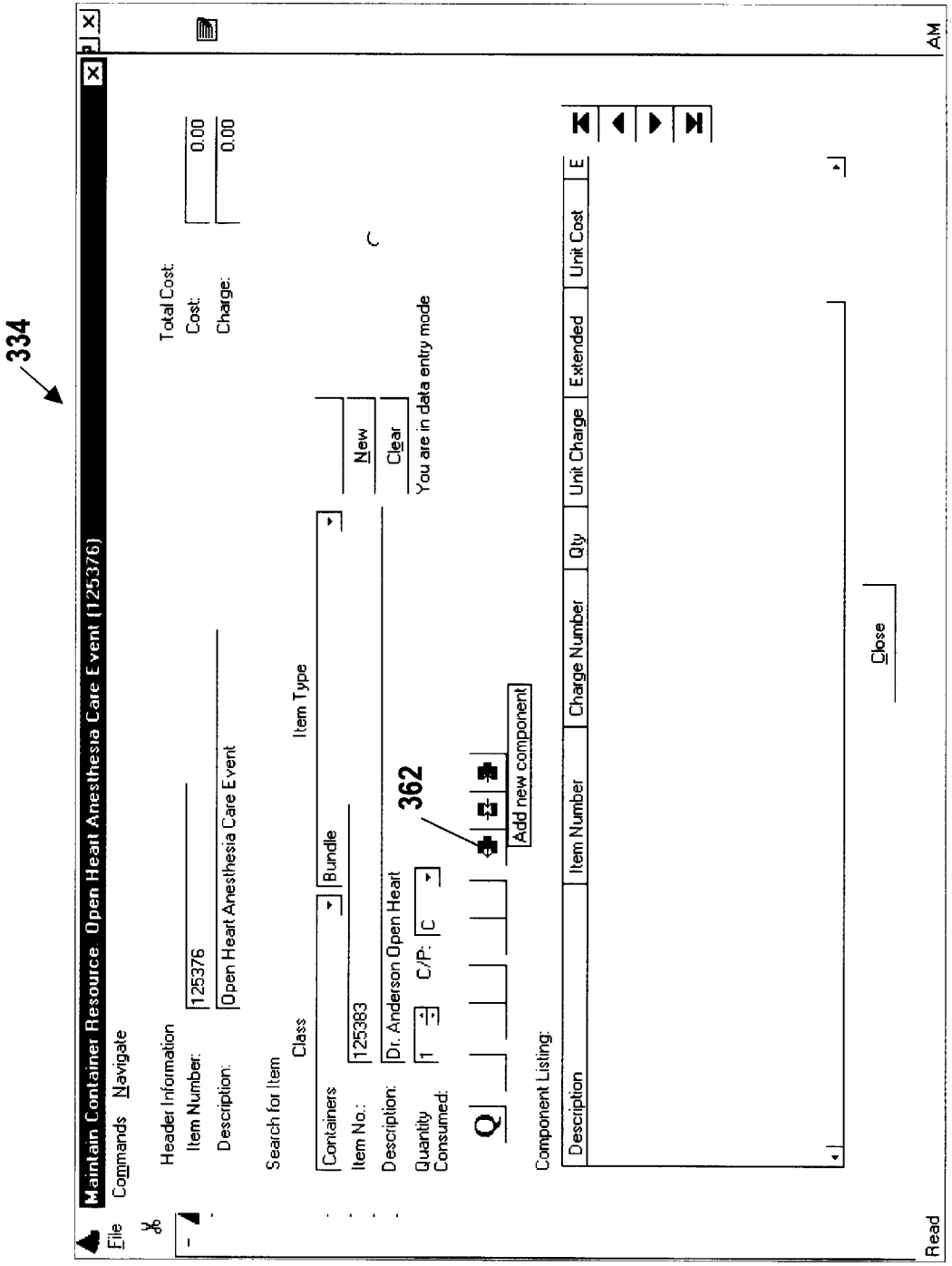
Figure 52:
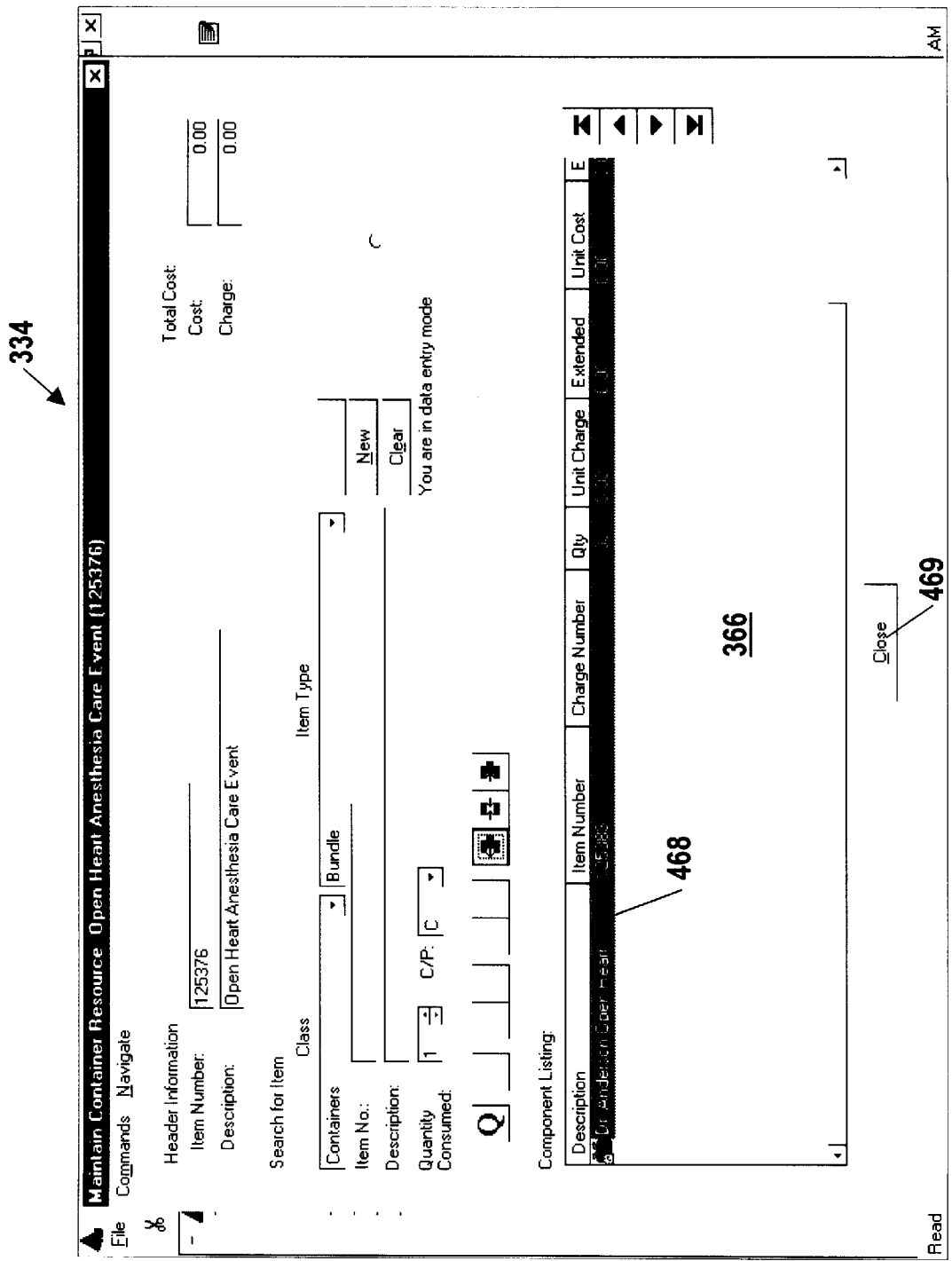
Figure 53:
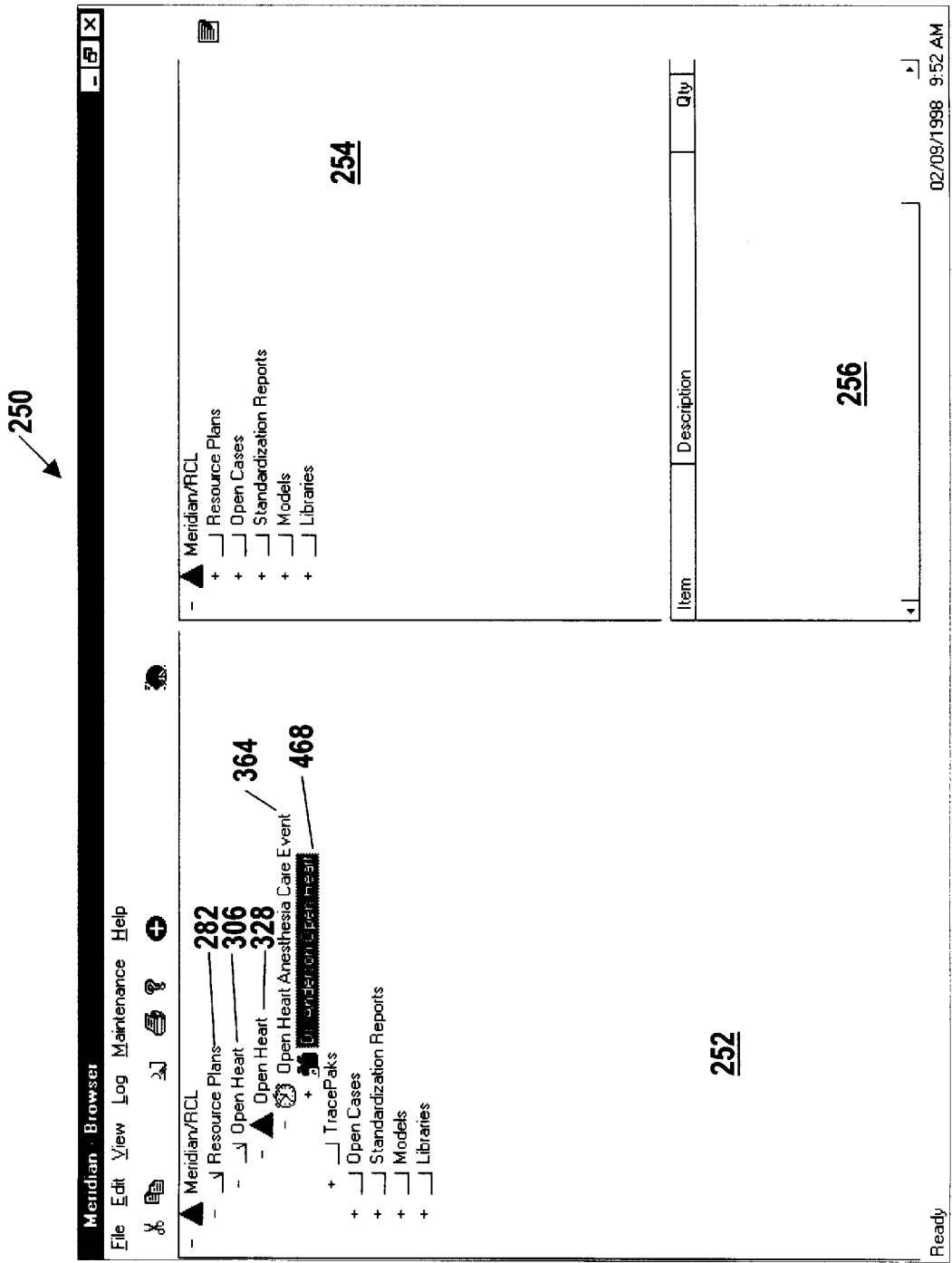

The newly described bundle object is created by pressing the OK button 430, which enters the item number for the bundle object in the Item Number field 354 and the name of the bundle object in the Description field 356 of the Maintain Container Resource window 334, as depicted in FIG. 50. The Add New Component button 362 is pressed as depicted in FIG. 51, and the Dr. Anderson Open Heart bundle object 468 is entered into the Component Listing field 366 of the Maintain Container Resource window 334, as depicted in FIG. 52. By pressing the Close button 469 the user is returned to the Browser window 250 depicted in FIG. 53, where the newly created Dr. Anderson Open Heart bundle object 468 is depicted as an element of the Open Heart Anesthesia Care Event 364 of the Open Heart procedural pathway 328.

Figure 54:
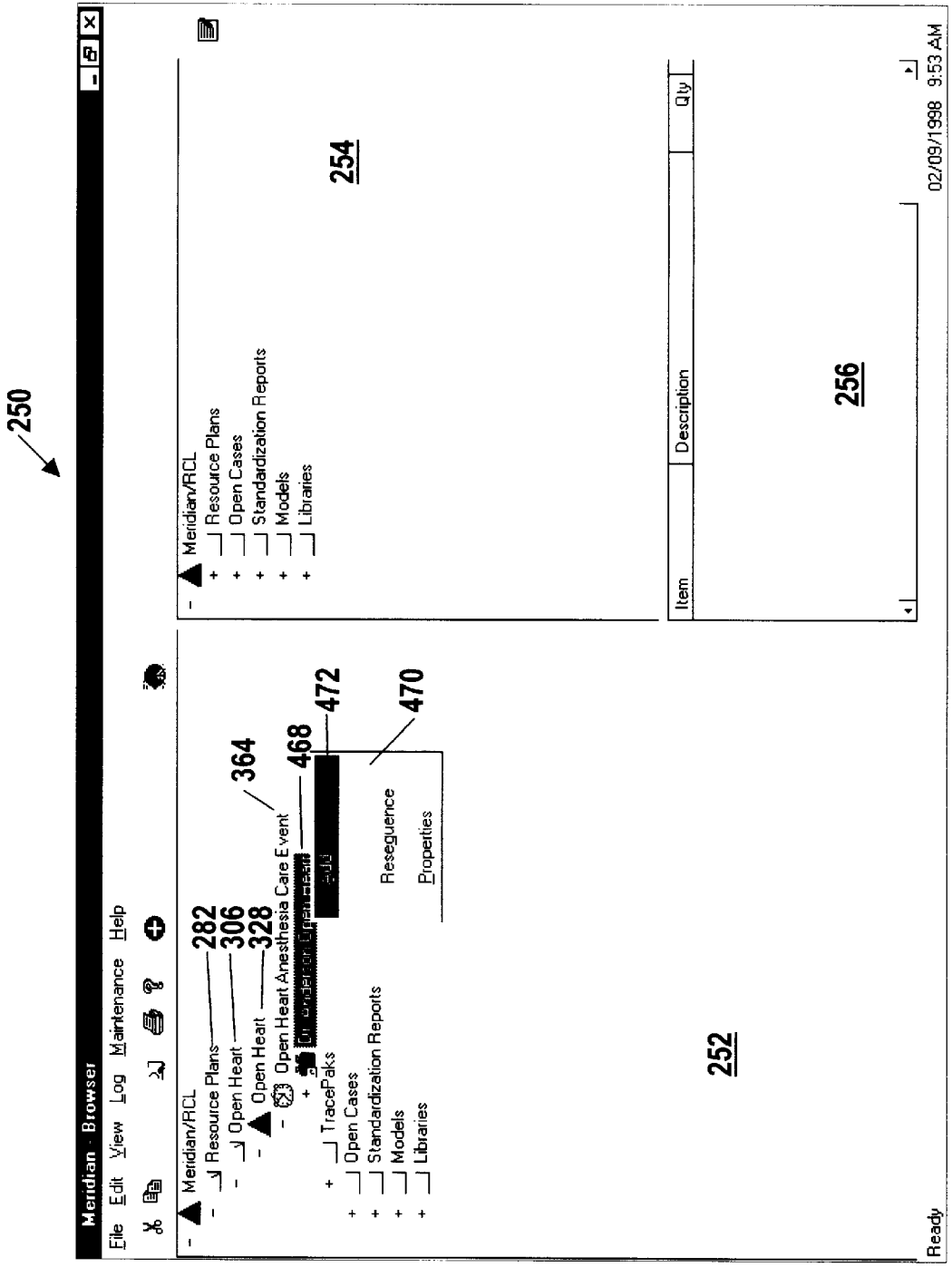
Figure 55:
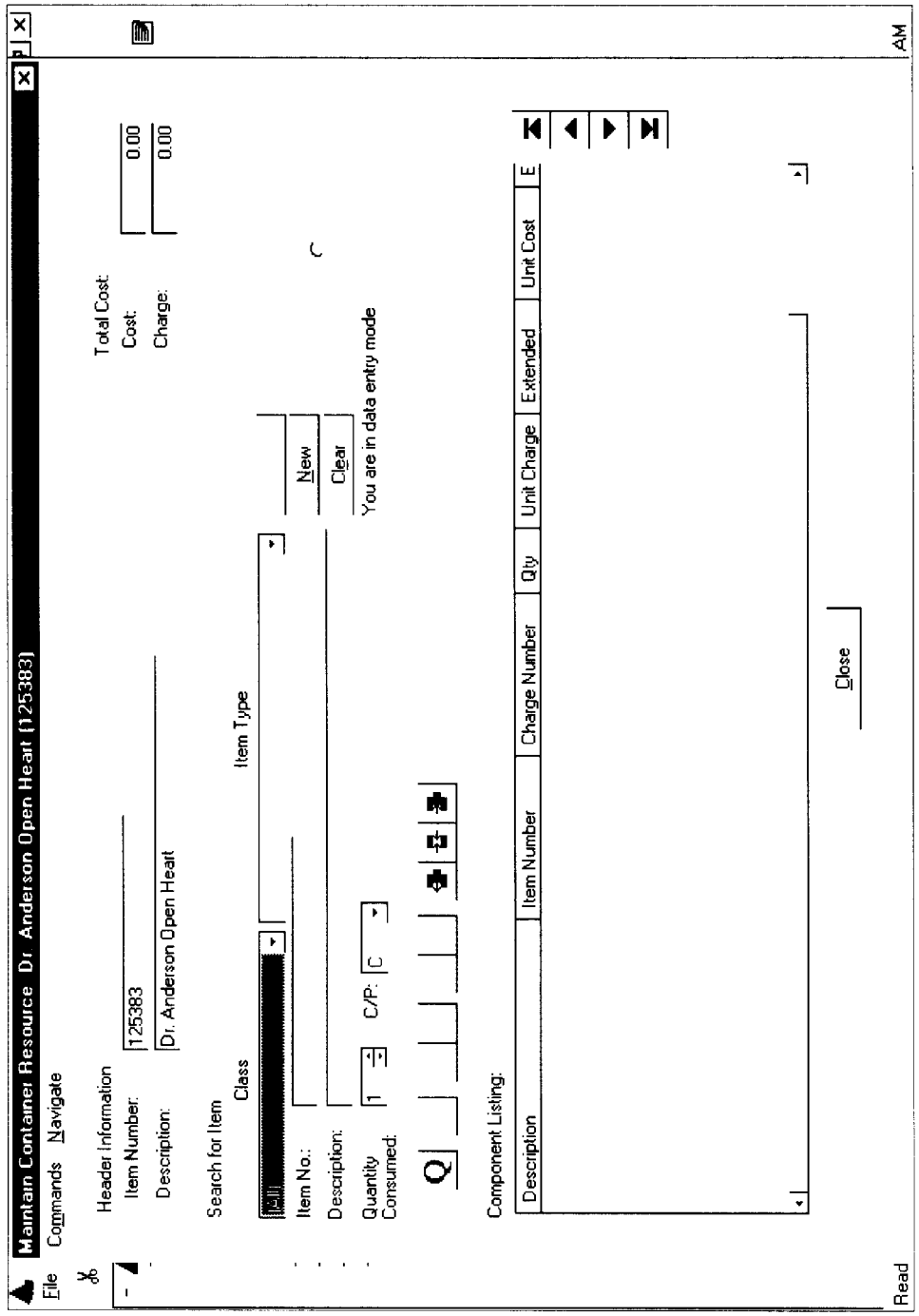

Specific items, such as those required by "Dr. Anderson," are added to the Dr. Anderson Open Heart bundle object 468 by right clicking on the Dr. Anderson Open Heart bundle object 468, which brings up the Bundle menu 470, as depicted in FIG. 54. By selecting the Add function 472, the Maintain Container Resource window 334 is displayed, as depicted in FIG. 55. Thus, the next series of figures depicts how specific supplies are added to the bundle object that was created.

Figure 56:
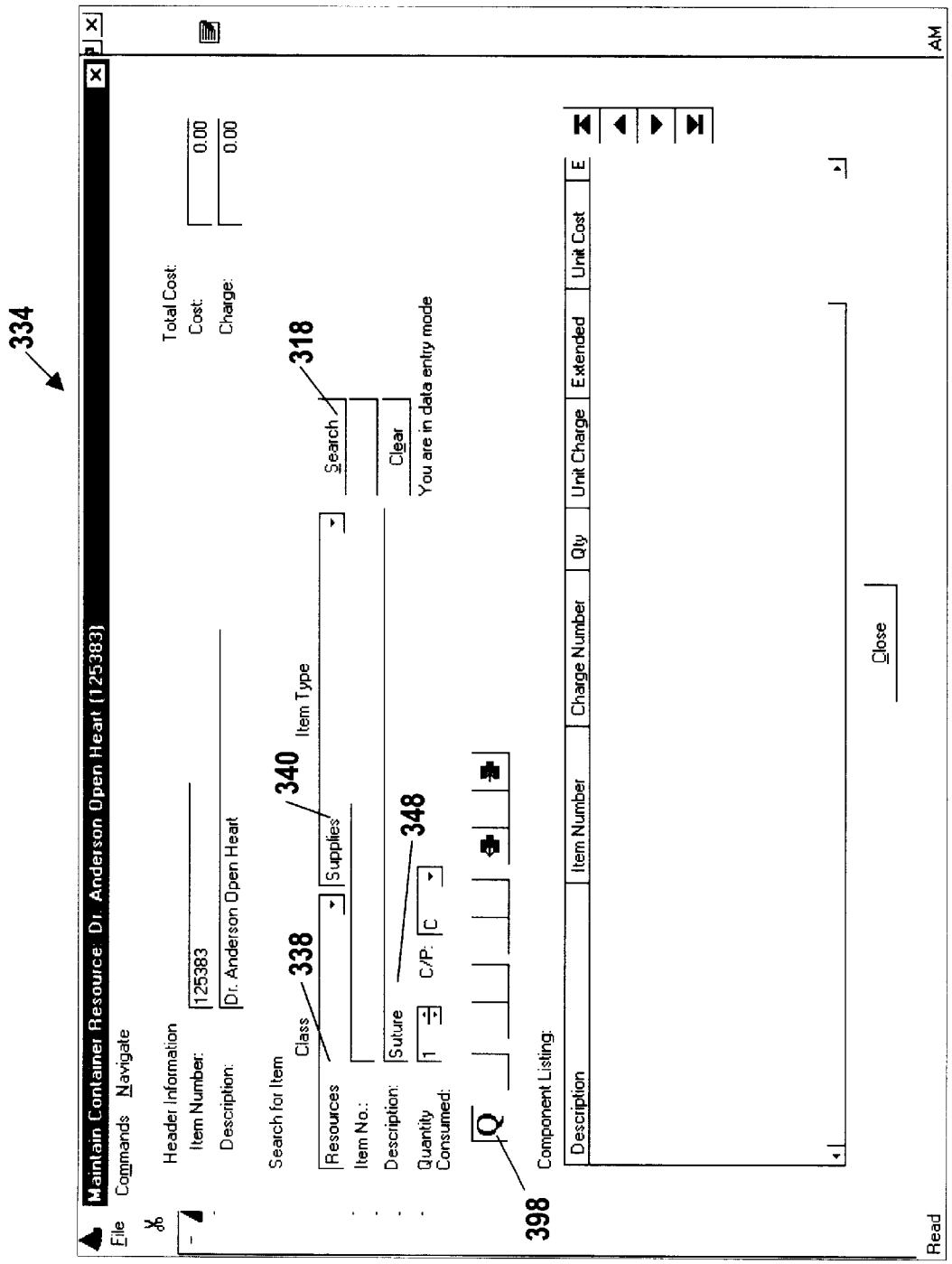

In FIG. 56 the Resources class has been entered into the Class field 338 and the Supplies item type has been entered into the Item Type field 340. Further, the word "Suture" has been entered by the user into the Description field 348. By depressing the Query Mode button 398, the Search button 318 is enabled. By then pressing the Search button 318, a search is activated which will search for all previously existing supply objects that contain the word "suture" in their assigned descriptions.

Figure 57:
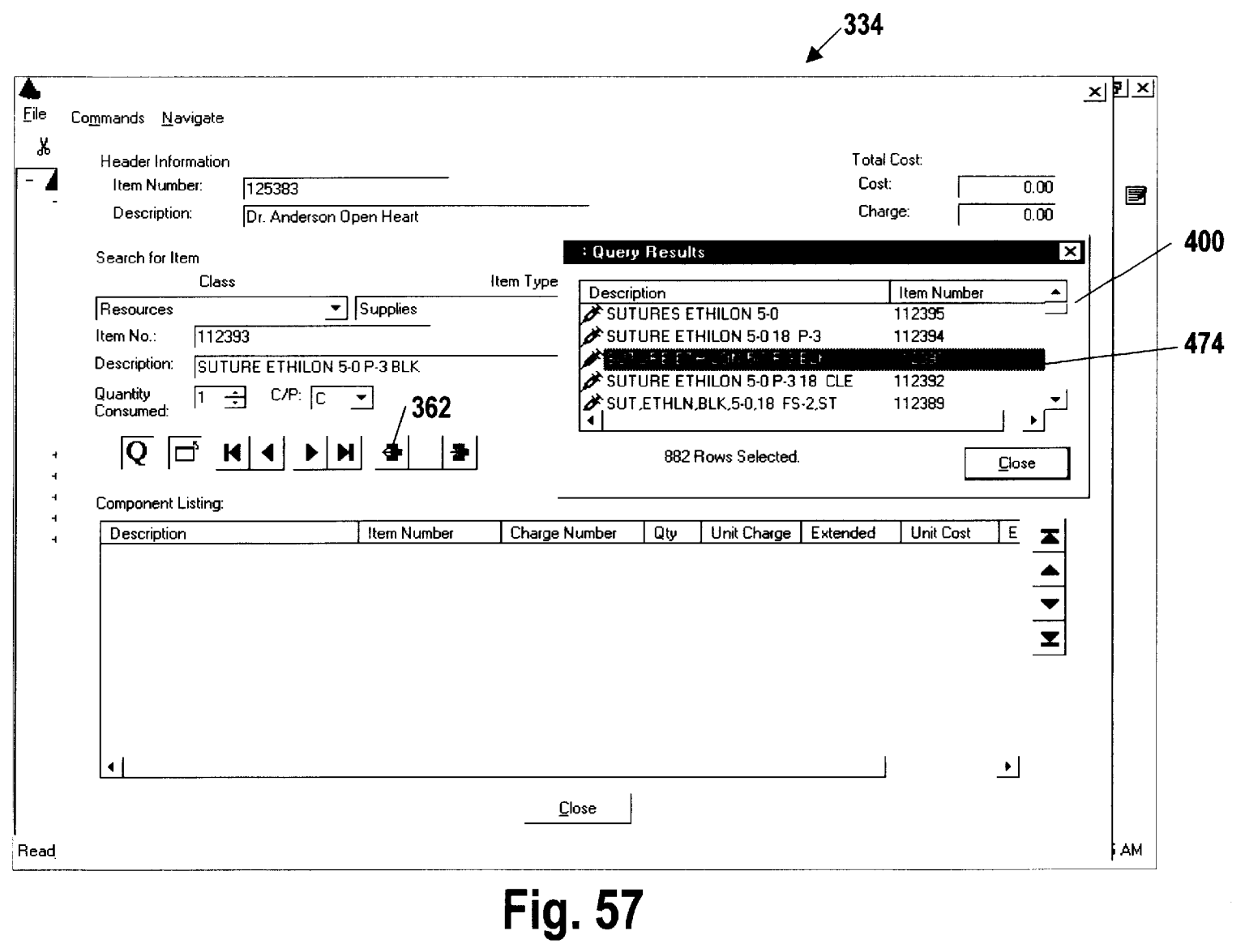
Figure 58:
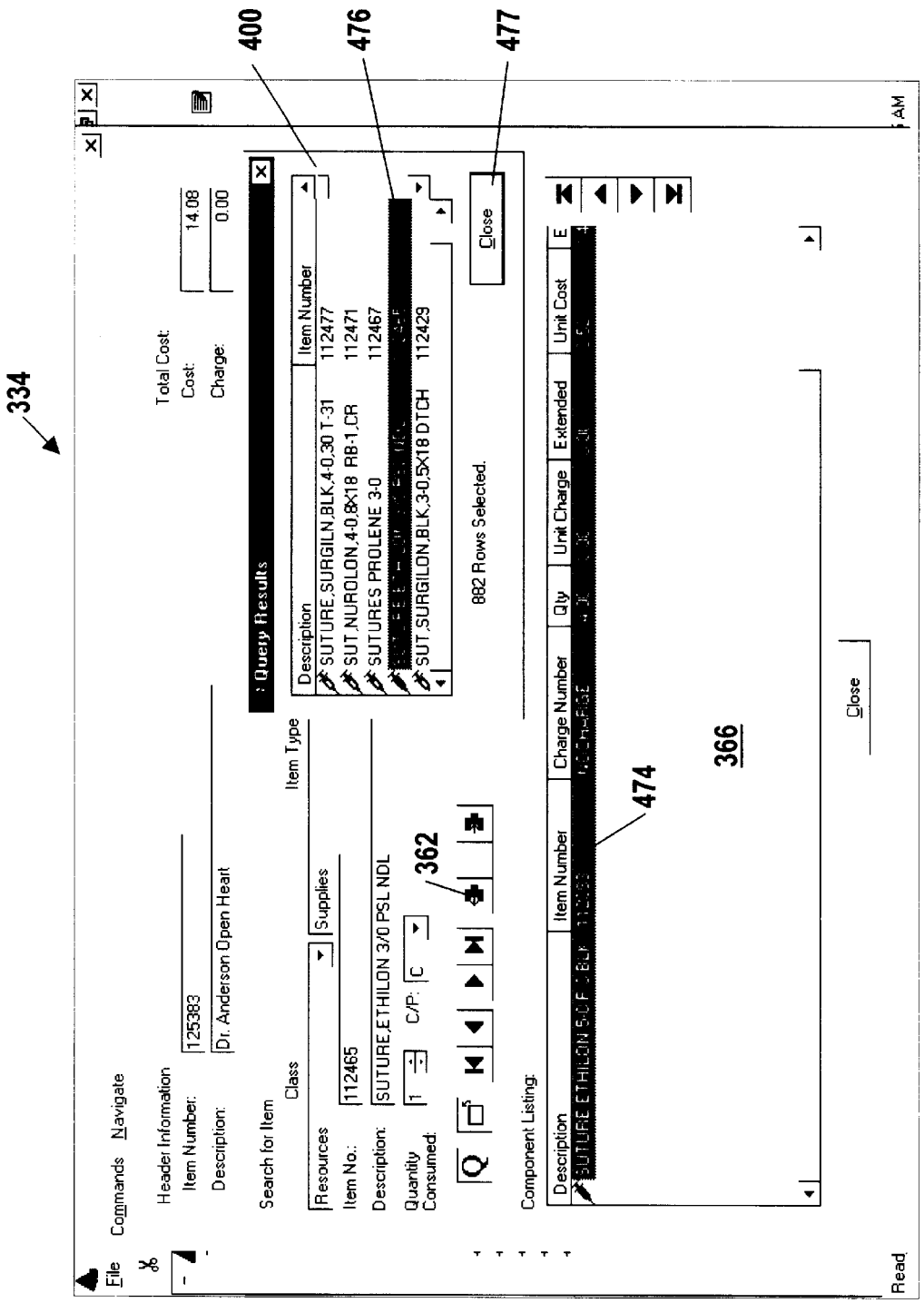
Figure 59:
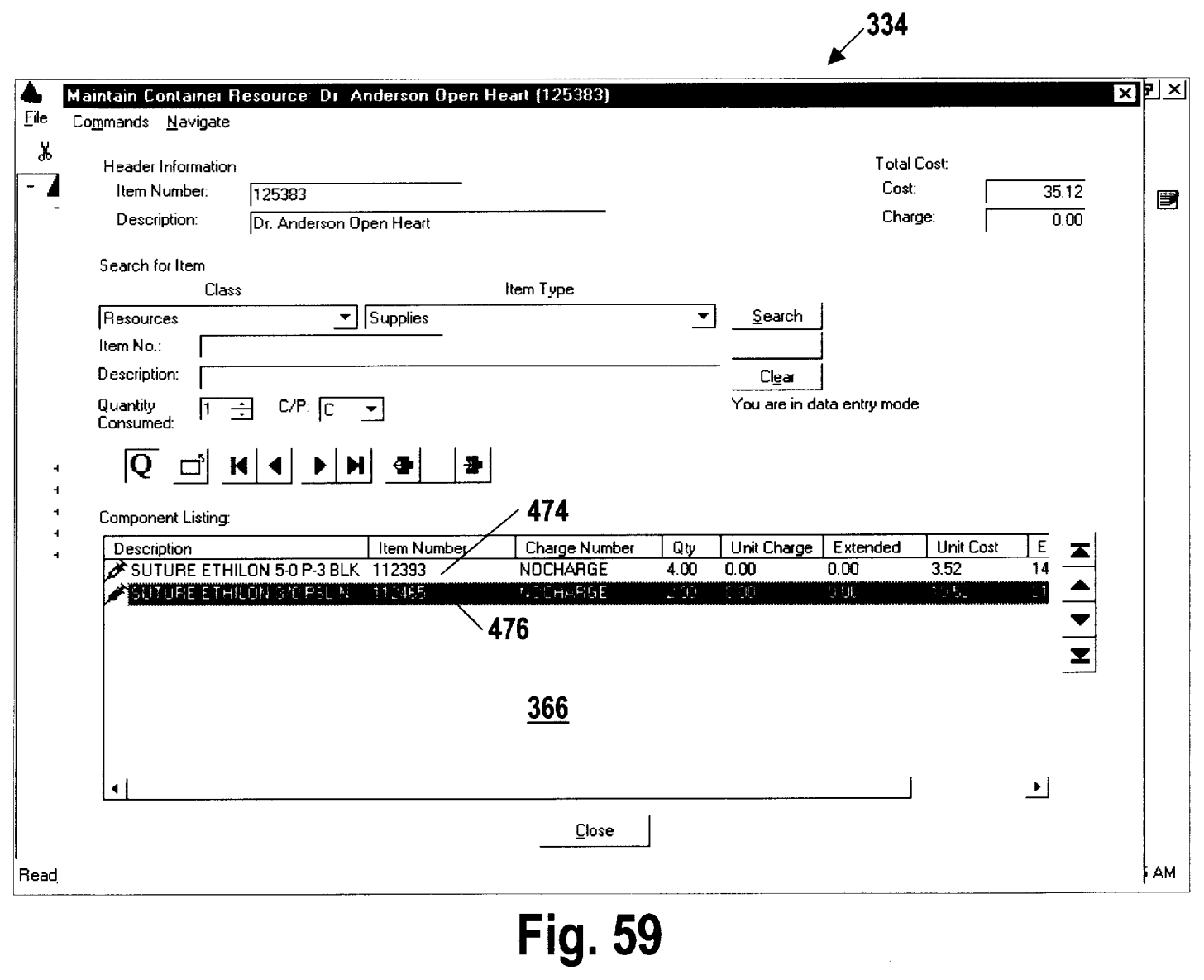

The results of the search are displayed in the Query Results window 400, as depicted in FIG. 57. In this example, the Suture Ethilon 5-0 P-3 BLK 474 is selected. This Suture 474 is added to the bundle object by pressing the Add New Component button 362 in the Maintain Container Resource window 334, which enters the Suture 474 into the Component Listing field 366, as depicted in FIG. 58. Additional sutures may also be selected from the Query Results window 400, such as the Suture Ethilon 3/0 PSL NDL 476, which is also added to the Component Listing field 366 by pressing the Add New Component button 362 as described above. The Query Results window 400 is closed by pressing the Close button 477, and the two sutures 474 and 476 are displayed in the Component Listing field 366 as depicted in FIG. 59.

Figure 60:
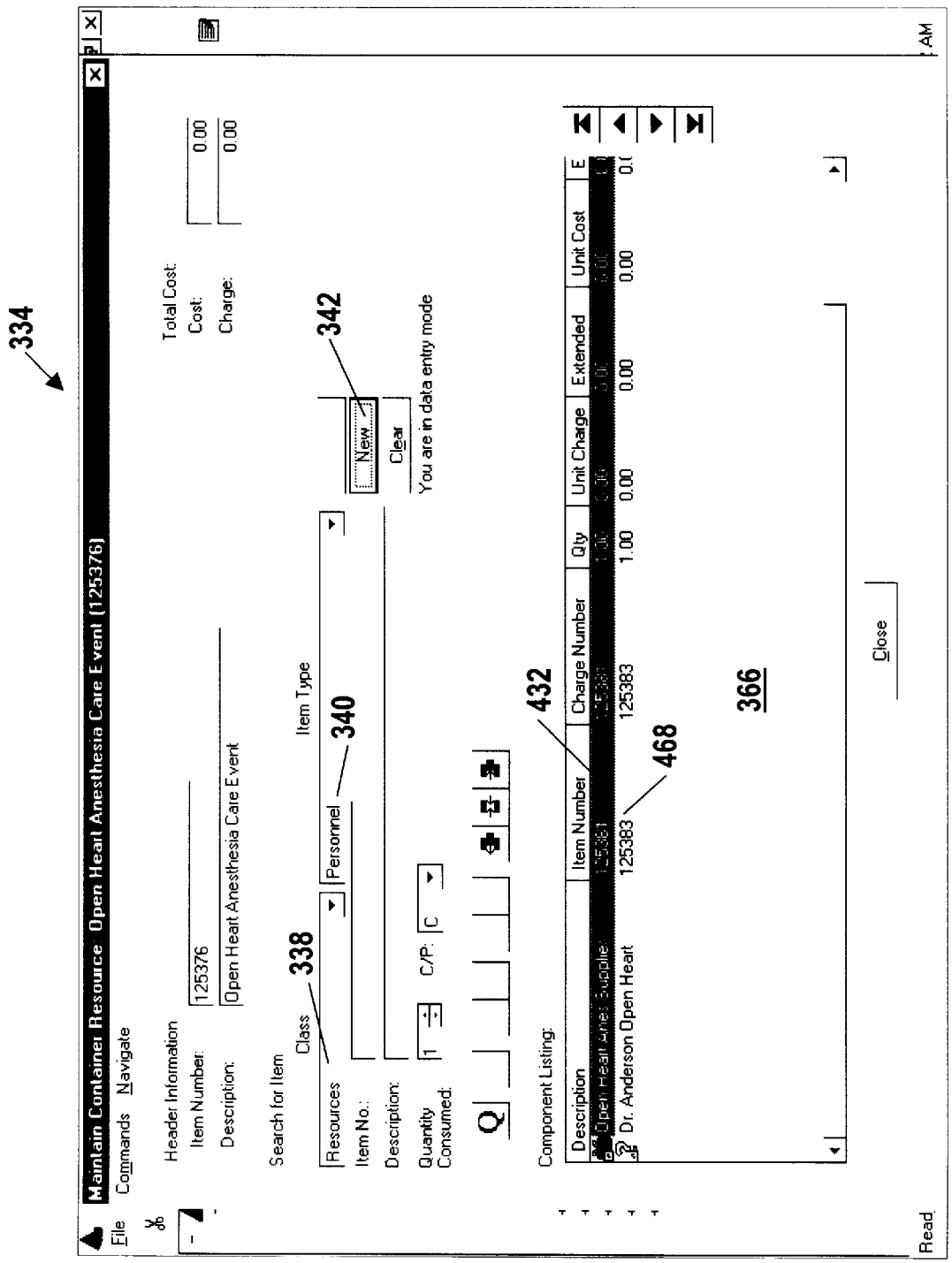

Beginning with FIG. 60, the steps for adding a personnel resource object to the Open Heart Anesthesia Care Event object 364 are described. As described above, the Open Heart Anesthesia Care Event object 364 is selected from the Browser window 250, the Care Event menu 420 is invoked by right clicking, the Add function 422 is selected, and the Maintain Container Resource window 334 is displayed, as depicted in FIG. 60.

Figure 61:
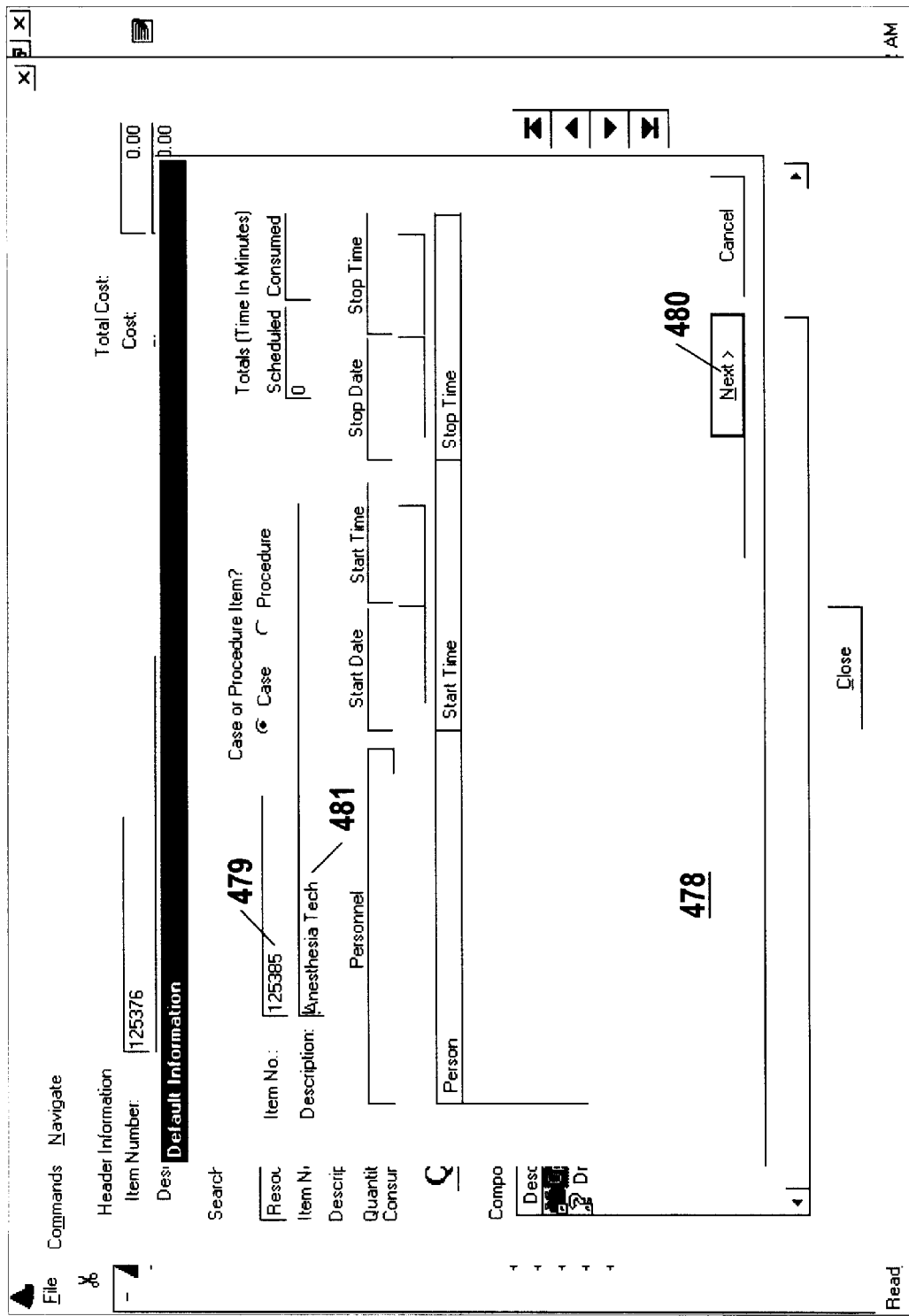

The Component Listing field 366 displays the Open Heart Anesthesia Supplies bundle object 432 and the Dr. Anderson Open Heart supply bundle object 468 previously created. The Resources class is selected in the Class field 338 and the personnel item type is selected in the Item Type field 340. By pressing the New button 342, the Default Information window 478 is displayed, as depicted in FIG. 61.

As described above, a new default value for the item number is automatically presented in the Item Number field 479, and the user may enter a name for the new personnel resource object in the Description field 481. In this example, the new personnel resource object is given the name of Anesthesia Tech. Other information may also be entered into the Default Information window 478, such as the amount of time that should be scheduled for the anesthesia technician to perform the care event being defined in the pathway. The entry of information is continued by pressing the Next button 480.

Figure 62:
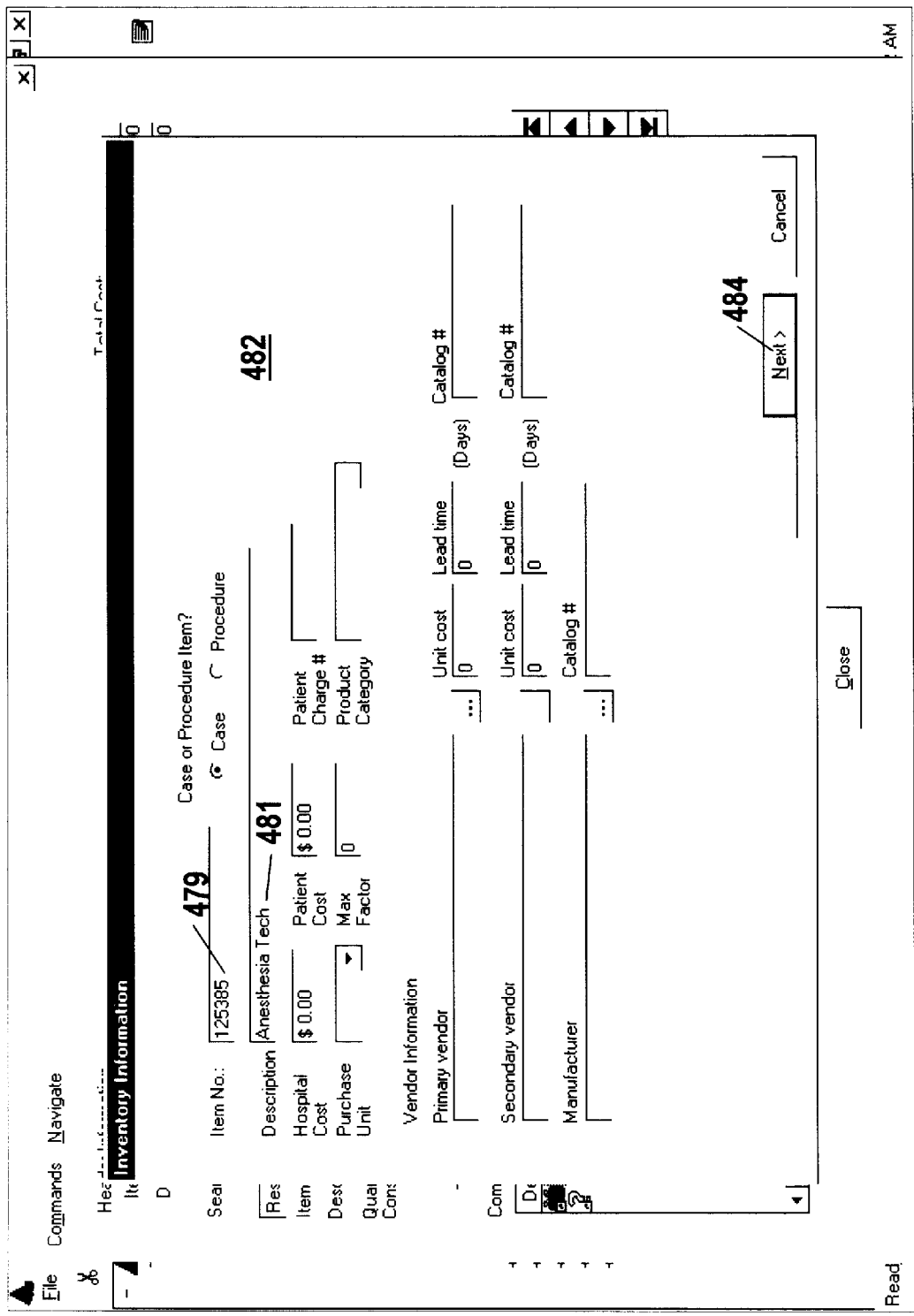

FIG. 62 depicts the Inventory Information window 482. As before, the item number assigned and the description entered are carried along through the various windows in the Item Number field 479 and the Description field 481, respectively. In the Inventory Information window 482, additional information relative to the proper and orderly inventory management of the described personnel resource is entered, such as a patient charge number and a catalog number. The entry of information is continued by pressing the Next button 484.

Figure 63:
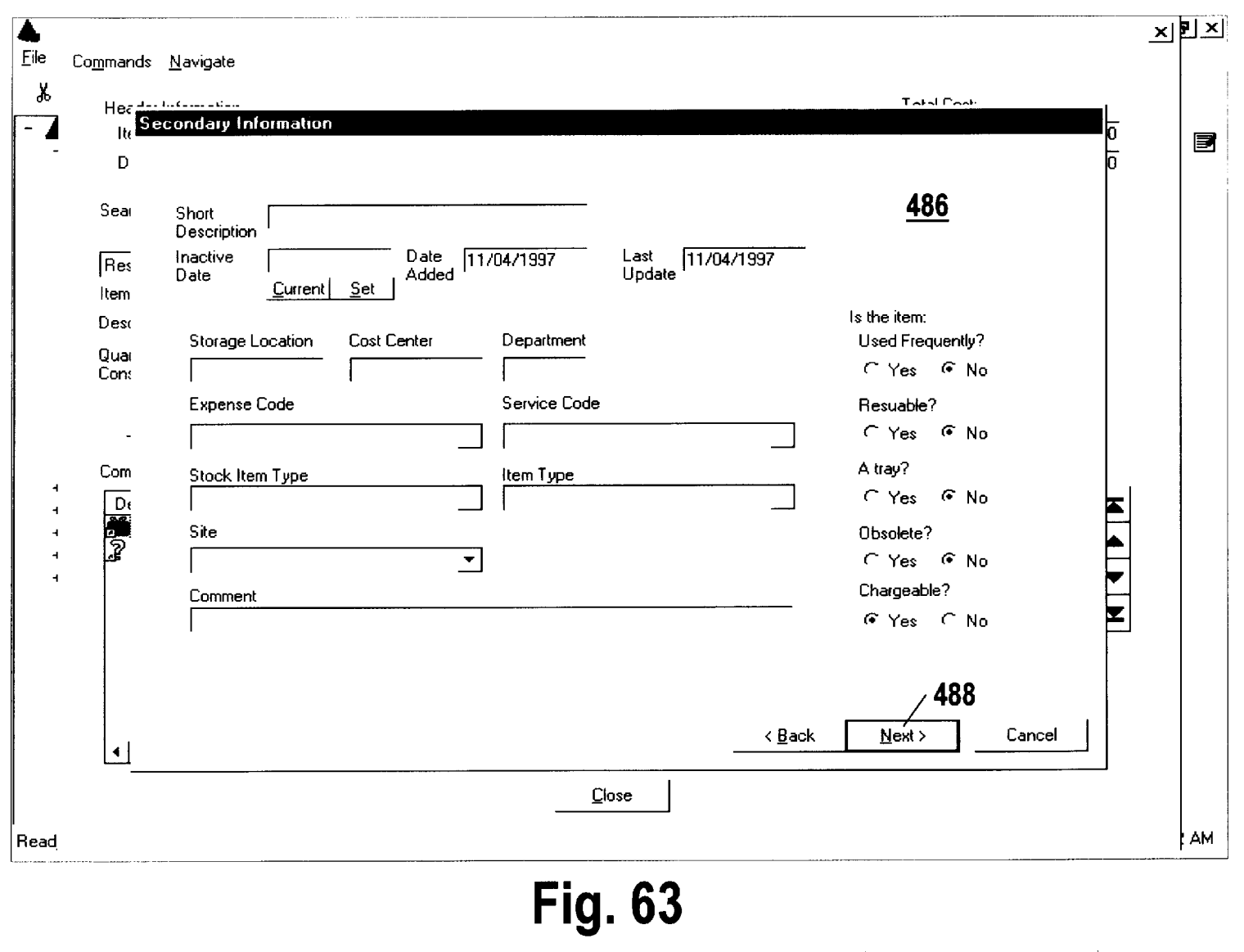
Figure 64:
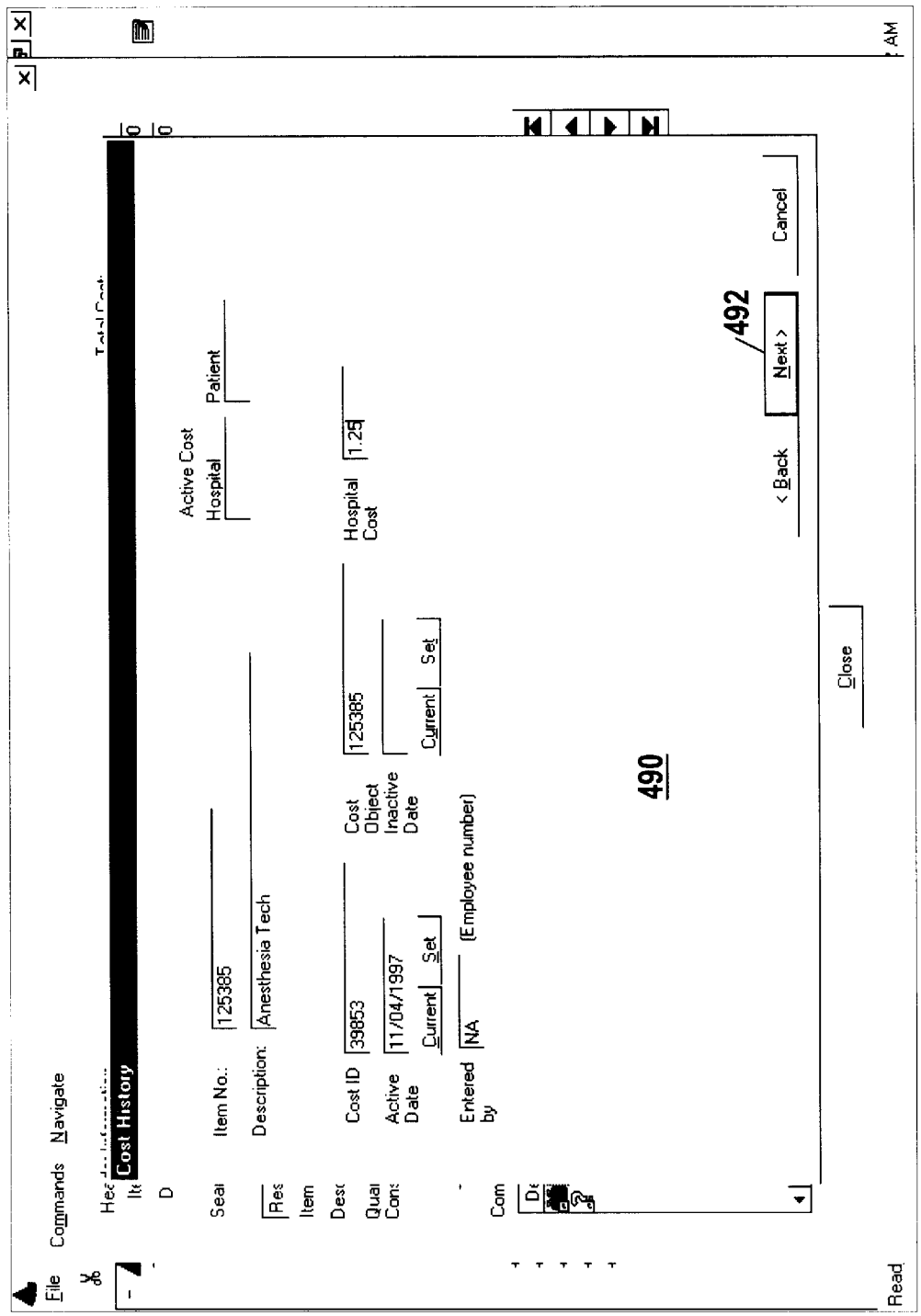

FIG. 63 depicts the Secondary Information window 486, in which other information relative to the personnel object being defined is entered. The information entry process is continued by pressing the Next button 488, which displays the Hospital Cost History window 490, as depicted in FIG. 64. In this window, information relative to the cost to the hospital of the personnel resource object is entered. Pressing the Next button 492 continues the data entry process.

Figure 65:

The Patient Cost History window 494 is next displayed, as depicted in FIG. 65. As described above, the Patient Cost History window 494 allows the information management system user to enter information about the personnel resource object relative to the billing rate of the resource or, in other words, the amount that the hospital will charge the patient for the consumed resource.

Figure 66:
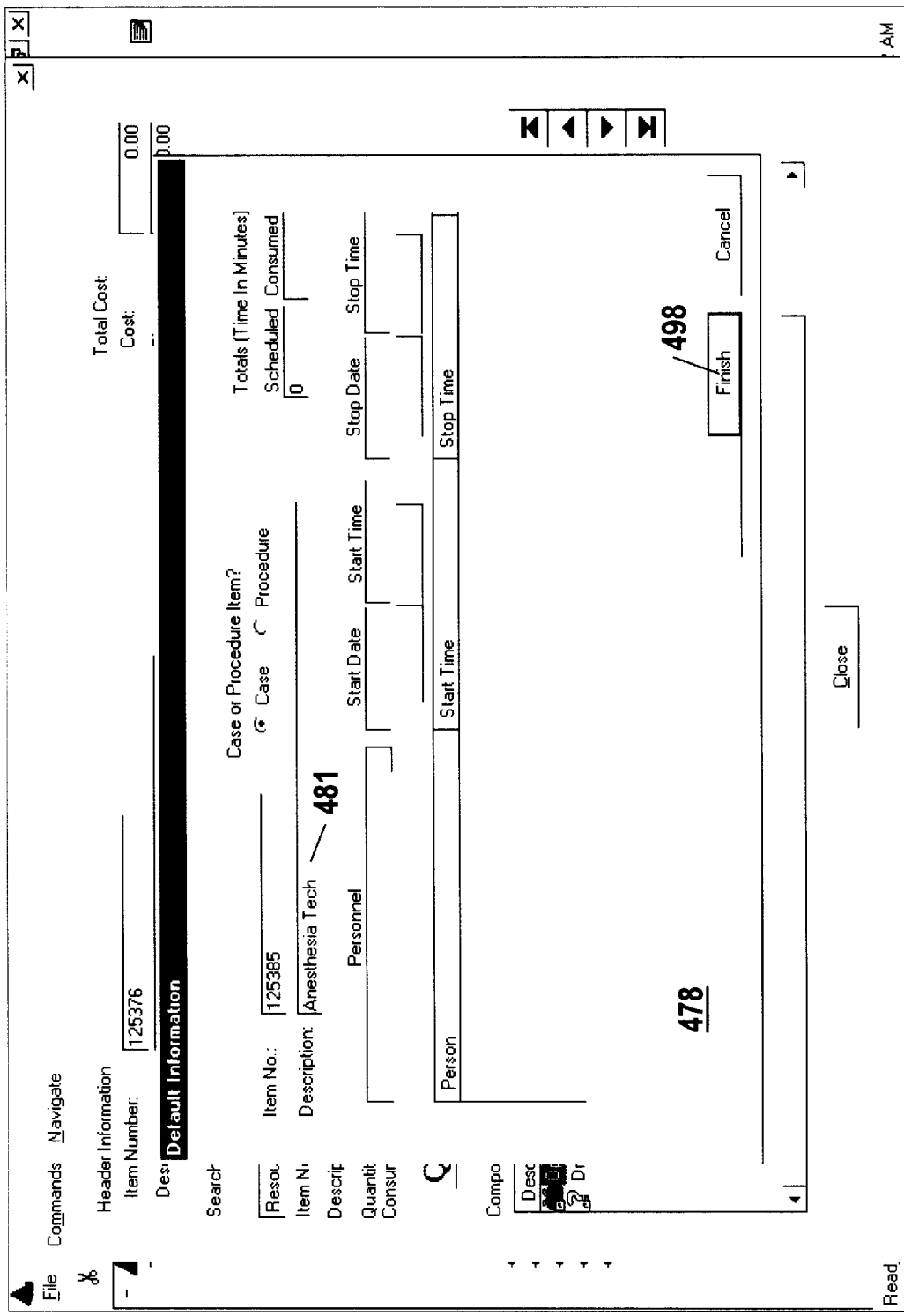
Figure 67:
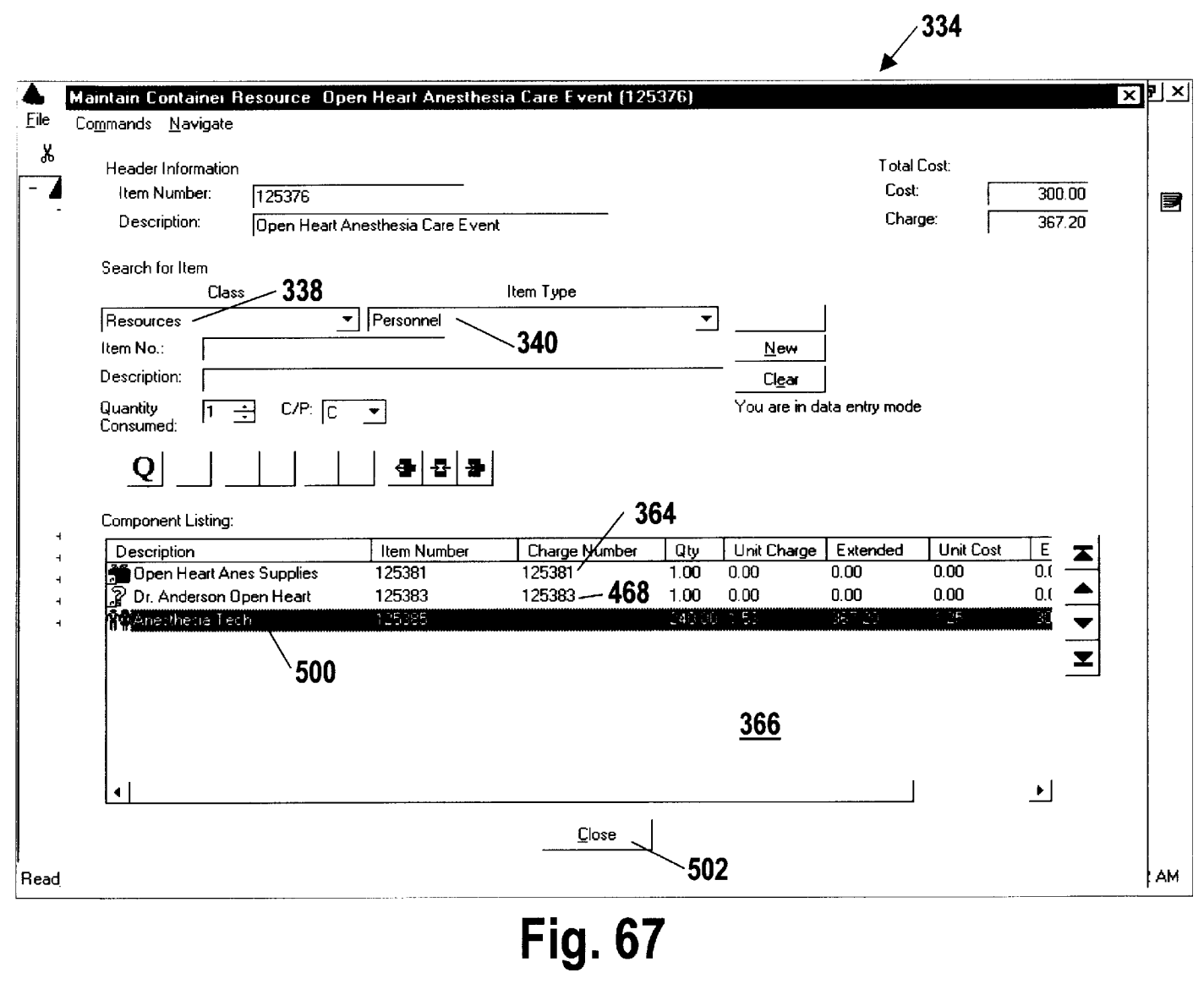

The data entry process is completed by pressing the Finish button 496, which returns the user to the Default Information window 478, depicted in FIG. 66. Pressing the Finish button 498 returns the user to the Maintain Container Resource window 334, as depicted in FIG. 67. In the Maintain Container Resource window 334, the newly created Anesthesia Tech personnel resource object 500 is now listed in the Component Listing field 366. Pressing the Close button 502 returns the user to the Browser window 250.

Figure 68:
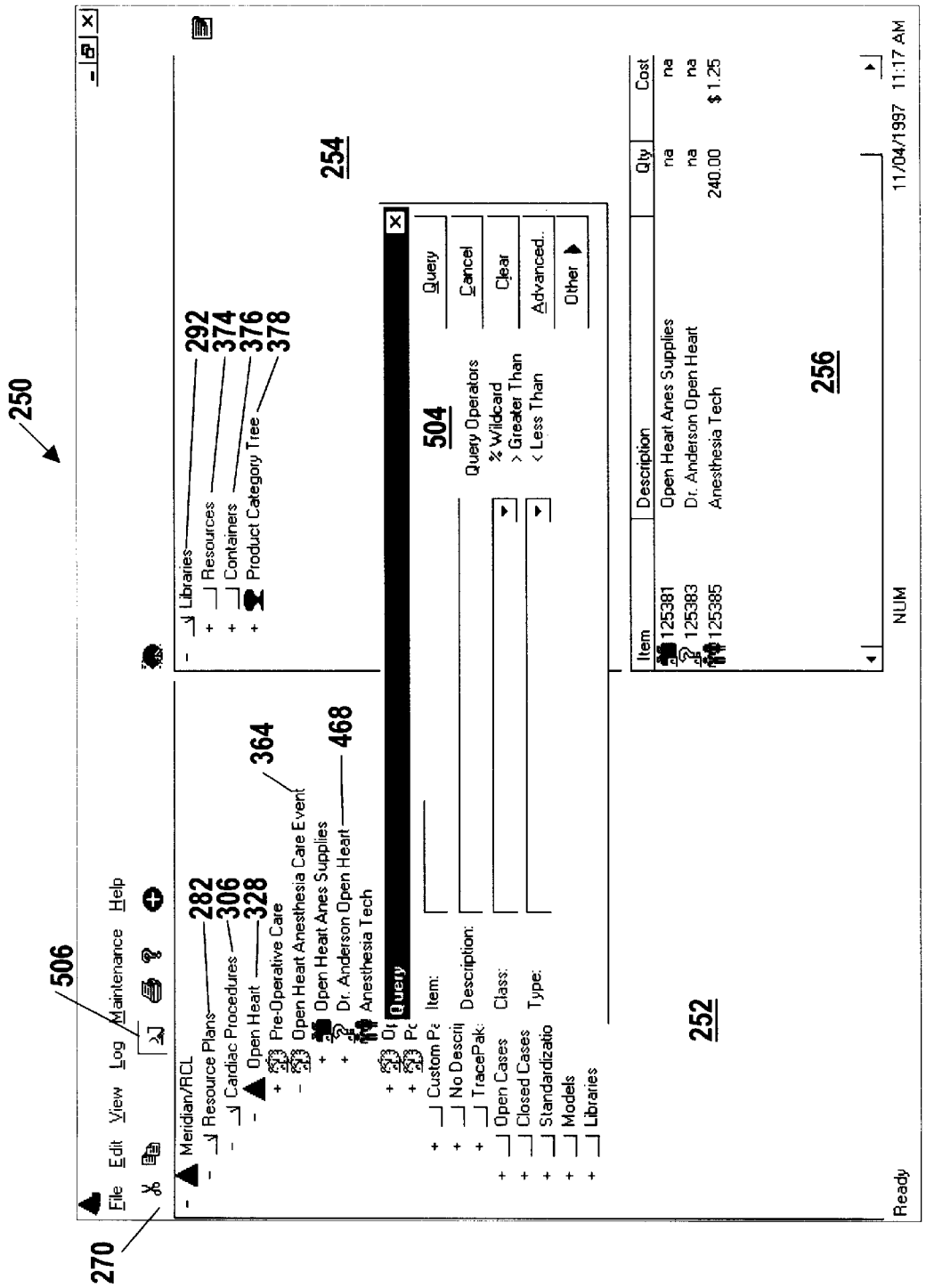

Beginning with FIG. 68, methods of adding objects that have already been defined to container objects are described. In a first method of adding predefined objects, the Query button 506 on the Tool Bar 270 is pressed, bringing up the Query window 504. The Query window 504 is used to initiate searches on predefined objects located within the Libraries folder 292.

Figure 69:
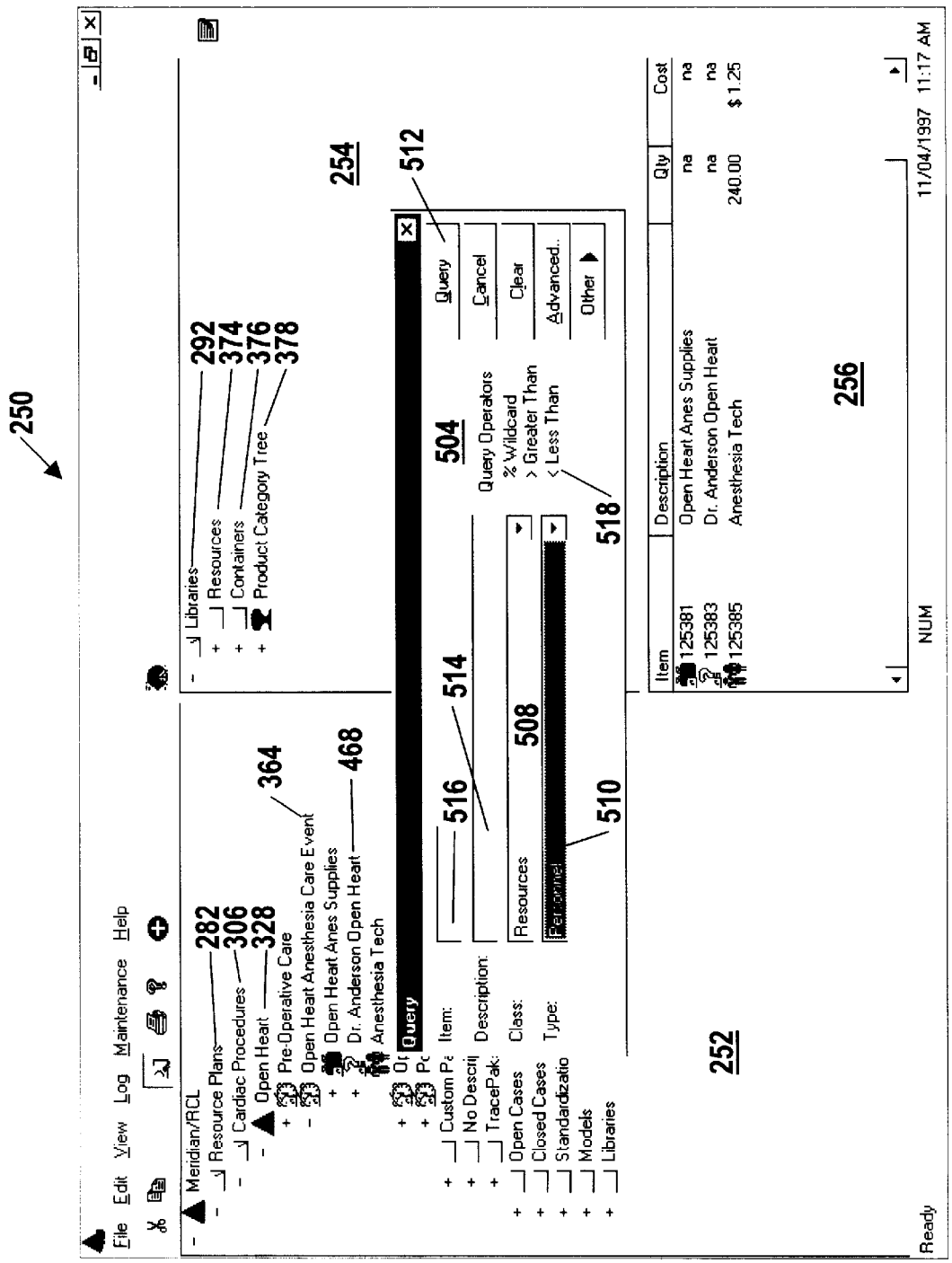

As depicted in FIG. 69, the query operation can be restricted in a variety of different ways. For example, typing a specific item number into the Item field 516 will search for a specific item number. In addition, the Query Operators 518 are used in association with the item number typed into the Item field 516, or any of the other fields mentioned below, to enable greater flexibility in the query operation. For example, the wildcard character "%" is used to represent any value that is within the position where the wildcard character is placed. Thus, performing a query on the item number 12345% finds item numbers 123450–123459. The wildcard character can be placed in other positions within the item number as well, and can also be placed in multiple positions within a single item number. Other Query Operators 518 include a Greater Than operator ">" that returns all item numbers greater than the item number entered, and a Less Than operator "<" that returns all item numbers less than the item number entered.

The query operation can also be restricted by the description of the object, which is entered in the Description field 514, the class of the object, which is entered in the Class field 508, or the type of the object, which is entered in the Type field 510. As mentioned above, the Query Operators 518 are used in conjunction with any or all of these fields. In addition, query restrictions may be entered within several of the fields described, providing a wide breadth of ability to finely restrict the query operation to just those objects desired.

In the example depicted in FIG. 69, two query criteria have been entered into the Query window 504. The class of the objects for which the query is being performed is restricted to the resources class by selecting Resources from the drop down menu within the Class field 508. In addition, the type of the objects for which the query is being performed is restricted to the personnel class by selecting Personnel from the drop down menu within the Type field 510. When the desired query criteria have been entered, the query operation is initiated by pressing the Query button 512.

Figure 70:
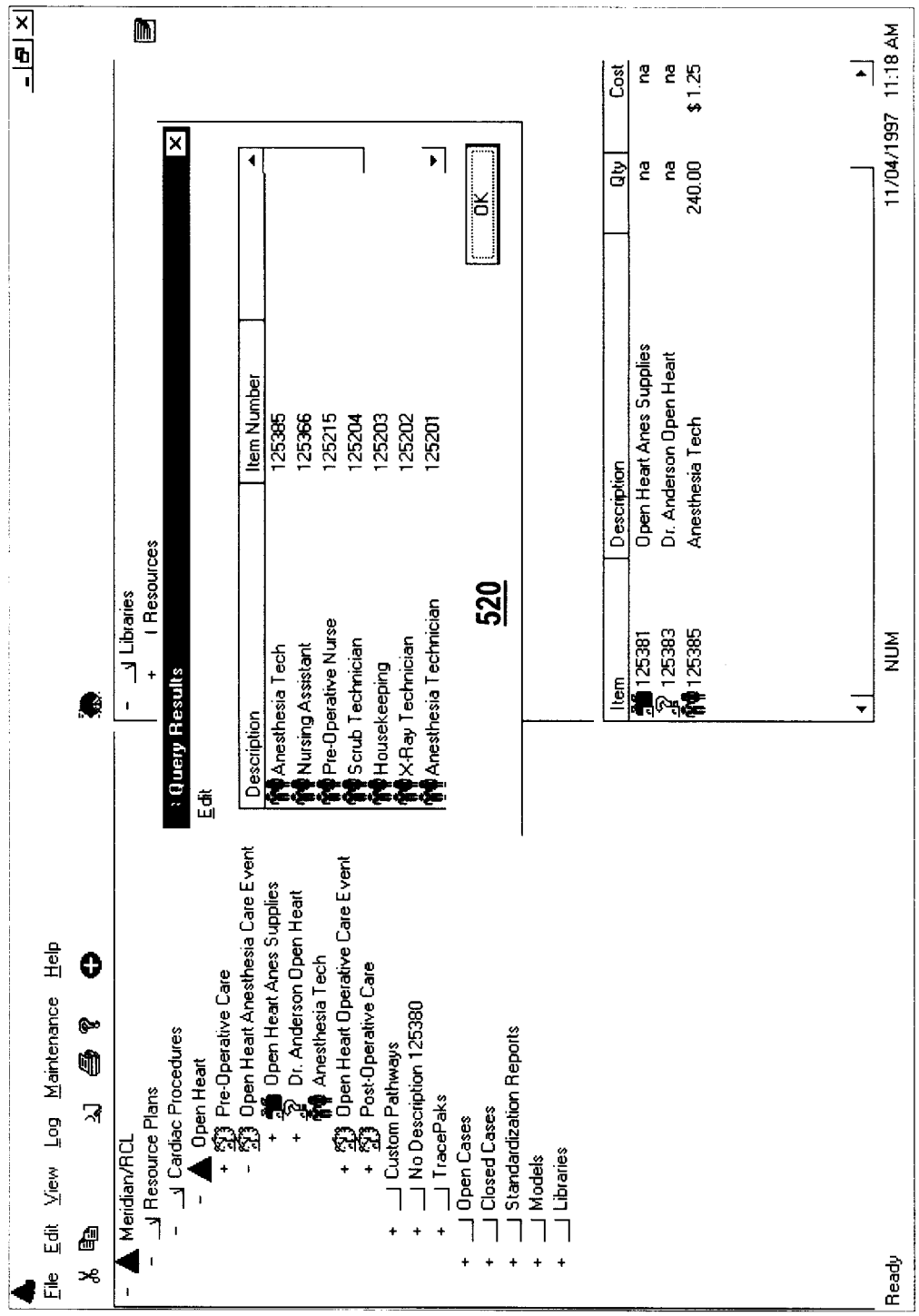
Figure 71:
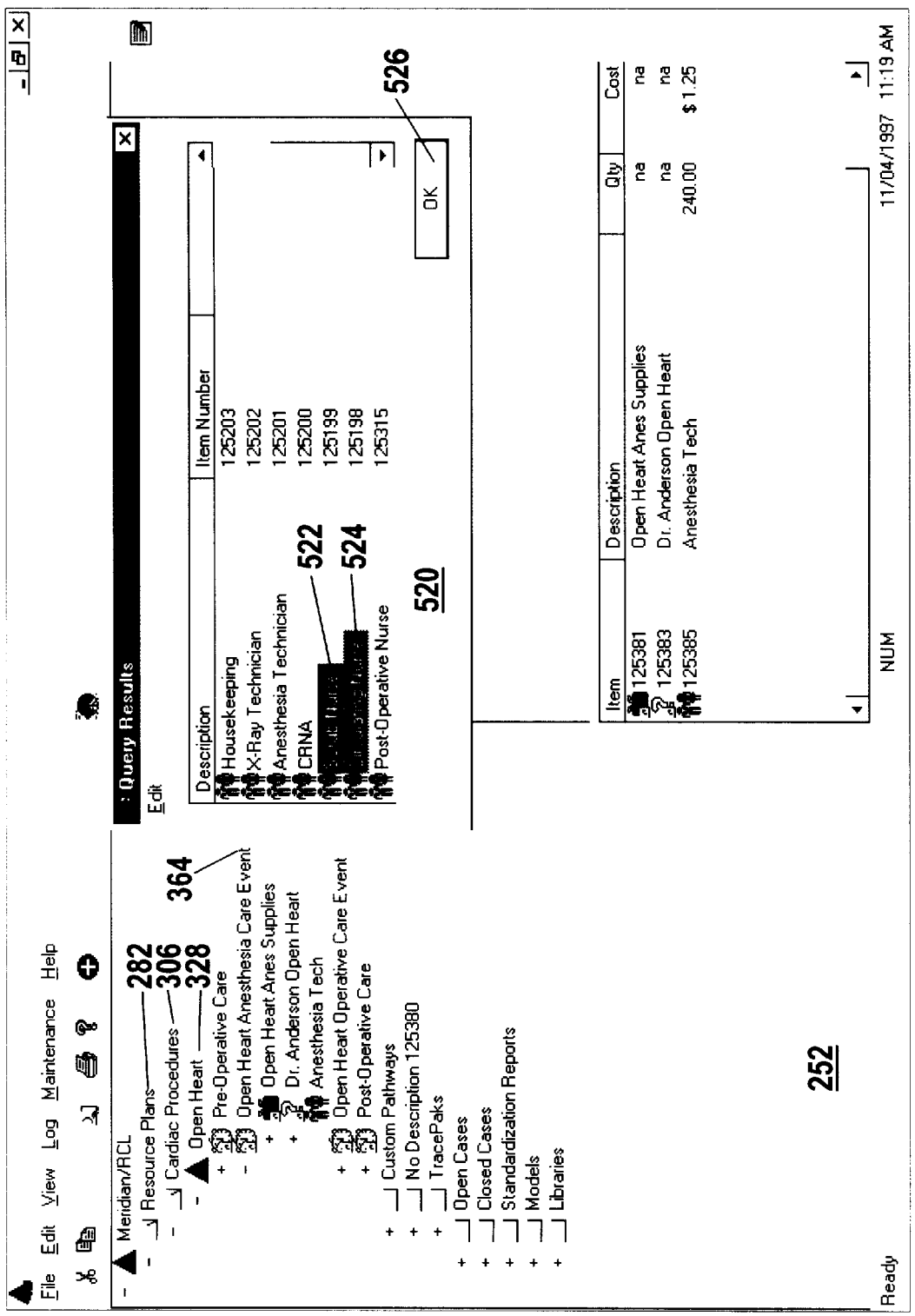

FIG. 70 depicts the Query Results window 520, from which two objects, the Scrub Nurse personnel resource object 522 and the Circulating Nurse personnel resource object 524, are selected as depicted in FIG. 71. Pressing the OK button 526 confirms the addition of the selected objects to the container object previously selected in the Nested Tree view 252. By pressing the OK button 526, the Referenced Item window 528 is invoked, as depicted in FIG. 72, and the user is given the opportunity to add the selected objects as either custom or standard objects to the previously selected container object.

By pressing the Yes button 530, the selected objects are added as standard objects to the container. When added in this manner, any changes made to the general template for the selected objects will be reflected in the objects as they reside within the container to which they have been added. By pressing the No button 532, the selected objects are added as custom objects to the container. When added in this manner, any changes made to the general template for the selected objects will not be reflected in the objects as they reside within the container to which they have been added. By pressing the Cancel button 534, the operation of adding the selected objects to the container is cancelled.

Figure 72:
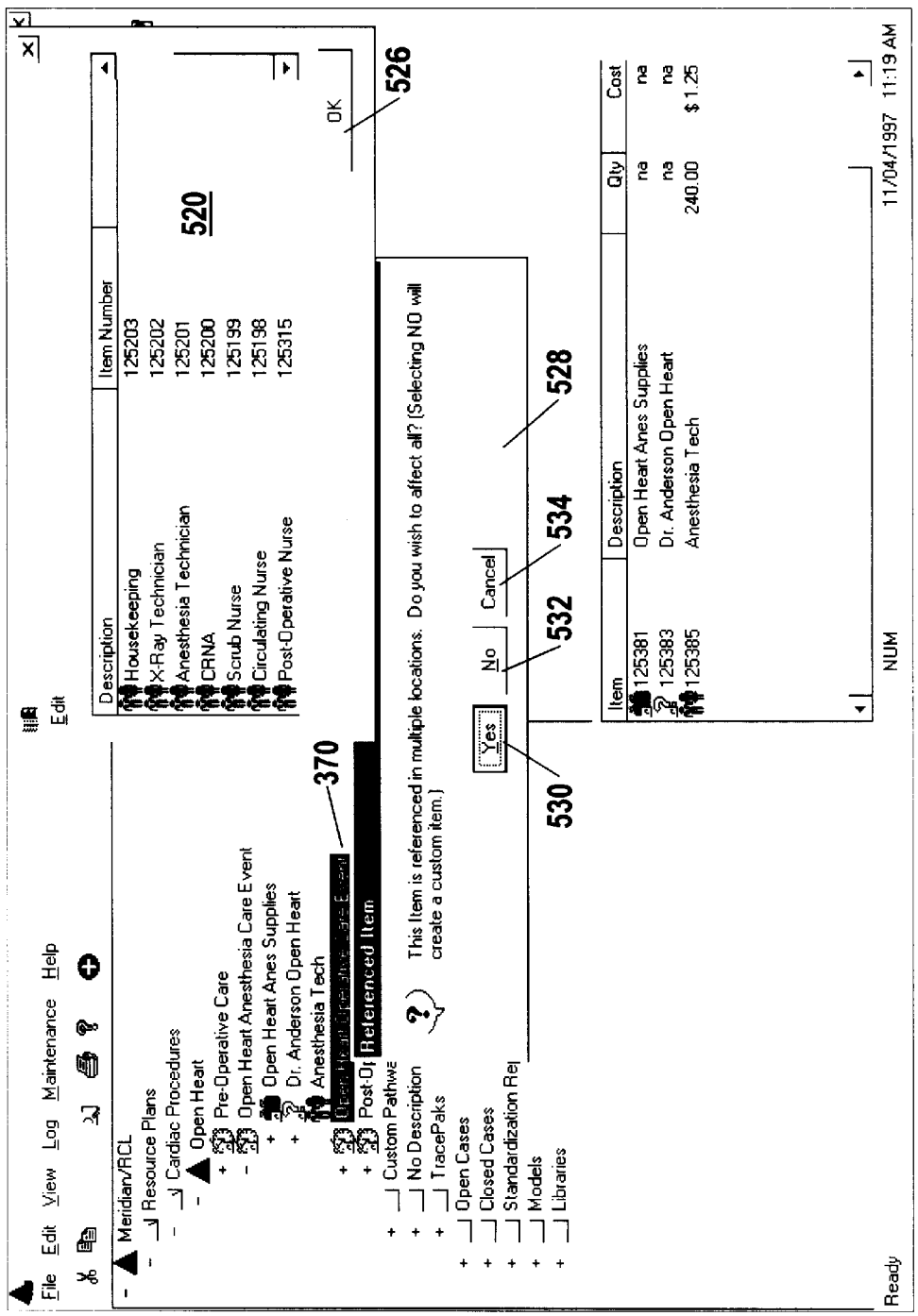
Figure 73:
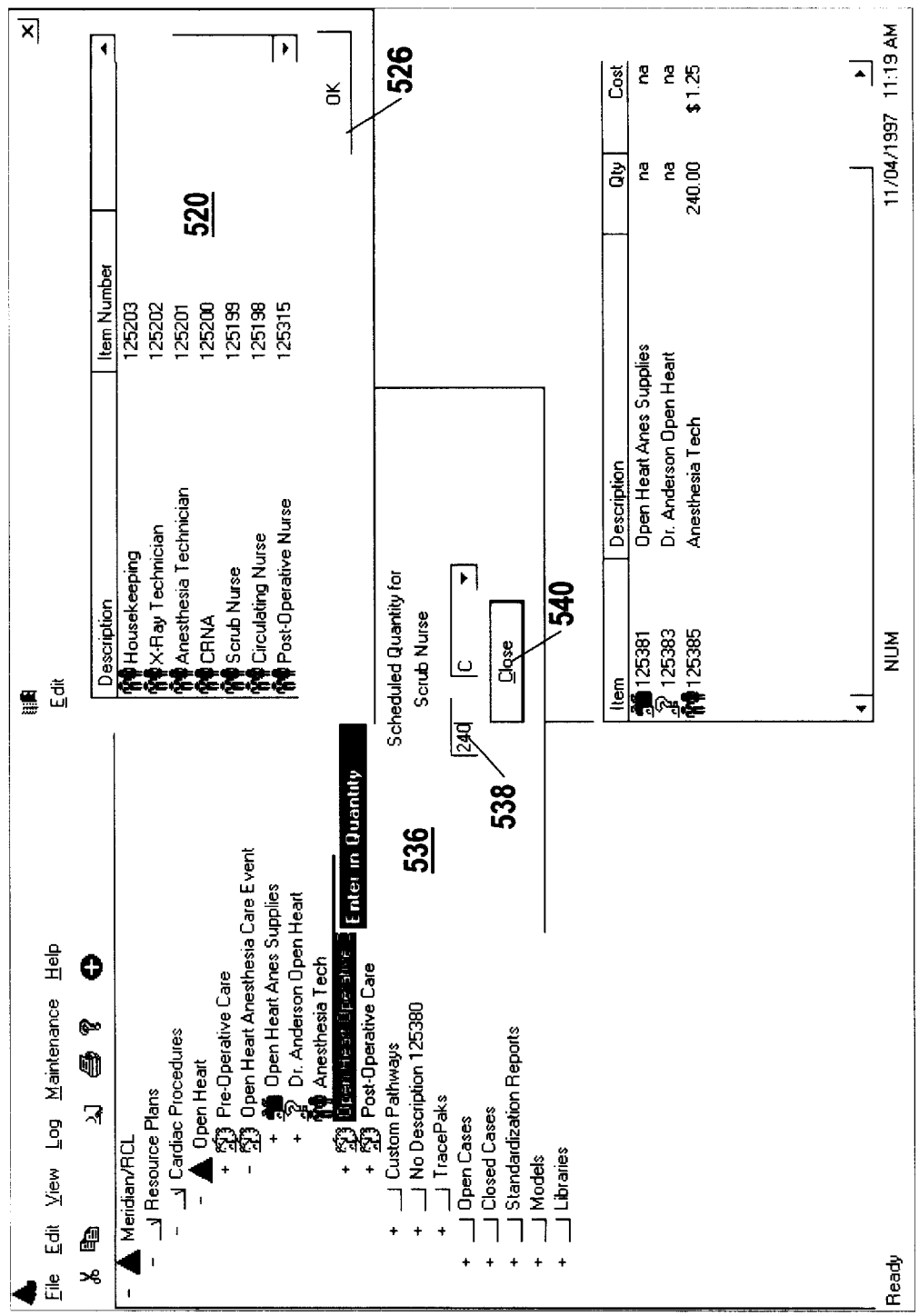

In the example depicted in FIG. 72, the Yes button 530 of the Referenced Item window 528 is pressed, which causes the display of the Enter In Quantity window 536, as depicted in FIG. 73. In the Enter In Quantity window 536, the user is presented with the opportunity to indicate the quantity desired for the specific object to be added to the container. In the example depicted in FIG. 73, the first object to be added to the container is a personnel resource object, thus, the quantity to be designated is the number of minutes for which the person indicated by the personnel resource object will be required for the operative care event container object. A value is entered by the user into the Quantity field 538, and the Close button 540 is pressed.

Figure 74:
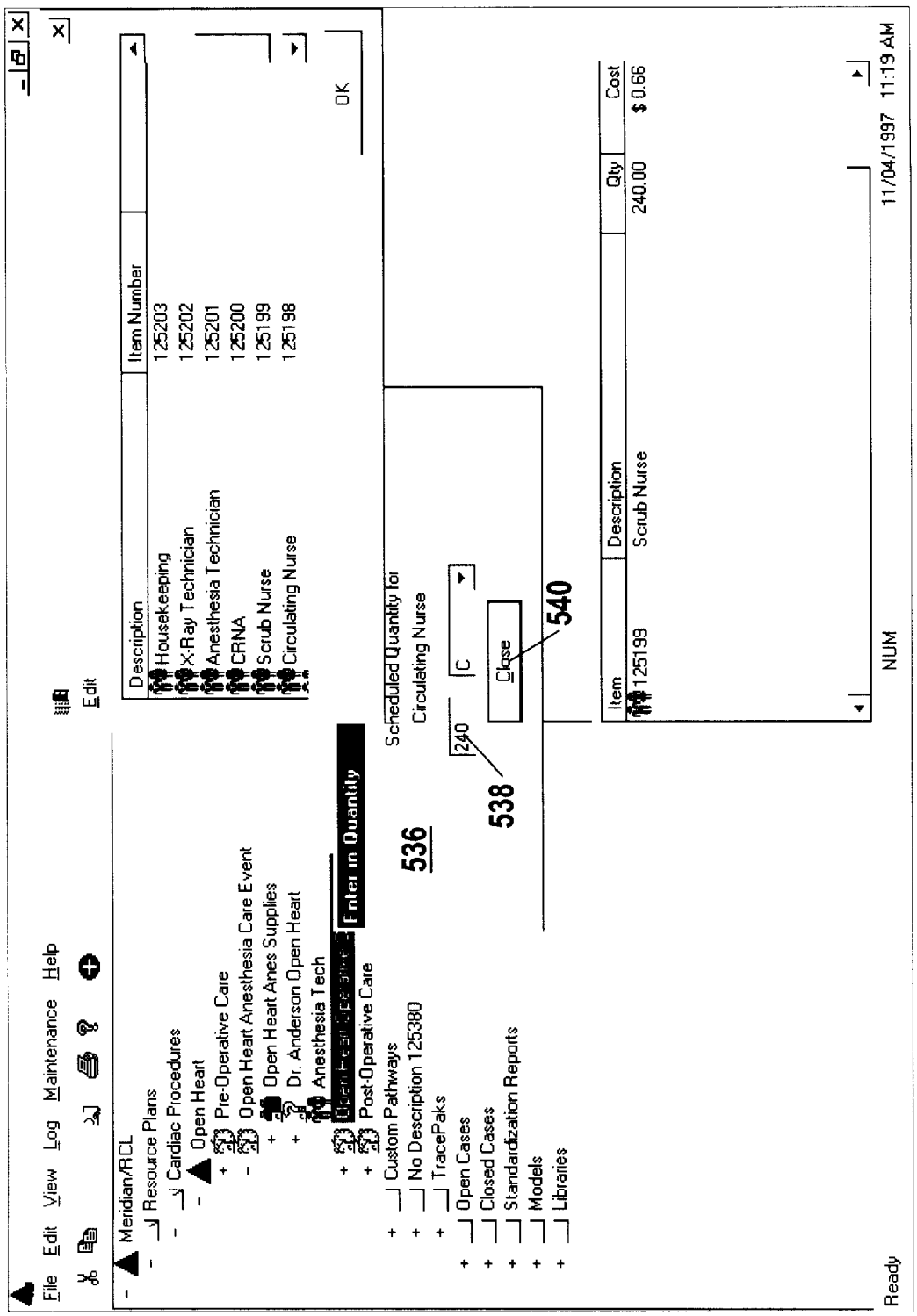
Figure 75:

In the current example, because two objects have been selected for addition to the container, pressing the Close button 540 invokes a second occurrence of the Enter In Quantity window 536, and the user is presented with an opportunity to enter the desired quantity for the second object in the Quantity field 538, as depicted in FIG. 74. Pressing the Close button 540 again accepts the added object with the designed quantity. If a third object had been selected for addition to the container, then a third occurrence of the Enter In Quantity window 536 is invoked. Thus, the number of Enter In Quantity windows 536 invoked is preferably equal to the number of objects selected for addition to the container. FIG. 75 depicts the previously selected Open Heart Operative Care Event container object 370 with the newly added Scrub Nurse personnel resource object 522 and Circulating Nurse personnel resource object 524.

Beginning with FIG. 75, a second method of adding previously defined objects to a container object is described. In this example, new resource objects are added to the Open Heart Operative Care Event container object 370. This second method is commenced by opening the Resources folder 374 in the Second Tree view 254 of the Browser window 250. The Resources folder 374 contains different types of predefined resources, which in the example depicted in FIG. 75 include Supplies 542, Personnel 544, Equipment 546, and Pharmacy/Medications 548. All of these different resource types are preferably contained within folders.

Figure 76:
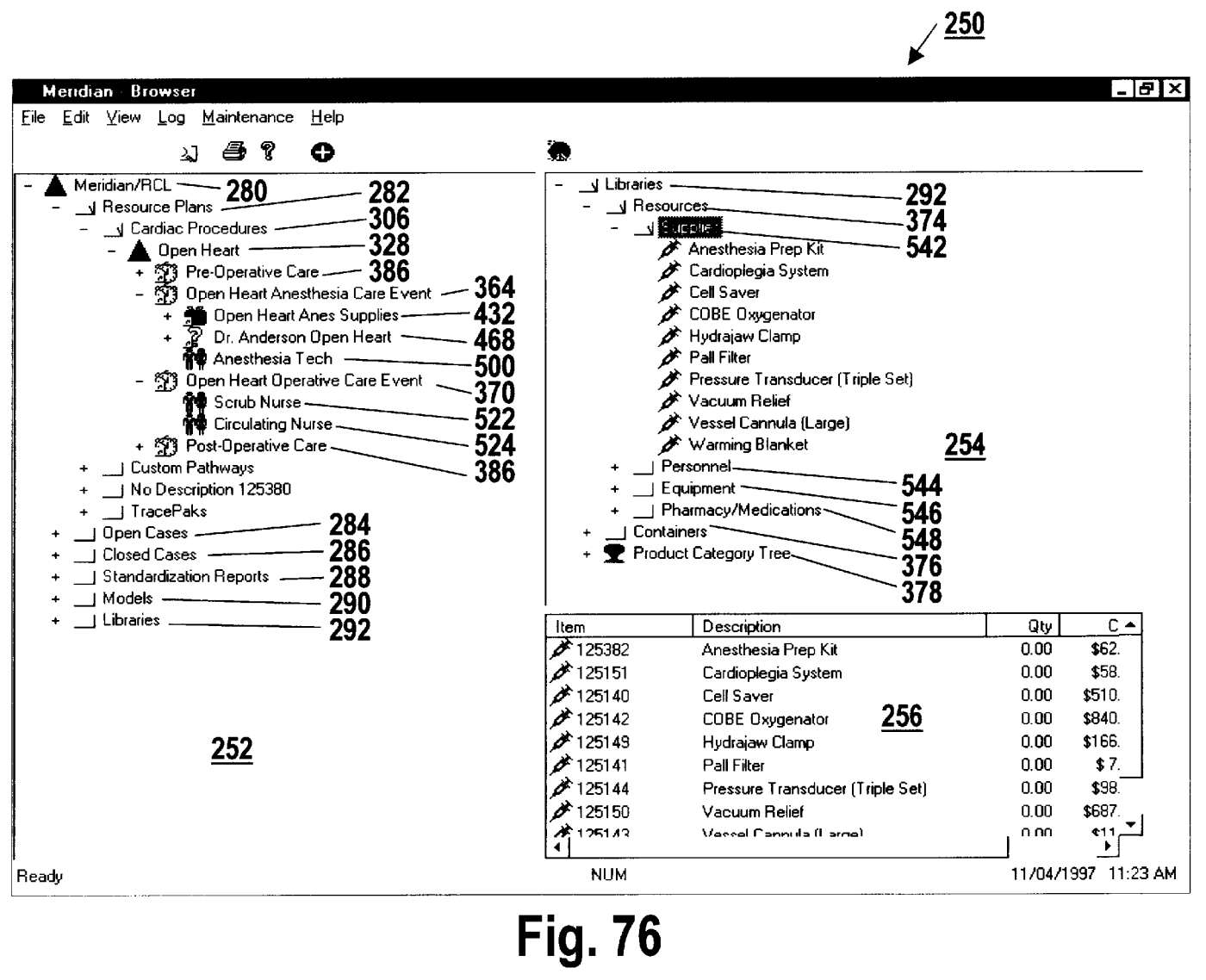
Figure 77:
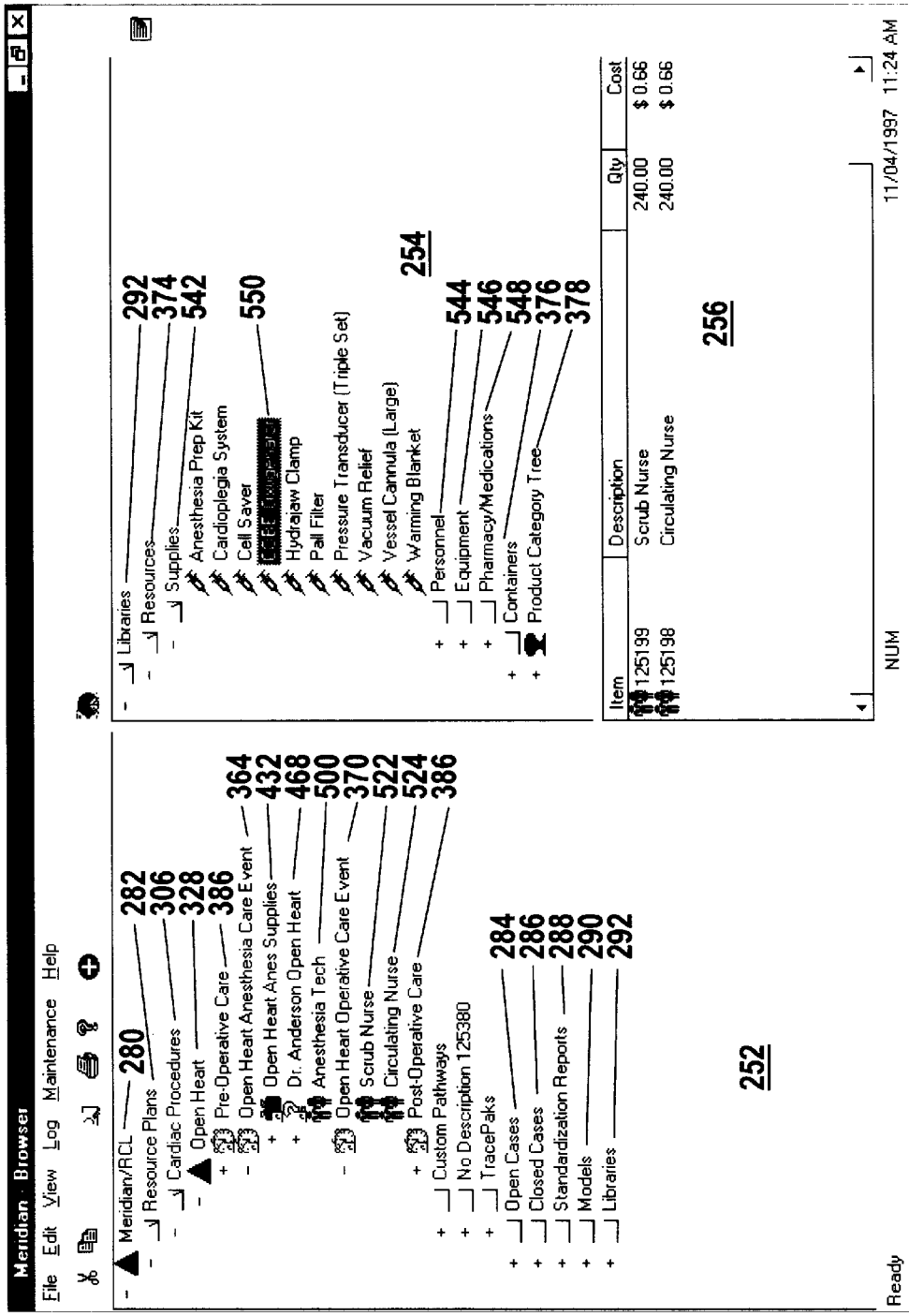

In FIG. 76, the Supplies folder 542 has been selected and opened, revealing the various supply resource objects located within the folder. These supply resource objects are displayed both in a hierarchical tree view within the Second Tree view 254, and in a list view within the List view 256. The desired supply resource object depicted in the Second Tree view 254 to be added to the container object depicted in the Nested Tree view 252 is selected. In the example depicted in FIG. 77, the desired supply resource object is a COBE Oxygenator 550. The List view 256 depicts the contents of the previously selected container object, which in this example is the Open Heart Operative Care Event container object 370. Thus, the List view 256 depicts the Scrub Nurse personnel resource object 522 and the Circulating Nurse personnel resource object 524 that were previously added to the Open Heart Operative Care Event container object 370.

The COBE Oxygenator supply resource object 550 is copied from the Second Tree view 254 to the Nested Tree view 252 by dragging it with the mouse to the Open Heart Operative Care Event container object 370, and dropping it there. Upon doing so, the Referenced Item window 528 appears, previously described during the recitation of the first method for adding predefined objects to a container, and the user is given the opportunity to add the selected object as either a custom or a standard object to the previously selected container object, as depicted in FIG. 78.

By pressing the Yes button 530, the selected object is added as a standard object to the container. When added in this manner, any changes made to the general template for the selected object will be reflected in the object as it resides within the container to which it has been added. By pressing the No button 532, the selected object is added as a custom object to the container. When added in this manner, any changes made to the general template for the selected object will not be reflected in the object as it resides within the container to which it has been added. By pressing the Cancel button 534, the operation of adding the selected object to the container is cancelled.

Figure 78:
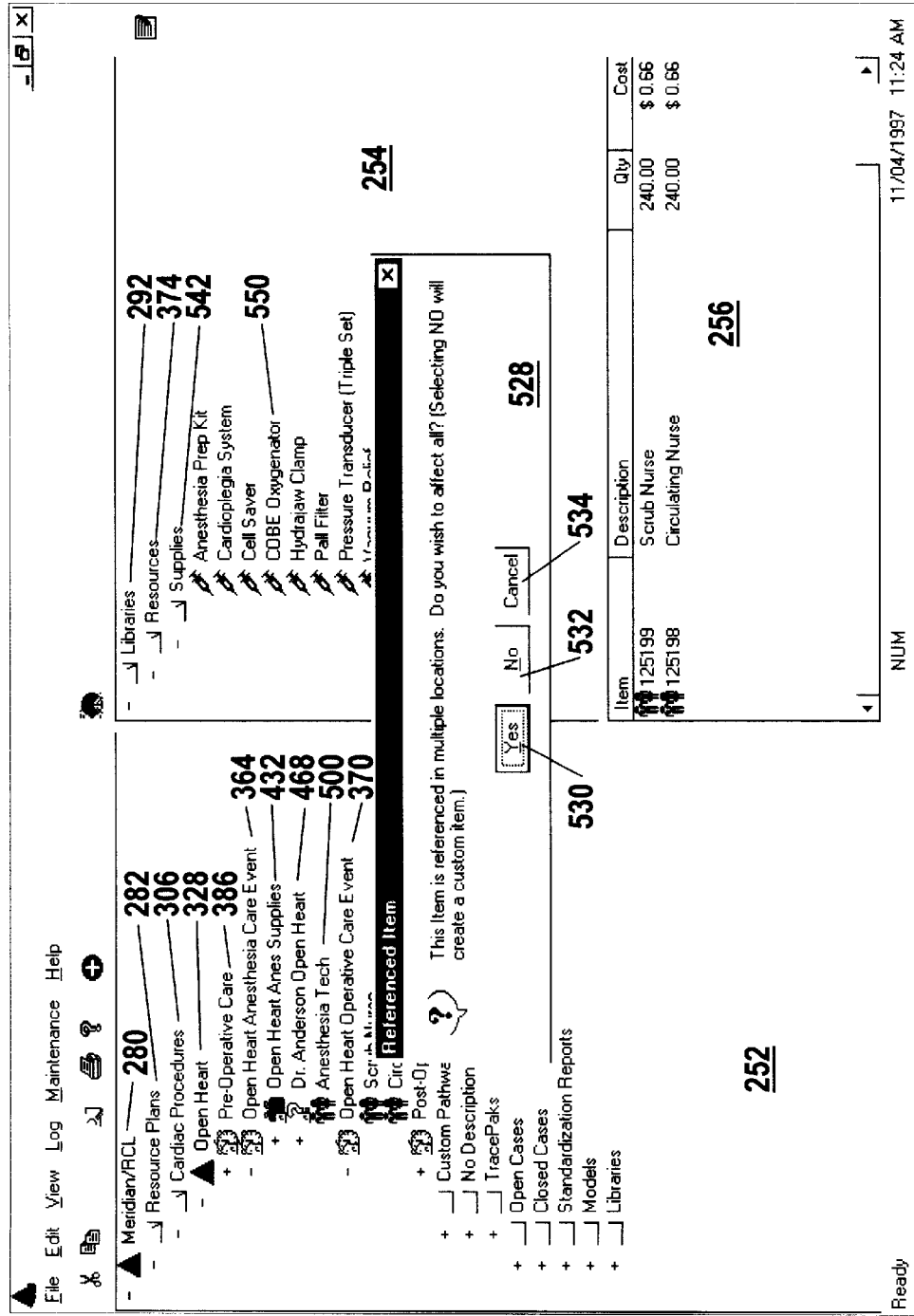
Figure 79:
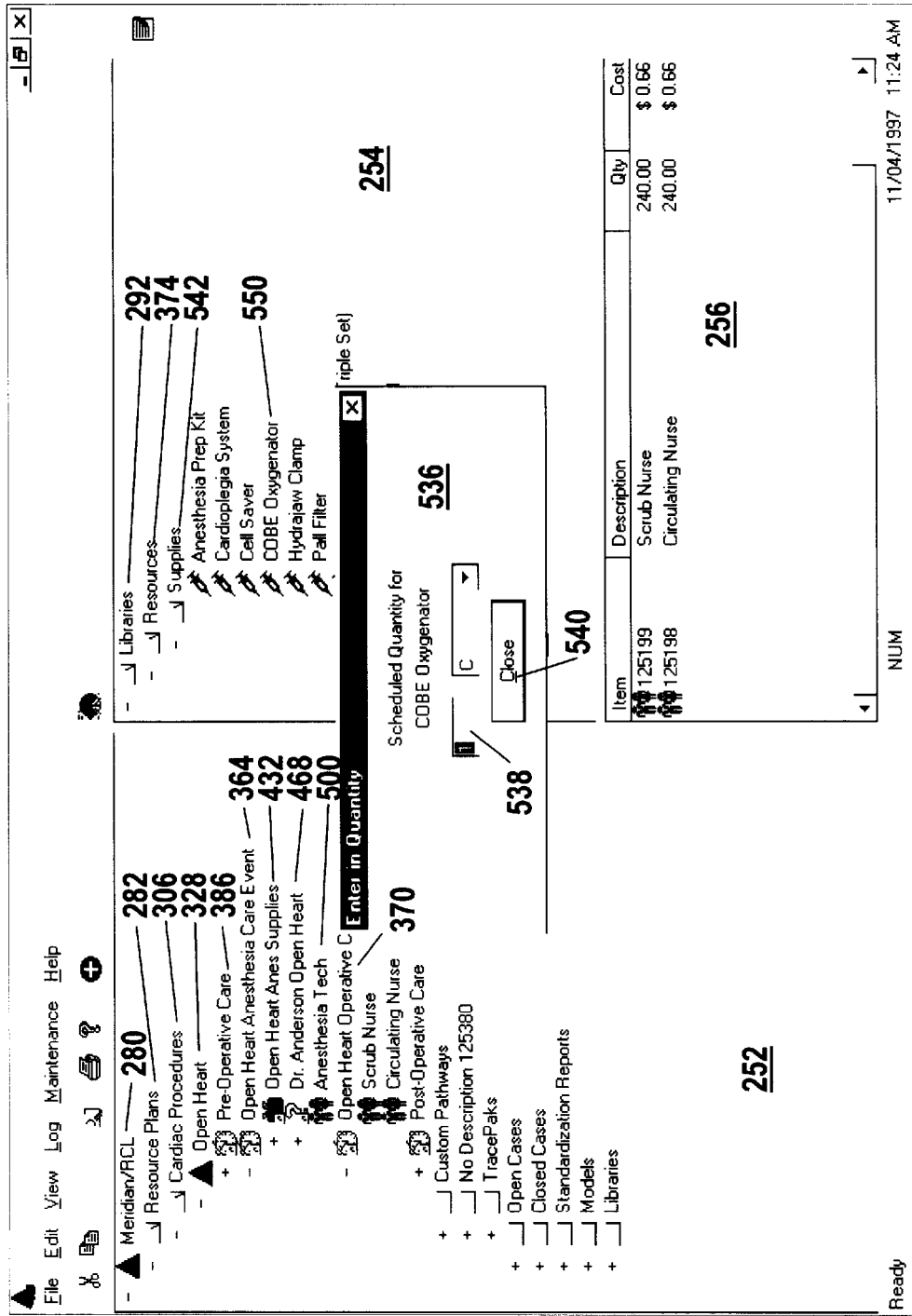

In the example depicted in FIG. 78, the Yes button 530 of the Referenced Item window 528 is pressed, which causes the display of the Enter In Quantity window 536, as depicted in FIG. 79, and as previously described. In the Enter In Quantity window 536, the user is presented with the opportunity to indicate the quantity desired for the specific object to be added to the container. In the example depicted in FIG. 79, the object to be added to the container is a supplies resource object, thus, the quantity to be designated is the number of the items indicated by the supplies resource object that are required for the operative care event container object. A value is entered by the user into the Quantity field 538, and the Close button 540 is pressed.

Figure 80:
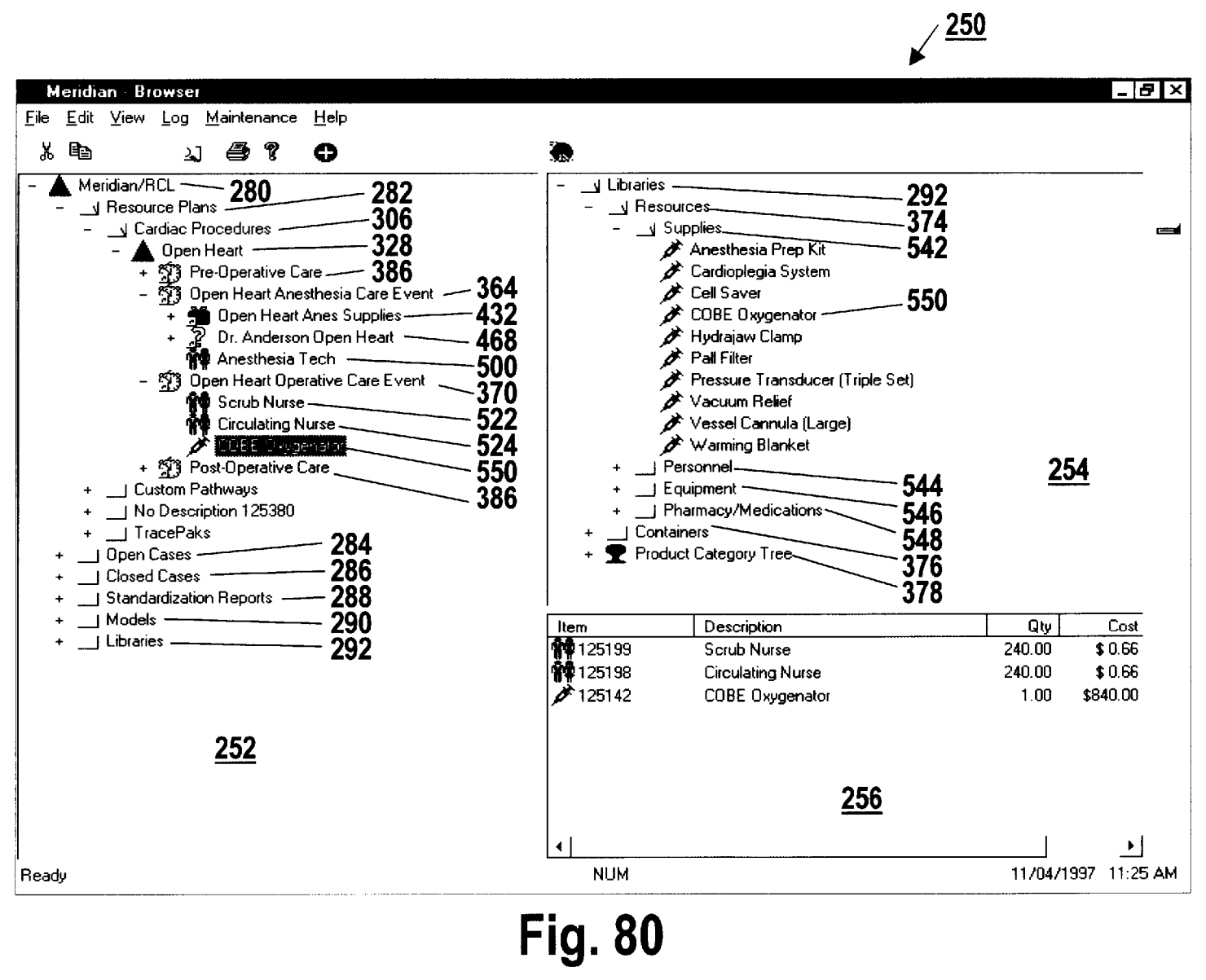

In the current example, because only one object has been selected for addition to the container, pressing the Close button 540 does not invoke a second occurrence of the Enter In Quantity window 536. However, as previously described, the number of Enter In Quantity windows 536 invoked is preferably equal to the number of objects selected for addition to the container. FIG. 80 depicts the previously selected Open Heart Operative Care Event container object 370 with the newly added COBE Oxygenator supply resource object 550.

FIG. 80 also depicts how the Nested Tree view 252, the Second Tree view 254, and the List view 256 of the Browser window 250 interrelate. The COBE Oxygenator supply resource object 550, originally depicted in the Second Tree view 254, is still depicted in the Second Tree view 254, but has been additionally copied to the Nested Tree view 252. The objects within the Open Heart Operative Care Event container object 370, being the Scrub Nurse personnel resource object 522, the Circulating Nurse personnel resource object 524, and the COBE Oxygenator supply resource object 550, are depicted both within the Nested Tree view 252 and the List view 256. In this exemplar embodiment, the Nested Tree view 252 and the Second Tree view 254 display identical hierarchical lists that can be independently expanded, contracted, and accessed.

Figure 81:
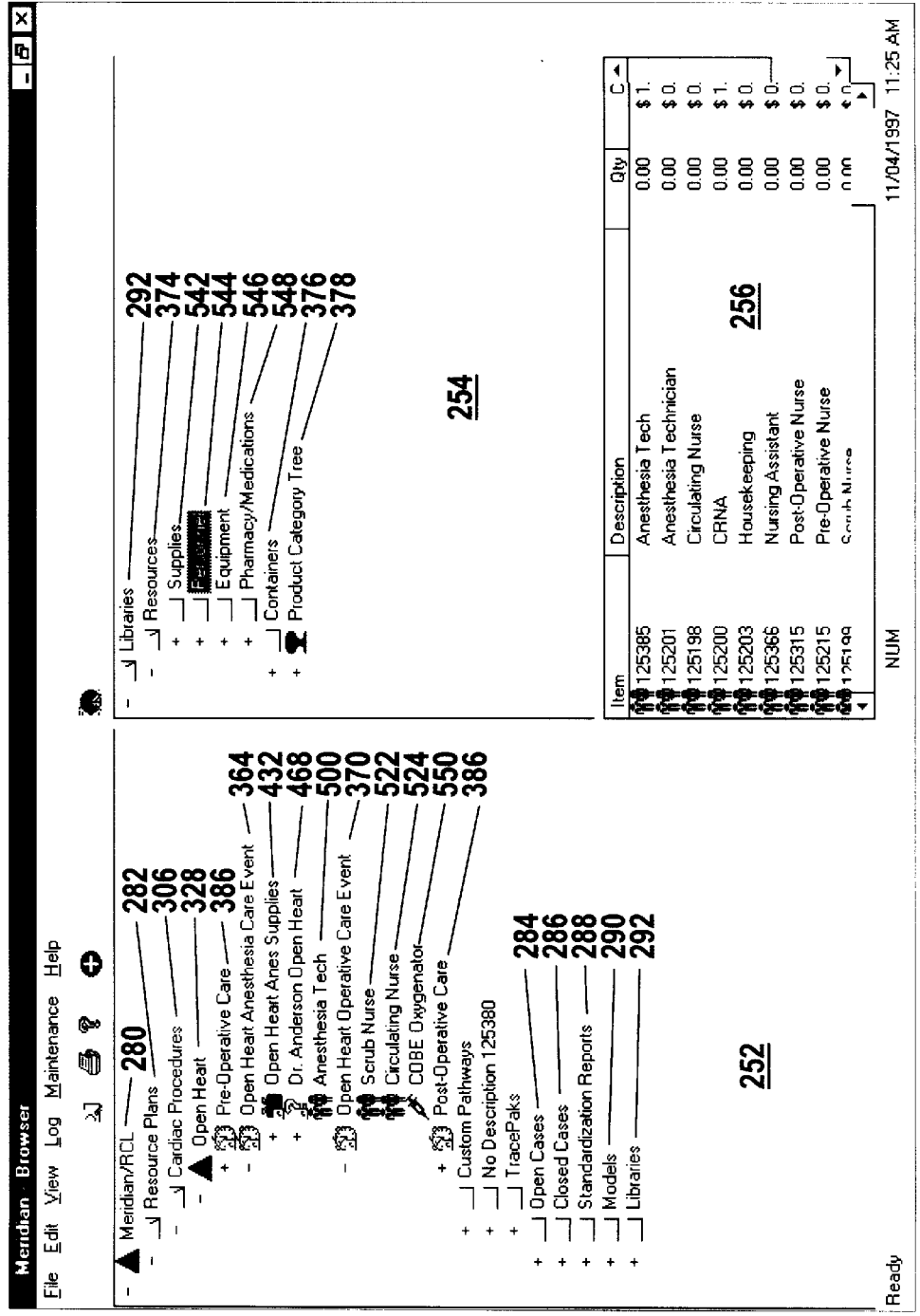
Figure 82:
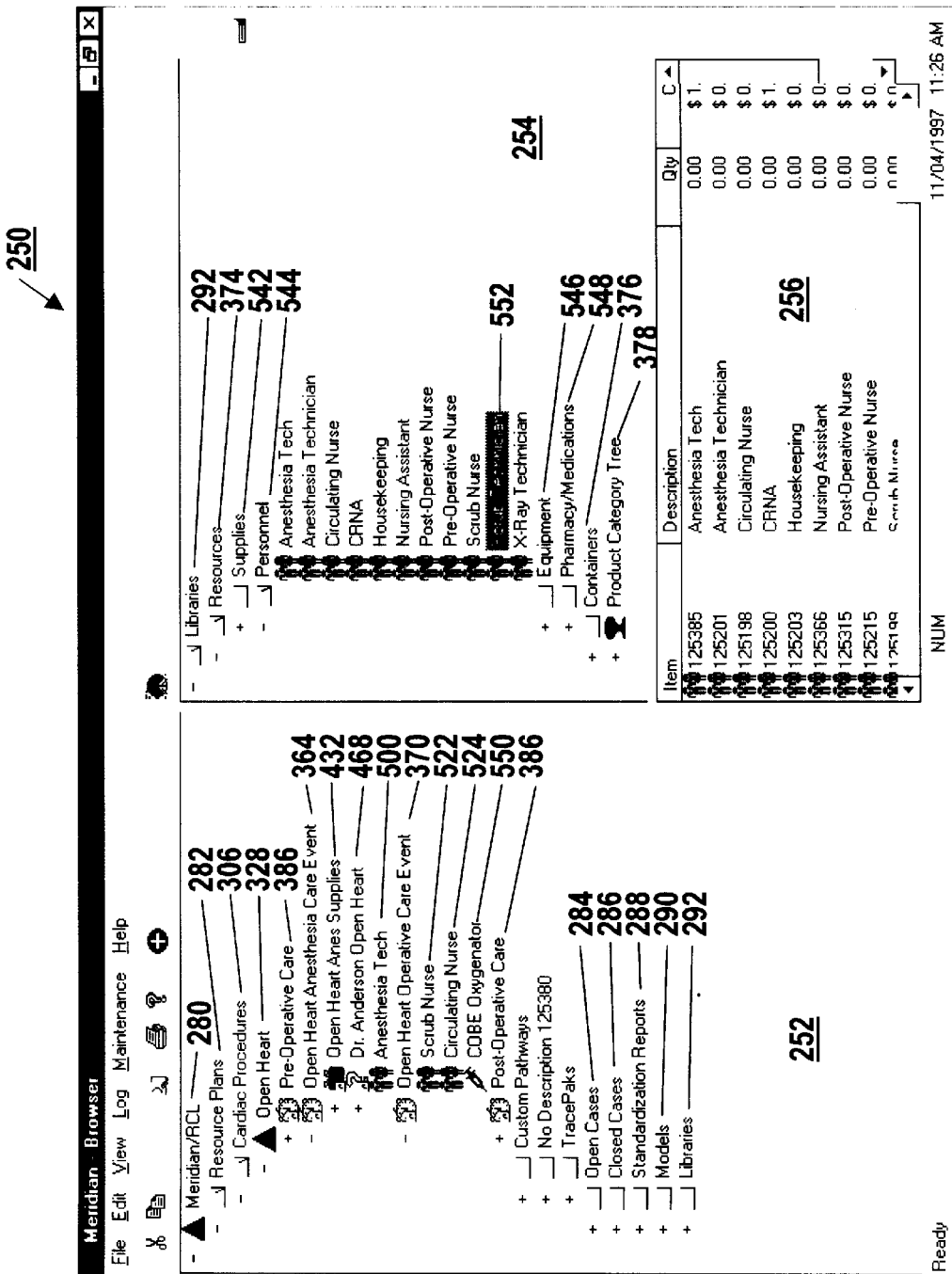

Beginning with FIG. 81, a method for adding a personnel resource object to the Open Heart Operative Care Event container object 370 is described. The container object to which the resource object is to be added is selected in the Nested Tree view 252, and then the appropriate folder for the resource object is selected in the Second Tree view 254. In the example depicted in FIG. 81, the appropriate folder is the Personnel folder 544. Opening the Personnel folder 544 displays the various predefined personnel objects within the Personnel folder 544, as depicted in FIG. 82. The predefined personnel objects within the Personnel folder 544 are depicted in a hierarchical tree form in the Second Tree view 254 and in a list form in the List view 256.

The personnel resource object to be added to the previously selected container object is selected in the Second Tree view 254. In the example depicted in FIG. 82, the selected object is the Scrub Technician personnel resource object 552, which is dragged with the mouse and dropped onto the Open Heart Operative Care Event container object 370 in the Nested Tree view 252. As previously described, this action brings up the Referenced Item window 528, previously described, and the user is given the opportunity to add the selected object as either a custom or a standard object to the previously selected container object, as depicted in FIG. 83.

By pressing the Yes button 530, the selected object is added as a standard object to the container. When added in this manner, any changes made to the general template for the selected object will be reflected in the object as it resides within the container to which it has been added. By pressing the No button 532, the selected object is added as a custom object to the container. When added in this manner, any changes made to the general template for the selected object will not be reflected in the object as it resides within the container to which it has been added. By pressing the Cancel button 534, the operation of adding the selected object to the container is cancelled.

Figure 83:
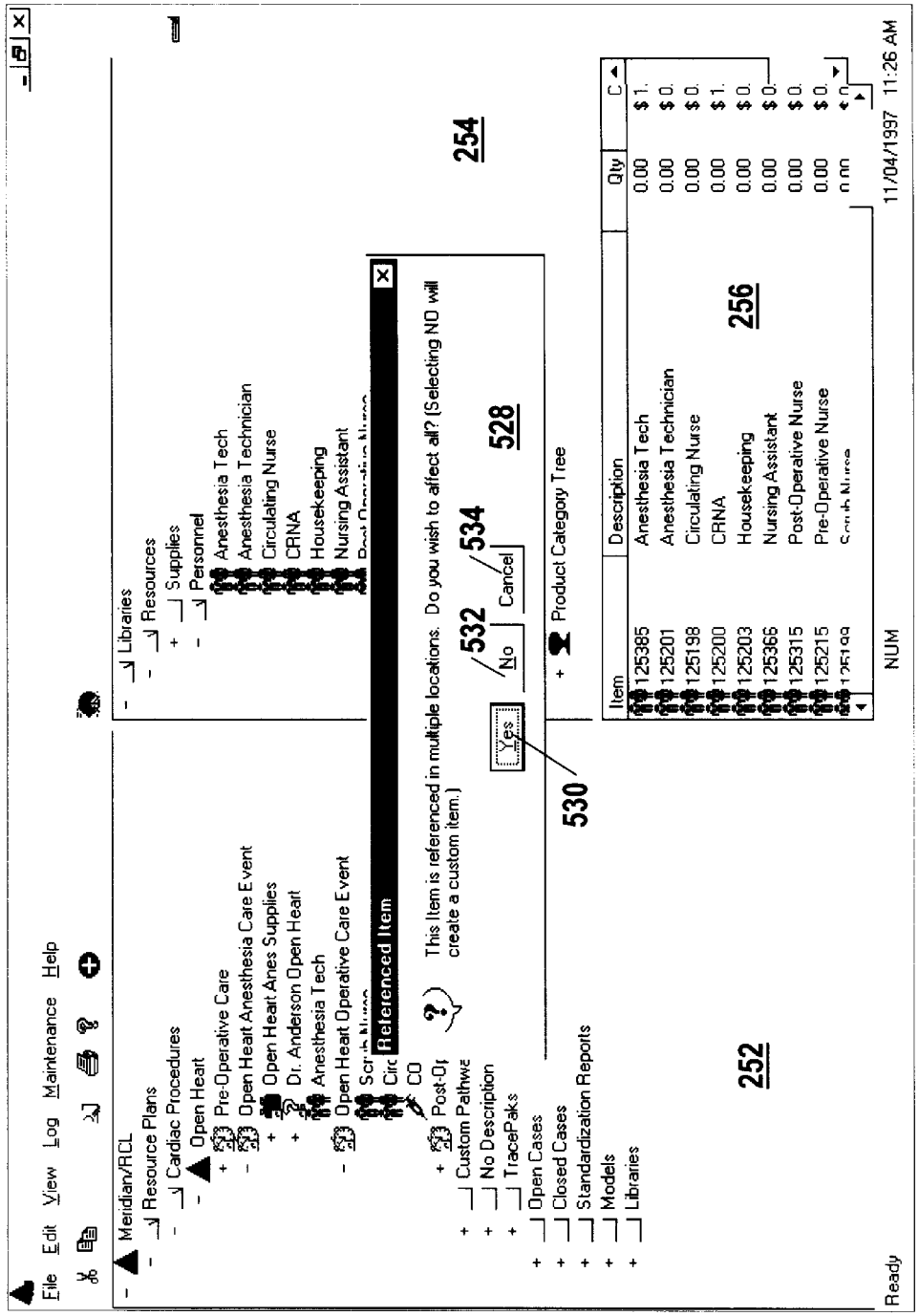
Figure 84:
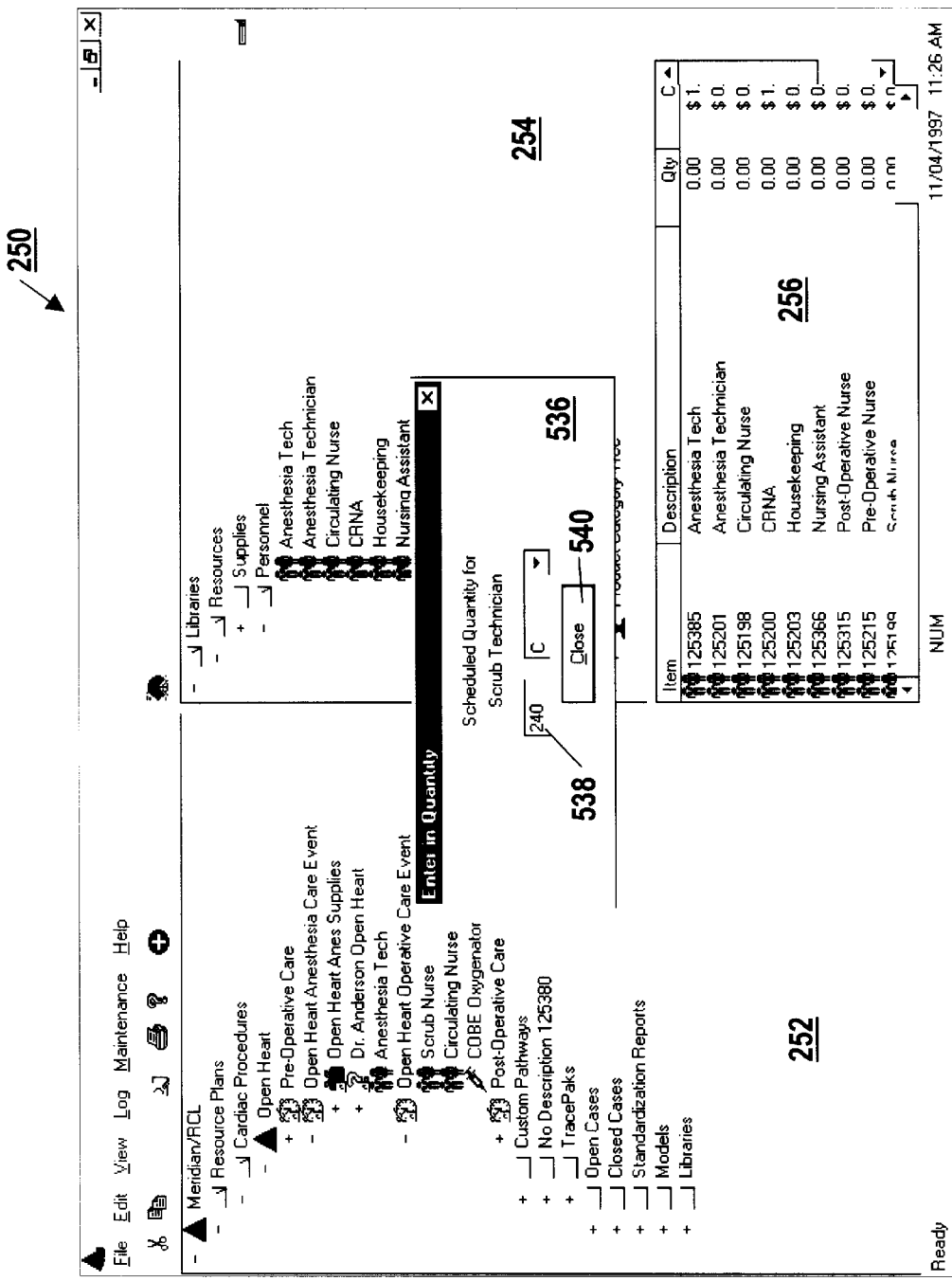
Figure 85:
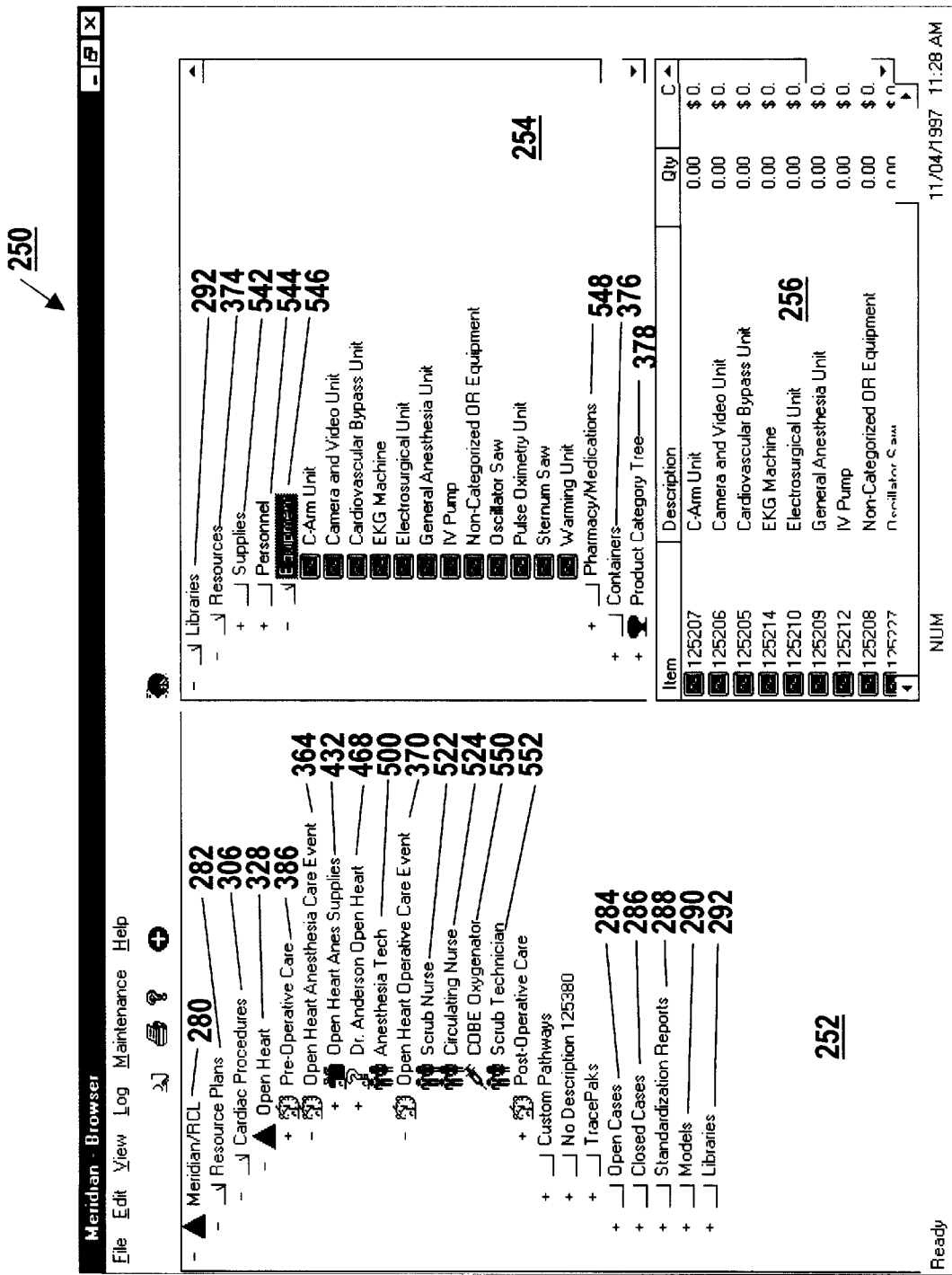

In the example depicted in FIG. 83, the Yes button 530 of the Referenced Item window 528 is pressed, which causes the display of the Enter In Quantity window 536, as depicted in FIG. 84, and as previously described. In the Enter In Quantity window 536, the user is presented with the opportunity to indicate the quantity desired for the specific object to be added to the container. In the example depicted in FIG. 84, the object to be added to the container is a personnel resource object, thus, the quantity to be designated is the amount of time from the person indicated by the personnel resource object that is required for the operative care event container object. A value is entered by the user into the Quantity field 538, and the Close button 540 is pressed. As depicted in FIG. 85, the newly added Scrub Technician personnel resource object 552 is depicted under the Open Heart Operative Care Event container object 370 in the Nested Tree view 252 of the Browser window 250.

Beginning with FIG. 85, a method for adding an equipment resource object to the Open Heart Operative Care Event container object 370 is described. The container object to which the resource object is to be added is selected in the Nested Tree view 252, and then the appropriate folder for the resource object is selected in the Second Tree view 254. In the example depicted in FIG. 85, the appropriate folder is the Equipment folder 546. Opening the Equipment folder 546 displays the various predefined equipment objects within the Equipment folder 546, as depicted in FIG. 85. The predefined equipment objects within the Equipment folder 546 are depicted in a hierarchical tree form in the Second Tree view 254 and in a list form in the List view 256.

Figure 86:
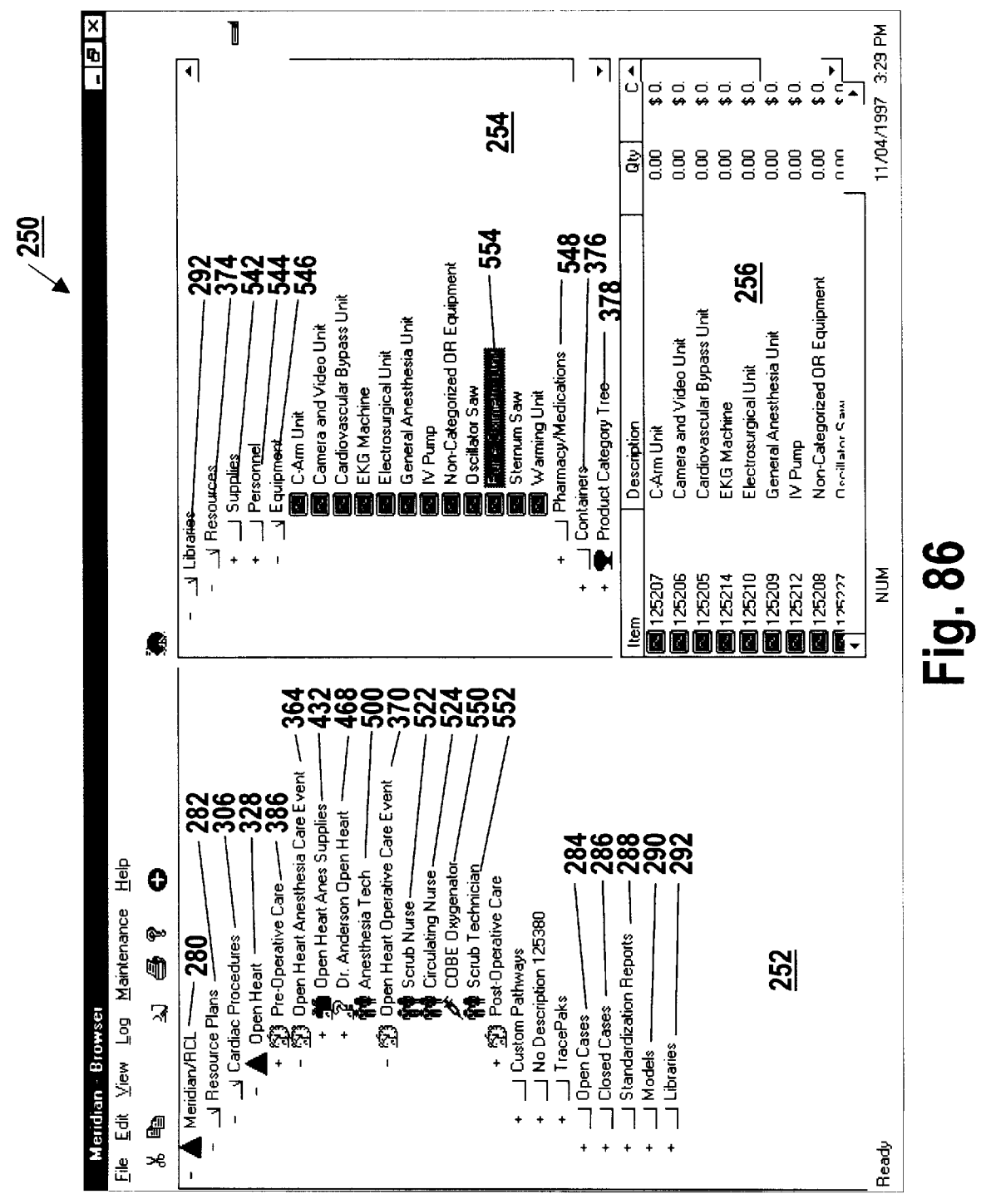

The equipment resource object to be added to the previously selected container object is selected in the Second Tree view 254. In the example depicted in FIG. 86, the selected object is the Pulse Oximetry Unit equipment resource object 554, which is dragged with the mouse and dropped onto the Open Heart Operative Care Event container object 370 in the Nested Tree view 252. As previously described, this action brings up the Referenced Item window 528, previously described, and the user is given the opportunity to add the selected object as either a custom or a standard object to the previously selected container object, as depicted in FIG. 87.

By pressing the Yes button 530, the selected object is added as a standard object to the container. When added in this manner, any changes made to the general template for the selected object will be reflected in the object as it resides within the container to which it has been added. By pressing the No button 532, the selected object is added as a custom object to the container. When added in this manner, any changes made to the general template for the selected object will not be reflected in the object as it resides within the container to which it has been added. By pressing the Cancel button 534, the operation of adding the selected object to the container is cancelled.

Figure 87:
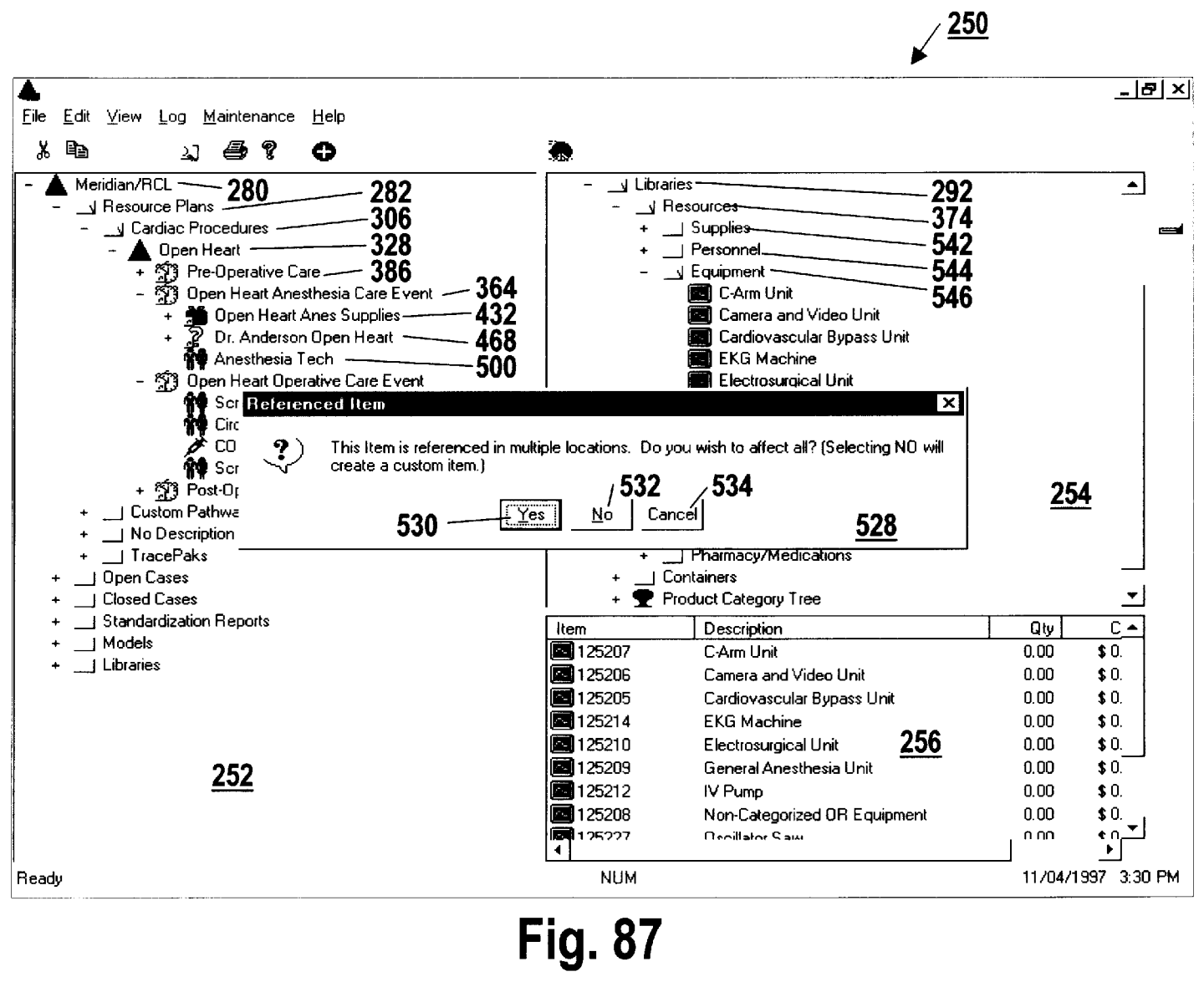
Figure 88:
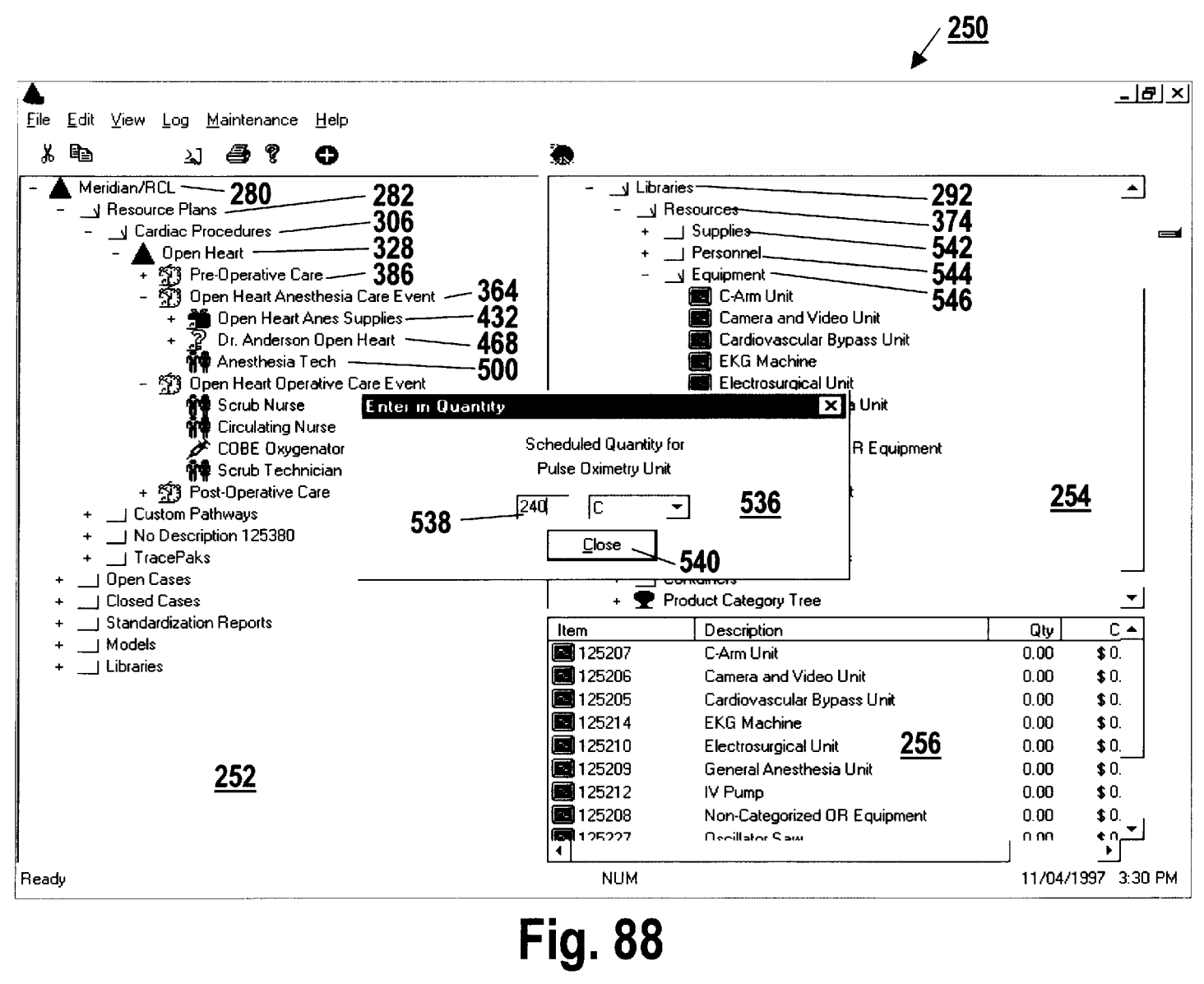
Figure 89:
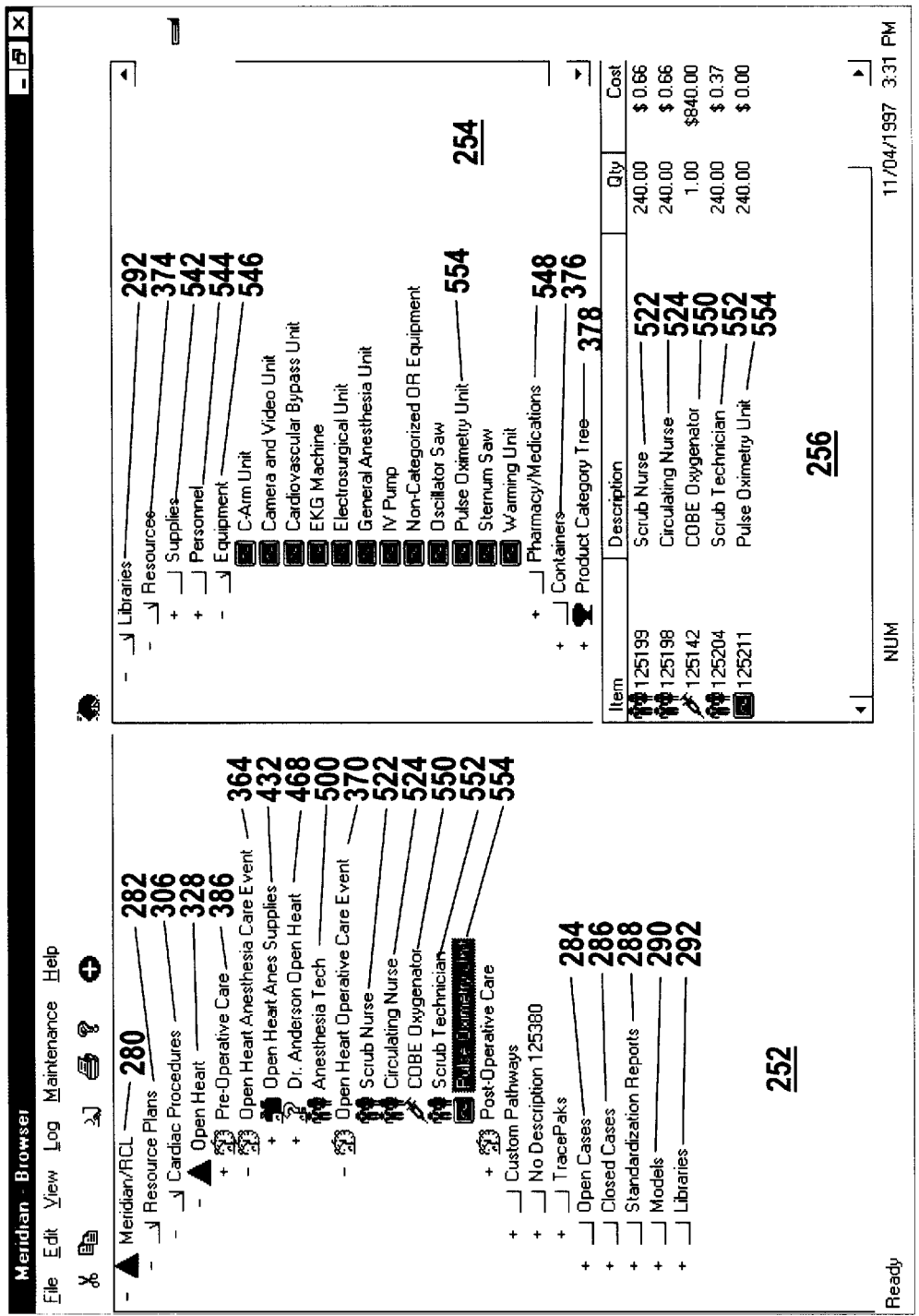

In the example depicted in FIG. 87, the Yes button 530 of the Referenced Item window 528 is pressed, which causes the display of the Enter In Quantity window 536, as depicted in FIG. 88, and as previously described. In the Enter In Quantity window 536, the user is presented with the opportunity to indicate the quantity desired for the specific object to be added to the container. In the example depicted in FIG. 88, the object to be added to the container is an equipment resource object, thus, the quantity to be designated is the amount of time on the equipment indicated by the equipment resource object that is required for the operative care event container object. A value is entered by the user into the Quantity field 538, and the Close button 540 is pressed. The newly added Pulse Oximetry equipment resource object 554 is depicted under the Open Heart Operative Care Event container object 370 in the Nested Tree view 252 of the Browser window 250, as depicted in FIG. 89.

Figure 90:
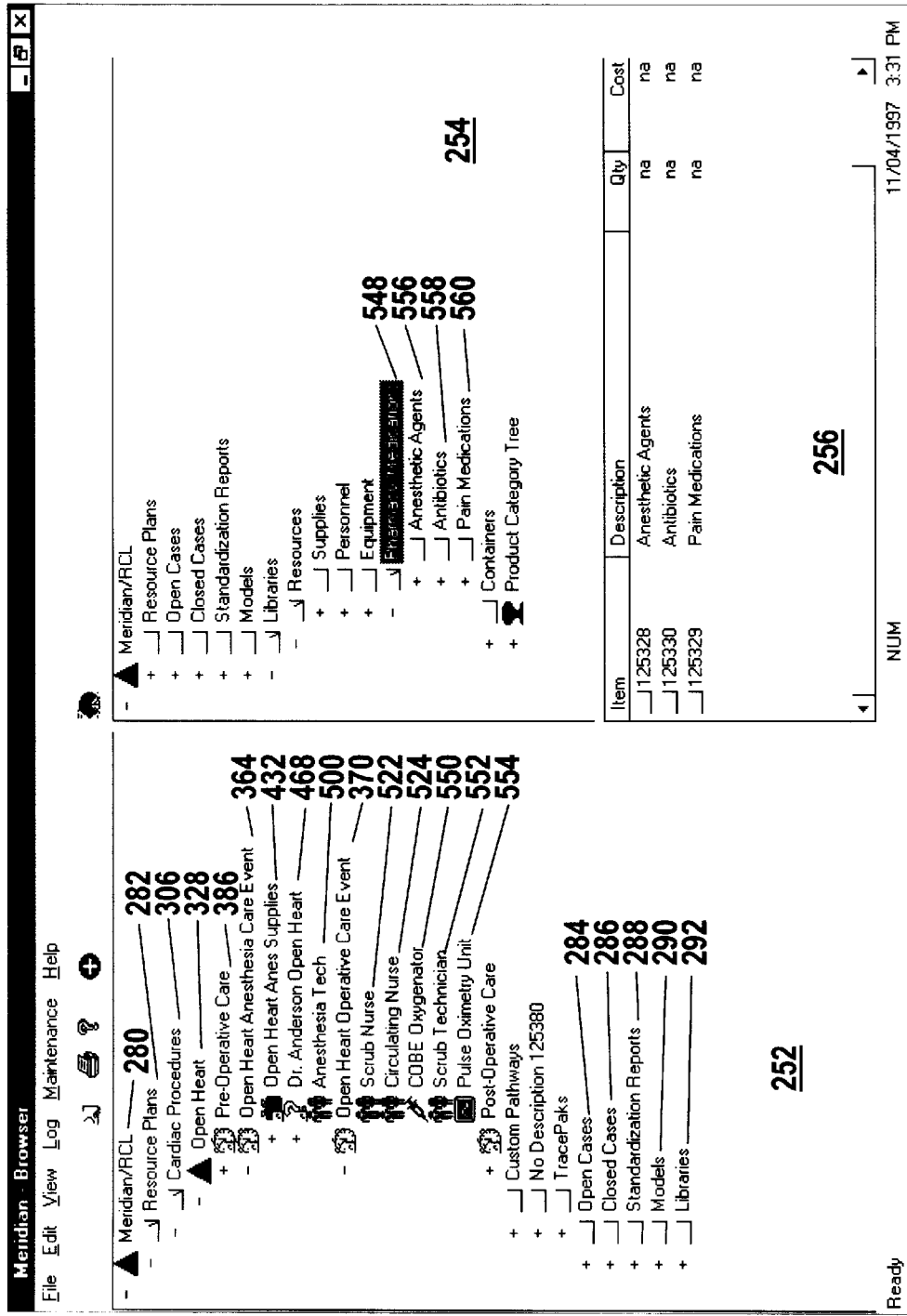

Beginning with FIG. 90, a method for adding a pharmacy/medication resource object to the Open Heart Operative Care Event container object 370 is described. The container object to which the resource object is to be added is selected in the Nested Tree view 252, and then the appropriate folder for the resource object is selected in the Second Tree view 254. In the example depicted in FIG. 90, the appropriate folder is the Pharmacy/Medications folder 548. Opening the Pharmacy/Medications folder 548 displays the various predefined equipment objects within the Pharmacy/Medications folder 548, as depicted in FIG. 90. The predefined objects within the Pharmacy/Medications folder 548 are depicted in a hierarchical tree form in the Second Tree view 254 and in a list form in the List view 256, and include the Anesthetic Agents folder 556, the Antibiotics folder 558, and the Pain Medications folder 560.

Figure 91:
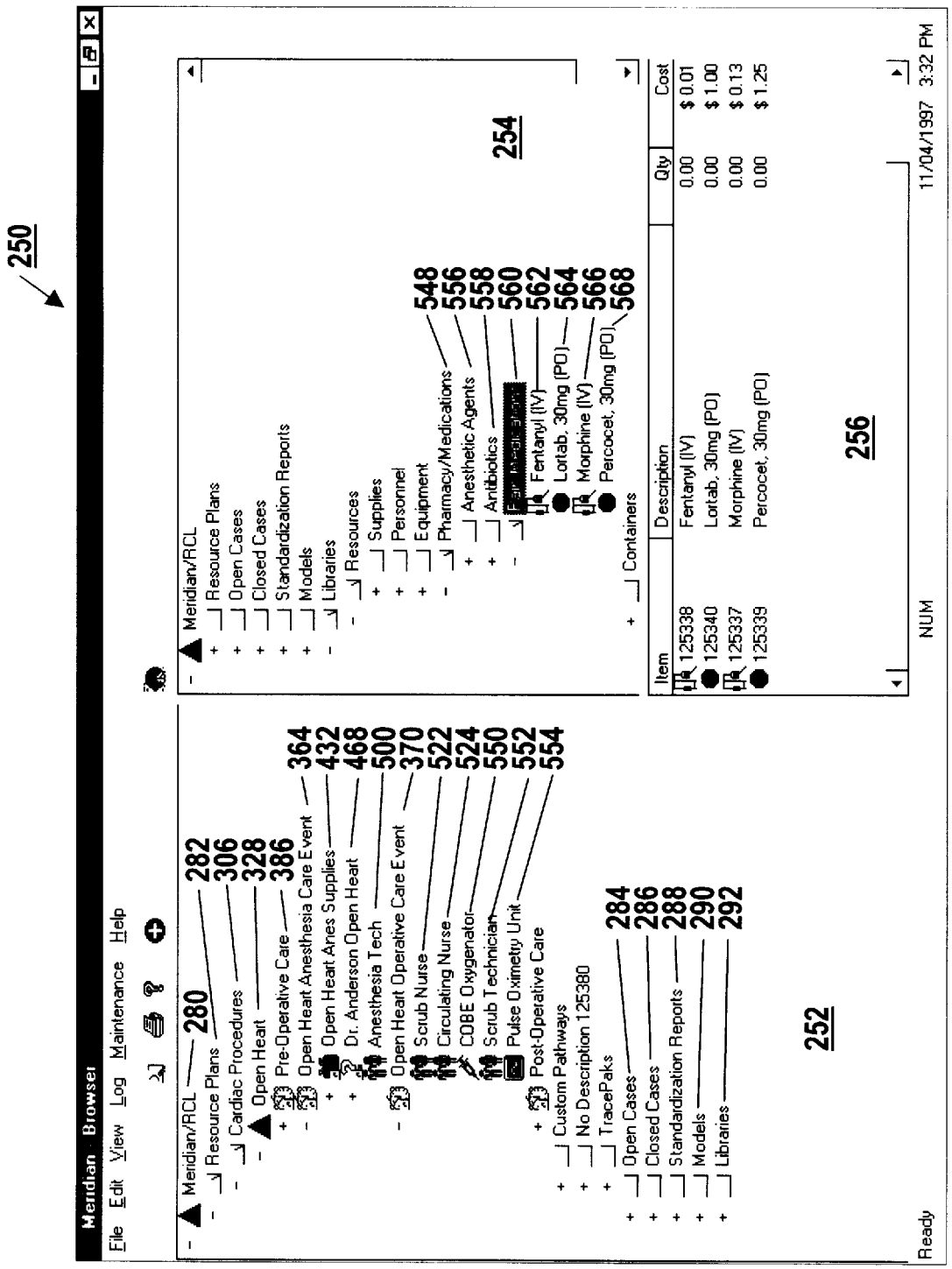

Opening the Pain Medications folder 560 in the Second Tree view 254 displays the additional objects located within that folder. In the example depicted in FIG. 91, these additional items include Fentanyl 562, Lortab 564, Morphine 566, and Percocet 568.

Figure 92:
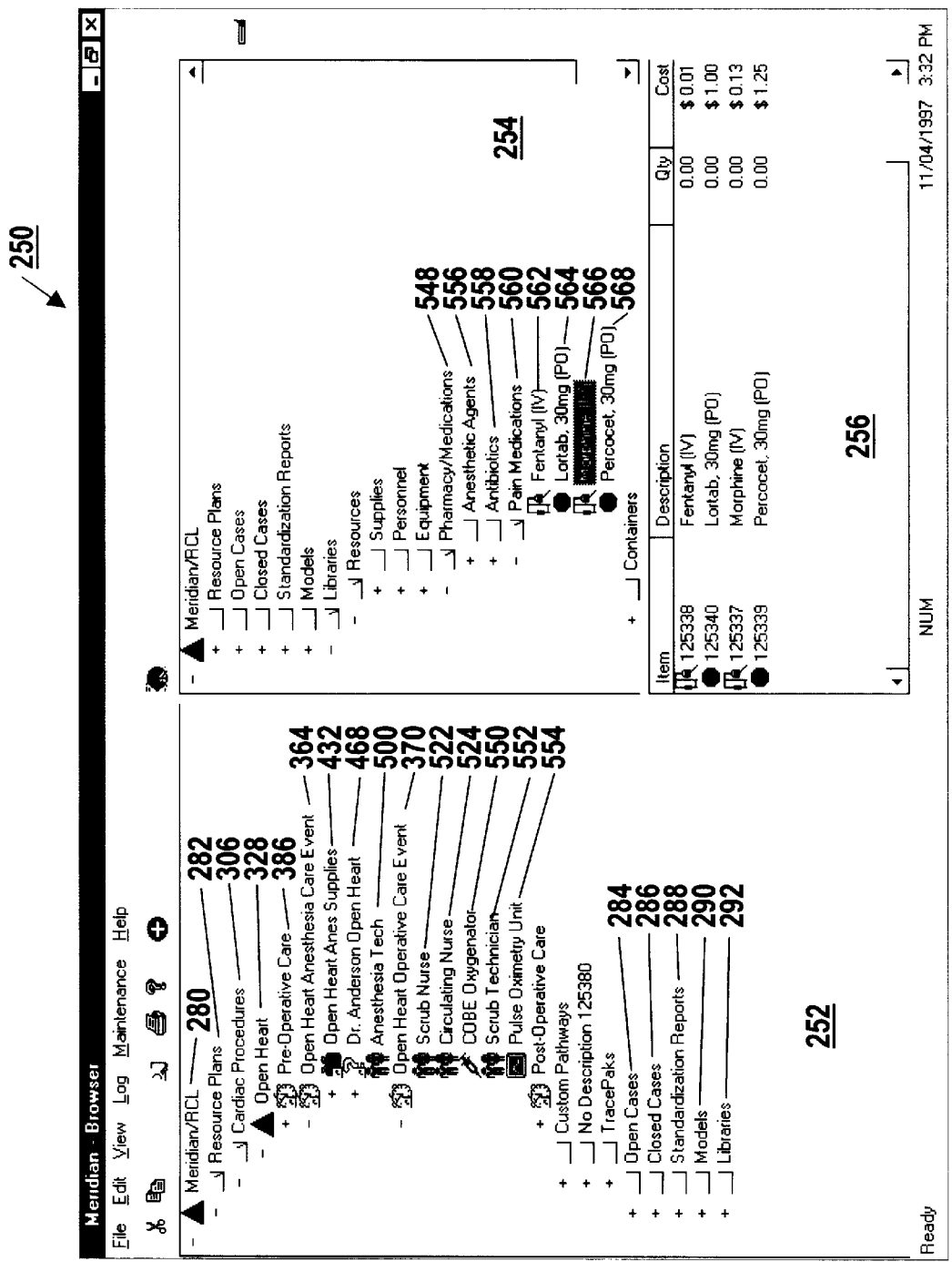

The pharmacy/medication resource object to be added to the previously selected container object is selected in the Second Tree view 254. In the example depicted in FIG. 92, the selected object is the Morphine (IV) pain medication pharmacy/medication resource object 566, which is dragged with the mouse and dropped onto the Open Heart Operative Care Event container object 370 in the Nested Tree view 252. As previously described, this action brings up the Referenced Item window 528, and the user is given the opportunity to add the selected object as either a custom or a standard object to the previously selected container object, as depicted in FIG. 93.

By pressing the Yes button 530, the selected object is added as a standard object to the container. When added in this manner, any changes made to the general template for the selected object will be reflected in the object as it resides within the container to which it has been added. By pressing the No button 532, the selected object is added as a custom object to the container. When added in this manner, any changes made to the general template for the selected object will not be reflected in the object as it resides within the container to which it has been added. By pressing the Cancel button 534, the operation of adding the selected object to the container is cancelled.

Figure 93:
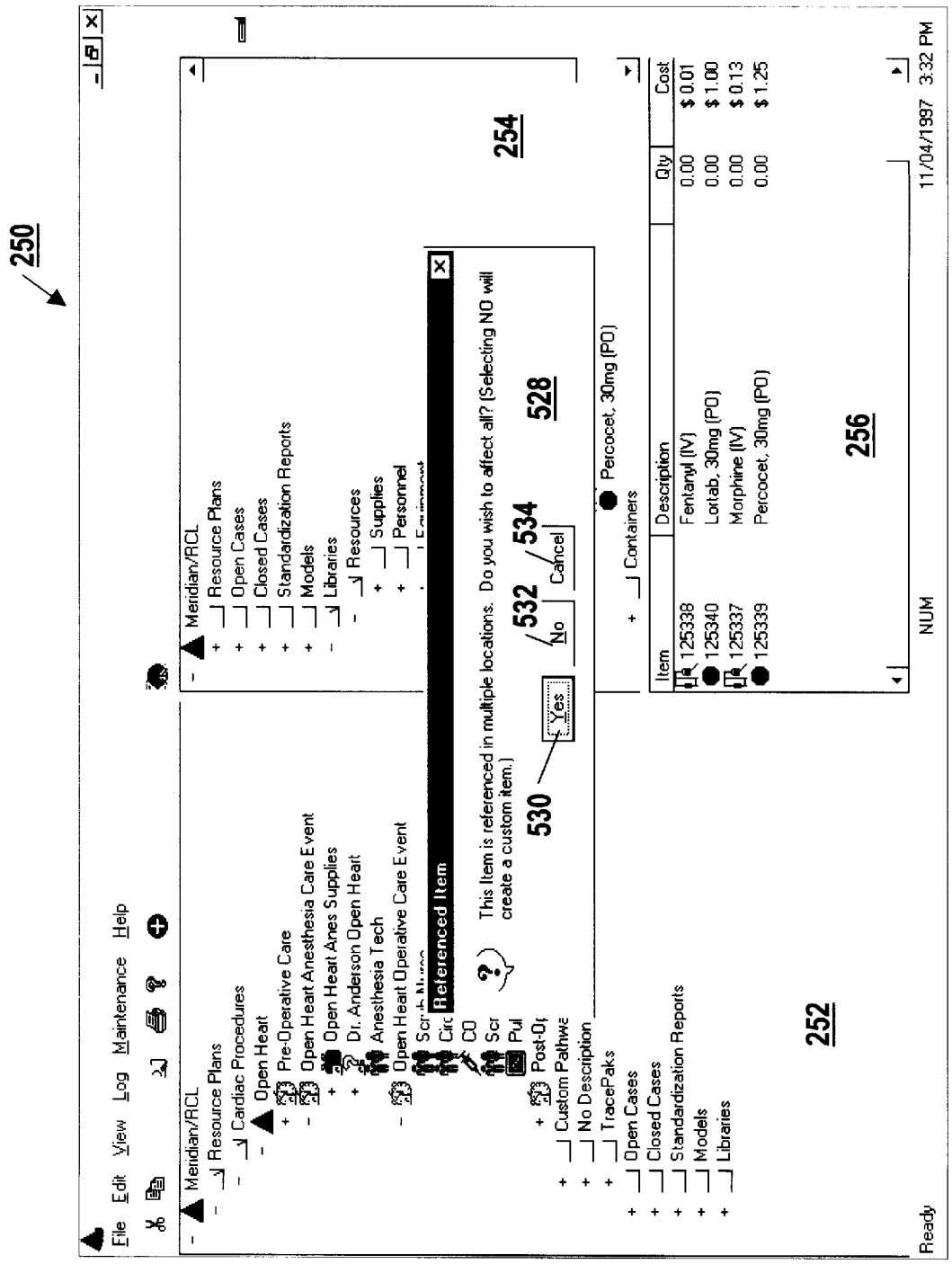
Figure 94:
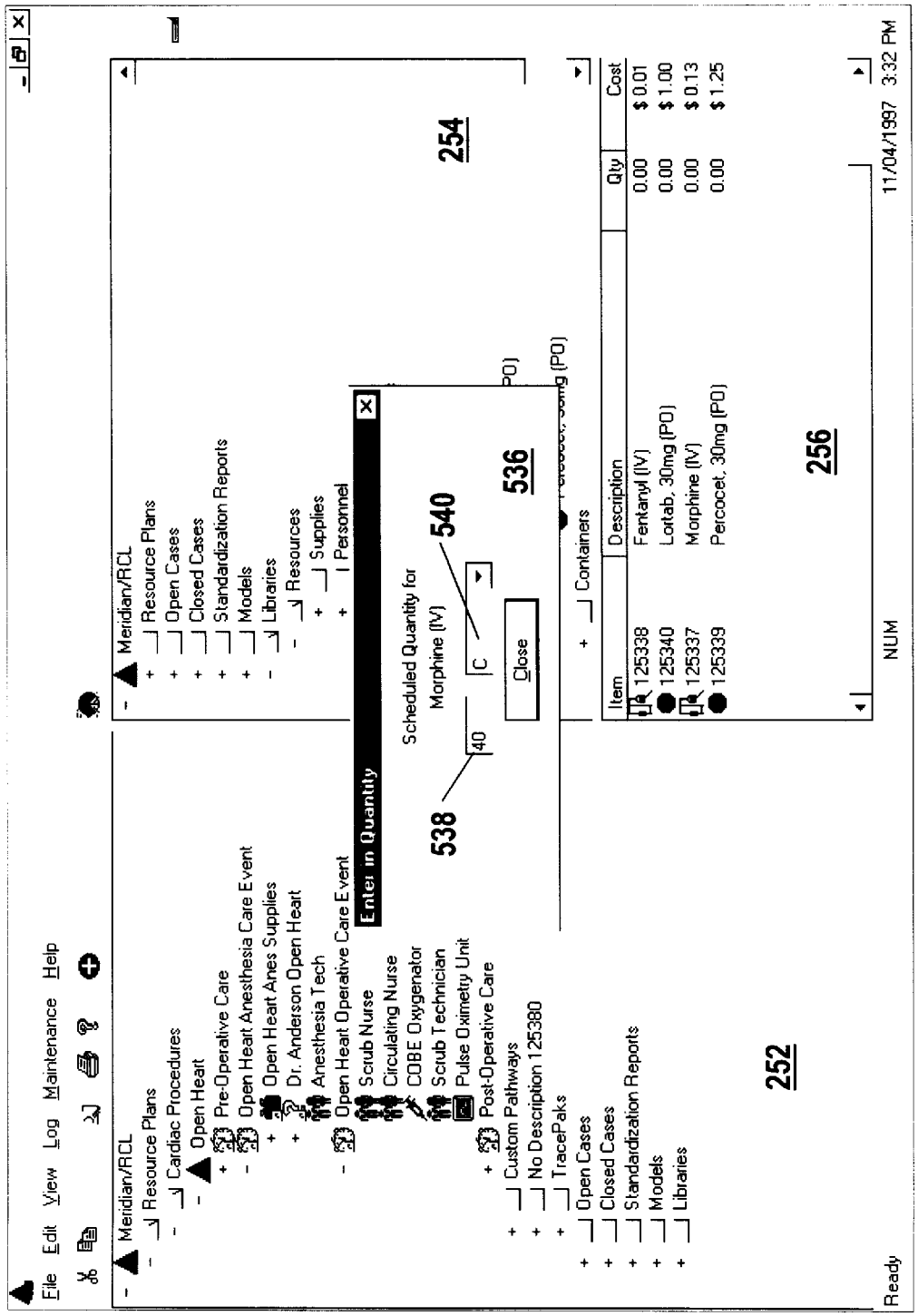
Figure 95:
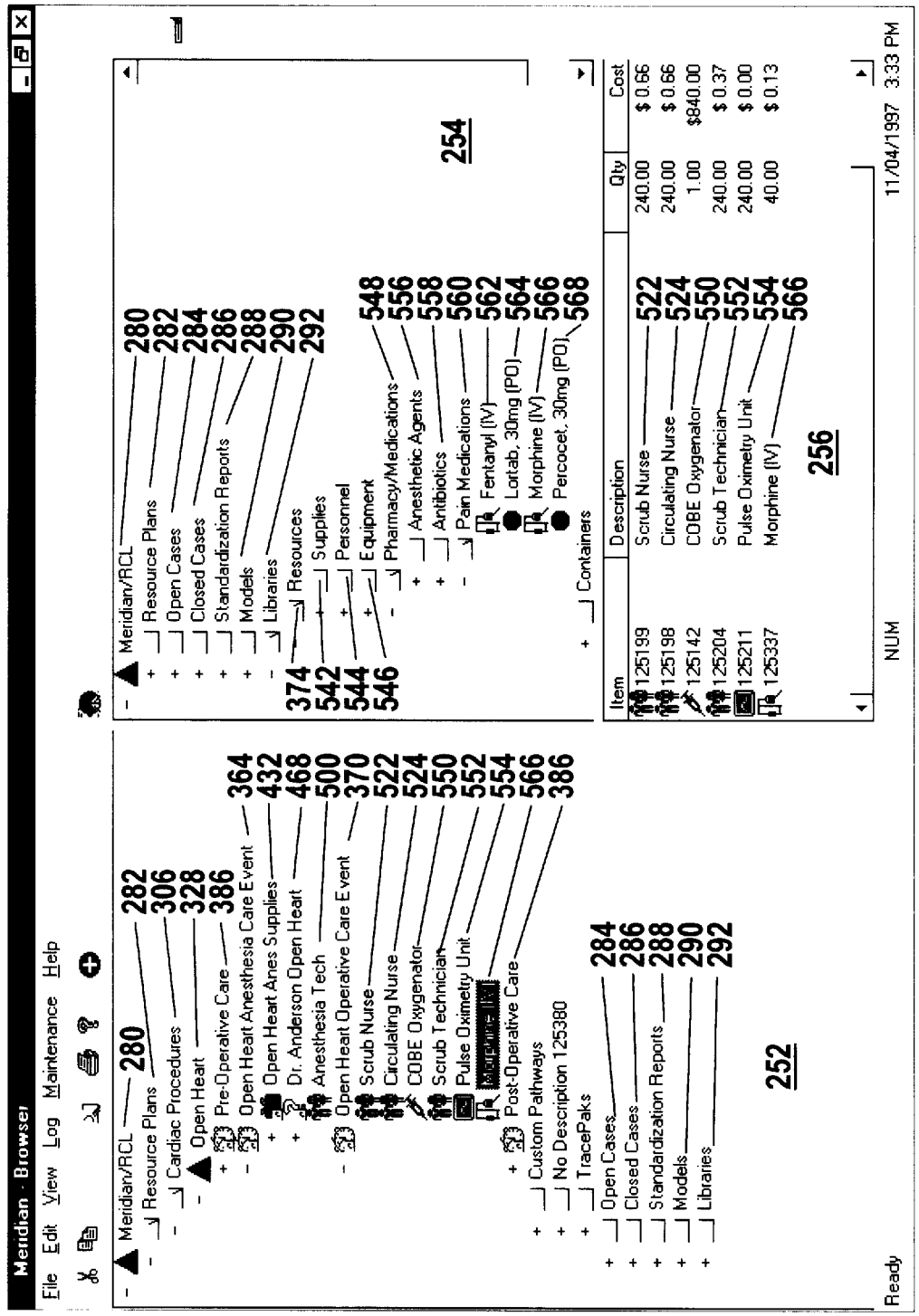

In the example depicted in FIG. 93, the Yes button 530 of the Referenced Item window 528 is pressed, which causes the display of the Enter In Quantity window 536, as depicted in FIG. 94, and as previously described. In the Enter In Quantity window 536, the user is presented with the opportunity to indicate the quantity desired for the specific object to be added to the container. In the example depicted in FIG. 94, the object to be added to the container is a pharmacy/medication resource object, thus, the quantity to be designated is the amount of medication indicated by the pharmacy/medication resource object that is required for the operative care event container object. A value is entered by the user into the Quantity field 538, and the Close button 540 is pressed. The newly added Morphine (IV) pain medication pharmacy/medication resource object 566 is depicted under the Open Heart Operative Care Event container object 370 in the Nested Tree view 252 of the Browser window 250, as depicted in FIG. 95.

Figure 96:
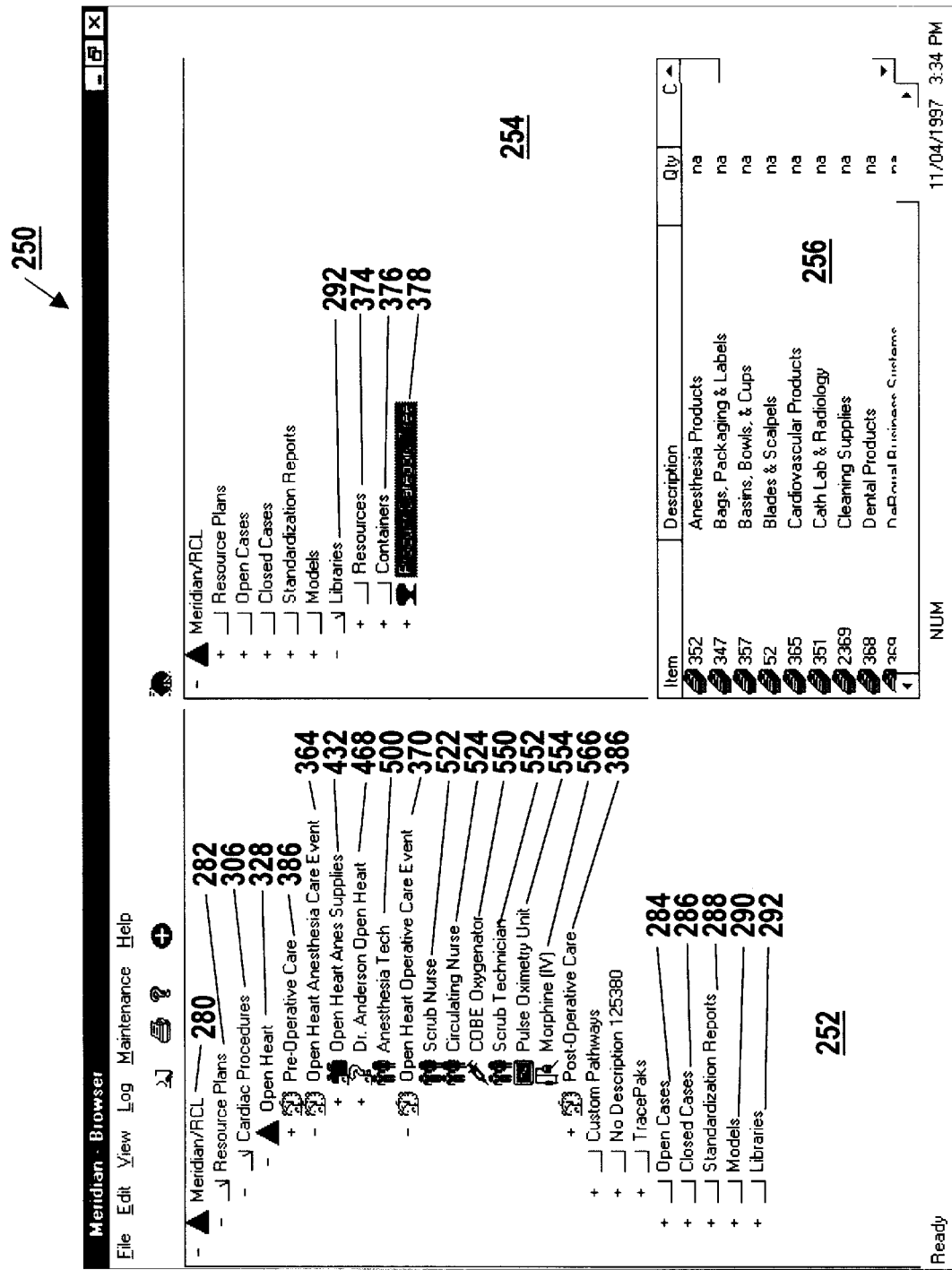

Beginning with FIG. 96, a method for adding an object from the Product Category Tree 378 to the Open Heart Operative Care Event container object 370 is described. The Product Category Tree 378 is a special container object, or folder, that contains a special selection of objects. In the example next explained, the Product Category Tree 378 contains predefined objects representing items that are available from DeRoyal Industries, Inc. Thus, the Product Category Tree 378 is representative of other special collections that could be available, such as product catalogs of other vendors.

Figure 97:
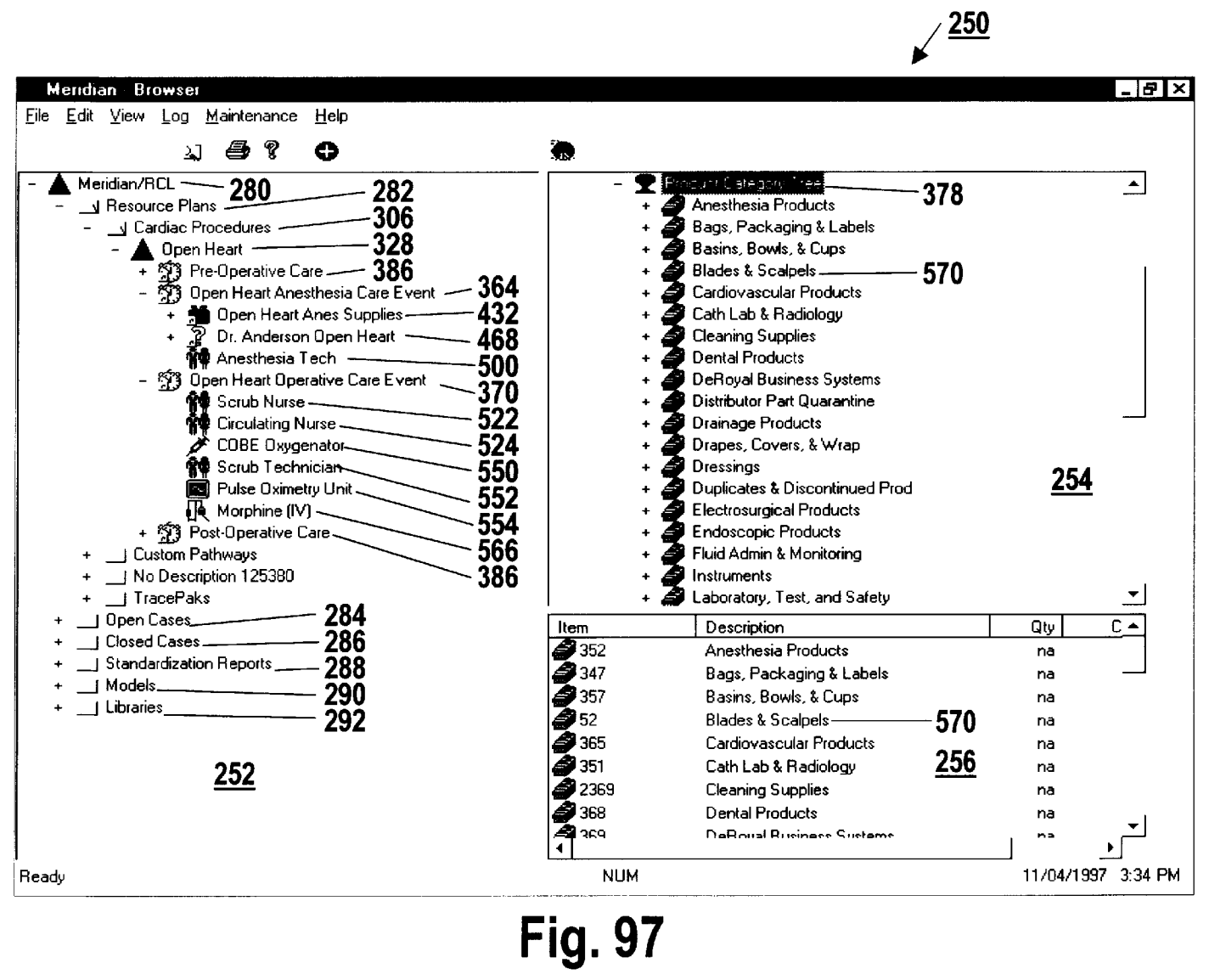
Figure 98:
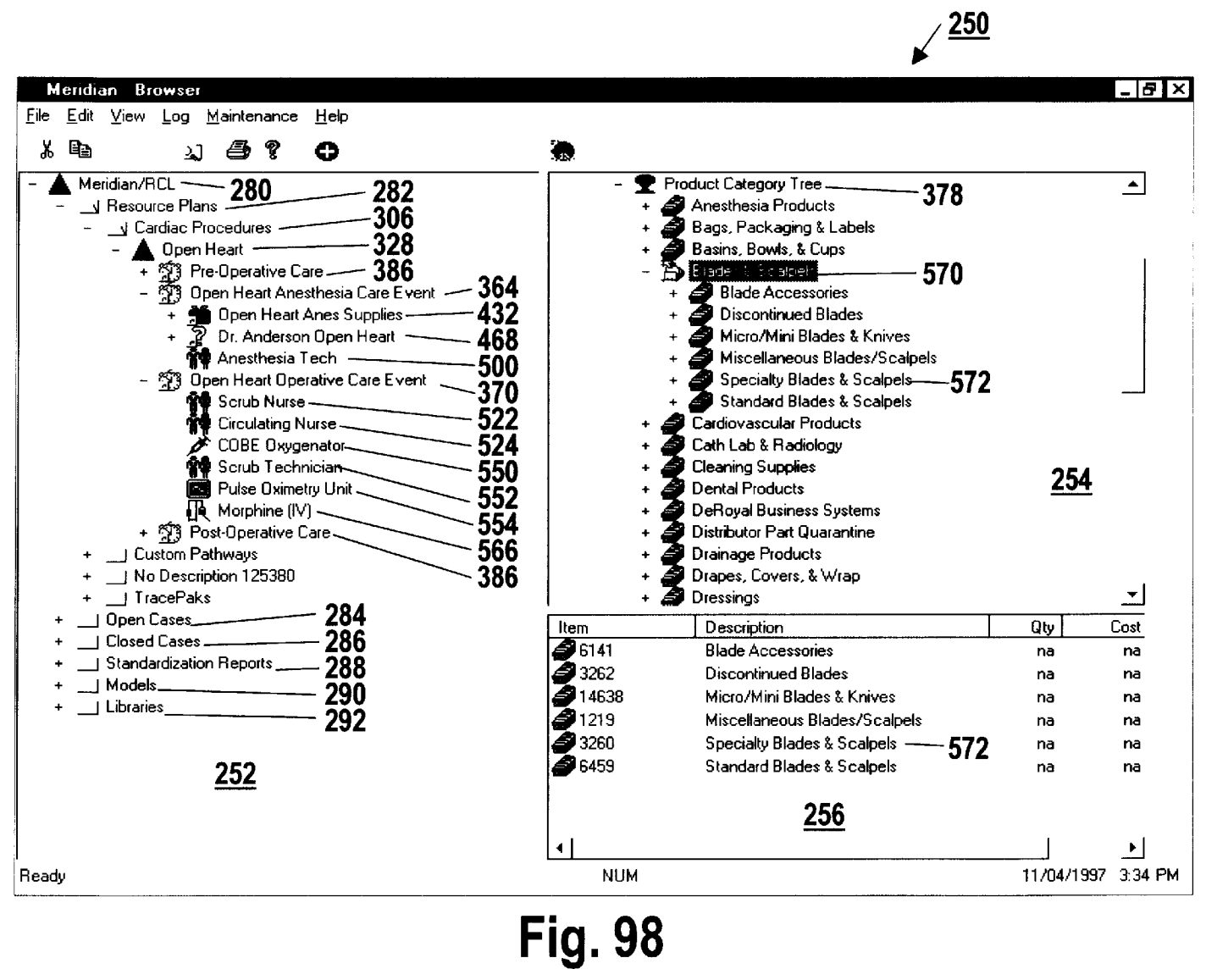

The container object to which the product category tree object is to be added is selected in the Nested Tree view 252, and then the appropriate folder is selected in the Second Tree view 254. Opening the Product Category Tree folder 378 displays the items inside of the Product Category Tree folder 378, which in the example depicted in FIG. 97 is a selection of additional container objects, including the Blades & Scalpels folder 570. Opening the Blades & Scalpels folder 570 displays the various predefined equipment objects within the Blades & Scalpels folder 570, as depicted in FIG. 98. The predefined blades & scalpels objects within the Blades & Scalpels folder 570 are depicted in a hierarchical tree form in the Second Tree view 254 and in a list form in the List view 256, as depicted in FIG. 98, and include the Specialty Blades & Scalpels folder 572. It is noted that these items are also folders, or in other words container objects, which themselves hold additional objects.

Figure 99:
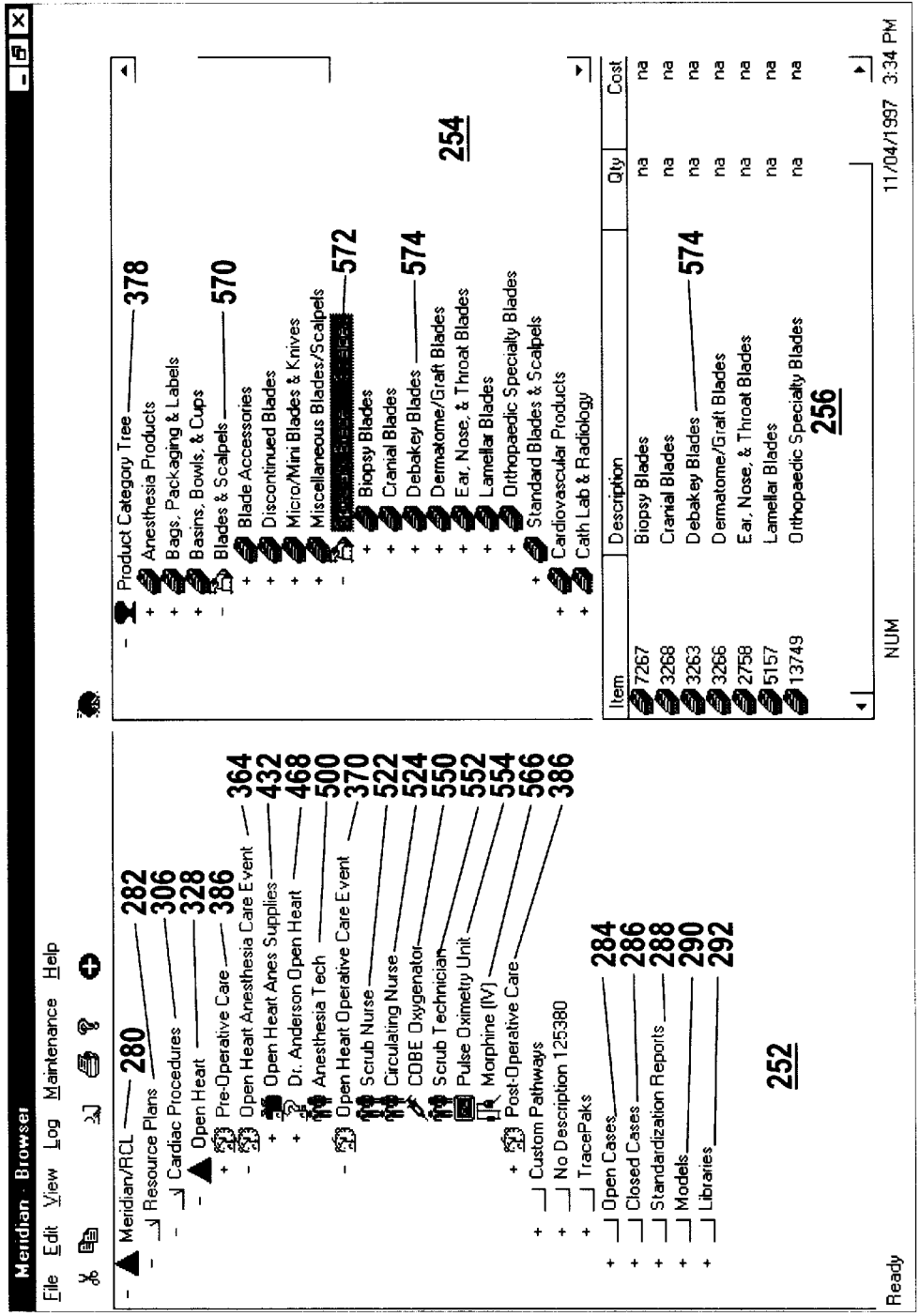
Figure 100:
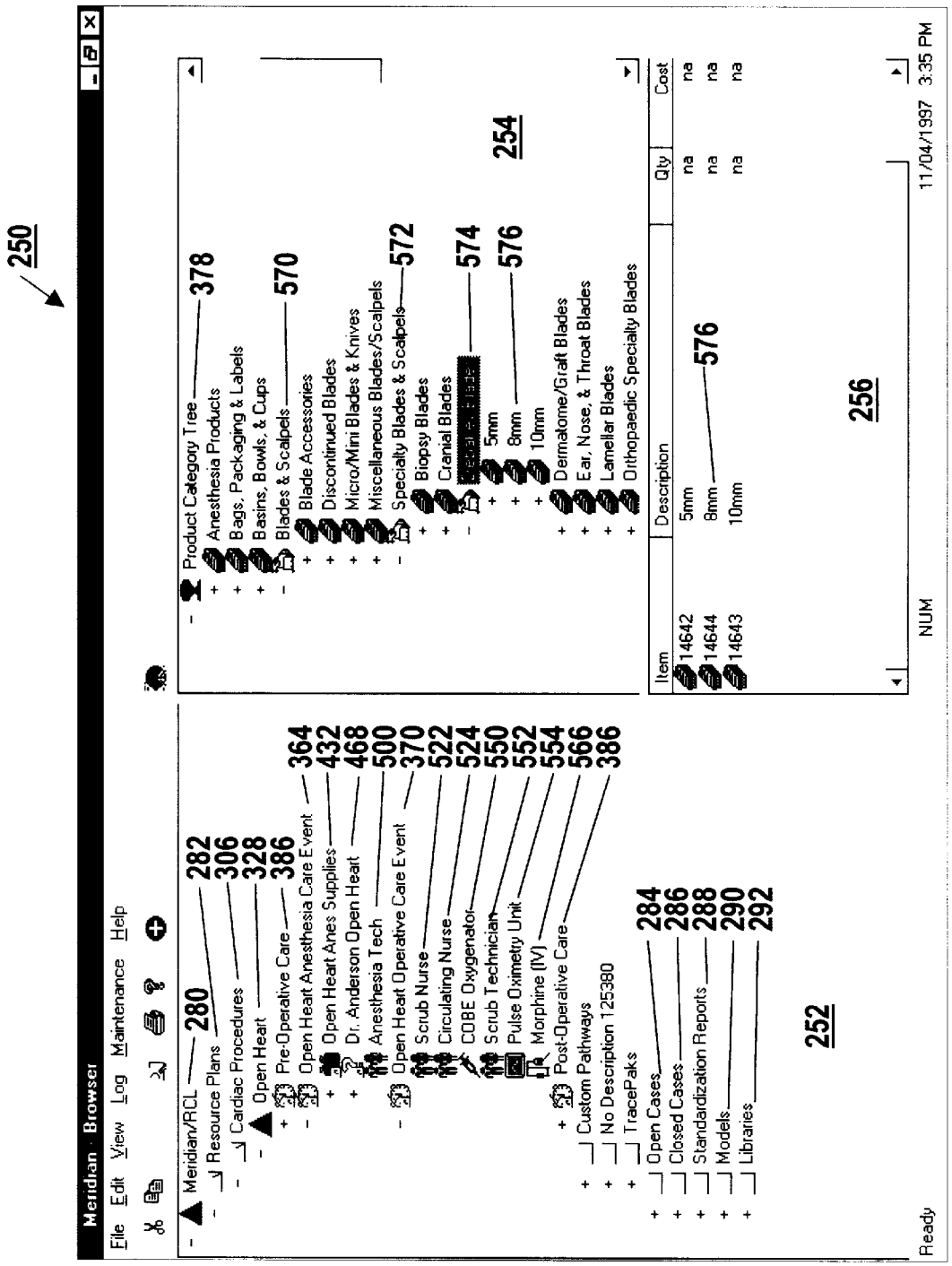
Figure 101:
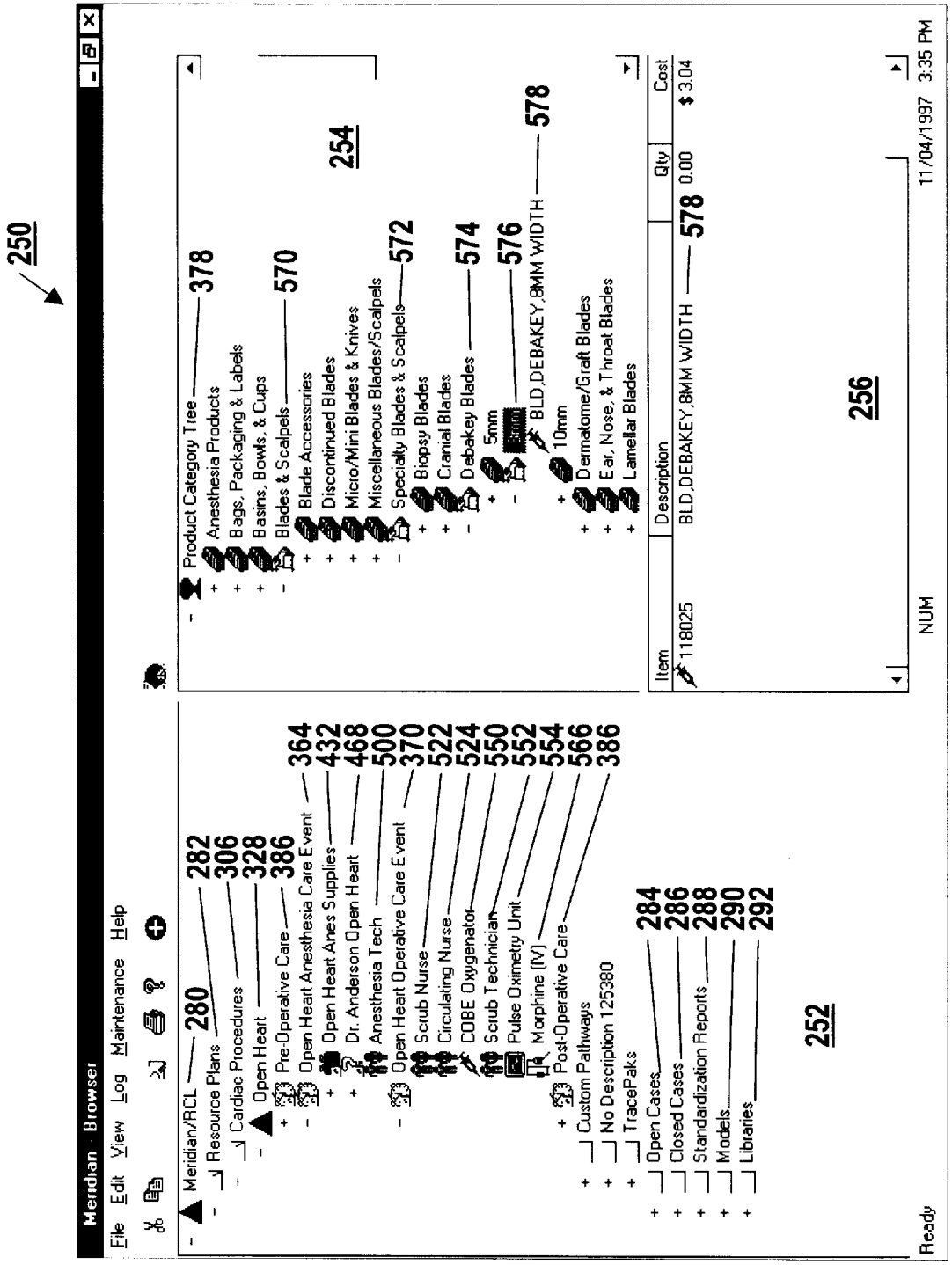

As depicted in FIG. 99, opening the Specialty Blades & Scalpels folder 572 in the Second Tree view 254 displays the additional objects located within that folder. In the example depicted in FIG. 99, these additional items include more container objects, including the Debakey Blades folder 574. The Debakey Blades folder 574 is selected and opened in FIG. 100, displaying additional container objects within the Debakey Blades folder 574, including the 8 mm container object 576. The 8 mm container object 576 is selected and opened as depicted in FIG. 101, displaying the Bld, Debakey, 8 mm Width supply resource object 578 located within the 8 mm container object 576.

Figure 102:
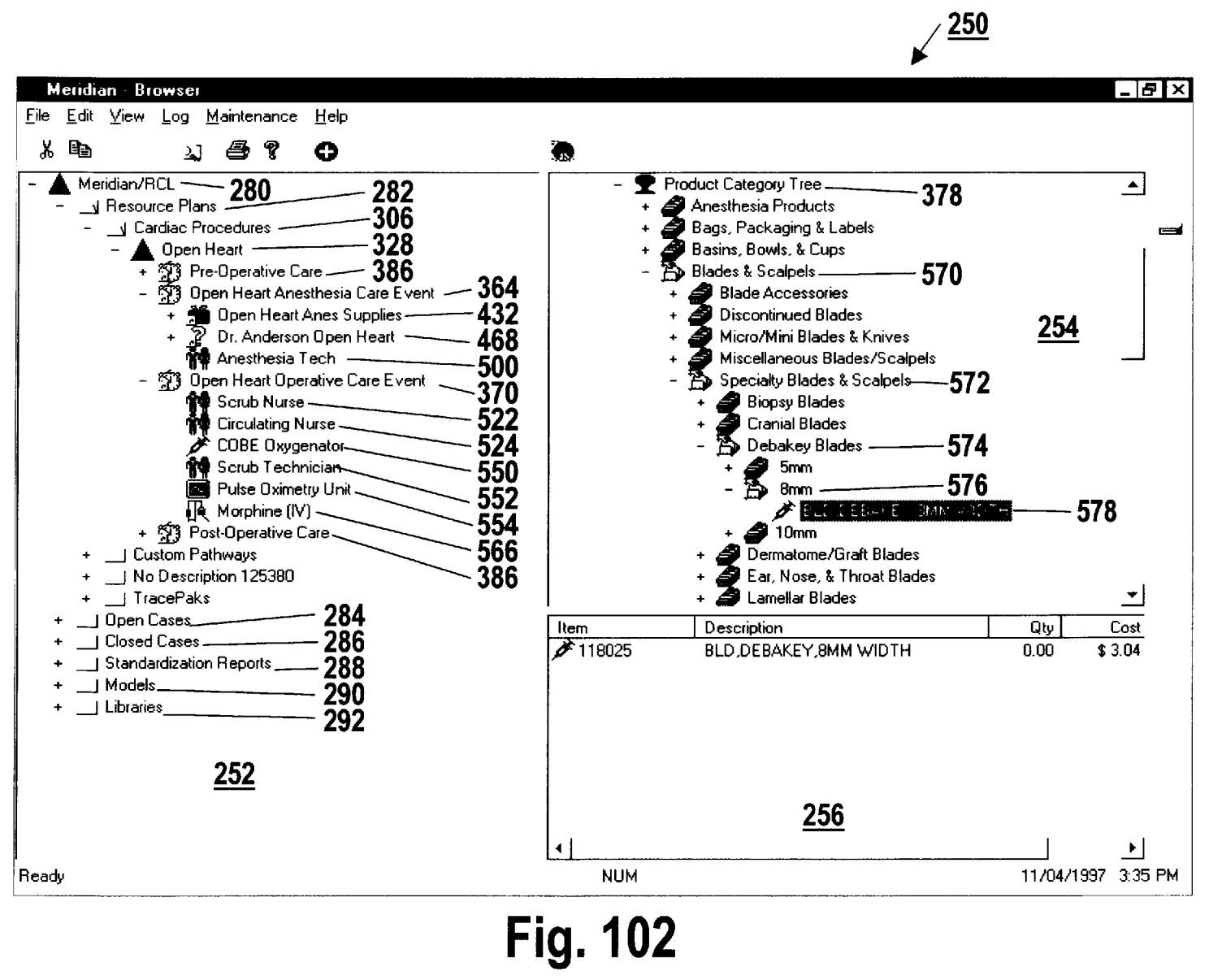

The supply resource object to be added to the previously selected container object is selected in the Second Tree view 254. In the example depicted in FIG. 102, the selected object is the Bld, Debakey, 8 mm Width supply resource object 578, which is dragged with the mouse and dropped onto the Open Heart Operative Care Event container object 370 in the Nested Tree view 252. As previously described, this action brings up the Referenced Item window 528, and the user is given the opportunity to add the selected object as either a custom or a standard object to the previously selected container object, as depicted in FIG. 103.

By pressing the Yes button 530, the selected object is added as a standard object to the container. When added in this manner, any changes made to the general template for the selected object will be reflected in the object as it resides within the container to which it has been added. By pressing the No button 532, the selected object is added as a custom object to the container. When added in this manner, any changes made to the general template for the selected object will not be reflected in the object as it resides within the container to which it has been added. By pressing the Cancel button 534, the operation of adding the selected object to the container is cancelled.

Figure 103:
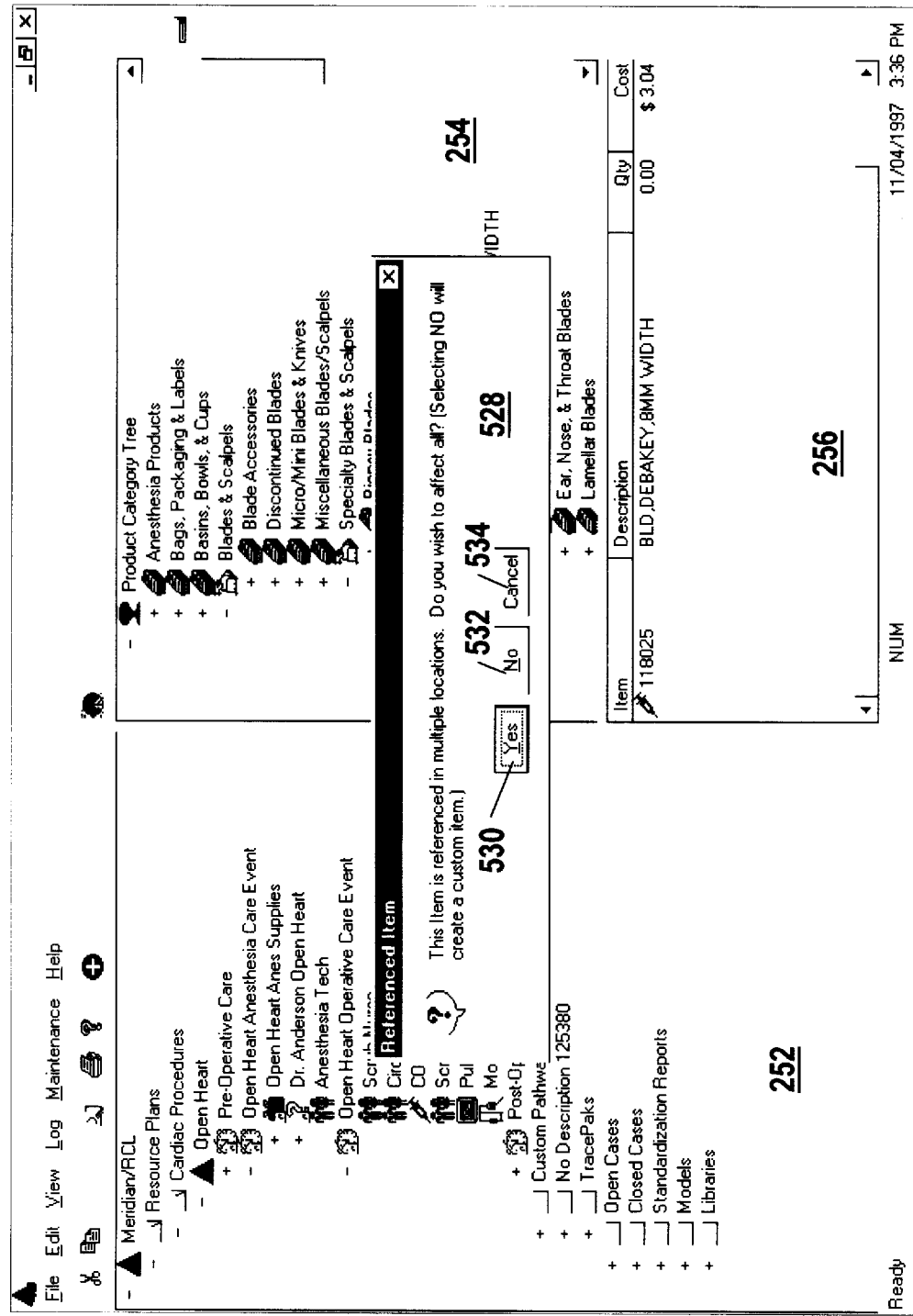
Figure 104:
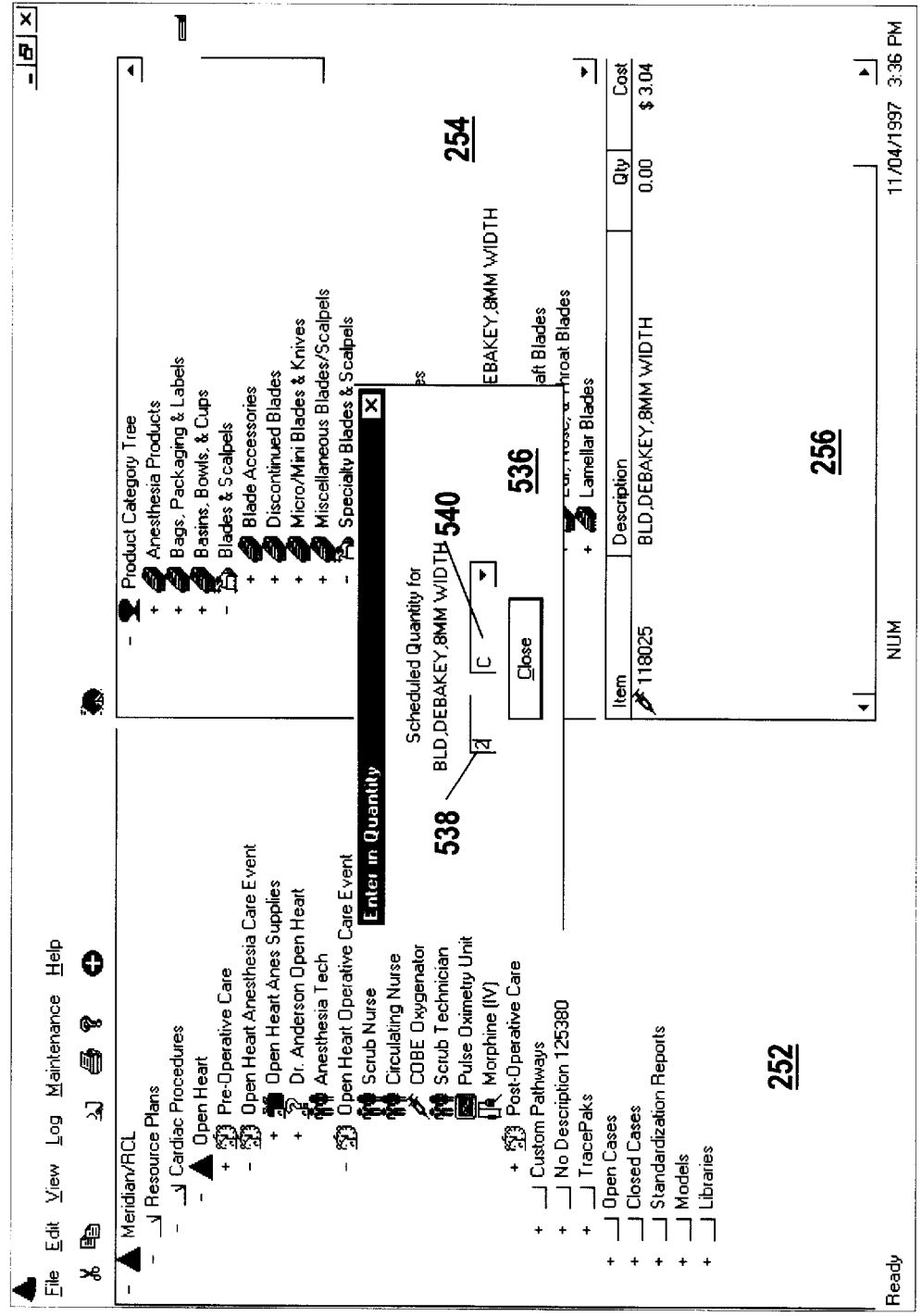
Figure 105:
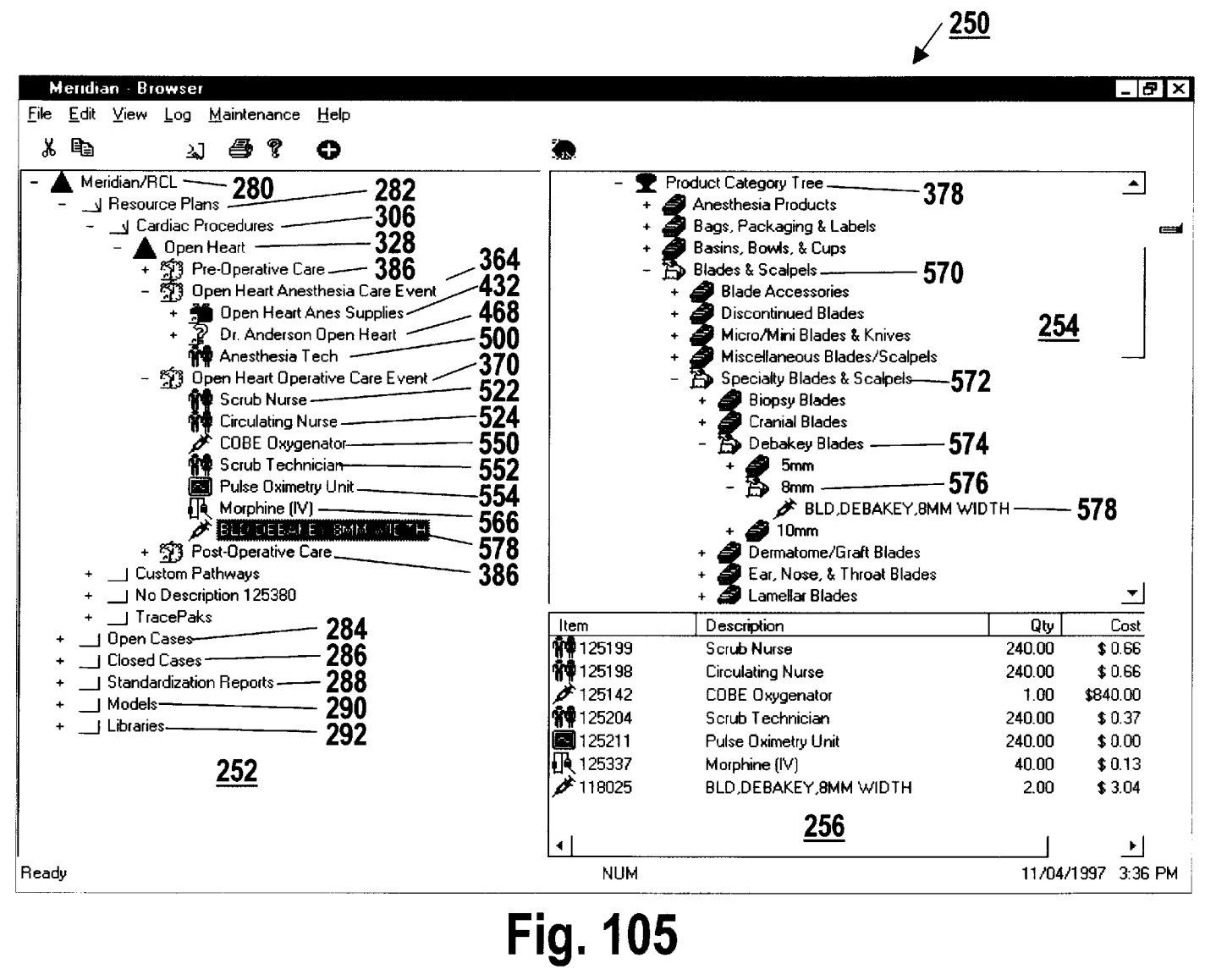

In the example depicted in FIG. 103, the Yes button 530 of the Referenced Item window 528 is pressed, which causes the display of the Enter In Quantity window 536, as depicted in FIG. 104, and as previously described. In the Enter In Quantity window 536, the user is presented with the opportunity to indicate the quantity desired for the specific object to be added to the container. In the example depicted in FIG. 104, the object to be added to the container is a supply resource object, thus, the quantity to be designated is the number of items indicated by the supply resource object that is required for the operative care event container object. A value is entered by the user into the Quantity field 538, and the Close button 540 is pressed. The newly added Bld, Debakey, 8 mm Width supply resource object 578 is depicted under the Open Heart Operative Care Event container object 370 in the Nested Tree view 252 of the Browser window 250, as depicted in FIG. 105.

The discussion above has briefly described some of the aspects of creating and working with procedural pathways. As a part of this discussion, the creation of different types of container objects has been described, including care event container objects and bundle container objects. In addition, the creation and maintenance of resource objects has been described, including supply resource objects, personnel resource objects, and equipment resource objects. Further, the nesting of these objects, one within another, has also been briefly described.

Figure 106:
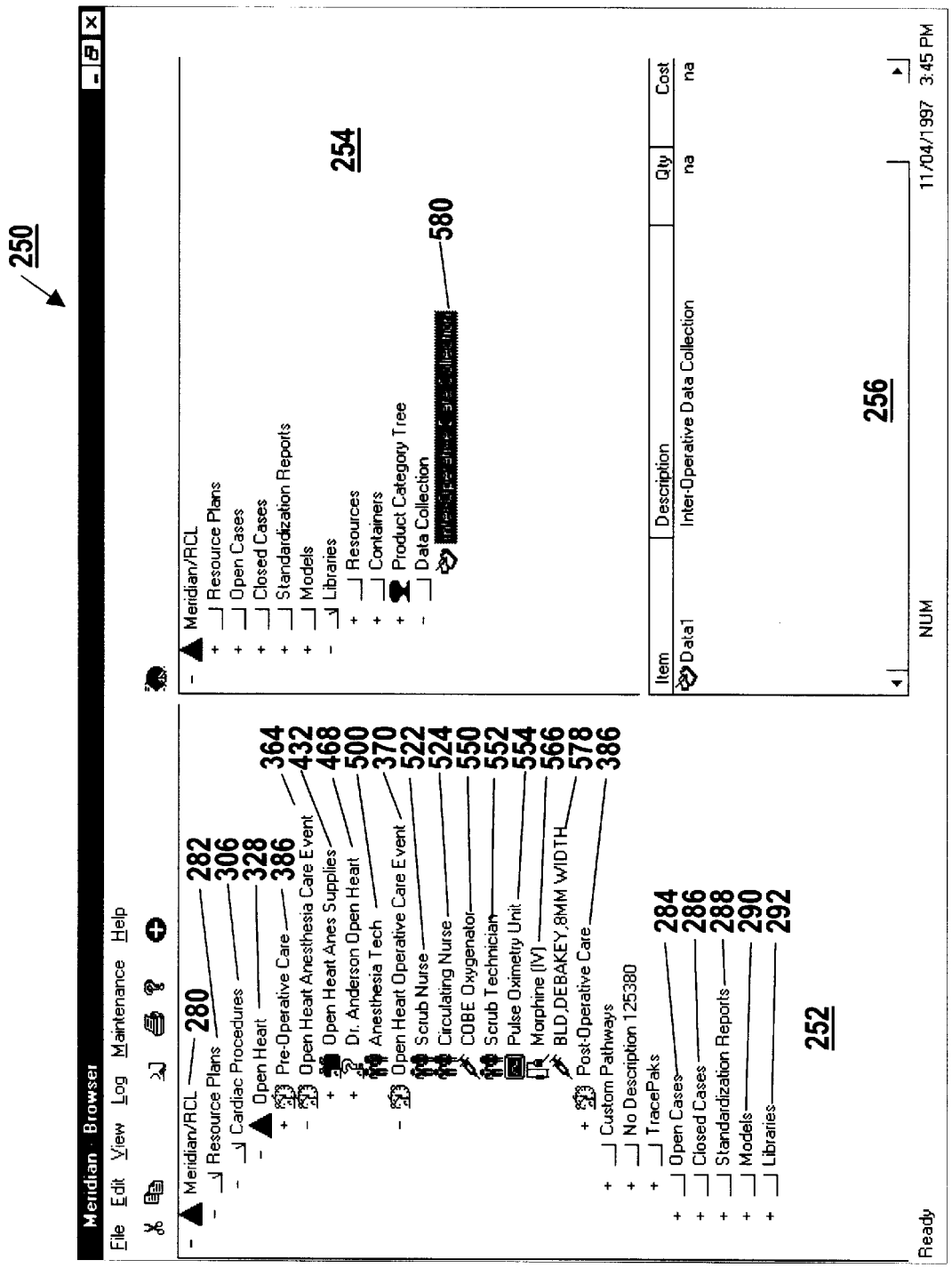

A third type of object, a data object, is depicted in FIG. 106. In this example, Inter-Operative Data Collection data object 580 is selected in the Second Tree view 254 of the Browser window 250. The Inter-Operative Data Collection data object 580 is representative of other data objects, which are not depicted in the figures. Data objects are used to hold information, such as may be necessary for the completion of a procedural pathway, or gathered during the performance of a procedural pathway.

For example, when a patient is admitted to the hospital, a data object could be created for the patient's demographic and clinical information. This data object could be a part of the admitting procedural pathway container object. As a part of the performance of the procedural pathway, a nurse, doctor, technician, or staff member could request or otherwise gather information from the patient and enter it into the management system. The information stored within the data object can be used to select various options within the current or later procedural pathways.

For example, the reason for admittance, such as a specific type of hip surgery, can be stored in the data object and used to select the correct procedural pathway for hip surgery. The patient's sex, also stored in the data object, can select the appropriate type of catheter, a supply resource object, in a bundle container object. The patient's height and weight can select the appropriate medication in a similar manner. Further, the designation of the patient's doctor, stored within the data object, can select the appropriate bundle container object specific to the designated physician. Thus, the data objects provide the management system with the ability to optionally select conditional branching routes within the various available procedural pathways, as well as with a location to store the data taken during the performance of those procedural pathways.

Figure 107:
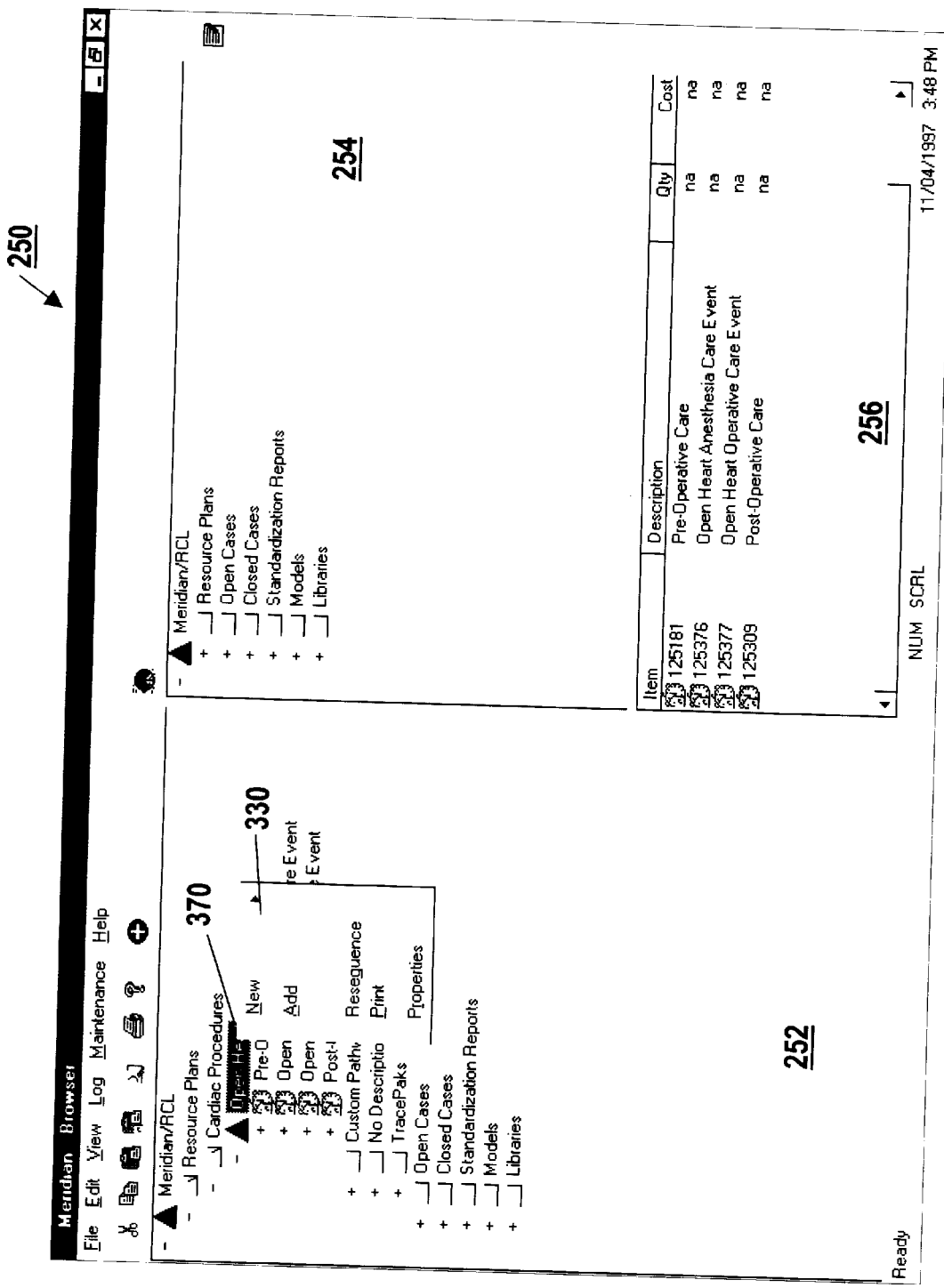
Figure 108:
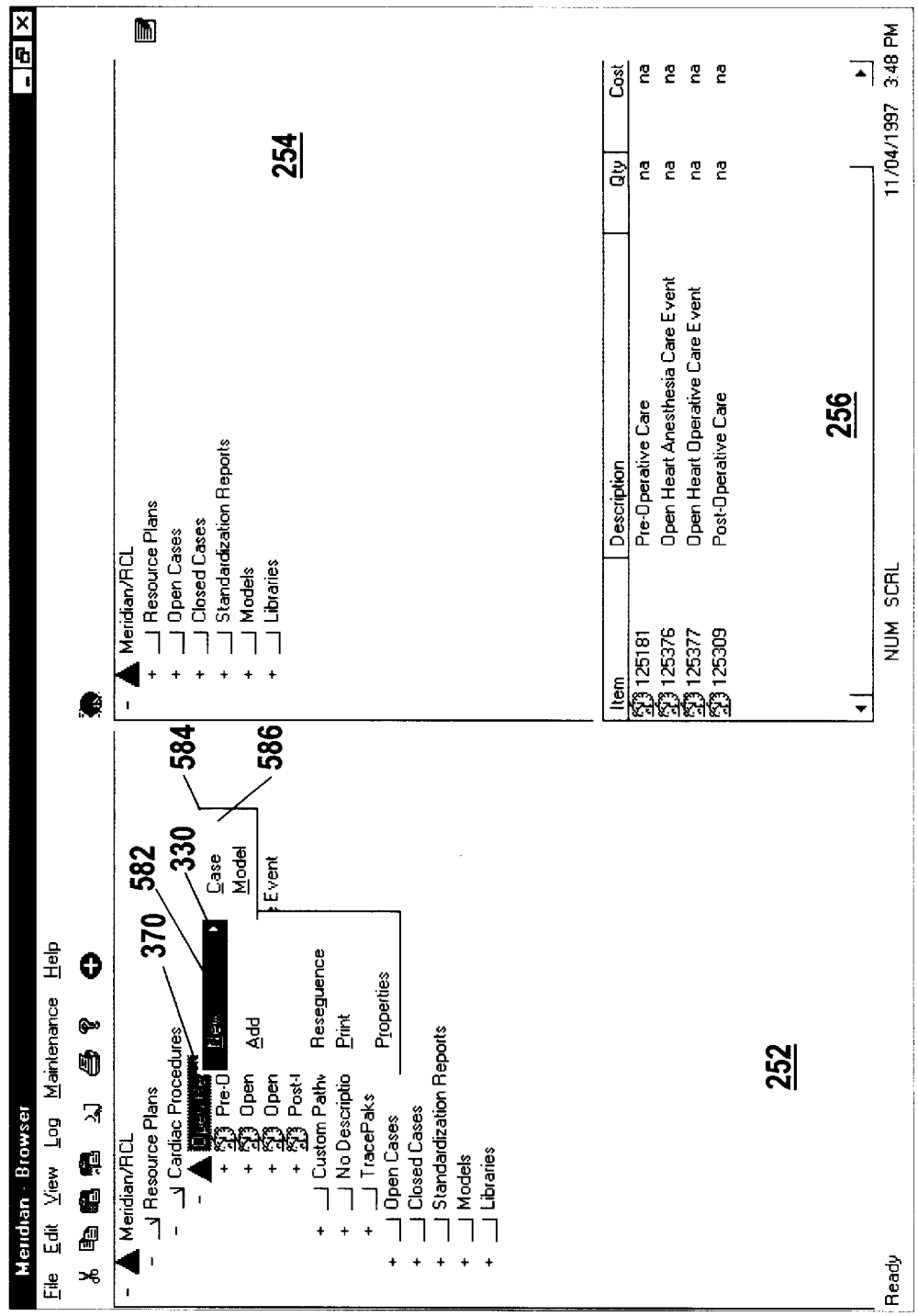
Figure 109:
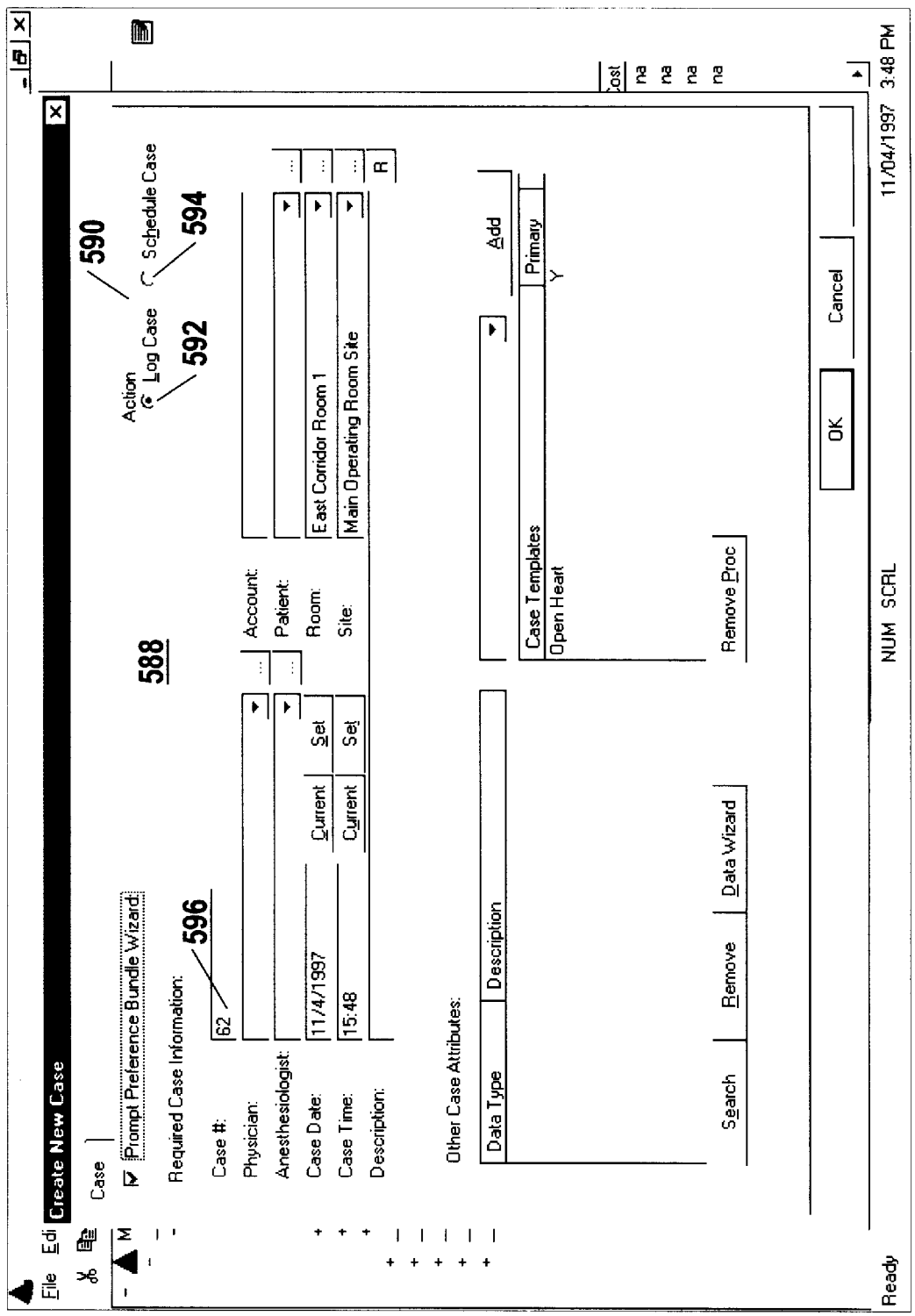

Commencing with FIG. 107, we turn aside from the description of creating pathways, and move now towards a description of the various ways in which the pathways can be used. In FIG. 107, the Open Heart Operative care event 370 is selected in the Nested Tree view 252 and the Procedural pathway Module menu 330 is invoked, such as by right clicking on the Open Heart Operative care event 370. FIG. 108 depicts the selection of the New function 582, which invokes the New submenu 584. Selecting the Case function 586 from the New submenu 584 invokes the Create New Case window 588, as depicted in FIG. 109.

The Create New Case window 588 receives information about a specific case that will follow the selected procedural pathway, which in this example is the Open Heart Operative care event 370. Thus, the Create New Case window 588 is used to copy the general template of the procedural pathway to an actual case, wherein the procedural pathway to be followed by an actual patient is charted, and where the procedural pathway as actually performed for the patient is recorded. The Action palette 590 allows the case to be logged, such as by selecting the Log Case function 592, or scheduled, such as by selecting the Schedule Case function 594.

Logging a case indicates that the patient has already completed the procedural pathway, the data has been gathered, and the case is being created to provide a record of what has already been accomplished. Scheduling a case indicates that the patient has not yet completed the procedural pathway, and the case is being created to provide a prompt for the data that needs to be gathered and the supplies, personnel, and equipment that need to be scheduled or consumed. In the example depicted in FIG. 109, the case is being logged after the procedural pathway has been completed, and so the Log Case function 592 is selected.

Figure 110:
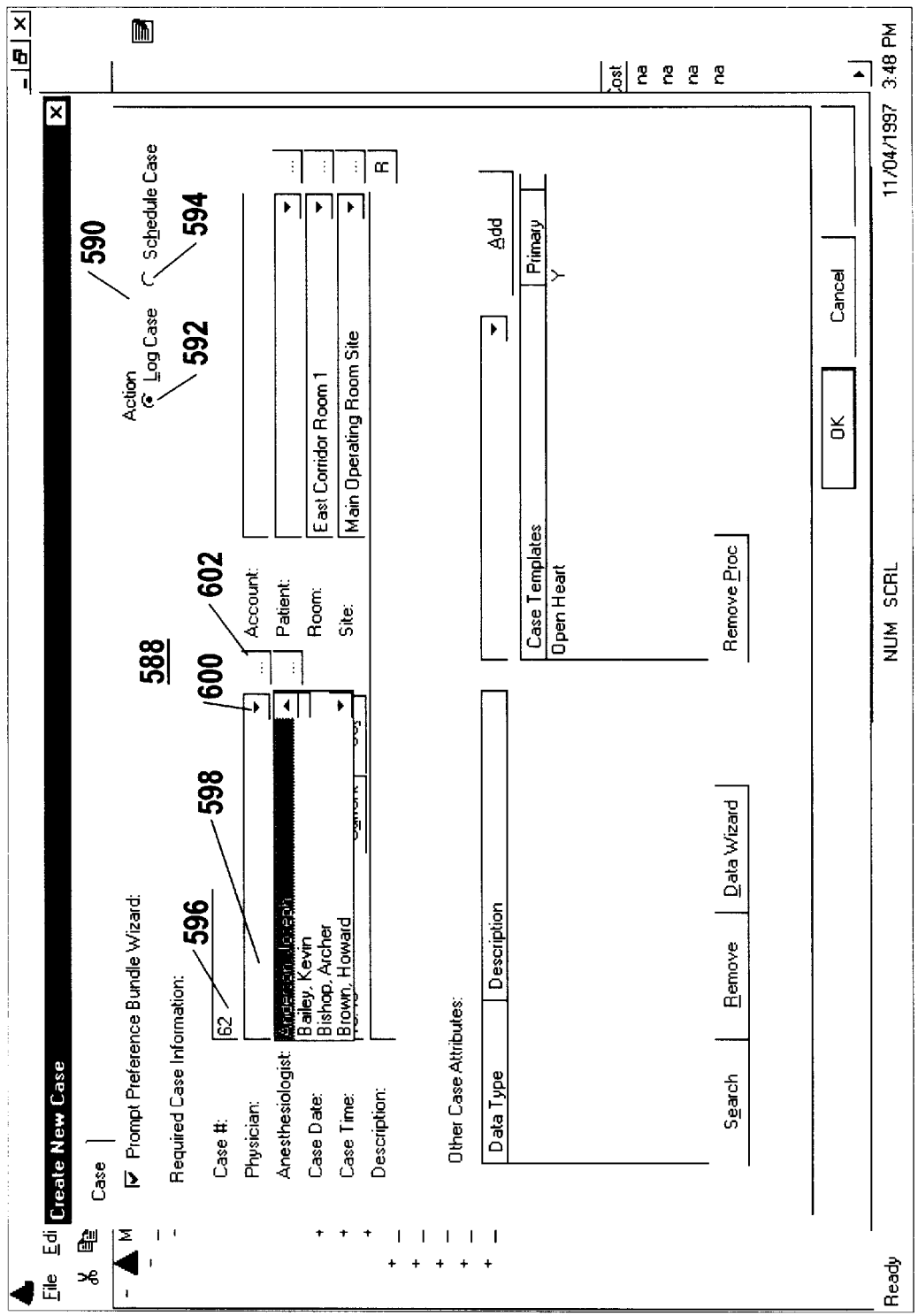

A case number is assigned to the case, which number is depicted in the Case # field 596. In the example depicted the case number has been automatically assigned by the management system. However, in alternate embodiments the user is able to select any case number desired, preferably a case number that has not been assigned to any other case. The patient's physician is selected from the Physician field 598, as depicted in FIG. 110. The correct physician can be selected in a variety of ways. For example, as depicted in FIG. 110, the Drop List button 600 is selected, invoking an alphabetized list of available physicians.

Alternately, the first few letters of the name of the correct physician can be typed into the Physician field 598 prior to or after selecting the Drop List button, which will cause the list of available physicians to automatically scroll to a position in the alphabetized list corresponding to the first few letters so typed. Further, the Criteria Selection button 602 may be selected to display additional selection criteria for selecting the appropriate physician. Once the correct physician has been identified, clicking on the name enters it in the Physician field 598, as depicted in FIG. 111.

Figure 111:
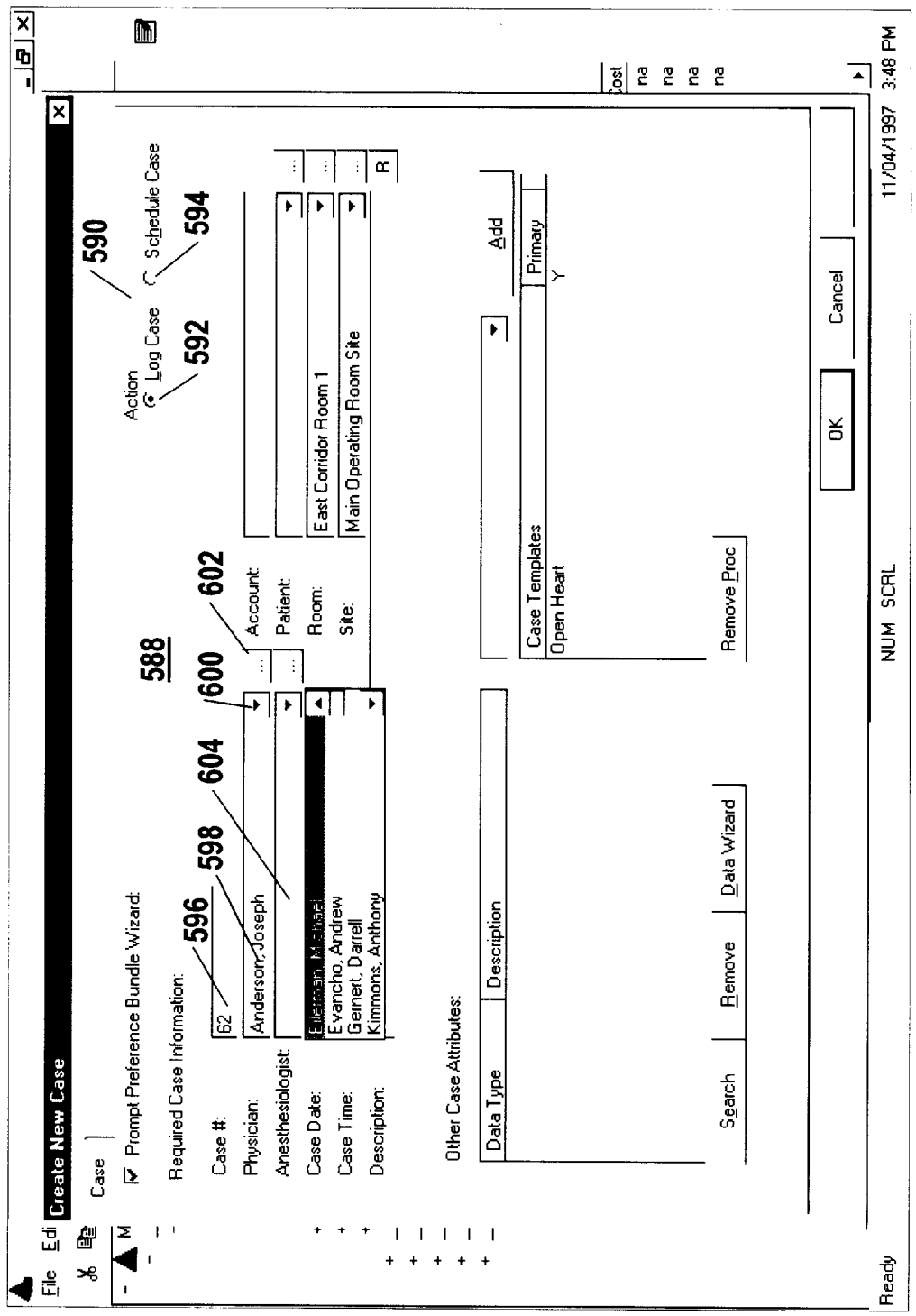
Figure 112:
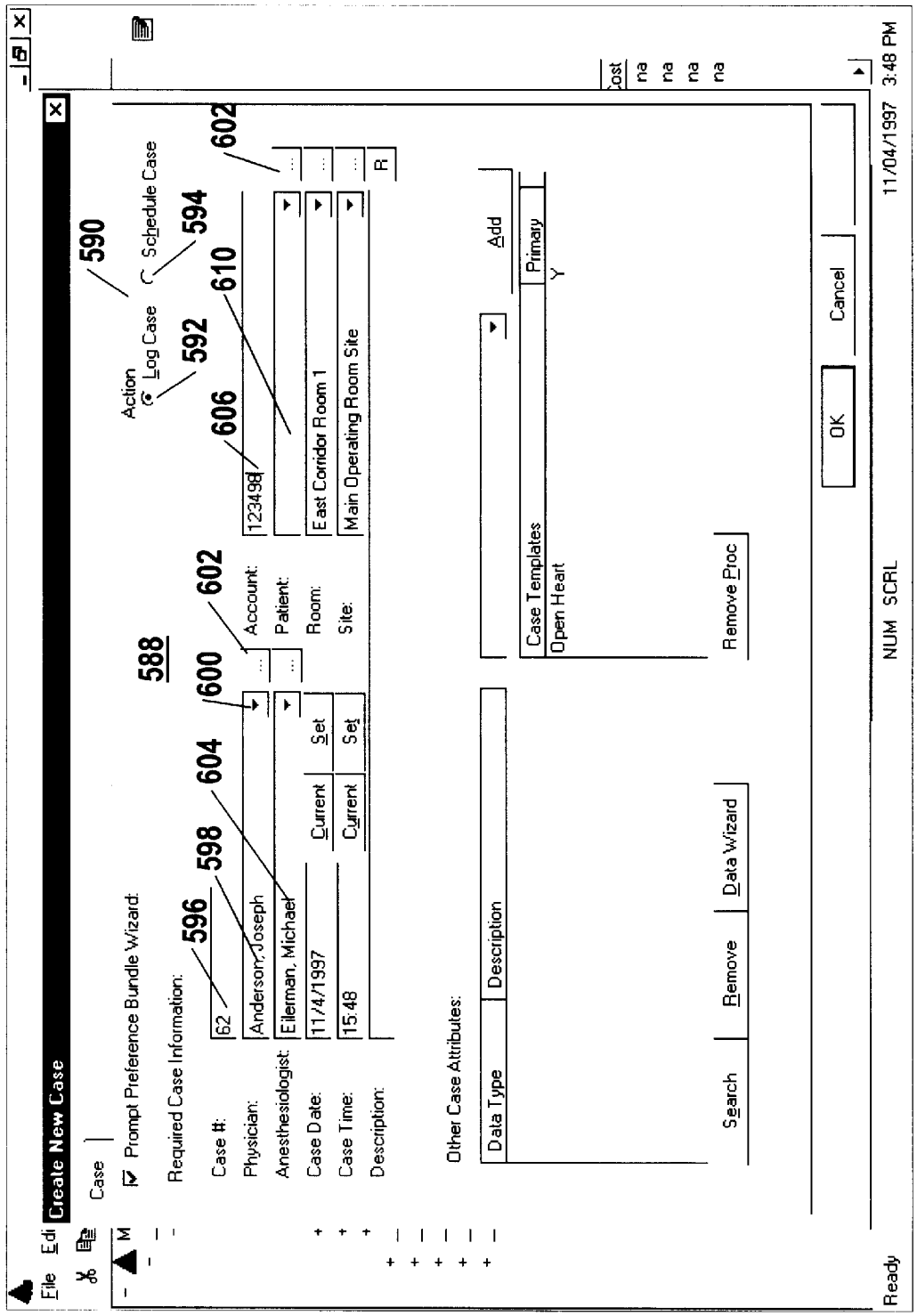

FIG. 111 also depicts the method of selecting the appropriate anesthesiologist in the Anesthesiologist field 604. Preferably, this is done in the same manner as that used to select the correct physician. Thus, the same options for locating the correct anesthesiologist are available, such as invoking the alphabetized list with the Drop List button 600 and displaying additional selection criteria with the Criteria Selection button 602. As before, when the correct anesthesiologist is located, the name is displayed in the Anesthesiologist field 604 by selecting it, as depicted in FIG. 112. The account number, associating the patient with this specific case, is entered into the Account field 606, also as depicted in FIG. 112.

Figure 113:
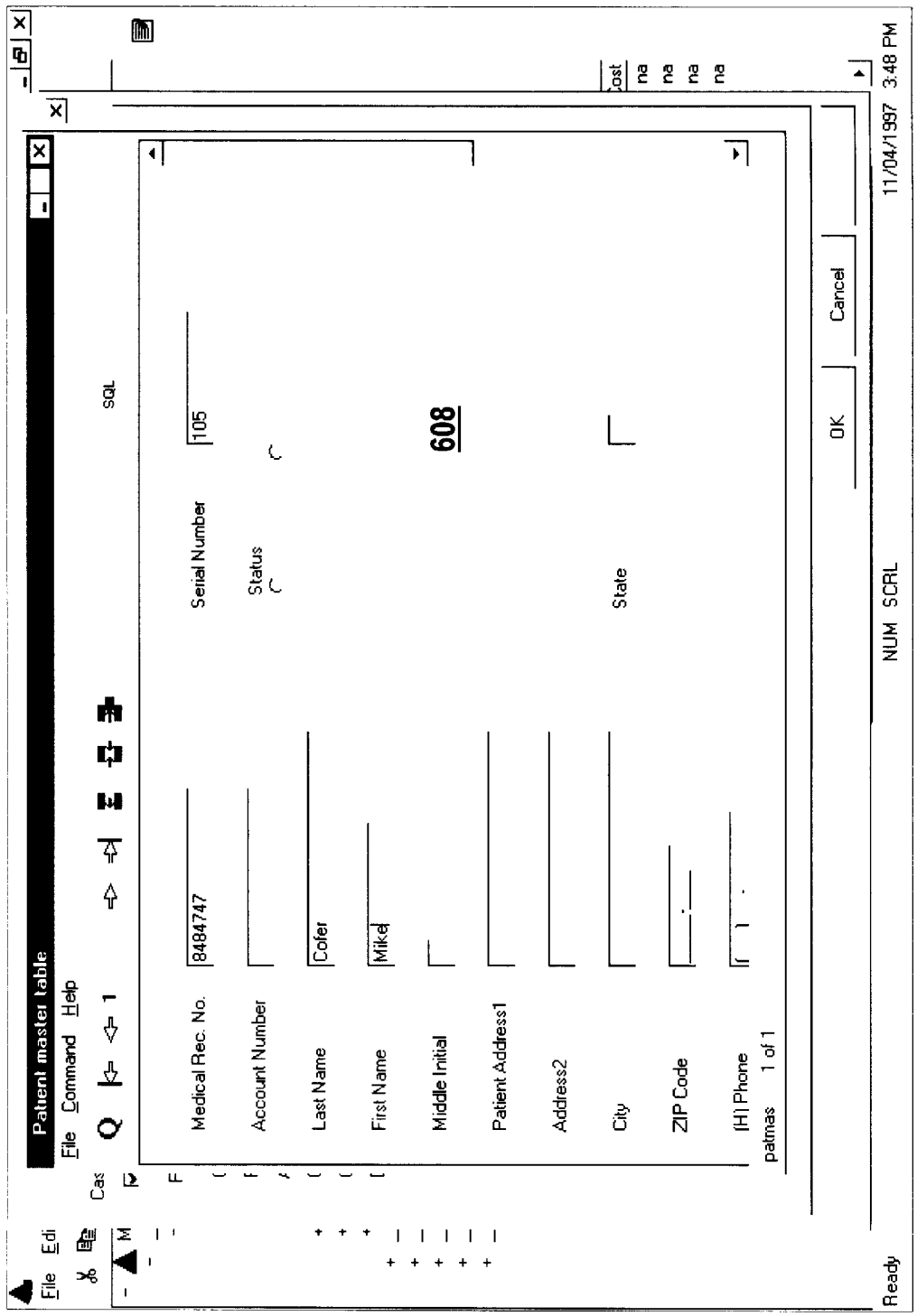

Selecting the Criteria Selection button 602 associated with the Patient field 110 invokes the Patient Master Table window 608, as depicted in FIG. 113. The Patient Master Table window 608 is used to locate the correct patient by matching one or more of a variety of identification information, such as medical record number, account number, last name, first name, middle initial, address, city, zip code, state, or other information, as depicted in FIG. 113. In this manner, a variety of information that may be more readily known or remembered about the patient may be used to select the correct patient. This screen may also be used to create a new patient designation that did not exist previously.

Figure 114:
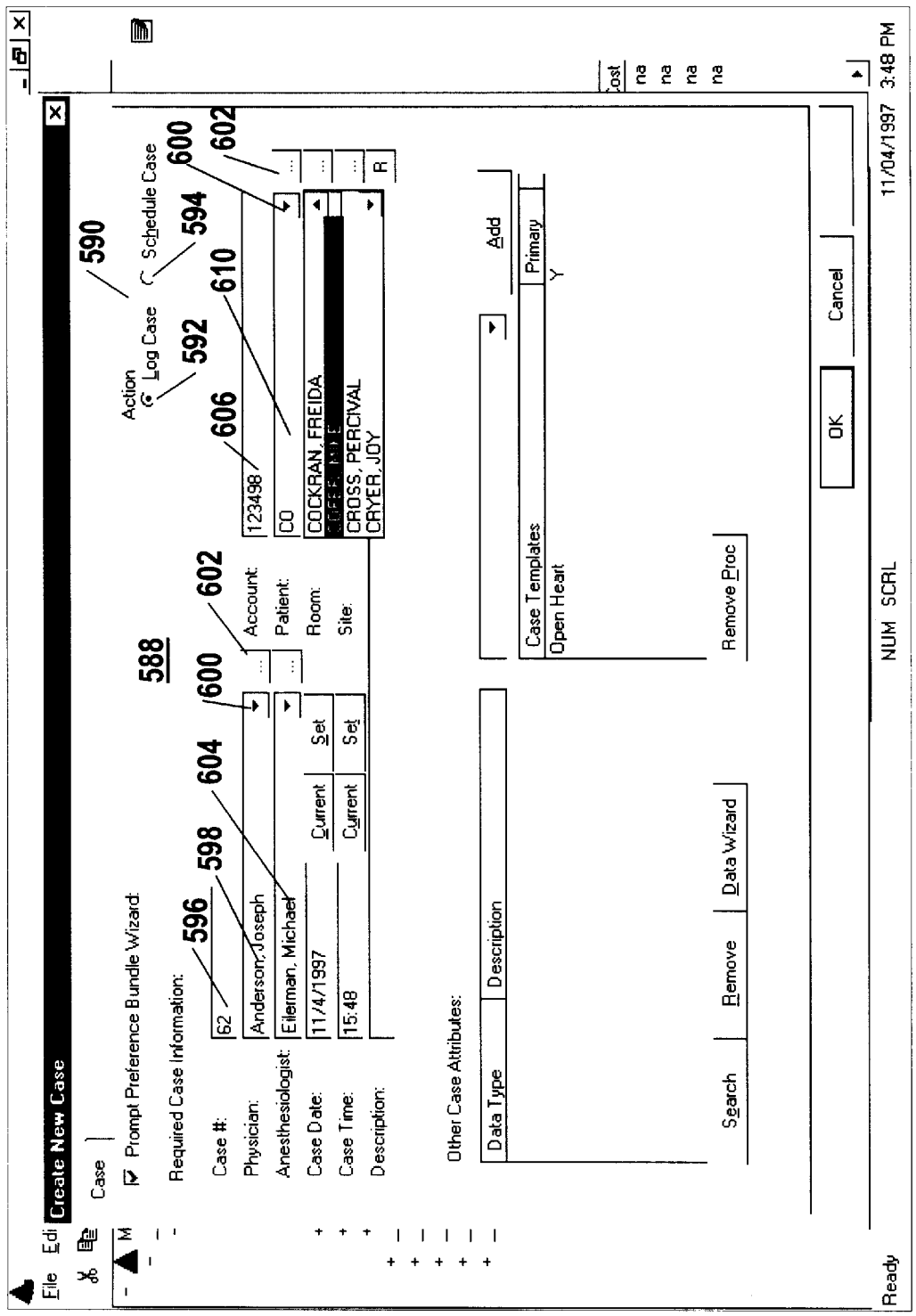

FIG. 114 depicts an alternate method of selecting the correct patient, by typing in the first few letters of the patient's name, as described above. As depicted, typing in the first two letters of the patient's name scrolls the alphabetized list of patient names to the first such name satisfying the search criteria. In this manner, the user can quickly scroll to the relevant portion of the patient name list, and thereby more readily locate and enter the correct name.

Figure 115:
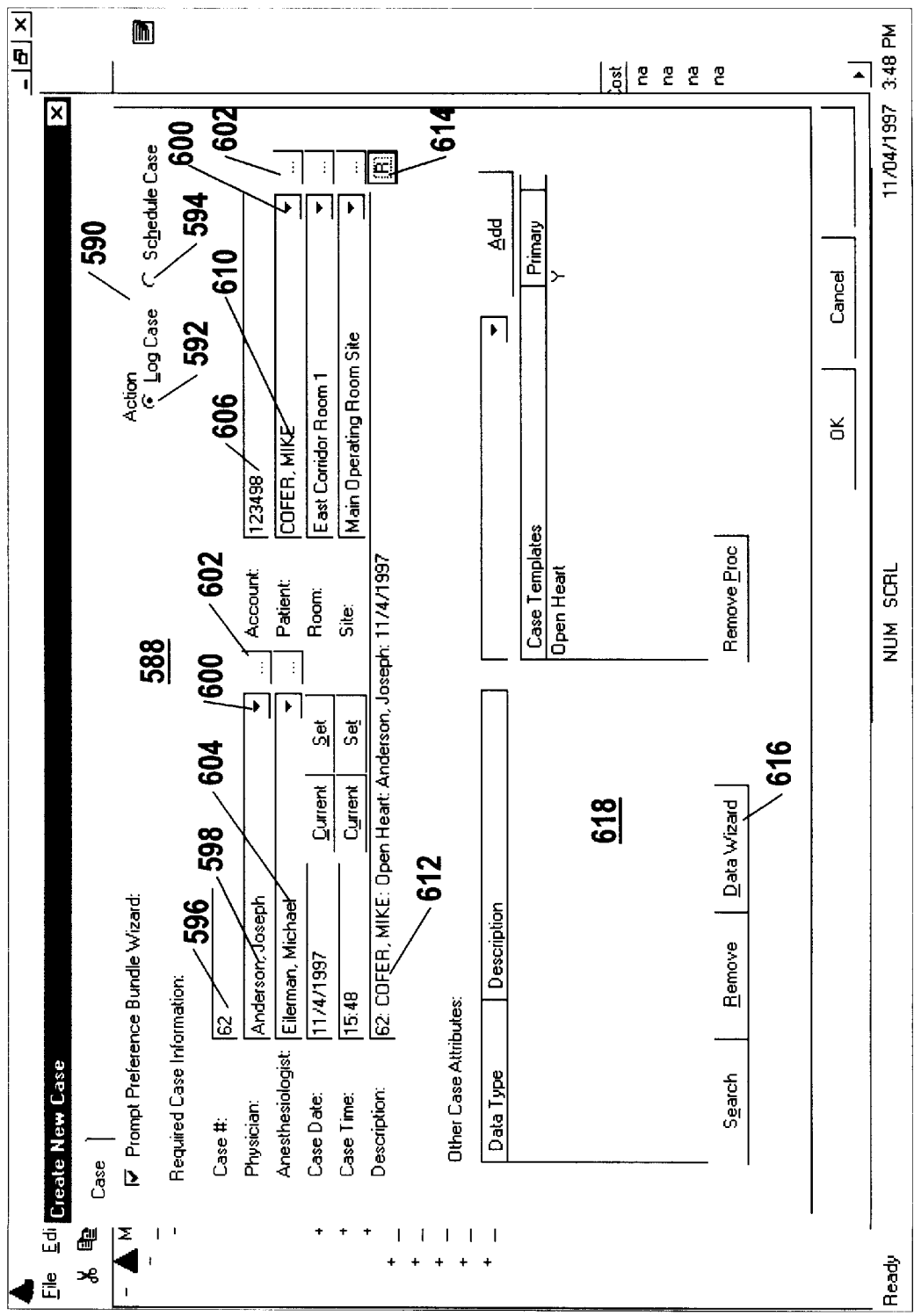

The Description field 612, depicted in FIG. 115, accepts a user defined description for the case. However, in many instances it may be better to have a standardized description for the cases that are created, rather than to allow each individual user to enter case descriptions that conform to the whim of each such user. Thus, the Retrieve Standard Description button 614 is provided, which operates to parse a selection of the information that is previously entered into the Create New Case window 588, and enter the parsed selection into the Description field 612. In this manner, all case descriptions contain a standardized selection of case information, allowing the cases to be more readily identified when using the description of the case. In a most preferred embodiment, the specific parsing and selection of information to be used as the description is user definable across the management system.

Figure 116:
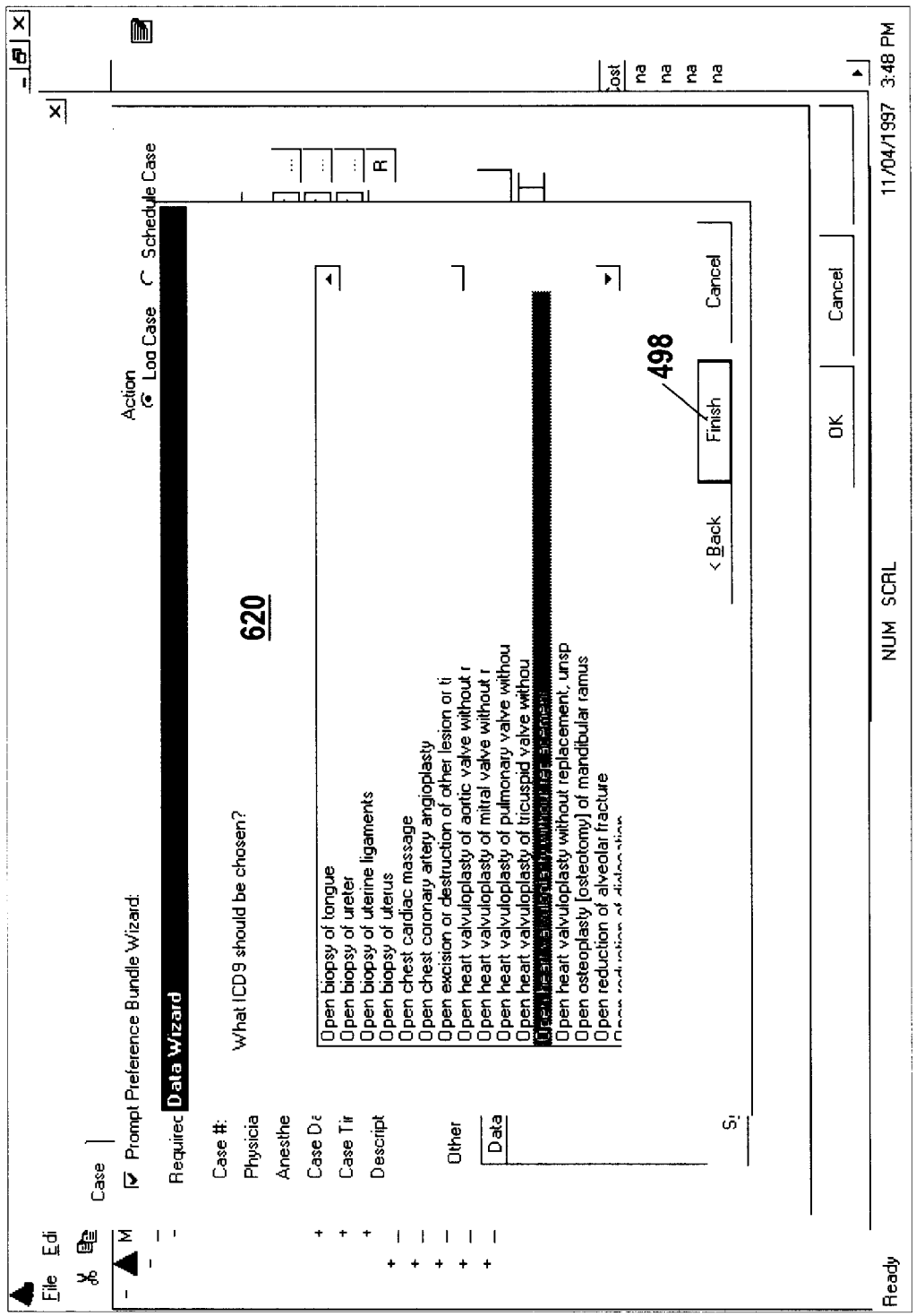
Figure 117:
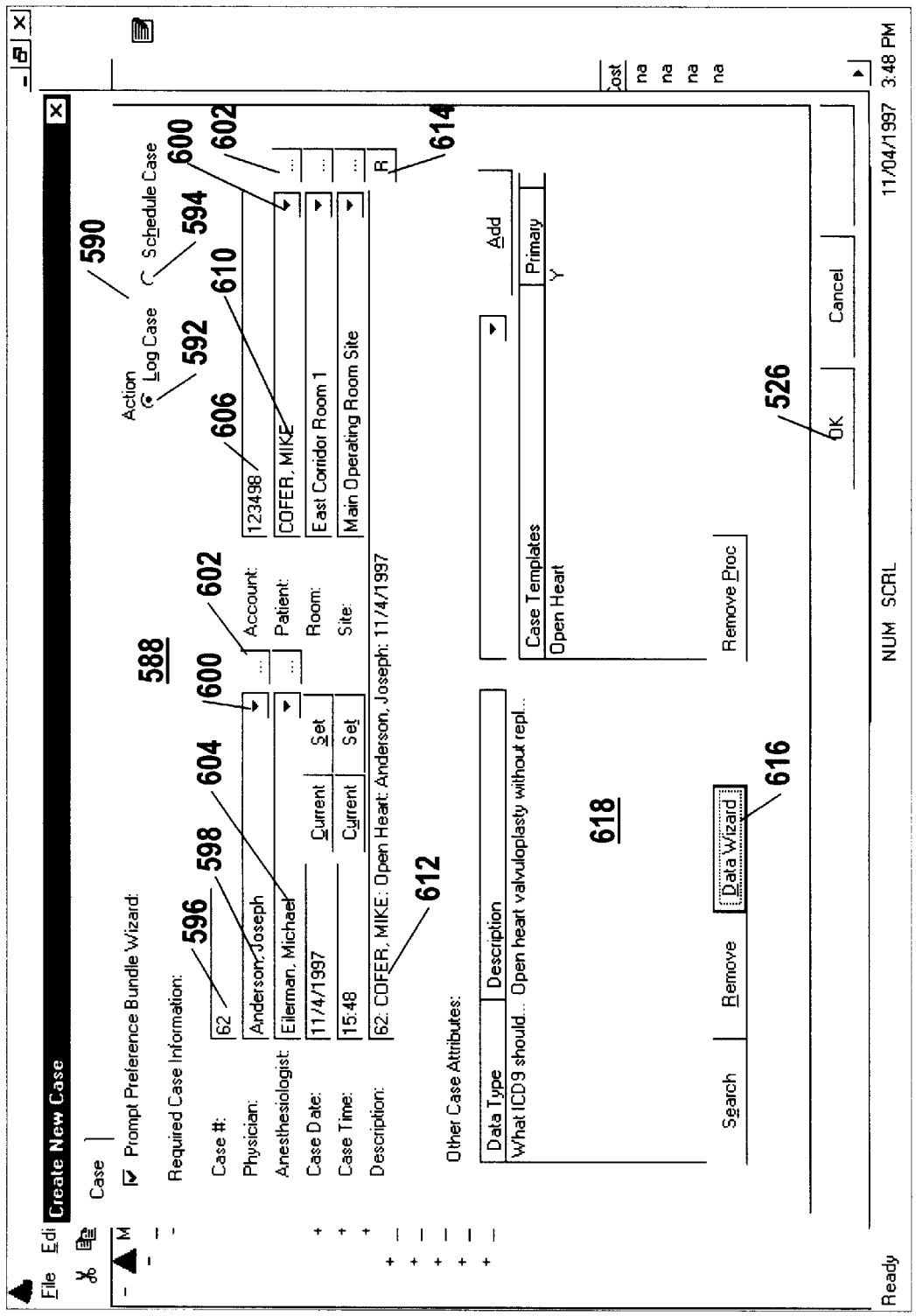

Other information about the case is selectively entered in the Other Case Attributes field 618. One especially convenient method of entering such information is by pressing the Data Wizard button 616, which invokes the Data Wizard window 620, as depicted in FIG. 116. The Data Wizard window 620 is preferably configured to allow for the convenient selection of standardized insurance carrier ICD9 codes, which codes the insurance carriers insist on receiving prior to authorizing payment for services. Thus, the Data Wizard window 620 presents an alphabetized scroll list of the ICD9 codes, from which the proper code can be selected and entered into the Other Case Attributes field 618 by pressing the Finish button 498, which procedure has been accomplished as depicted in FIG. 117.

Figure 118:
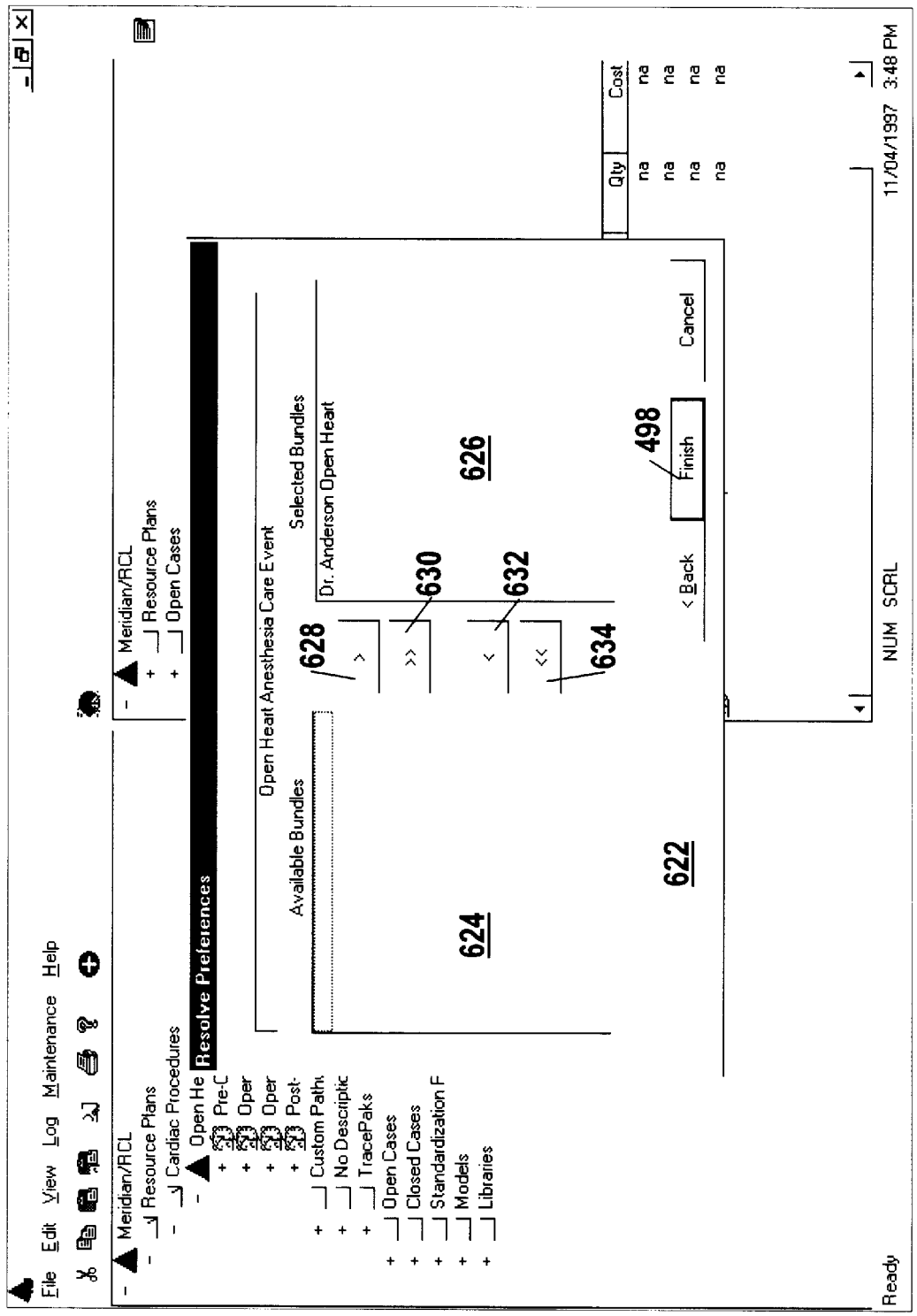

When the OK button 526 is pressed, signaling the completion of case data entry in the Create New Case window 588, the Resolve Preferences window 622 is invoked, as depicted in FIG. 118. The Resolve Preferences window 622 presents the user with the opportunity to selectively indicate or override the conditional branching that may otherwise be specified by the procedural pathway. For example, if the procedural pathway suggests that one or more of several bundle container objects may be required for the procedure, the user is presented with the opportunity to select the desired bundles from within the Resolve Preferences window 622. Most preferably, those preferences which are resolved by data that has already been entered in a data object are preselected by the management system and placed within the Selected Bundles field 626. However, all bundles related to the procedural pathway are preferably visible within the Available Bundles field 624, so that the user may override the automated selection made by the management system.

The user transfers bundle objects from the Available Bundles field 624 to the Selected Bundles field 626 by clicking on the desired bundle to highlight it, and then pressing the Add Selected Bundle button 628. Alternately, all bundle objects listed in the Available Bundles field 624 may be added to the Selected Bundles field 626 by pressing the Add All Bundles button 630. When the Add All Bundles button 630 is used, the individual bundle objects in the Available Bundles field 624 do not need to be highlighted, as all bundle objects will be transferred to the Selected Bundles field 626, whether they are highlighted or not.

Similarly, bundle objects displayed in the Selected Bundles field 626 may be transferred back to the Available Bundles field 624 by first clicking on the bundle object to be so transferred and then pressing the Remove Selected Bundle button 632, which removes the highlighted bundle object from the Selected Bundles field 626 and places it back within the Available Bundles field 624. Alternately, all bundle objects listed in the Selected Bundles field 626 may be transferred back to the Available Bundles field 624 by pressing the Remove All bundles button 634. When the Remove All Bundles button 634 is used, the individual bundle objects in the Selected Bundles field 626 do not need to be highlighted, as all bundle objects will be transferred to the Available Bundles field 624, whether they are highlighted or not. Pressing the Finish button 498 signals the management system that all bundle object preferences have been resolved and the user is ready to continue.

Figure 119:
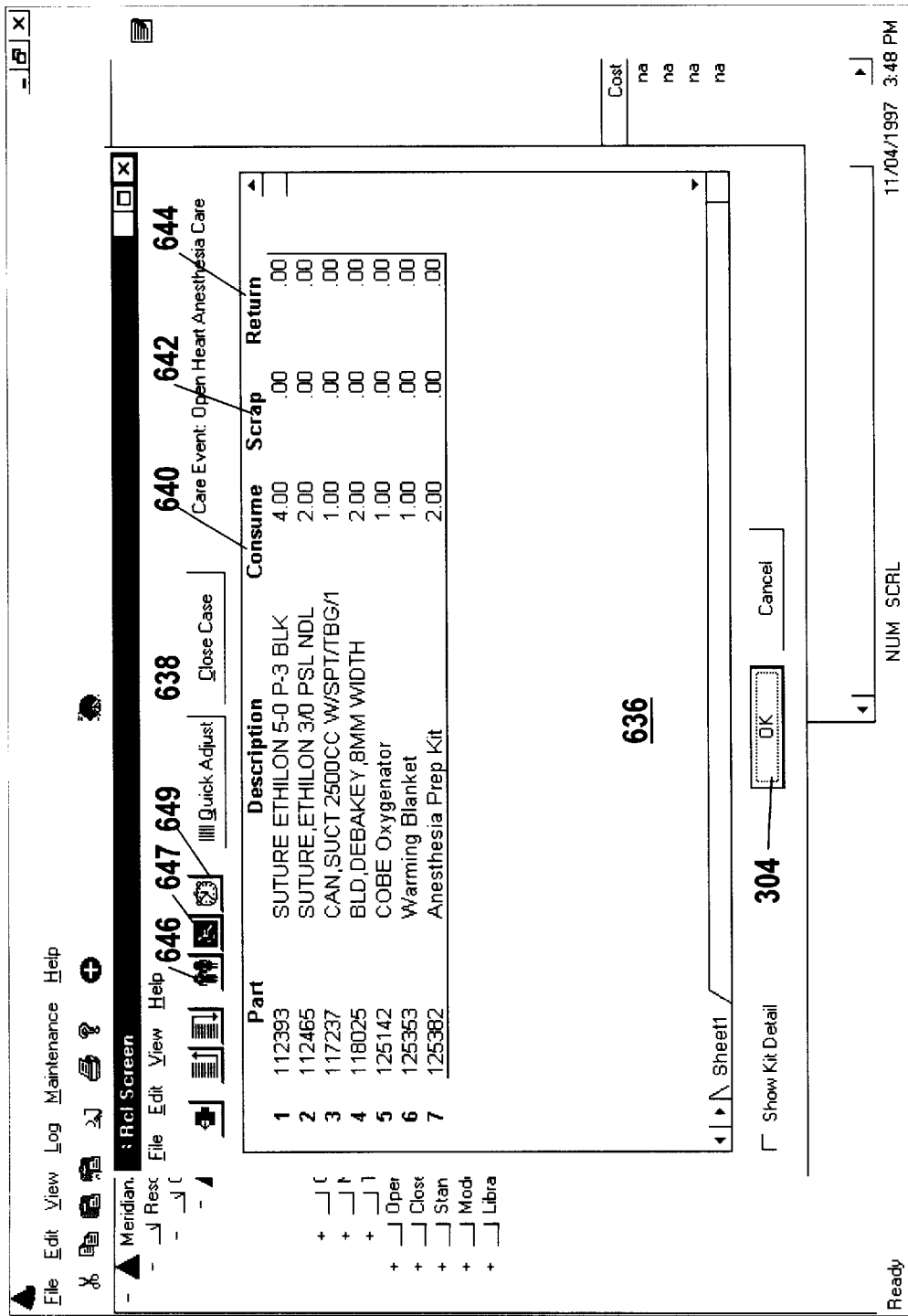

Upon clicking the Finish button 498, as depicted in FIG. 118, the Resource Consumption Log window 636 is invoked, as depicted in FIG. 119. In the Resource Consumption Log window 636, the user is presented with the opportunity to account for the various resources that were allocated to the procedural pathway during the bundle object selection just completed. The Resource Consumption Log window 636 is preferably presented at this point only when the case is being logged, or in other words, only when the procedural pathway has already been completed and the actual disposition of the resources is actually known. If the case is being creating as a scheduled case, then the procedural pathway has not as yet been completed, the disposition of the resources is not actually known, and the Resource Consumption Log window 636 is irrelevant at this point in time.

All of the resources allocated to the procedural pathway are depicted in a scrolling list within the Resource Consumption Log window 636. In the example depicted in FIG. 119, the list of allocated resources is quite short, and so there is no need to scroll the display in order to see the entire list. However, in a typical procedural pathway that would be used in an actual procedure, the list of allocated resources would tend to be much more lengthy.

The allocated resources are logged by confirming the actual disposition of the resources. The management system starts with the basic assumption that all of the resources allocated to the procedural pathway have been consumed. Thus, for each resource listed in the Description field 638 there is an associated value listed in the Consume Value field 640. The value listed in the Consume Value field 640 is a default value that is preferable equal to the value originally specified as the desired quantity of the resource when it was originally added to the container object.

However, not all of the resources may have been consumed. Some of the resources may have been scrapped, in which case they were not productively used. For example, the allocated number of resources may have been packaged together in a sterile package that, once it was opened, exposed all of the contents to the environment. Thus, any of that package contents that were not productively consumed had to be scrapped, or in other words, just thrown away. This, of course, is wasteful and leads to unnecessary expense, and so is a condition that is preferably tracked by the management system.

Other resources do not necessarily need to be scrapped if not productively consumed. In this case, the allocated resource can be returned to a stocking area, where it can be restaged for use in a subsequent clinical procedure. However, even though the resource itself is not needlessly destroyed, there is still wasted expense involved with preparing the resource for the clinical procedure when it was not actually required. Further, there is wasted expense involved with returning the unnecessary resource to the storage area, and making it available for alternate use. Therefore, this situation is also one that the management system preferably tracks. In either case, whether the allocated resource is scrapped or returned, the management system preferably analyzes the data and is able to suggest to the user that the allocated amount of the resource be adjusted to a value more nearly resembling the actual productive consumption of the resource in the procedural pathway described.

The disposition of the resource is depicted in FIG. 120, in which an entry in the Consume Value field 640 has been selected and altered. The original value for the entry, as depicted in FIG. 119, was 4. However, in the example depicted in FIG. 120, only 2 of the items were actually productively consumed, and so this value has been entered in the Consume Value field 640. The other two units of the resource, those of the four allocated that were not consumed, are preferably accounted for. Thus, the user selects the appropriate of either the Scrap Value field 642 or the Return Value field 644, or both, and enters the appropriate value in the fields according to the actual disposition of the resources. In the example depicted in FIG. 121, the Return Value field 644 has been selected, in which the user may enter the number of units of the resource that have been returned to stores.

Figure 122:
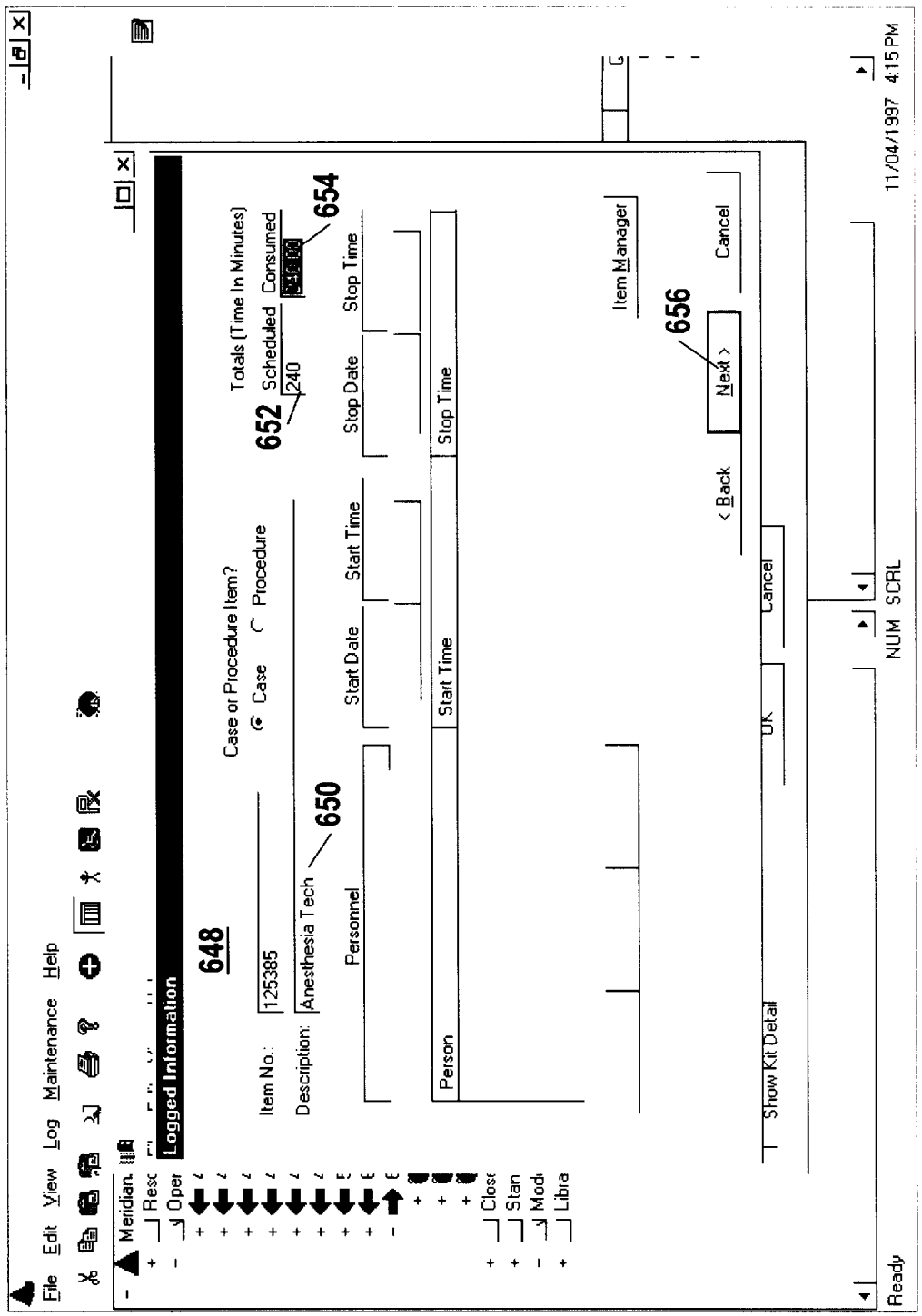

When all such corrections to the actual disposition of the several resources allocated to the procedural pathway have been completed, the user may next confirm utilization of the allocated personnel resources in a manner similar to that described above, by pressing the Personnel Utilization button 646, which invokes the Logged Information window 648, as depicted in FIG. 122. In the Logged Information window 648 the user is presented with the opportunity to account for the actual amount of time used of the various personnel that were allocated to the procedural pathway. The Description field 650 displays the description of the first personnel resource specified in the procedural pathway. The Scheduled Total field 652 indicates the total number of minutes of personnel resource time that were allocated to the procedure. The Consumed Totals field 654 allows the user to enter in the actual amount of time that was productively consumed in the course of the procedure.

In the example depicted in FIG. 122, the consumed value equals the scheduled value, indicating that all of the scheduled time was productively used. However, the user could also enter a value in the Consumed Total field 654 that is either greater than or less than the value displayed in the Scheduled Totals field 652. If the value entered into the Consumed Total field 654 is greater than the value displayed in the Scheduled Totals field 652, then it is an indication that the procedure demanded a greater amount of time from the personnel resource than was initially allocated. Such a situation may create severe scheduling problems, if the person represented by the personnel resource has another procedure to participate in, and the current procedure is taking longer than originally anticipated. This is a situation that is preferably tracked by the management system, so that personnel time management and scheduling can be optimized.

Alternately, if the value entered into the Consumed Total field 654 is less than the value displayed in the Scheduled Totals field 652, then it is an indication that the procedure required a lesser amount of time from the personnel resource than was initially allocated. Although it is hoped that the excess time not consumed for the procedure was "returned" and productive use was made thereof, it is far more likely that the excess time was "scrapped." Therefore, the management system assumes that the time was lost in an unproductive manner, and there is, in the embodiment depicted, no provision for specifying the actual disposition of the scheduled time that was not consumed. This too is a situation that is preferably tracked by the management system, so that personnel resources are used to their fullest, thus reducing the excess expense associated with under utilized personnel resources.

Figure 123:
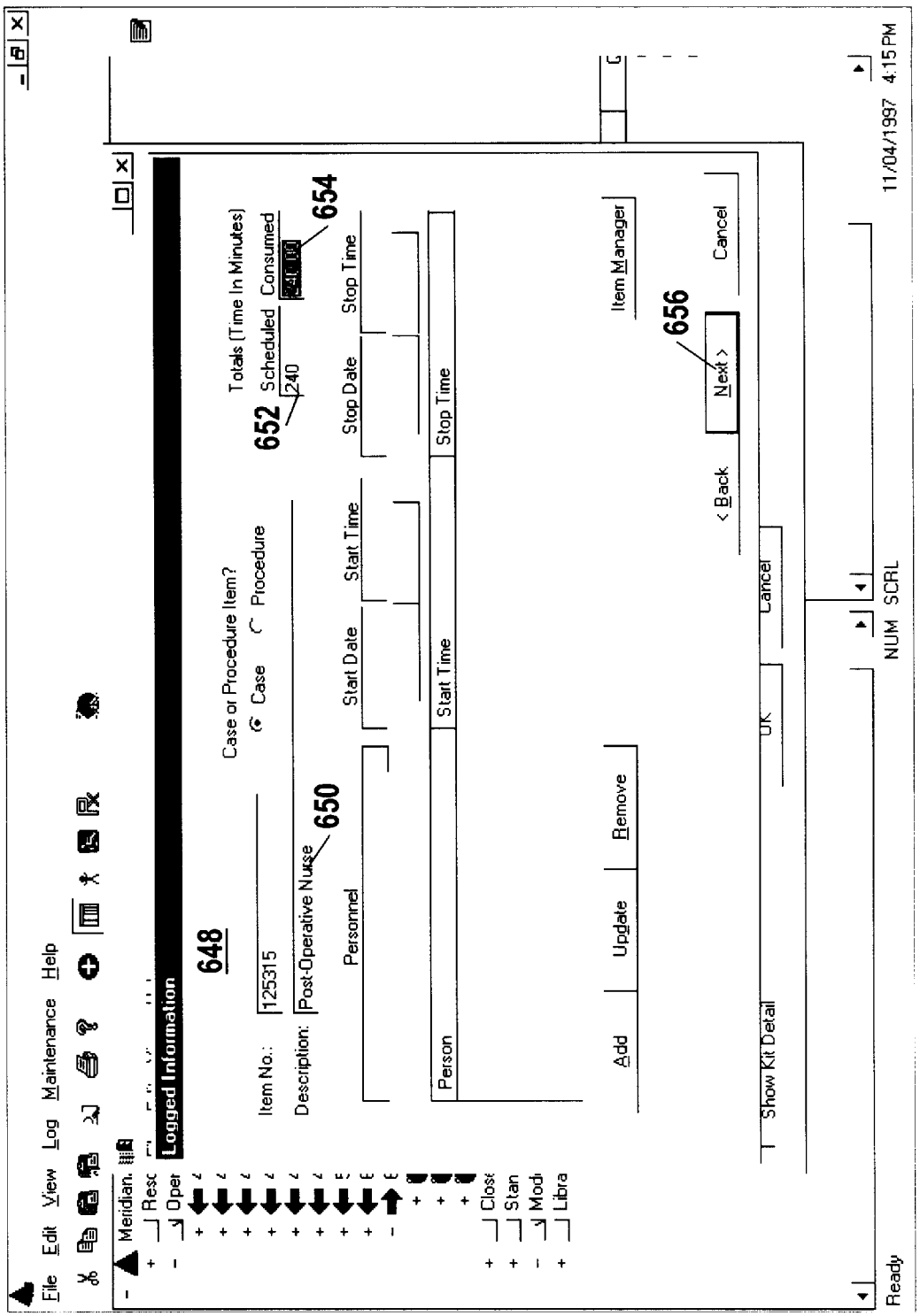

When the consumed time for the personnel resource indicated in the Description field 650 has been entered into the Consumed Totals field 654, the Next button 656 is clicked, and the user is brought to a second instance of the Logged Information window 648, which represents a second personnel resource, if such has been allocated to the procedural pathway. Thus, a separate personnel Logged Information window 648 is depicted for each personnel resource that has been allocated to the procedural pathway. FIG. 123 depicts the second instance of the Logged Information window 648, in which the time actually consumed by the next personnel resource, listed in the Description field 650, is entered into the Consumed Totals field 654, in a manner the same as that described above. When this time has been entered, the Next button 656 is clicked.

Figure 121:
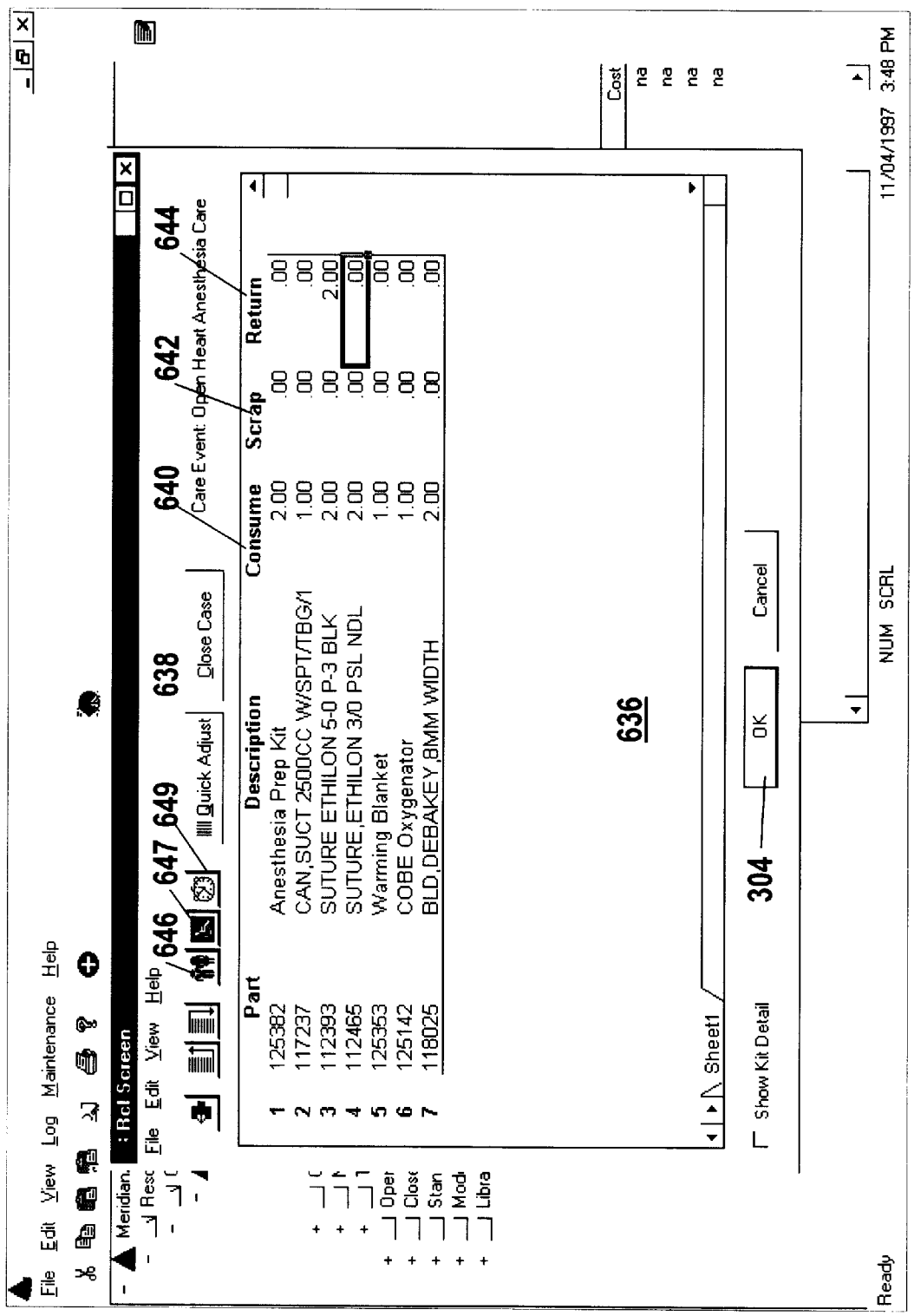
Figure 124:
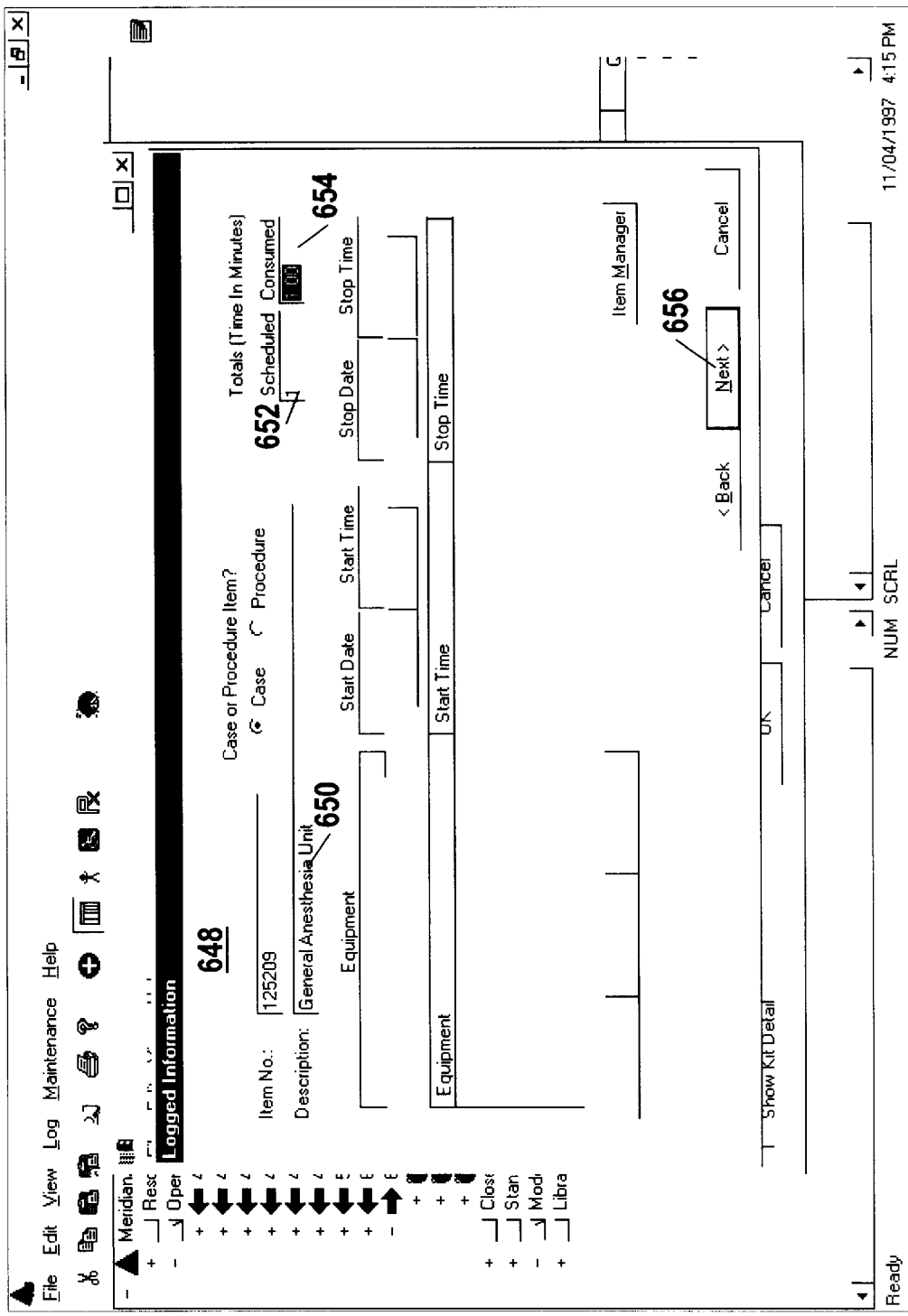

In the example depicted, only two personnel resources have been allocated to the procedural pathway, and so no more personnel Logged Information windows 648 are required. Thus, pressing the Next button 656 as described above invokes an instance of the Logged Information window 648 that displays an equipment resource in the Description field 650, as depicted in FIG. 124. It is possible to enter the consumed time for the various equipment resources directly from the Resource Consumption Log window 636, by pressing the Equipment Utilization button 647, as depicted in FIG. 121. By so doing, the Logged Information windows 648 associated with personnel resources may be bypassed. The amount of allocated time for the equipment resource that was actually consumed is entered in the Consumed Totals field 654, in a manner similar to that described above, and the Next button 656 is clicked.

Figure 125:
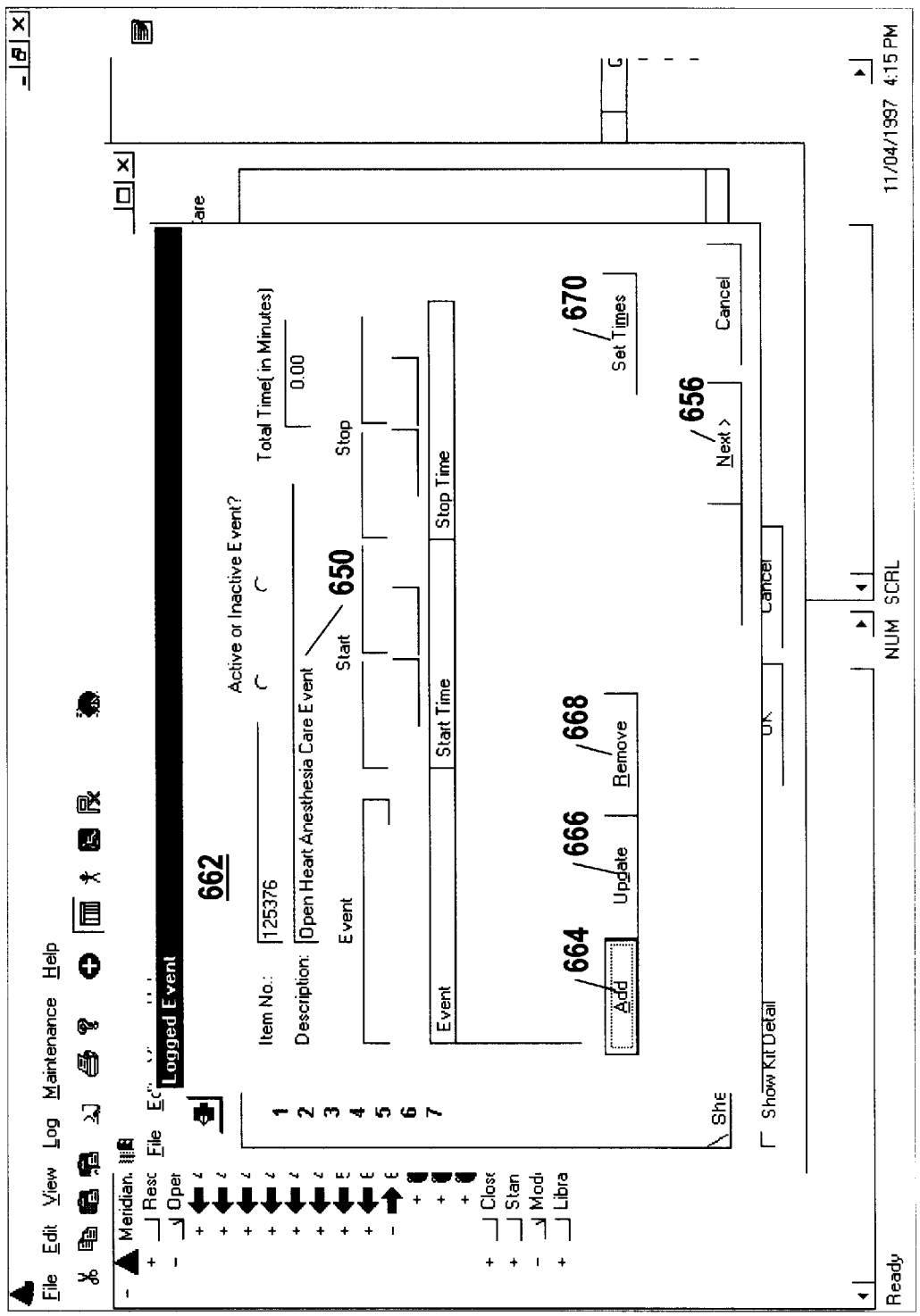

Had there been additional equipment resources allocated to the procedural pathway, then additional instances of the equipment Logged Information window 648 would preferably have been invoked. However, in the example depicted, only one such equipment resource was allocated. Thus, clicking the Next button 656 invokes the Logged Event window 662, as depicted in FIG. 125, in which the total time for the procedural pathway, as described in the Description field 650, is accounted for. The name of the procedural pathway is depicted in the Description field 650, and the user is given the opportunity to add, update, remove, or set the times for the procedure represented by the procedural pathway.

Figure 126:
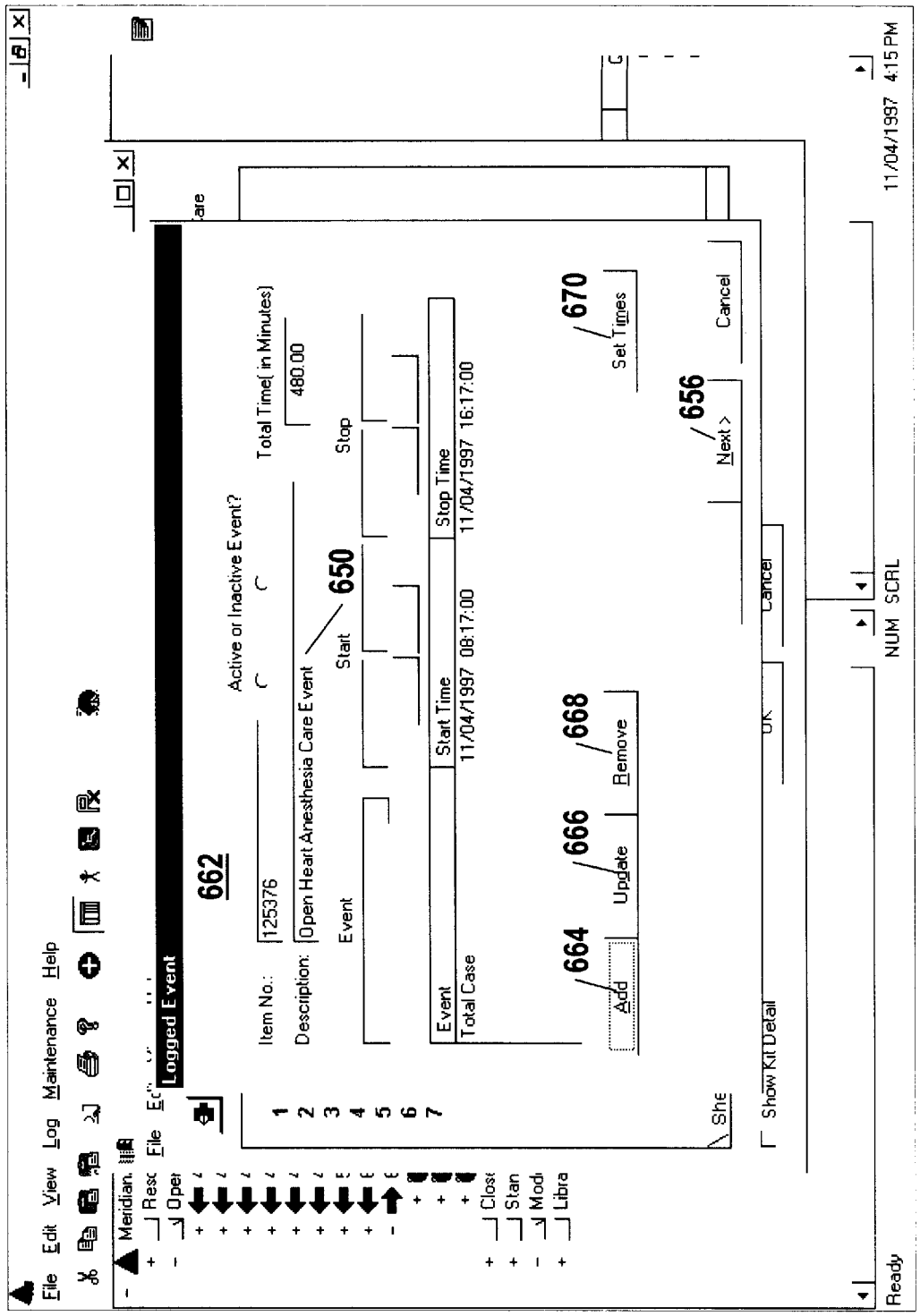

For example, pressing the Add button 664 adds all of the time previously described in the Logged Information windows 648 described above. This creates an entry in the Logged Event window 662, as depicted in FIG. 126. The entry so created by clicking the Add button 664 can be deleted by pressing the Remove button 668. Additionally, the start and stop times listed in the entry can be changed by clicking on the Set Times button 670, which preferably invokes a dialog for accomplishing the task. If all of the allocated time for the personnel resources and equipment resources had been productively consumed, such that no adjustment to the allocated times had been necessary, then the user could have by passed all of the Logged Information windows 648 described above and gone directly to the Logged Event window 662 by pressing the Event Times button 649, as depicted in FIG. 121.

Figure 127:
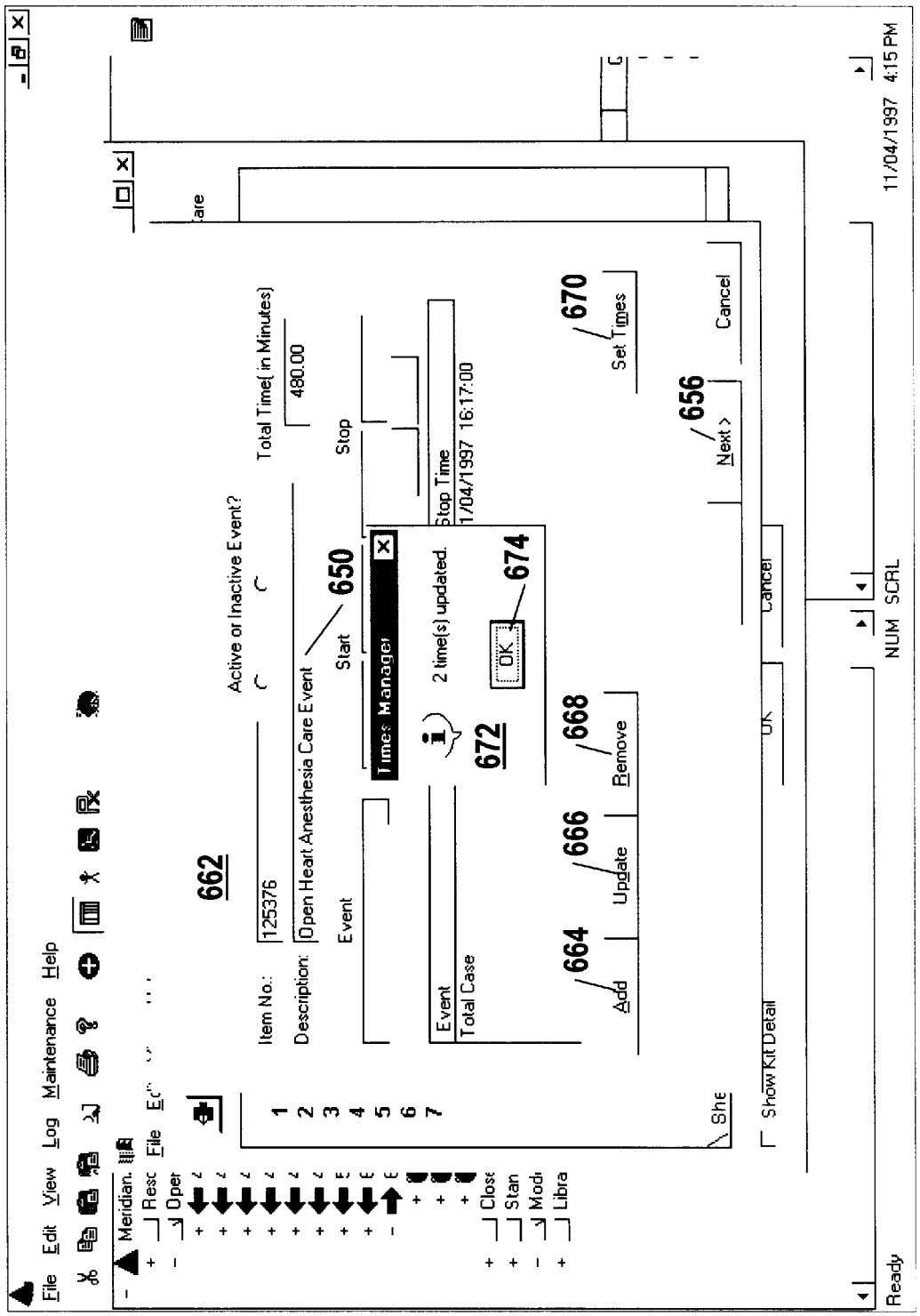
Figure 128:
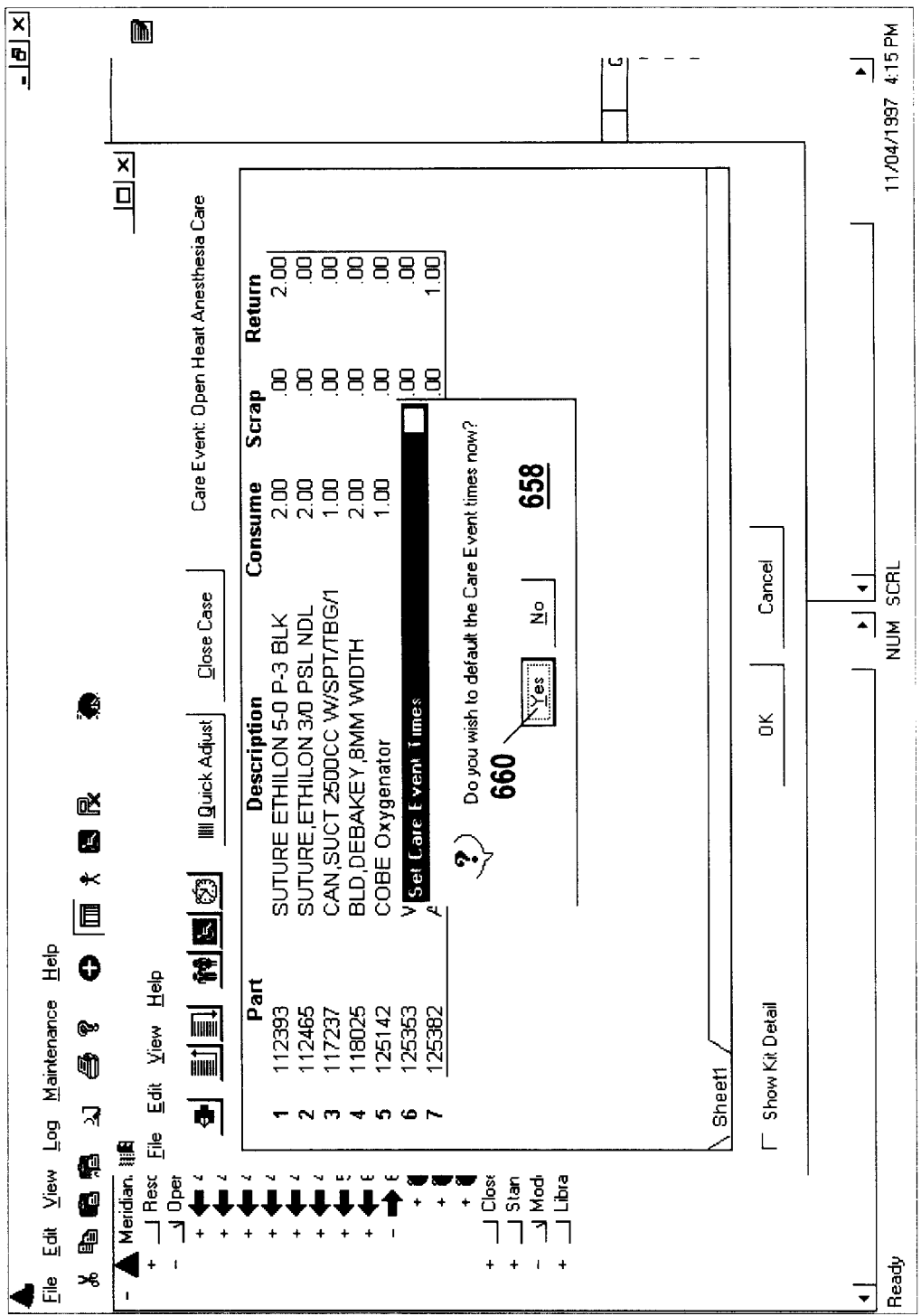

The event set times are updated with the information specified in the Logged Event window 662 by pressing the Update button 666, which invokes the Times Manager dialog box 672, as depicted in FIG. 127. The Times Manger dialog box 672 confirms that the times have been updated. The user proceeds by clicking the OK button 674, which returns control to the Logged Event window 662. Clicking the Next button 566 in the Logged Event window 662 invokes the Set Care Event Times dialog box 658, depicted in FIG. 128, in which all of the times specified in the above procedures are posted to the management system by pressing the Yes button 660.

Figure 129:
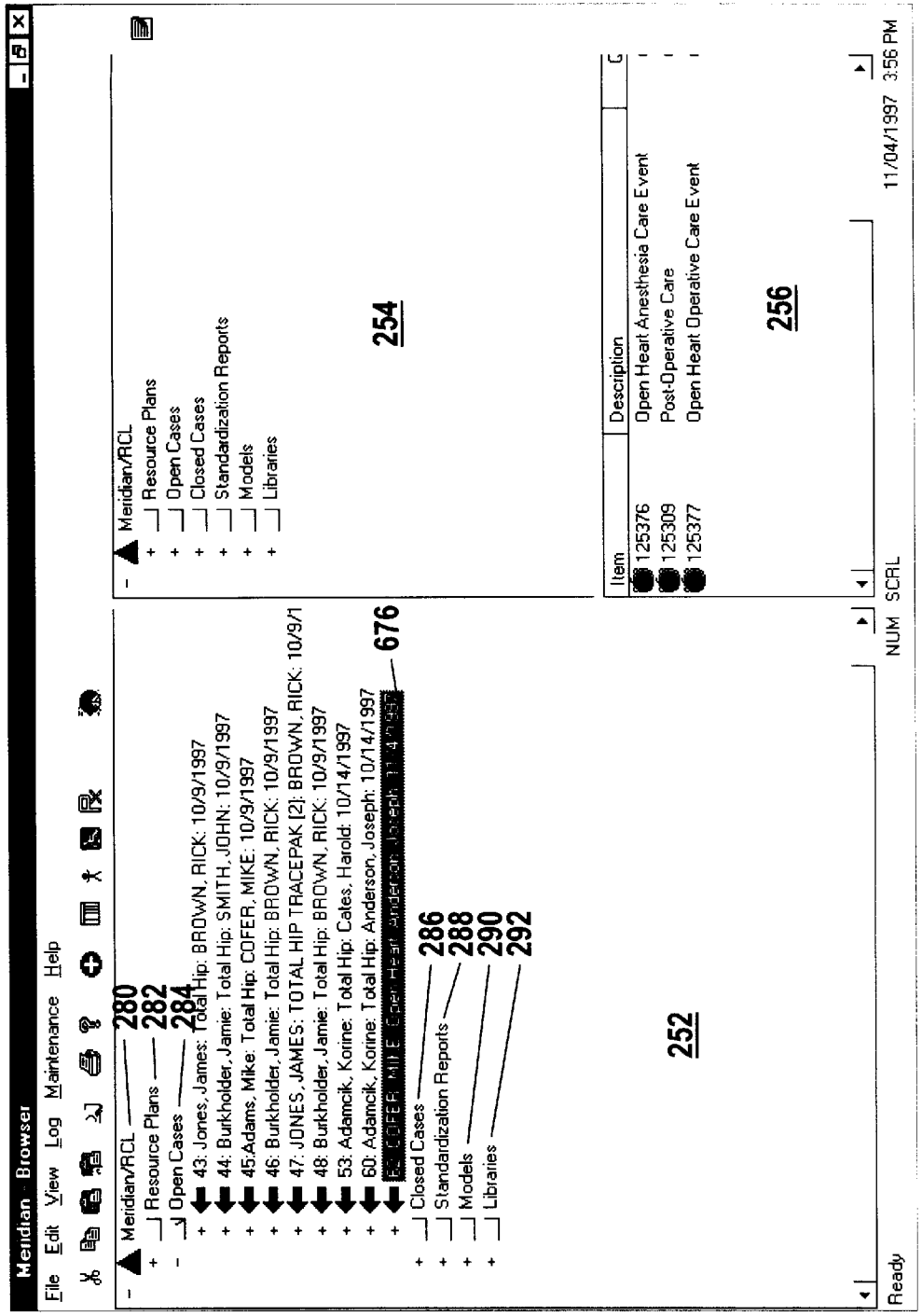

The new case 676 created by the procedure specified above is placed within the Open Cases node 284 in the Nested Tree view 252 of the Browser window 250, as depicted in FIG. 129. As a preferable default, the new case 676 is given the default description that was specified in the Description field 612, as depicted in FIG. 115. Cases listed under the Open Cases node 284 preferably differ from those listed under the Closed Cases node 286 in several respects. As a point of conception, open cases are those that are scheduled but pending, still in progress, or completed but not yet logged. Closed cases are those that have been completed and logged. Thus, changes may still be made to an open case, whereas changes cannot be made to a closed case, unless it is reopened. The management system preferably uses only closed cases in its automated analysis routines, so as to not base results and conclusions on cases that have not been fully logged.

Figure 130:
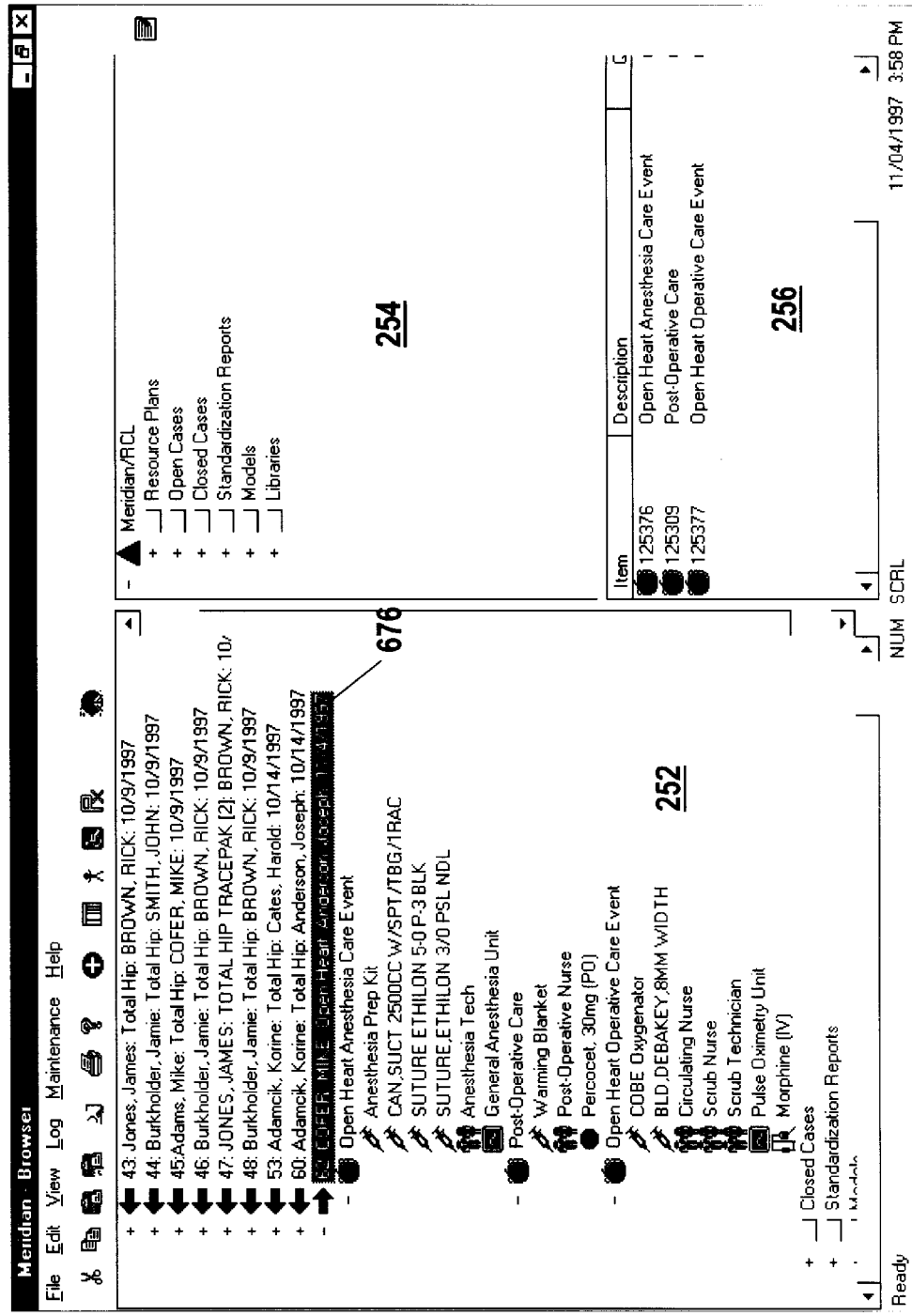

Resources allocated to a specific case can be designated as having been consumed, scraped, or returned in a quicker manner than the more complete logging method described above. This quicker procedure may be used when, for example, only a specific portion of the procedural pathway of the case has been accomplished, and only the resources specified for that portion of the pathway are to be accounted for. This procedure is initiated by expanding the case 676 in the Nested Tree view 252, as depicted in FIG. 130. The case 676 can be expanded in any one of several different ways, such as by selecting the case by clicking on it and then pressing the enter key on the keyboard, double clicking on the case 676, or clicking on the plus sign next to the name of the case 676.

Figure 131:
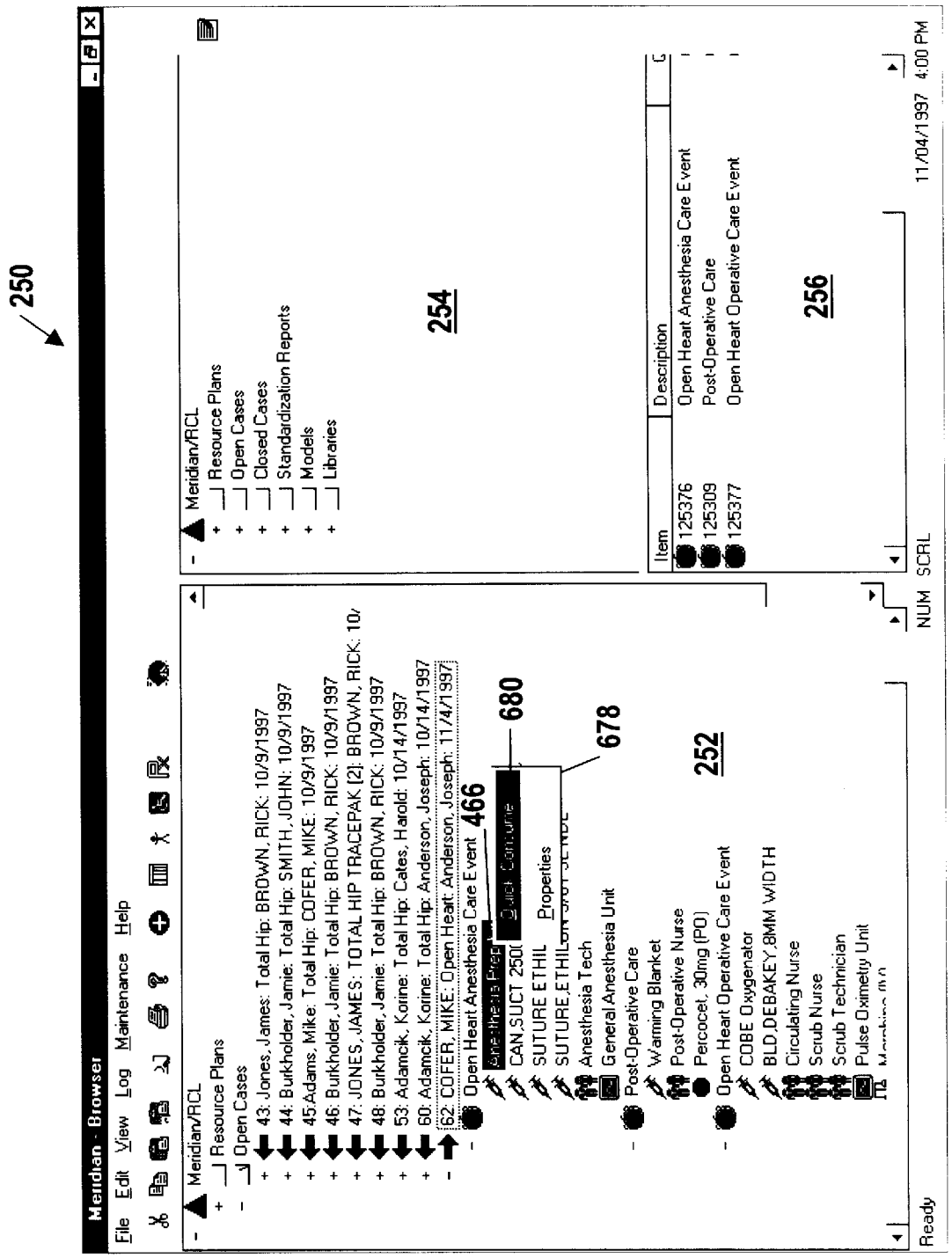
Figure 132:
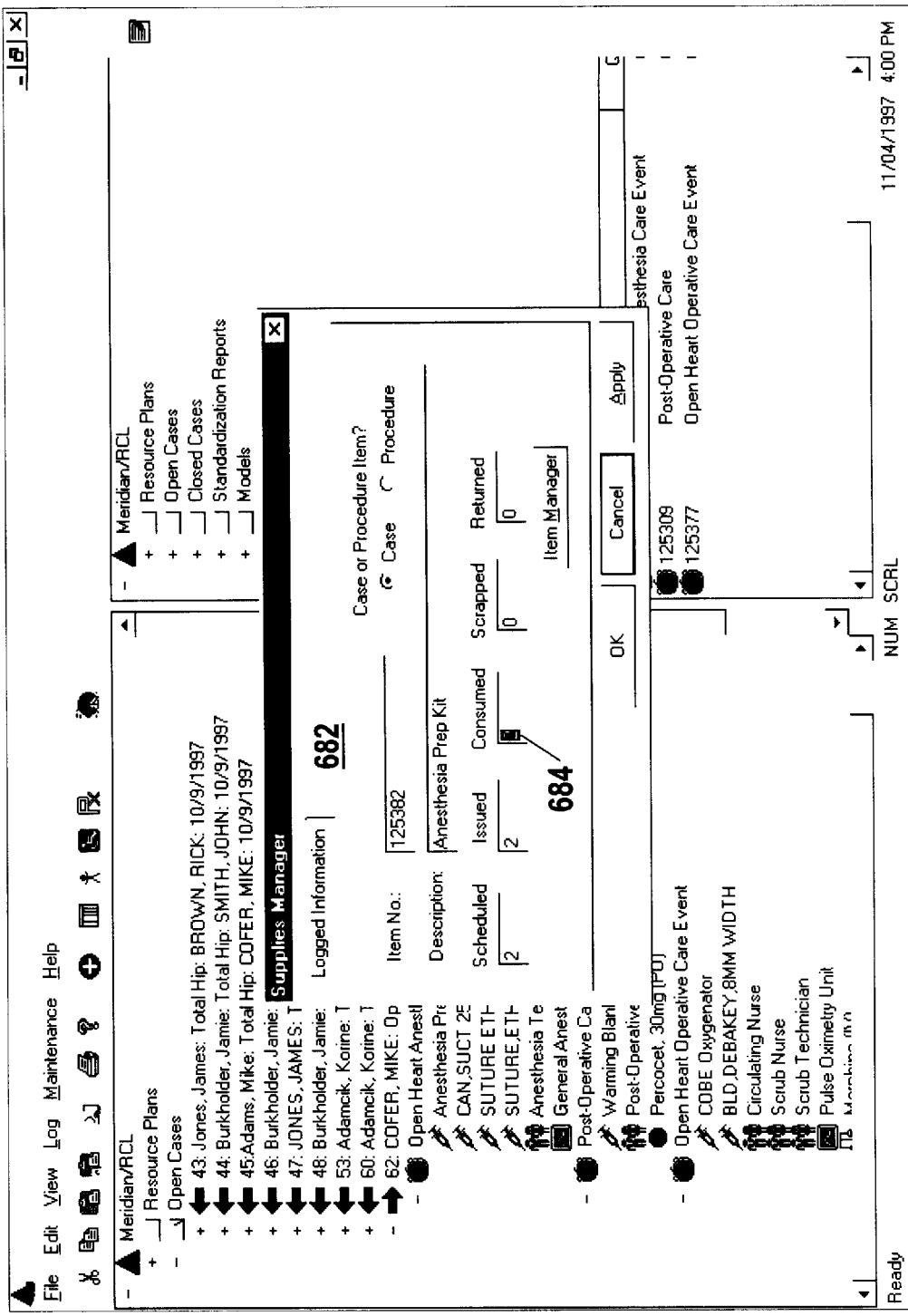

Once the case 676 has been opened, the resource to be accounted for is selected, as depicted in FIG. 131. In the example of FIG. 131, the Anesthesia Prep Kit supply resource object 466 has been selected, and the Supply Resource menu has been invoked, such as by right clicking on the Anesthesia Prep Kit supply resource object 466. It is noted at this point that the menu associated with the Anesthesia Prep Kit supply resource object 466 under the Open Cases node 284 is a different menu than that associated with the Anesthesia Prep Kit supply resource object 466 under the Resource Plans node 282. Thus, even though the Anesthesia Prep Kit supply resource object 466 has been copied from one node to another, the management system treats the objects differently according to the location of the object, and presents menu options that are context sensitive to the location of the object. Selecting the Quick Consume function 680 invokes the Supplies Manager 682, depicted in FIG. 132, in which information about the number of units allocated to the case, and the disposition of the number of units allocated, is depicted.

Figure 133:
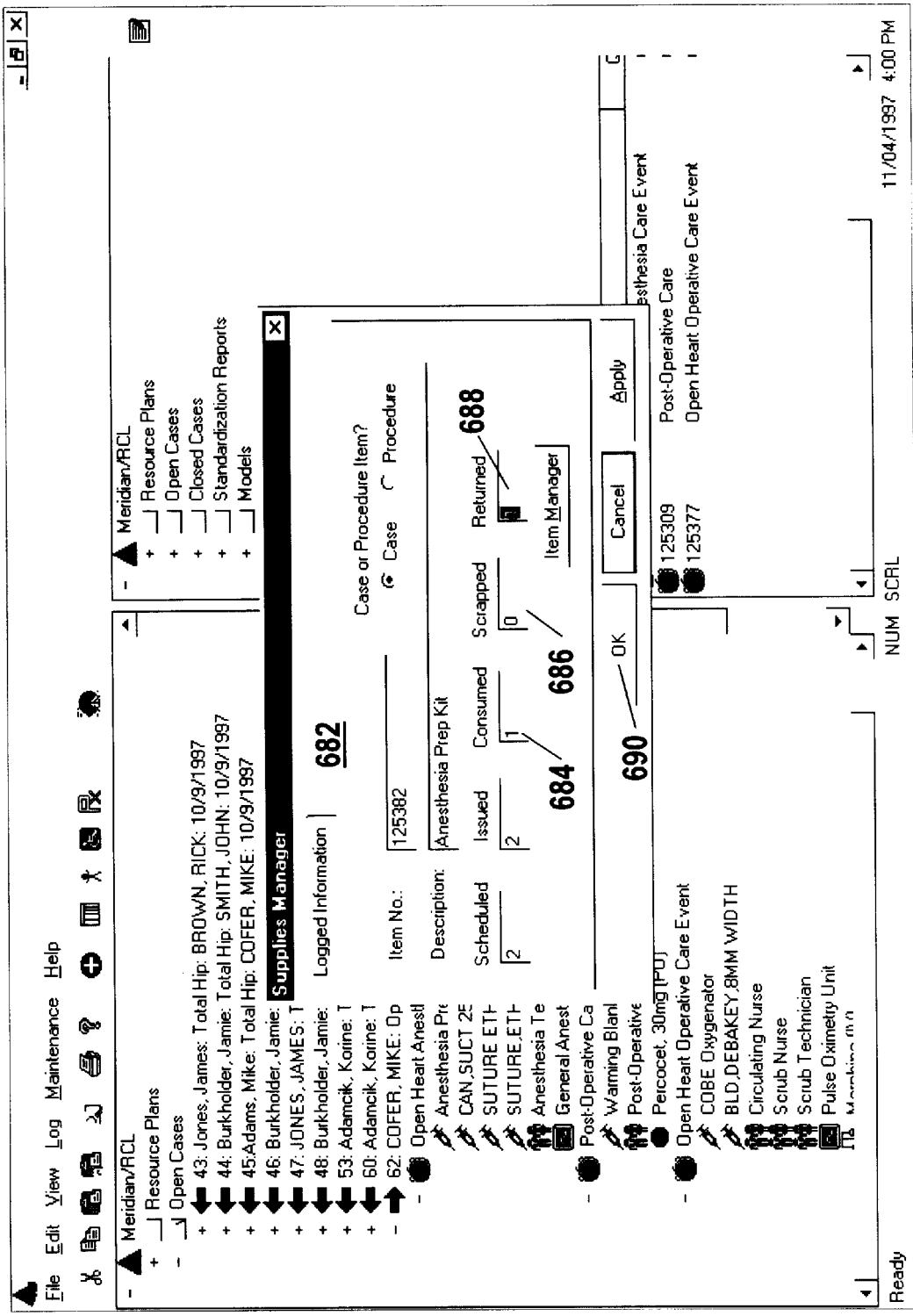

The number of units allocated, as described in the procedural pathway, is initially displayed in the Consumed field 684. Thus, the management system initially assumes that the scheduled number of units will all be consumed. If, however, such is not the case, then the user merely changes the value entered in the Consumed field 684. As soon as this event occurs, the Scrapped field 686 and the Returned field 688 become active and editable, as depicted in FIG. 133. Thus, the user can specify the number of units that are either scrapped or returned. Pressing the OK button 690 completes the procedure and posts the disposition of the resources to the management system.

One of the many tremendous benefits of the management system according to the present invention is the ability to extract detailed information and analysis from the data that is collected from the cases. As an overview in retrospect, the initial description provided herein was of creating procedural pathways within the Resource Plans node 282. These procedural pathways represented standard templates that are used to schedule and allocate the various available resources required to complete the procedure represented by the procedural pathway.

Figure 134:
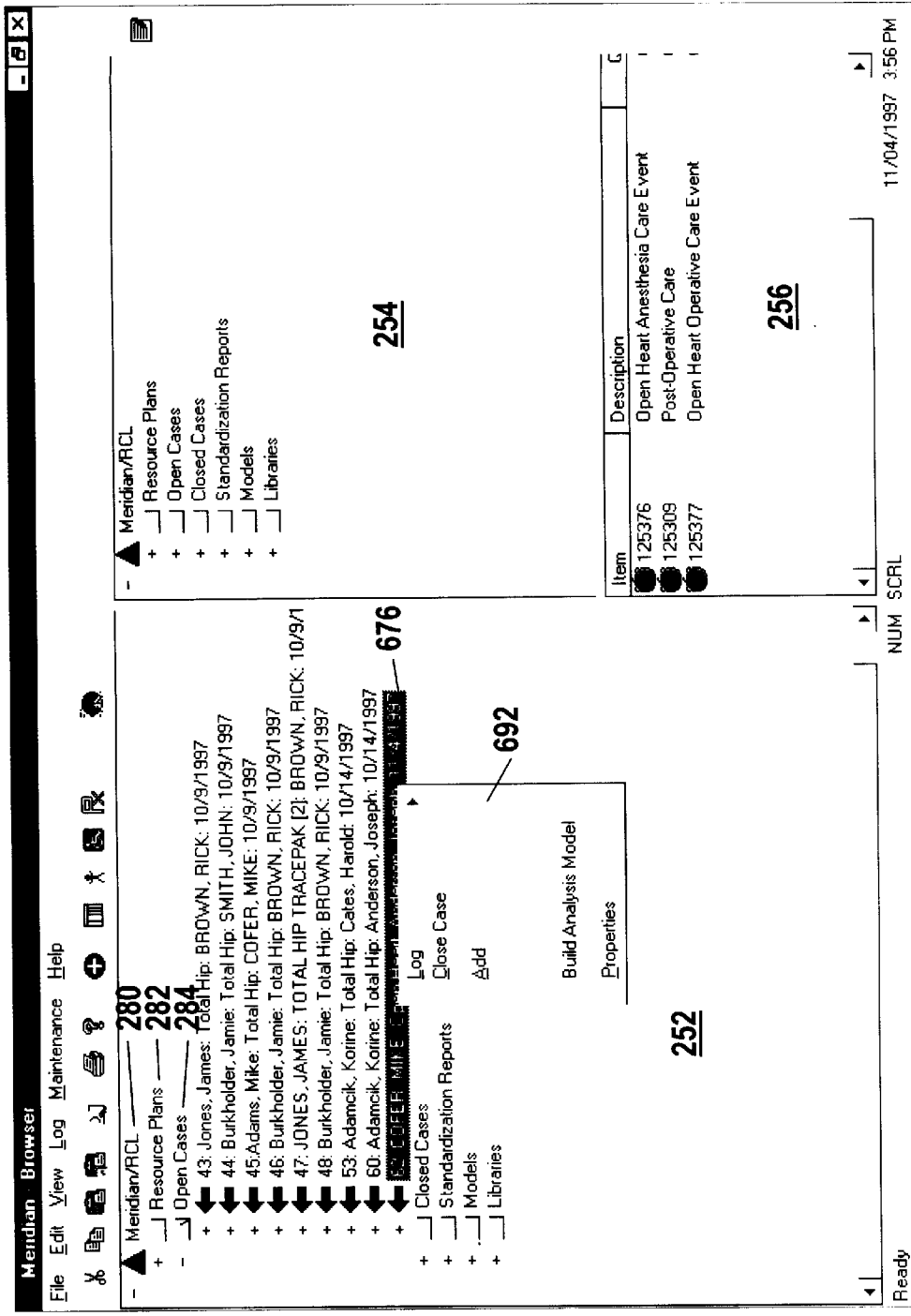
Figure 135:
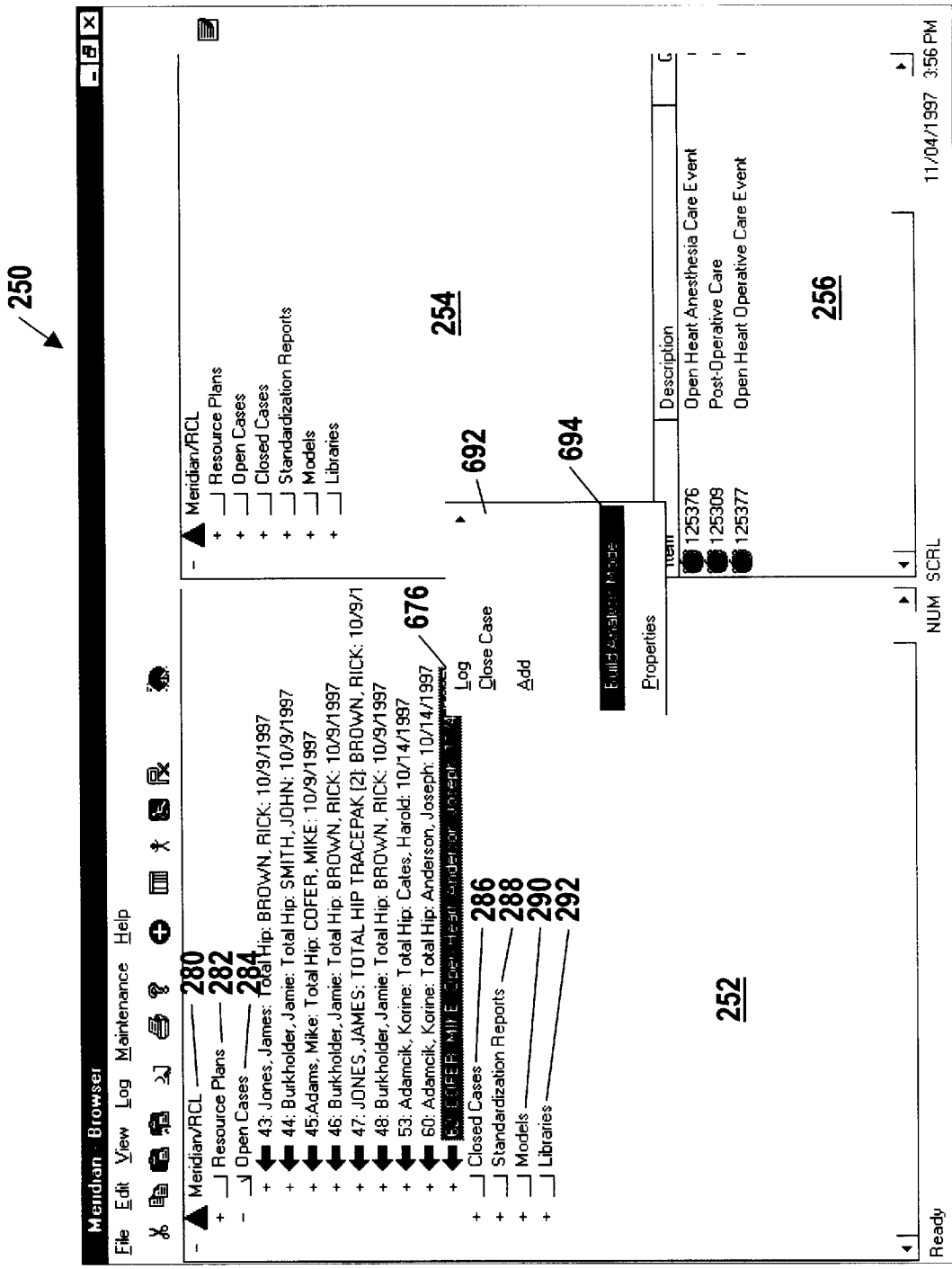
Figure 136:
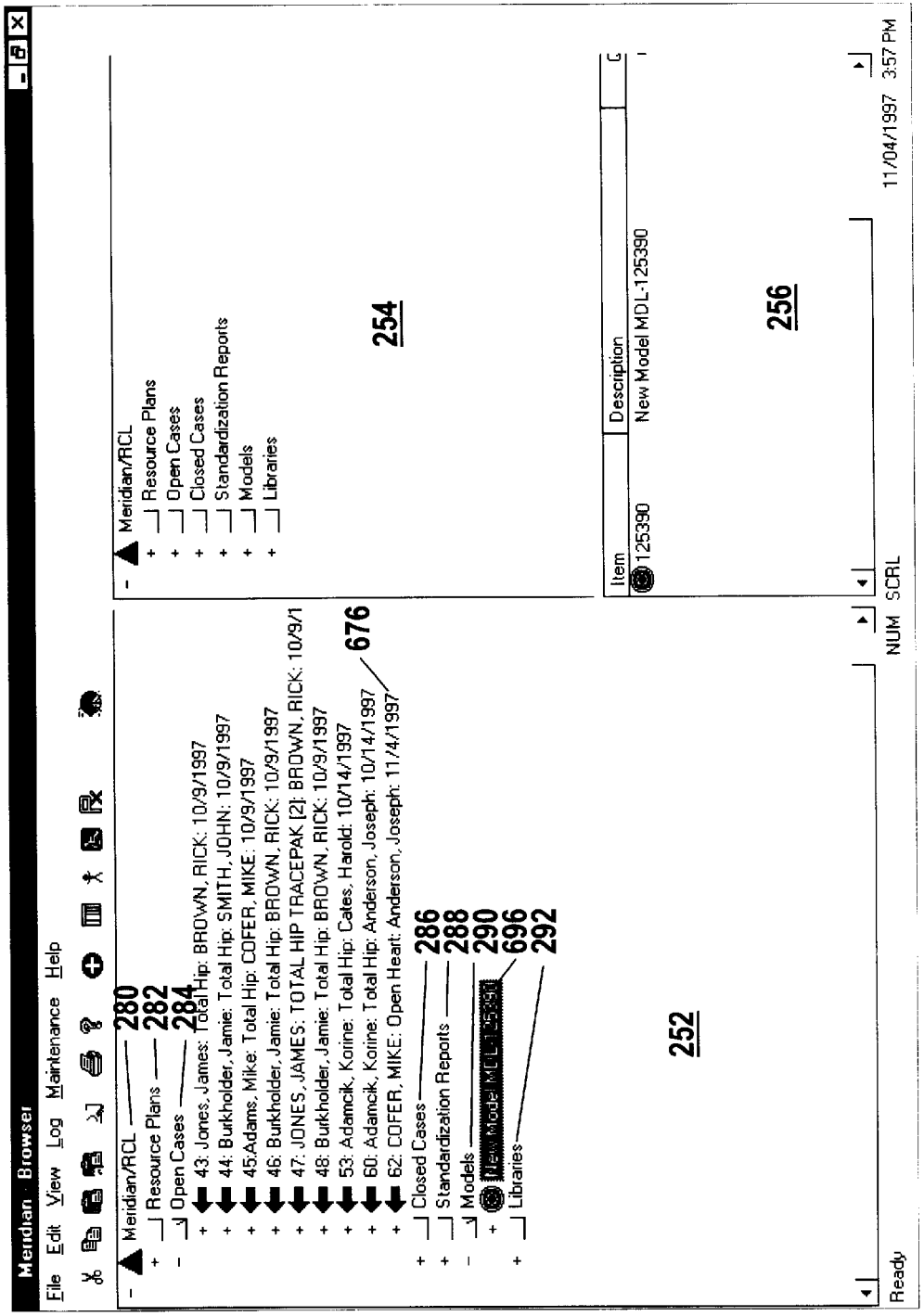

After a procedural pathway is constructed, an actual case is copied from the procedural pathway to the Open Cases node 284. The actual disposition of the resources allocated to the case, as based on the procedural pathway, is specified. Once the disposition of the resources has been accomplished, the case can be used in a model to analyze the efficiency of the procedural pathway and the utilization of resources. This analysis procedure is commenced by invoking the Open Case menu 692, as depicted in FIG. 134, such as by right clicking on the new case 676, and selecting the Build Analysis Model function 694, as depicted in FIG. 135. A new model 696 is thereby created under the Models node 290, which new model 696 is preferably given a standardized name by the management system, as depicted in FIG. 136.

Figure 137:
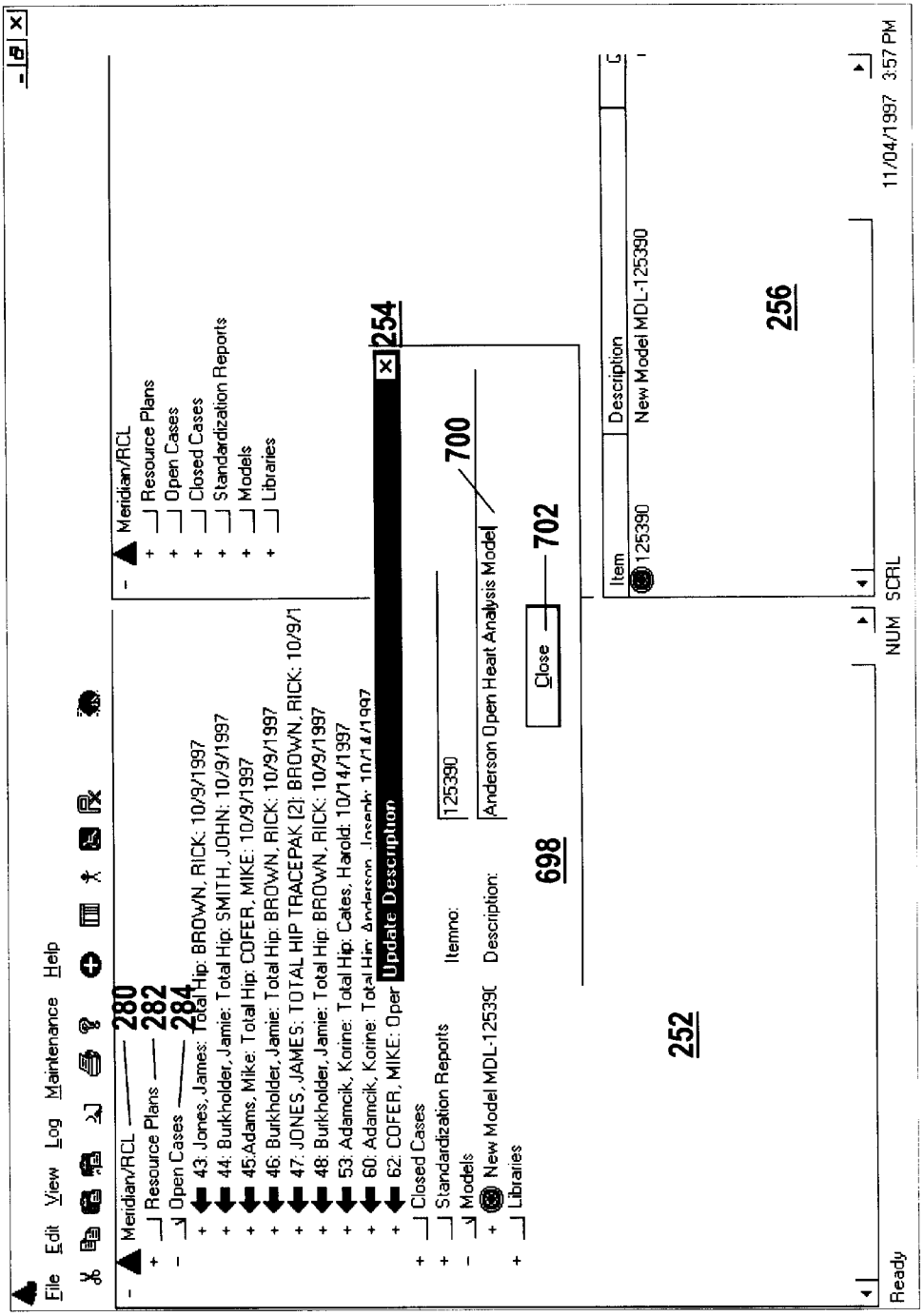
Figure 138:
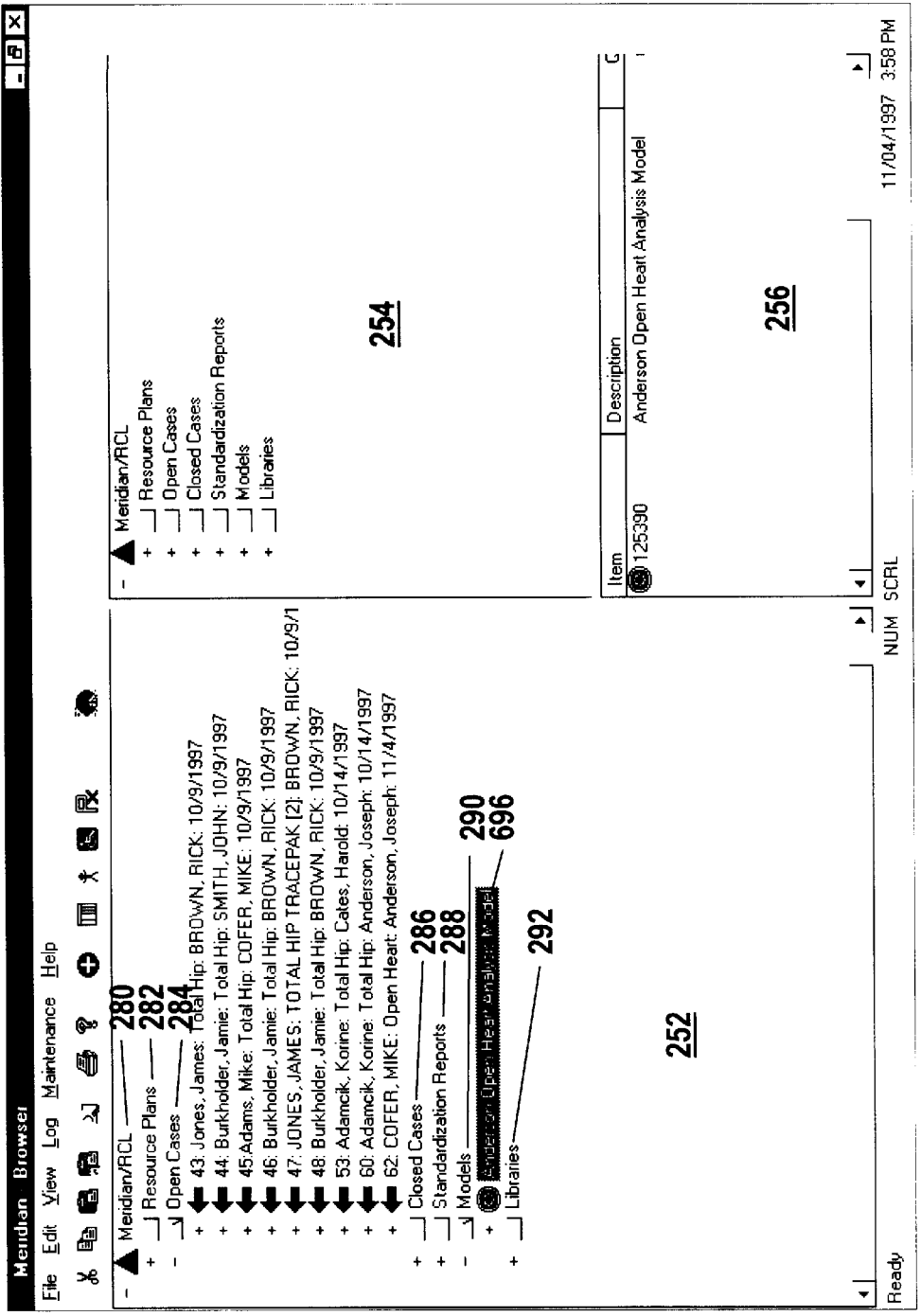

A more descriptive name is given to the new model 696 by invoking the Update Description dialog box 698, as depicted in FIG. 137, such as by pressing the F2 key on the keyboard when the new model 696 is highlighted. The desired description for the new model 696 is entered into the Description field 700, and the selection of the new description is posted to the management system by clicking the Close button 702. The renamed model 696 is depicted in FIG. 138.

Figure 139:
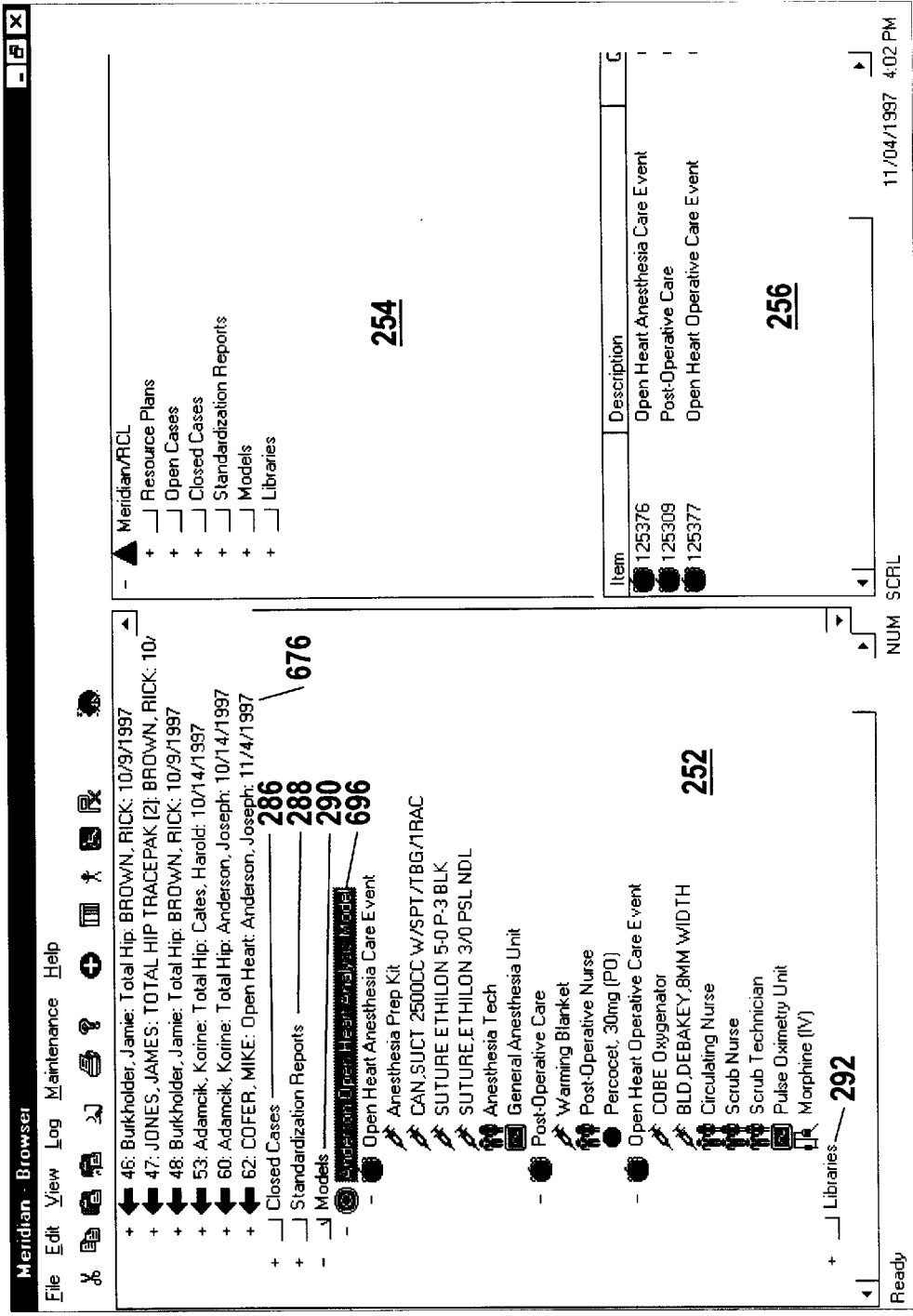

FIG. 139 depicts the contents of the model 696, which appear identical to the contents of the corresponding case 676, on which the model is based, the contents of which case 676 appear similar to the contents of the corresponding procedural pathway 370. However, in reality, the various objects which are the contents of the model 696, case 676, and pathway 370 are not identical. One evidence of this is that the contextual menus for the corresponding objects within the model 696, case 676, and pathway 370 are not the same. Each of the contextual menus provide a different set of functions, which functions are specifically related to the purpose and character of the objects. Further, while the objects in one node do correlate and track with their counterpart objects in other nodes, they contain different types of data, specific to their intended functions. This becomes further evident in the discussion below, which describes more of the analysis functions of the management system.

Figure 140:
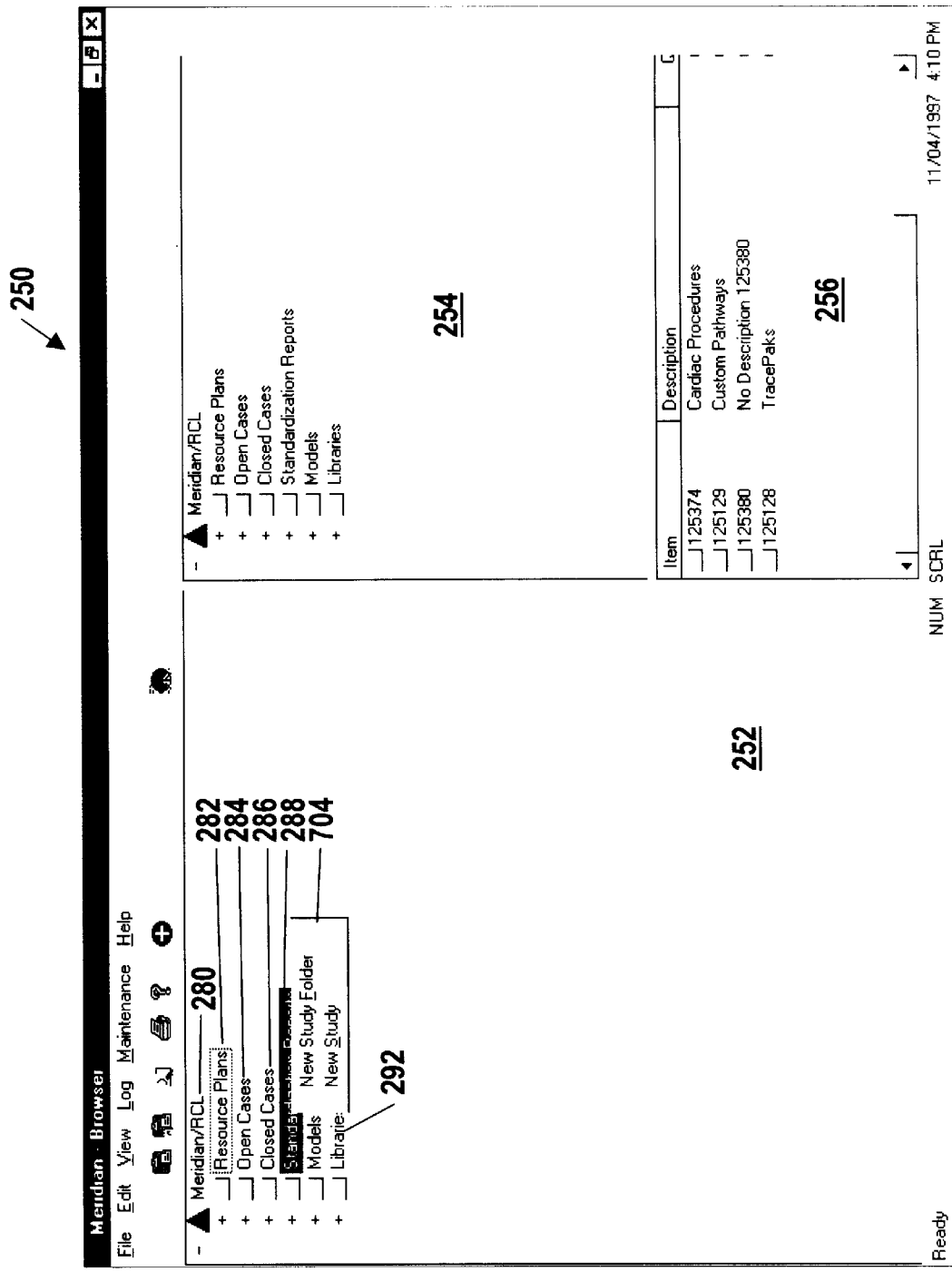
Figure 141:
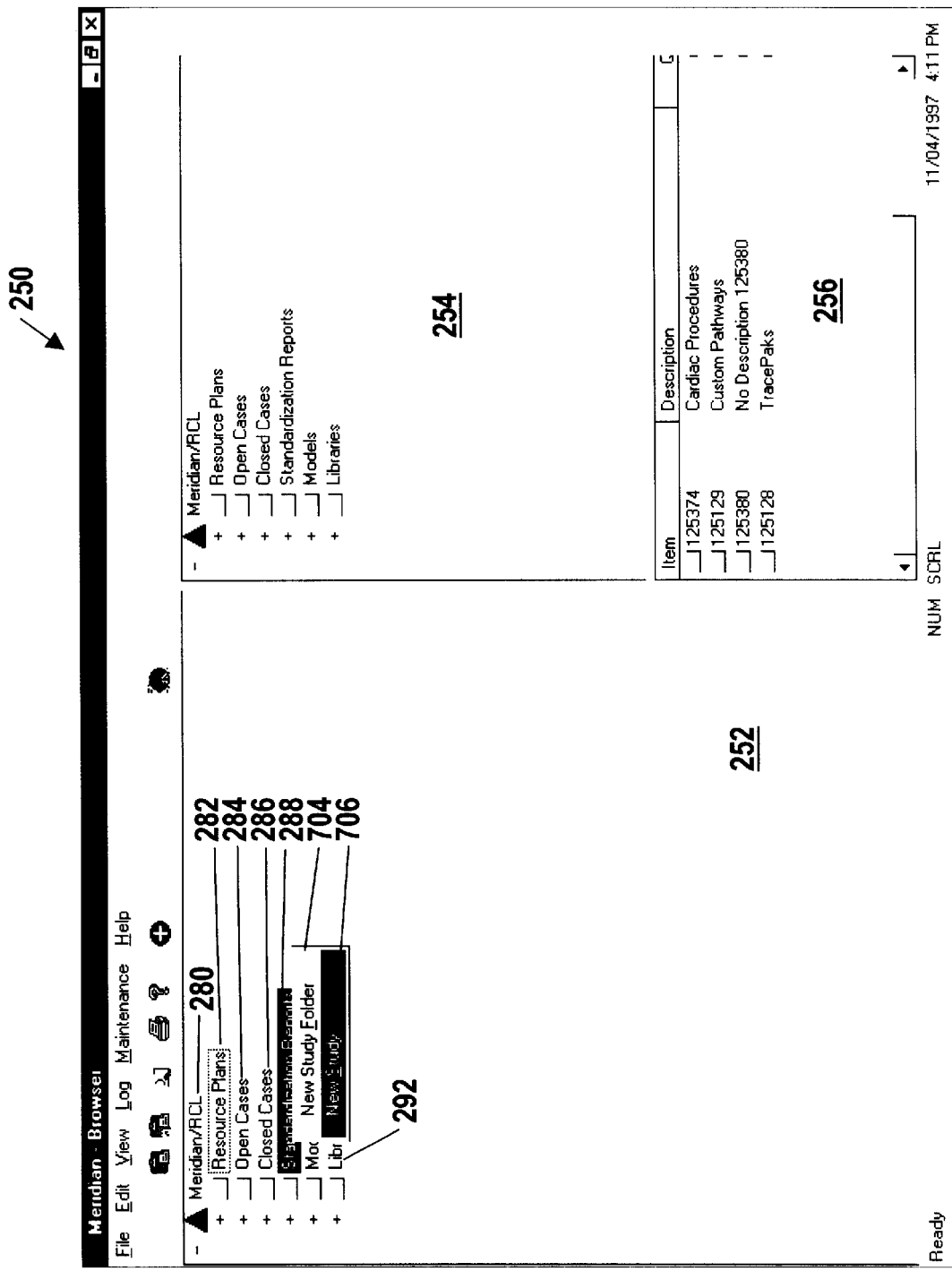
Figure 142:
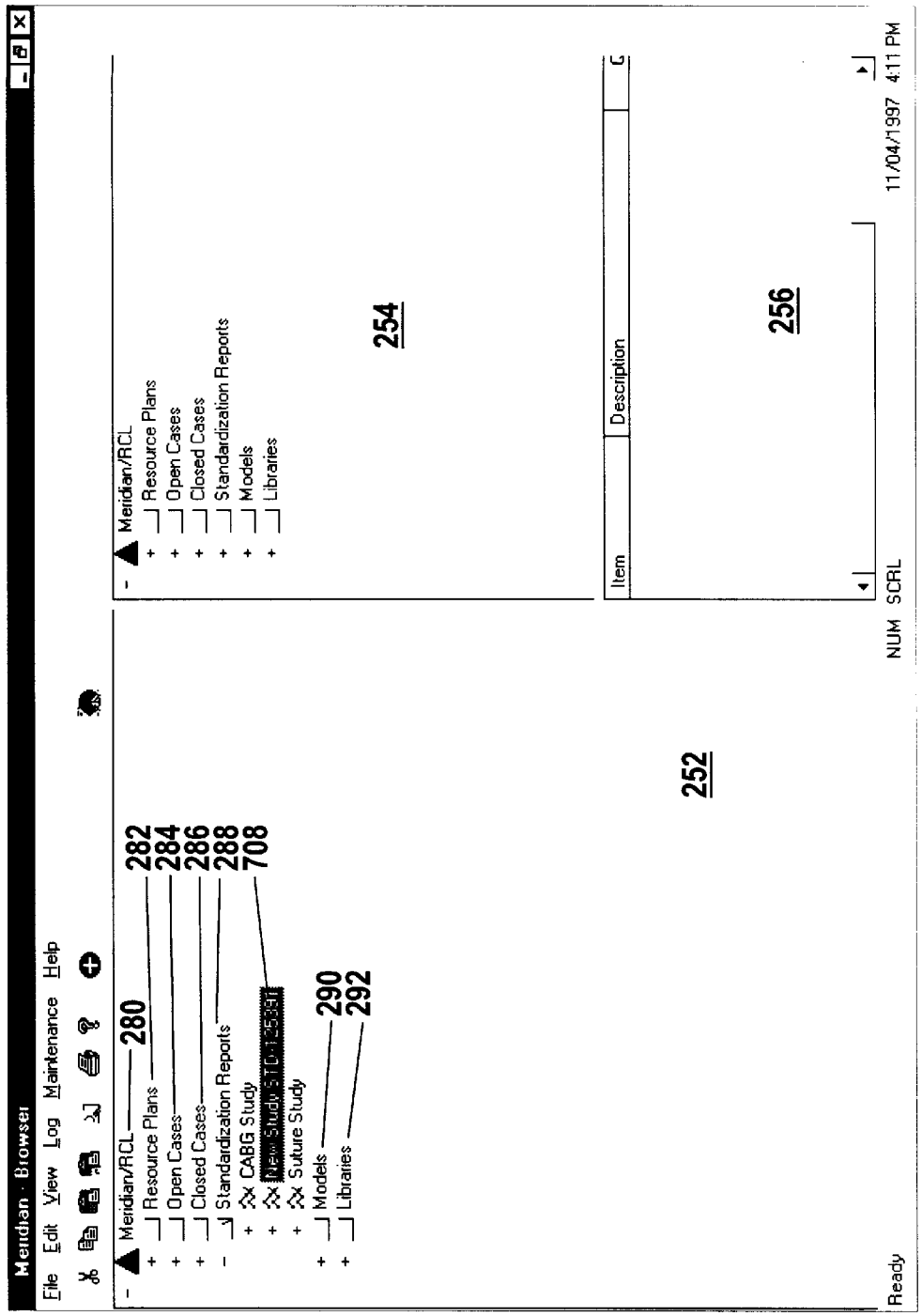
Figure 143:
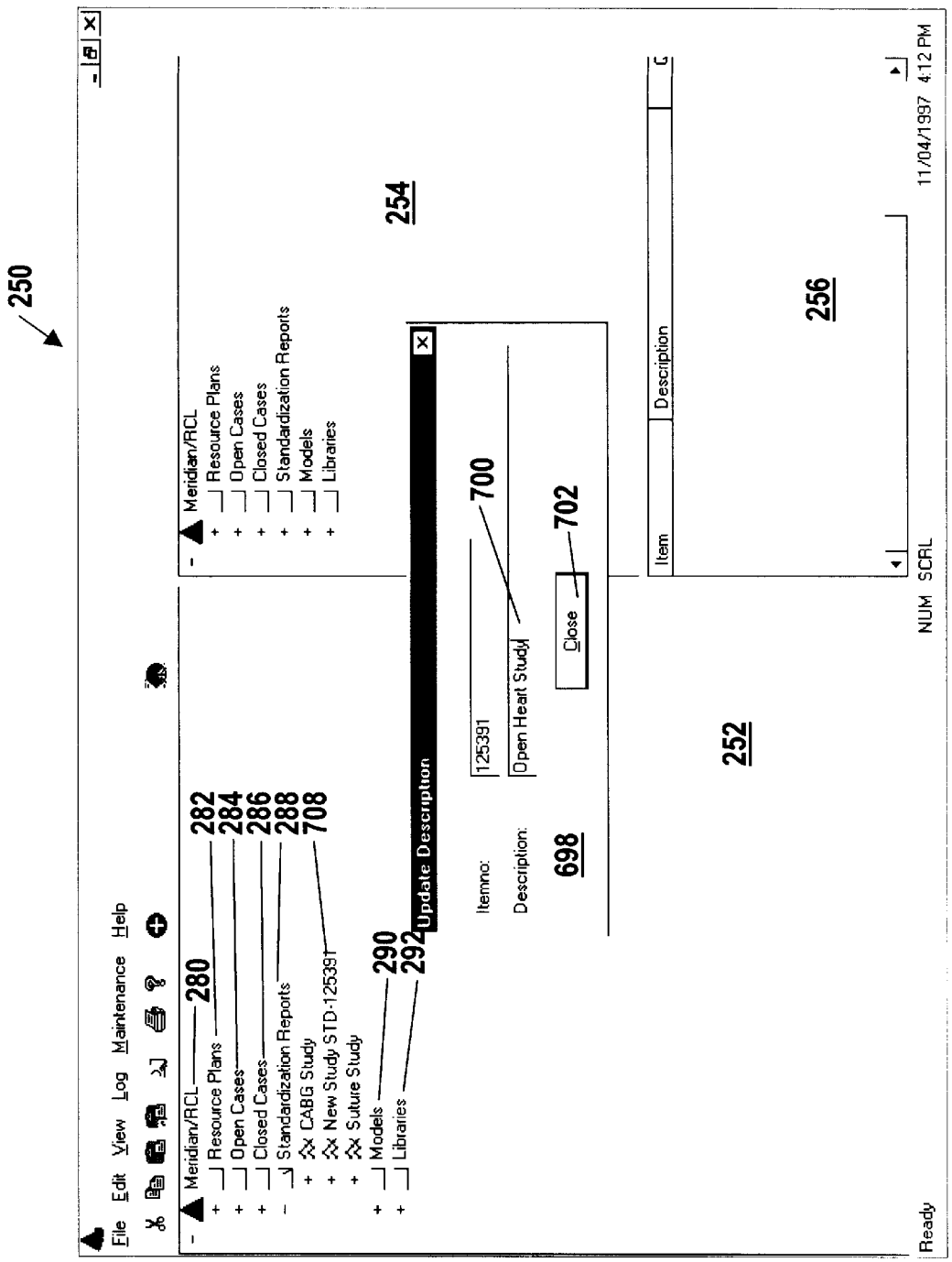
Figure 144:

A discussion of the preferred method of creating a new study, in which an analysis can be performed, is commenced with reference to FIG. 140. The Standardization Reports node 288 is selected, and the Standardization Reports menu is invoked in one of the methods described above. The New Study function 706 is selected from the Standardization Reports menu 704, as depicted in FIG. 141, and a new study 708 is created, with a default name as preferably determined by the management system, as depicted in FIG. 142. The new study is given a new name by invoking the Update Description dialog box 698, as described above, entering the desired new name, and clicking the Close button 702, as depicted in FIG. 143. The renamed study is displayed as depicted in FIG. 144.

Figure 145:
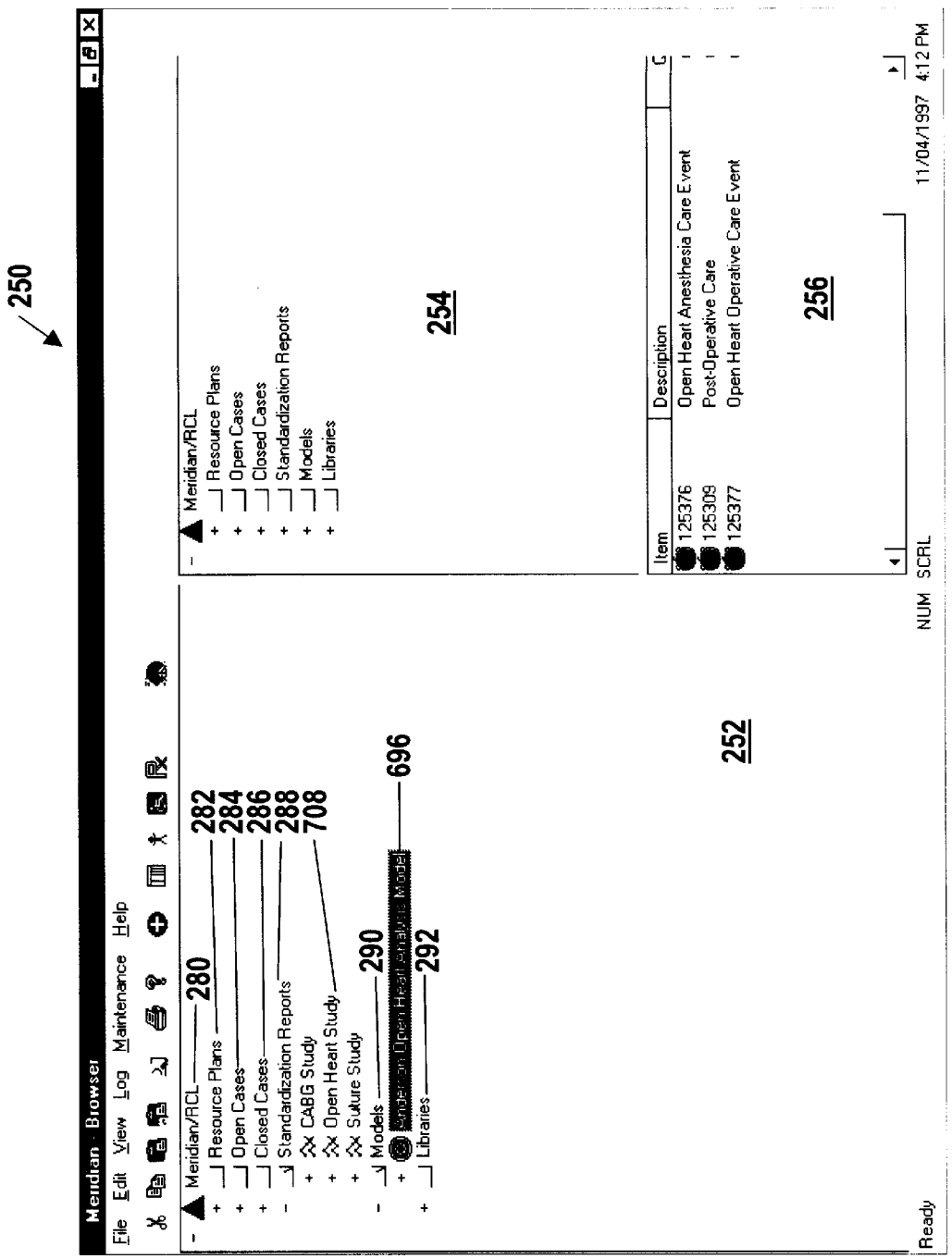
Figure 146:
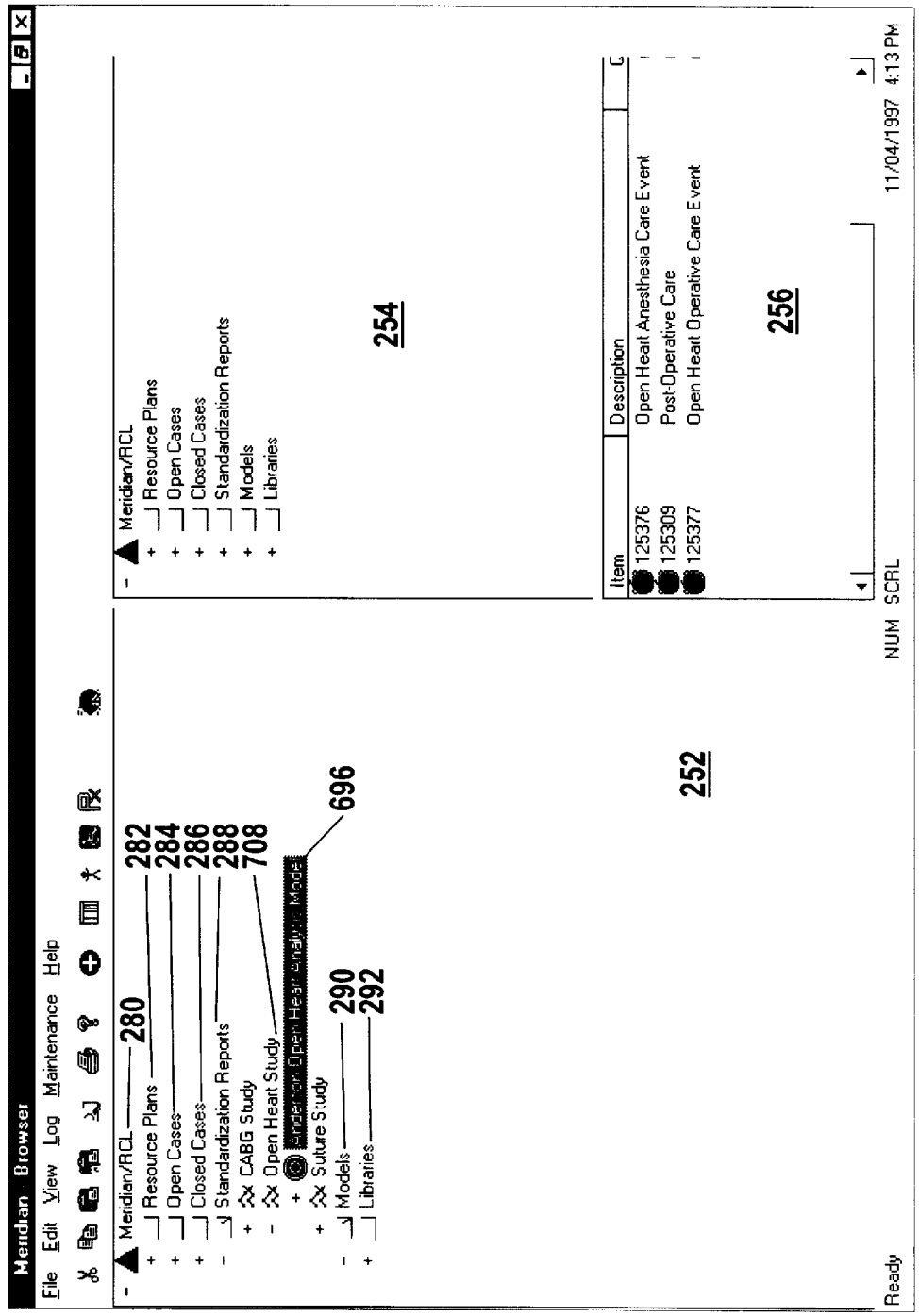

The model on which the study is to be based is selected, as depicted in FIG. 145. In the example of FIG. 145, the Anderson Open Heart Analysis Model 696 is selected for the new Open Heart Study 708. The study is created by moving the Open Heart Analysis Model 696 from the Models node 290 to the appropriate study 708 within the Standardization Reports node 288, as depicted in FIG. 146. Again it is mentioned at this juncture, that although the objects that are copied and moved from one node to another appear to retain their exact identity and function, this is not the case. Copying and moving the objects from one node to another modifies the object to retain a portion of its prior characteristics, and a link to the prior associated object, but endows the new object with additional functionality, as described throughout this discussion. It is this ability to retain specific aspects of the precursor object while accepting aspects of the successor object that allows the management system according to the present invention to provide such power with such an easily understood interface.

Figure 147:
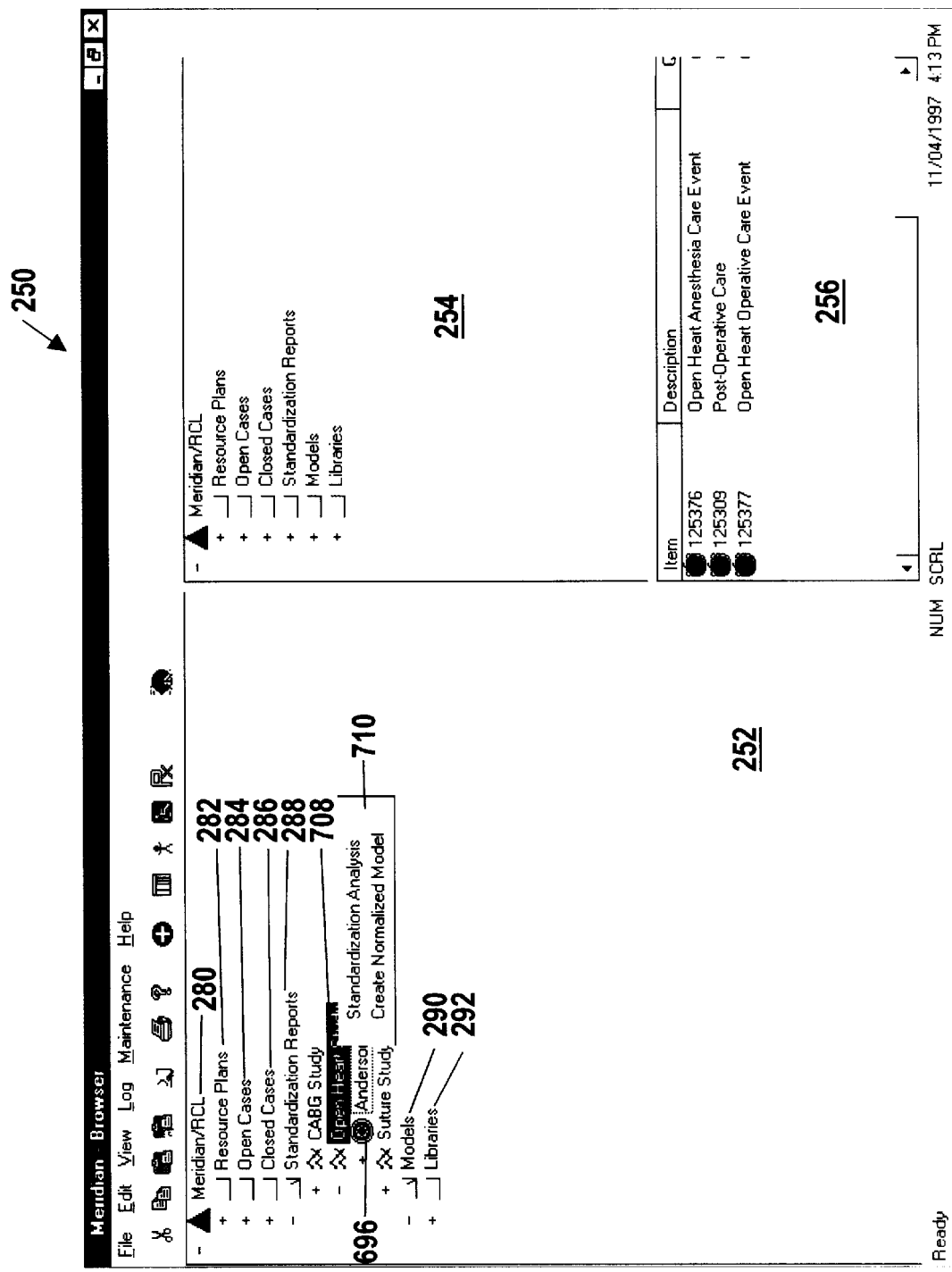

The analysis is commenced by invoking the Analysis menu 710 from the selected model 696 inside of the appropriate study 708, as depicted in FIG. 147. From this menu, the management system of the exemplar embodiment provides the ability for the user to create many different kinds of reports. For example, reports can be generated which track how well the resources allocated to a given procedural pathway correlate to the actual usage of those resources.

The foregoing description of the preferred and exemplar embodiments of the present invention is for the purposes of illustration and not limitation. The preferred and exemplar embodiments are capable of numerous modifications, substitutions and deletions without departing from the scope of the invention as set forth in the following claims. For example, while the preferred and exemplar embodiments are described as being implemented in the Windows 95 or Windows NT environment using ActiveX or OLE controls from Microsoft Corp., the modular software object approach described could be implemented in other standards or operating environments such as Delphi. Furthermore, while the objects described above are preferentially written in Visual C++, any other common programming language may be used as well. Finally, while the computer environment is preferentially a PC environment, either networked or stand alone, other computer systems such as RISC servers, workstations, mainframes, or access to processors through the Internet may be substituted.

What is claimed is:

1. A system for managing health care services, comprising:
   a) computing means having;
      i) input means for receiving patient health care information,
      ii) storage means for storing data corresponding to the patient health care information,
      iii) processing means for processing software objects corresponding to health care services management instructions and the patient health care information and producing health care services management output, and
      iv) display means for visually presenting the health care services output,
   b) the software objects including data software objects having;
      i) means for receiving the patient health care information, and
      ii) means for providing the patient health care information through a standardized interface,
   c) the software objects including resource software objects for associating resources with information relating to the resources, including;
      i) personnel resource software objects having;
         (1) means for associating a health care personnel resource with information relating to the health care personnel resource, including at least one of a personnel resource billing rate, a personnel resource pay rate, and a personnel resource time requirement, and
         (2) means for providing the information relating to the health care personnel resource through the standardized interface,
      ii) equipment resource software objects having;
         (1) means for associating a health care equipment resource with information relating to the health care equipment resource, including at least one of an equipment resource billing rate, an equipment resource cost, and an equipment resource time requirement, and
         (2) means for providing the information relating to the health care equipment resource through the standardized interface, and iii) supply resource software objects including;
(1) bundle supply resource software objects having;
(a) means for associating health care supply resources with information relating to health care supply resources, including at least one of a supply resource billing rate and a supply resource cost, and
(b) means for providing the information relating to health care supply resources through the standardized interface, and
(2) conditional bundle supply resource software objects having;
(a) means for associating health care supply resources with information relating to health care supply resources, including at least one of supply resource billing rates and supply resource costs, and
(b) means for selectively providing the information relating to health care supply resources through the standardized interface based at least in part on the patient health care information provided by at least one of the data software objects, and
d) the software objects including node software objects including at least a pathway node software object having;
i) means for selectively creating the data software objects,
ii) means for selectively creating the resource software objects,
iii) means for selectively linking the standardized interface of the data software objects and resource software objects into configurable procedural pathways associated with health care treatment plans,
iv) means for selectively adapting the information provided through the standardized interface of the data software objects, and resource software objects, and
v) means for providing the data software objects, and resource software objects, with a first set of functions specifically adapted to the pathway node software object.

2. The system of claim 1, further comprising container software objects having;
a) means for selectively associating groups of data software objects, resource software objects, and container software objects, and
b) means for associating the groups with information relating to at least one of a health care procedure and a health care resource kit.

3. The system of claim 1, wherein the node software objects further comprise a case node software object having:
a) means for receiving the procedural pathways from the pathway node software object and converting the procedural pathways into at least one of an open case software object and a closed case software object,
b) means for providing open case software objects and closed case software objects to the pathway node software object,
c) means for selectively adapting the information provided through the standardized interface of the data software objects and resource software objects, and
d) means for providing the data software objects and resource software objects with a second set of functions specifically adapted to the case node software object.

4. The system of claim 1, wherein the node software objects further comprise a model node software object having:
a) means for receiving the closed case software objects from the case node software object and converting the closed case software objects into analysis model software objects,
b) means for providing analysis model software objects to the case node software object,
c) means for selectively adapting the information provided through the standardized interface of the data software objects and resource software objects, and
d) means for providing the data software objects and resource software objects with a third set of functions specifically adapted to the model node software object.

5. The system of claim 4, wherein the node software objects further comprise a report node software object having:
a) means for receiving the analysis model software objects from the model node software object and converting the analysis model software objects into configurable report software objects
b) means for providing configurable report software objects to the model node software object,
c) means for selectively adapting the information provided through the standardized interface of the data software objects and resource software objects, and
d) means for providing the data software objects and resource software objects with a fourth set of functions specifically adapted to the model node software object.

6. The system of claim 1, wherein the node software objects further comprise a library node software object having;
a) means for selectively creating the data software objects,
b) means for selectively creating the resource software objects,
c) means for selectively creating container software objects,
d) means for selectively linking the standardized interface of the data software objects, resource software objects, and container software objects into configurable sets associated with the health care services,
e) means for selectively adapting the information provided through the standardized interface of the data software objects, resource software objects, and container software objects, and
f) means for providing the data software objects, resource software objects, and container software objects with a fifth set of functions specifically adapted to the model node software object.

7. The system of claim 1, further comprising means for scheduling health care services resources based at least in part on the health care services management output.

8. The system of claim 1, further comprising means for billing patients based at least in part on the health care services management output.

9. The system of claim 1, further comprising means for ordering supplies based at least in part on the health care services management output.

10. A system for managing health care services, comprising:
a) computing means having;
i) input means for receiving health care services information and health care services management instructions,
ii) storage means for storing data corresponding to the health care services information,
iii) processing means for selectively processing commands corresponding to the health care services management instructions based on the health care services information and producing health care services management output, and iv) display means for visually presenting the health care services output, b) data software objects having;
    i) means for receiving patient health care information, and
    ii) means for providing the patient health care information through a standardized interface, c) resource software objects for associating resources with information relating to the resources, including;
    i) personnel resource software objects having;
        (1) means for associating a health care personnel resource with information relating to the health care personnel resource, including at least one of a personnel resource billing rate, a personnel resource pay rate, and a personnel resource time requirement, and
        (2) means for providing the information relating to the health care personnel resource through the standardized interface,
    ii) equipment resource software objects having;
        (1) means for associating a health care equipment resource with information relating to the health care equipment resource, including at least one of an equipment resource billing rate, an equipment resource cost, and an equipment resource time requirement, and
        (2) means for providing the information relating to the health care equipment resource through the standardized interface,
    iii) supply resource software objects including;
        (1) bundle supply resource software objects having;
            (a) means for associating health care supply resources with information relating to health care supply resources, including at least one of a supply resource billing rate and a supply resource cost, and
            (b) means for providing the information relating to health care supply resources through the standardized interface, and
        (2) conditional bundle supply resource software objects having;
            (a) means for associating health care supply resources with information relating to health care supply resources, including at least one of supply resource billing rates and supply resource costs, and
            (b) means for selectively providing the information relating to health care supply resources through the standardized interface based at least in part on the patient health care information provided by at least one of the data software objects, and d) container software objects having;
    i) means for selectively associating groups of data software objects, resource software objects, and container software objects, and
    ii) means for associating the groups with information relating to at least one of a health care procedure and a health care resource kit, and e) node software objects including;
    i) a pathway node software object having;
        (1) means for selectively creating the data software objects,
        (2) means for selectively creating the resource software objects,
        (3) means for selectively creating the container software objects,
        (4) means for selectively linking the standardized interface of the data software objects, resource software objects, and container software objects into configurable procedural pathways associated with health care treatment plans,
        (5) means for selectively adapting the information provided through the standardized interface of the data software objects, resource software objects, and container software objects, and
        (6) means for providing the data software objects, resource software objects, and container software objects with a first set of functions specifically adapted to the pathway node software object,
    ii) a case node software object having;
        (1) means for receiving the procedural pathways from the pathway node software object and converting the procedural pathways into at least one of an open case software object and a closed case software object,
        (2) means for providing open case software objects and closed case software objects to the pathway node software object,
        (3) means for selectively adapting the information provided through the standardized interface of the data software objects, resource software objects, and container software objects, and
        (4) means for providing the data software objects, resource software objects, and container software objects with a second set of functions specifically adapted to the case node software object,
    iii) a model node software object having;
        (1) means for receiving the closed case software objects from the case node software object and converting the closed case software objects into analysis model software objects,
        (2) means for providing analysis model software objects to the case node software object,
        (3) means for selectively adapting the information provided through the standardized interface of the data software objects, resource software objects, and container software objects, and
        (4) means for providing the data software objects, resource software objects, and container software objects with a third set of functions specifically adapted to the model node software object,
    iv) a report node software object having;
        (1) means for receiving the analysis model software objects from the model node software object and converting the analysis model software objects into configurable report software objects,
        (2) means for providing configurable report software objects to the model 95 node software object,
        (3) means for selectively adapting the information provided through the standardized interface of the data software objects, resource software objects, and container software objects, and
        (4) means for providing the data software objects, resource software objects, and container software objects with a fourth set of functions specifically adapted to the model node software object, and
    v) a library node software object having;
        (1) means for selectively creating the data software objects,
        (2) means for selectively creating the resource software objects, (3) means for selectively creating the container software objects, (4) means for selectively linking the standardized interface of the data software objects, resource software objects, and container software objects into configurable sets associated with the health care services, (5) means for selectively adapting the information provided through the standardized interface of the data software objects, resource software objects, and container software objects, and (6) means for providing the data software objects, resource software objects, and container software objects with a fifth set of functions specifically adapted to the model node software object.

11. An information management system for managing information relating to providing health care services, comprising:
   a) a general purpose computer system having;
      i) storage means for storing data corresponding to the information,
      ii) processing means for processing management instructions,
      iii) display means for visually presenting the information, and
      iv) input means for receiving the management instructions and the information; and
   b) information management software installed on the general purpose computer system and having software objects, each of the software objects providing a health care information management function and corresponding to an aspect of providing health care services, wherein the software objects are combined in procedural pathways corresponding to sets of health care procedures.

12. The information management system of claim 11, wherein the software objects further comprise node software objects for creating, altering characteristics of, and the management of the software objects.

13. The information management system of claim 12, wherein the characteristics of the software objects further comprise predefined options for modifying or manipulating a selected one of the software objects.

14. The information management system of claim 12, wherein the management of the software objects further comprises analyzing health care information associated with a selected one of the software objects.

15. The information management system of claim 11, wherein the software objects further comprise container software objects for containing the software objects, and corresponding to at least one of health care procedures, health care information, and health care resource groups.

16. The information management system of claim 15, wherein the container software objects further comprise care event container software objects for containing the software objects, and corresponding to health care procedures.

17. The information management system of claim 15, wherein the container software objects further comprise bundle container software objects for containing the software objects, and corresponding to health care resource groups.

18. The information management system of claim 11, wherein the software objects further comprise resource software objects corresponding to resources to be used in the provision of health care services.

19. The information management system of claim 18, wherein the resource software objects further comprise equipment resource software objects corresponding to equipment to be used in the provision of health care services.

20. The information management system of claim 18, wherein the resource software objects further comprise personnel resource software objects corresponding to personnel to be used in the provision of health care services.

21. The information management system of claim 18, wherein the resource software objects further comprise supply resource software objects corresponding to supplies to be used in the provision of health care services.

22. The information management system of claim 11, wherein the software objects further comprise data software objects corresponding to health care information associated with the provision of health care services.

23. The information management system of claim 11, wherein the software objects further comprise:
   a) node software objects for creating, altering characteristics of, and managing the software objects,
   b) container software objects for containing the software objects, and corresponding to at least one of health care procedures, health care information, and health care resource groups,
   c) resource software objects corresponding to resources to be used in the provision of health care services, and
   d) data software objects corresponding to health care information.

24. The information management system of claim 23, wherein the node software objects, container software objects, resource software objects, and data software objects are combined in cases corresponding to sets of health care procedures designated for a patient.

25. The information management system of claim 24, wherein the cases are selectively designated as open, corresponding to sets of health care procedures that are planned for a patient.

26. The information management system of claim 24, wherein the cases are selectively designated as closed, corresponding to sets of health care procedures that are completed for a patient.

27. The information management system of claim 23, wherein the node software objects, container software objects, resource software objects, and data software objects are combined in a library of predefined care event containers corresponding to predefined health care procedures.

28. The information management system of claim 23, wherein the node software objects, container software objects, resource software objects, and data software objects are combined in a library of predefined bundle containers corresponding to predefined health care resource groups.

29. The information management system of claim 23, wherein the node software objects, container software objects, resource software objects, and data software objects are combined in a library of procedural pathways having predefined care event containers corresponding to predefined health care procedures and predefined bundle containers corresponding to predefined health care resource groups, corresponding to predefined sets of health care procedures.

30. The information management system of claim 29, wherein at least a portion of the predefined bundle containers are selectively included based at least in part on the health care information in the data software objects.

31. The information management system of claim 23, wherein at least a portion of the resource software objects are selectively included within a procedural pathway node software object based at least in part upon user entered information in the data software objects.

32. An information management system for managing information relating to providing health care services, comprising:
a) a general purpose computer system having;
   i) storage means for storing data corresponding to the information,
   ii) processing means for processing management instructions,
   iii) display means for visually presenting the information, and
   iv) input means for receiving the management instructions and the information; and
b) information management software installed on the general purpose computer system and having software objects, each of the software objects providing a health care information management function and corresponding to an aspect of providing health care services, the software objects including;
   i) node software objects for creating, altering characteristics of, and managing the software objects,
   ii) container software objects for containing the software objects, and corresponding to at least one of health care procedures, health care information, and health care resource groups,
   iii) resource software objects corresponding to resources to be used in the provision of health care services, and
   iv) data software objects corresponding to health care information;
c) the node software objects, container software objects, resource software objects, and data software objects combined in procedural pathways corresponding to sets of health care procedures.

33. The information management system of claim 32, wherein at least a portion of the resource software objects are selectively combined within the procedural pathways based at least in part upon user entered information in the data software objects.

34. An information management system for managing information relating to providing health care services, comprising:
a) a general purpose computer system having;
   i) storage means for storing data corresponding to the information,
   ii) processing means for processing management instructions,
   iii) display means for visually presenting the information, and
   iv) input means for receiving the management instructions and the information; and
b) information management software installed on the general purpose computer system and having software objects, each of the software objects providing a health care information management function and corresponding to an aspect of providing health care services, the software objects including;
   i) node software objects for creating, altering characteristics of, and managing the software objects,
   ii) container software objects for containing the software objects, and corresponding to at least one of health care procedures, health care information, and health care resource groups,
   iii) resource software objects corresponding to resources to be used in the provision of health care services, and
   iv) data software objects corresponding to health care information; and
c) the node software objects, container software objects, resource software objects, and data software objects provided in a hierarchical form, corresponding to a sequential order of health care procedures to be performed, health care resources to be provided, and health care information to be gathered and recorded.

35. The information management system of claim 34, wherein at least a portion of the resource software objects are selectively provided based at least in part on the health care information recorded within the data software objects.

36. A method for managing health care services, comprising:
a) entering patient health care information into a computing means with an input means,
b) storing data corresponding to the patient health care information in a storage means,
c) processing software objects corresponding to health care services management instructions and the patient health care information on a processing means, and thereby producing health care services management output with the processing means, the processing further including;
   i) selectively creating data software objects, equipment resource software objects, personnel resource software objects, bundle supply resource software objects, and conditional bundle supply resource software objects with a pathway node software object,
   ii) receiving the patient health care information with the data software object,
   iii) providing the patient health care information through a standardized interface,
   iv) associating a health care equipment resource with information relating to the health care equipment resource with the equipment resource software object, the information relating to the health care equipment resource including at least one or an equipment resource billing rate, and equipment resource cost, and an equipment resource time requirement,
   v) providing the information relating to the health care equipment resource through the standardized interface,
   vi) associating a health care personnel resource with information relating to the health care personnel resource with the personnel resource software object, the information relating to the health care personnel resource including at least one of a personnel resource billing rate, a personnel resource pay rate, and a personnel resource time requirement,
   vii) providing the information relating to the health care personnel resource through the standardized interface,
   viii) associating health care supply resources with information relating to health care supply resources with the bundle supply resource software object, the information relating to health care supply resources including at least one of a supply resource billing rate and a supply resource cost,
   ix) providing the information relating to the health care supply resources through the standardized interface,
   x) associating health care supply resources with information relating to health care supply resources with the conditional bundle supply resource software object, the information relating to health care supply resources including at least one of supply resource billing rates and supply resource costs,
   xi) selectively providing the information relating to health care supply resources through the standardized interface based at least in part on the patient health care information provided by at least one of the data software objects, xii) selectively linking the standardized interface of the data software objects, equipment resource software objects, personnel resource software objects, bundle supply resource software objects, and conditional bundle supply resource software objects with the pathway node software object, xiii) selectively adapting the information provided through the standardized interface of the data software objects, equipment resource software objects, personnel resource software objects, bundle supply resource software objects, and conditional bundle supply resource software objects with the pathway node software object, and xiv) providing the data software objects, equipment resource software objects, personnel resource software objects, bundle supply resource software objects, and conditional bundle supply resource software objects with a first set of function specifically adapted to the pathway node software object, and d) visually presenting the health care services output on a display means.

* * * * *